United States Patent
Stankey et al.

(10) Patent No.: US 11,390,882 B2
(45) Date of Patent: Jul. 19, 2022

(54) EXPRESSION VECTOR

(71) Applicant: VARIGEN BIOSCIENCES CORPORATION, Middleton, WI (US)

(72) Inventors: Robert Joseph Stankey, Madison, WI (US); David Mead, Middleton, WI (US)

(73) Assignee: VARIGEN BIOSCIENCES CORPORATION, Middleton, WI (US)

( * ) Notice: Subject to any disclaimer, the term of this patent is extended or adjusted under 35 U.S.C. 154(b) by 93 days.

(21) Appl. No.: 16/815,399

(22) Filed: Mar. 11, 2020

(65) Prior Publication Data

US 2020/0291430 A1  Sep. 17, 2020

Related U.S. Application Data

(60) Provisional application No. 62/817,345, filed on Mar. 12, 2019.

(51) Int. Cl.
*C12N 15/70* (2006.01)
*C12N 15/86* (2006.01)
*C12N 15/52* (2006.01)

(52) U.S. Cl.
CPC ............ *C12N 15/86* (2013.01); *C12N 15/52* (2013.01); *C12N 15/70* (2013.01)

(58) Field of Classification Search
CPC .................................................... C12N 15/86
See application file for complete search history.

(56) References Cited

U.S. PATENT DOCUMENTS

| | | |
|---|---|---|
| 4,766,072 A | 8/1988 | Jendrisak et al. |
| 5,017,488 A | 5/1991 | McAllister et al. |
| 5,830,693 A | 11/1998 | Shimizu et al. |
| 6,117,651 A | 9/2000 | Schultz et al. |
| 9,546,202 B2 | 1/2017 | Felber et al. |
| 2004/0053273 A1 | 3/2004 | Kobayashi et al. |
| 2008/0241894 A1 | 10/2008 | Plaetinck et al. |
| 2008/0292918 A1 | 11/2008 | Finnerty et al. |
| 2009/0075283 A1 | 3/2009 | Liu et al. |
| 2011/0111413 A1 | 5/2011 | Padgett et al. |

FOREIGN PATENT DOCUMENTS

| WO | WO2017151059 A1 | 9/2017 |
| WO | WO2020/185831 A1 | 9/2020 |

OTHER PUBLICATIONS

Bankevich et al., *SPAdes: A New Genome Assembly Algorithm and Its Applications to Single-Cell Sequencing*. Journal of Computational Biology, 2012. 19(5): p. 455-477.
Boyer et al., A complementation analysis of the restriction and modification of DNA in *Escherichia coli*, J Mol Biol, 1969. 41(3): p. 459-7.
Brettin et al., RASTtk: A modular and extensible implementation of the RAST algorithm for building custom annotation pipelines and annotating batches of genomes, 2015, Sci Rep 5, 8365.
Figurski et al., Replication of an origin-containing derivative of plasmid RK2 dependent on a plasmid function provided in trans. Proc Natl Acad Sci U S A, 1979. 76(4): p. 1648-52.
Gomez-Escribano et al., *Engineering Streptomyces coelicolor for heterologous expression of secondary metabolite gene clusters*. Microb Biotechnol, 2011. 4(2): p. 207-215.
Gustafsson et al., Codon bias and heterologous protein expression, Trends in Biotechnology, 2004. (22)7: 346-353.
Guy, et al., *genoPlotR: comparative gene and genome visualization in R*. Bioinformatics, 2010. 26(18): p. 2334-233.
Handelsman et al., 1998, Chem. Biol. 5: R245-R249.
Herai et al., *Hyper-inducible expression system for streptomycetes*. Proc Natl Acad Sci U S A, 2004. 101(39): p. 14031-14035.
International Search Report and Written Opinion issued in corresponding application PCT/US2020/021986, dated Aug. 6, 2020, 33 pages.
Matsumoto et al., Development of nitrilase promoter-derived inducible vectors for Streptomyces. Bioscience Biotechnology and Biochemistry, 2016. 80(6): p. 1230-1237.
Skinnider et al., Genomic charting of ribosomally synthesized natural product chemical space facilitates targeted mining. P Natl Acad Sci USA 201,;113:E6343-51.
Tellez et al., *Preparative purification and library construction of BAC DNA using reversible electrophoresis gels*. Abstracts of Papers of the American Chemical Society, 2000. 219: p. U192-U192.
Taitt et al., *Antimicrobial resistance determinants in Acinetobacter baumannii isolates taken from military treatment facilities*. Antimicrob Agents Chemother, 2014. 58(2): p. 767-81.
Van Heel et al., BAGEL3: Automated identification of genes encoding bacteriocins and (non-)bactericidal posttranslationally modified peptides. Nucleic Acids Res 2013,41:W448-53.
Villalobos et al., Gene Designer: a synthetic biology tool for constructing artificial DNA segments, 2006, BMC Bioinformatics 7: 285.
Tracanna et al., Mining prokaryotes for antimicrobial compounds: from diversity to function, FEMS Microbiology Reviews, vol. 41, Issue 3, May 1, 2017, pp. 417-429.
Wang et al., *Development of a Synthetic Oxytetracycline-Inducible Expression System for Streptomycetes Using de Novo Characterized Genetic Parts*. ACS Synthetic Biology, 2016. 5(7): p. 765-773.
Weber et al., antiSMASH 3.0—a comprehensive resource for the genome mining of biosynthetic gene clusters, *Nucleic Acids Research*, vol. 43, Issue W1, Jul. 1, 2015, pp. W237-W243.
Welch et al., (2009) Design Parameters to Control Synthetic Gene Expression in *Escherichia coli*. PLoS ONE 4(9): e7002. https://doi.org/10.1371/journal.pone.0007002.

(Continued)

*Primary Examiner* — Maryam Monshipouri
(74) *Attorney, Agent, or Firm* — Casimir Jones, S.C.; Thomas A. Isenbarger

(57) ABSTRACT

Disclosed herein are recombinant methods of activating expression of one or more biosynthetic gene clusters comprising more than one gene, the method comprising a recombinant DNA expression vector that possess two opposable inducible promoters that drives expression of a biosynthetic gene cluster exogenously from outside of the cluster to produce polyketides or non-ribosomal peptides in a heterologous host.

20 Claims, 9 Drawing Sheets

Specification includes a Sequence Listing.

(56) References Cited

OTHER PUBLICATIONS

Wild et al., *Conditionally amplifiable BACs: Switching from single-copy to high-copy vectors and genomic clones.* Genome Res, 2002. 12(9): p. 1434-1444.
Wu et al., SGDB: a database of synthetic genes re-designed for optimizing protein over-expression. Nucleic Acids Res. 2007 D76-9.
GenBank_DQ143963.2.
GenBank_CP007053.1.
GenBank_CP035491.1.

EXPRESSION VECTOR

This application claims priority to U.S. provisional patent application Ser. No. 62/817,345, filed Mar. 12, 2019, which is incorporated herein by reference in its entirety.

STATEMENT REGARDING FEDERALLY SPONSORED RESEARCH OR DEVELOPMENT

This invention was made with government support under grant numbers 5R44AI085840-04 and R43AT008295 awarded by the National Institutes of Health. The United States government has certain rights to the invention.

FIELD

Provided herein is technology related to expression and discovery of natural products and biologically active agents and particularly, but not exclusively, to compositions, methods, systems, and materials for expressing biologically active agents by recombinant DNA technology. The technology finds use in, e.g., the fields of agriculture, chemistry, medicinal chemistry, medicine, molecular biology, and pharmacology.

BACKGROUND

Small molecule compounds produced by bacteria, fungi, and plants hold tremendous potential for new pharmaceuticals, therapeutic agents, and industrially useful compounds. Over 60% of clinically useful anticancer drugs and 49% of anti-infective drugs in use today are derived from secondary metabolites called natural products (NP). Despite this record, pharmaceutical companies have cultivated millions of microbes searching for new bioactive natural product compounds only to rediscover known chemical scaffolds >99% of the time. In contrast, whole genome sequencing and metagenomic approaches (e.g., studies of DNA isolated from complex microbial communities) reveal an immense diversity of genes encoding unknown metabolites that are missed by conventional cultivation-based screening approaches. Culture-independent studies (e.g., metagenomics) reveal that only a small fraction of NP pathways have been expressed to produce a known metabolite. Accessing these compounds promises to reinvigorate drug discovery pipelines and provide novel routes to synthesize complex chemicals.

Polyketides, ribosomally synthesized and post-translationally modified peptides, and nonribosomal peptides are important classes of natural products responsible for the development of many human therapeutic, veterinary, and agricultural products (e.g., FK506, lovastatin, avermectin, vancomycin, daptomycin, and teixobactin). Genes encoding NP are usually arranged in contiguous units called biosynthetic gene clusters (BGCs) in bacteria and fungi, making it possible to identify their contents, e.g., using bioinformatic analysis tools (e.g., antiSMASH (Weber et al. 2015), BAGEL3 (van Heel A J, de Jong A, Montalban-Lopez M et al. BAGEL3: Automated identification of genes encoding bacteriocins and (non-)bactericidal posttranslationally modified peptides. Nucleic Acids Res 2013; 41:W448-53, incorporated herein by reference), and PRISM (Skinnider M A, Johnston C W, Edgar R E et al. Genomic charting of ribosomally synthesized natural product chemical space facilitates targeted mining. P Natl Acad Sci USA 2016; 113:E6343-51, incorporated herein by reference)) to recognize structural motifs found within the encoded enzymes. Some enzymes that synthesize these compounds—e.g., polyketide synthases (PKS) or nonribosomal peptide synthases (NRPS)—typically exist as large multi-modular scaffolds that have been the target of various molecular engineering methods directed to producing more of the small molecule compounds or improved analogs of existing pharmaceuticals. Further complicating things, many NP biosynthetic pathways comprise dozens of genes and are often 5 to 200 kilobases (kb) in size; thus, special tools and technologies are often used for biosynthesis of NPs.

A major bottleneck in NP discovery is the production of sufficient metabolite for biochemical, structural, and/or cytotoxicity analyses. Classical strain improvement and process development programs sometimes involve years of work to increase the yield of a compound from the natural producing organism and have achieved greater than 100-fold increases in titers. A number of microorganisms have been optimized through random mutagenesis for bulk production of highly valuable compounds, including penicillins, macrolide antibiotics, and lovastatins. However, this conventional approach to strain improvement is not feasible during the early stages of discovering or characterizing NPs.

Ribosome and RNA polymerase engineering, regulatory gene activation, the use of eliciting agents, epigenetic perturbations, testing multiple media recipes, and many of the other recent methods developed to improve NP expression are low throughput and are limited to being applied to one pathway or one organism at a time. Refactoring a NP pathway in a native host organism to insert promoters or modify regulatory elements is a relatively new method to overproduce metabolites that involves the use of specialized genome editing tools, a genetically tractable host, and months of effort to identify the proper combination of genetic elements that increase metabolite production. An alternative method comprises cloning the pathway onto a shuttle vector and moving the cloned pathway into a surrogate "heterologous host" species that is often engineered to enhance the production and discovery of secondary metabolites. This process does not always produce detectable metabolites or sufficient metabolite to characterize the molecule further. Accordingly, such approaches often involve additional efforts to modify the cloned pathway to overexpress the proteins needed to produce the small molecule.

The development of new drugs from NP biosynthetic pathways is labor intensive and very expensive. Current methods involve specific and particularized tailoring and precise genetic modifications for each pathway, most of which involve multiple gene products encoded by very large gene clusters that are difficult to manipulate. Nevertheless, heterologous expression of entire BGCs in a genetically tractable host is one of the most promising approaches to connect BGCs to their NP. Heterologous expression permits the characterization of BGCs from cultured microbes and from metagenomic DNA and provides a technology for accessing potentially new and valuable compounds. However, BGCs often are 20-200 kb in size and their manipulation involves use of specialized cloning methods and autonomously replicating bacterial chromosome vectors called bacterial artificial chromosomes (BACs) or cosmid/fosmid cloning vectors. Cloning methods often entail producing a clone library of large DNA inserts (e.g., comprising 5 to 10 to 100 kb or more) from a genome or metagenome and then screening the clone library by PCR or other sequence-specific methods to locate a clone comprising the desired BGC. While such approaches have proven to be successful, constructing and managing such a clone library and then finding an entire pathway on one clone is challenging. Some recombination-based technologies have been developed to address library construction by circumventing the entire genome library construction approach of obtaining a BGC. However, these technologies are also lengthy and complicated. For example, recent strategies using CRISPR/Cas9 as a universal restriction endonuclease have been used in vitro to excise a BGC precisely for further manipulation. Such approaches have led to rapid improvements in directly cloning BGCs from essentially any bacterial or fungal genome that has been sequenced.

Heterologous expression of biosynthetic gene clusters in a genetically tractable host can provide a more directed strategy for natural product discovery and a variety of new tools have been developed recently to investigate the vast number of BGCs identified by sequencing microbes. The heterologous expression process usually comprises five steps: assembling a high quality sequence of a target genome or metagenome, identifying a target BGC, cloning the BGC or genes of a BGC that provide a biosynthetic pathway, expressing the genes of the pathway in a heterologous host, and detecting the metabolite produced by the host. Briefly, in some approaches, BGCs are identified from sequenced genomes or metagenomic clones using computational tools such as AntiSMASH. Various DNA cloning and/or assembly tools and engineered heterologous hosts are then used for expression of the large biosynthetic gene clusters. To identify the target natural products, the resulting metabolite profiles are evaluated and characterized by advanced metabolomics and detection techniques such as mass spectrometry and antibiosis activity against pathogenic microbes.

Despite improvements in molecular biological tools, significant issues remain for heterologous expression technologies. For instance, moving a BGC between organisms, even closely related ones, can drastically change the productivity of a pathway because regulatory gene pathways are not fully conserved between species. Accordingly, it is not surprising that most natural product biosynthetic gene clusters identified in microbial genomic and metagenomic sequencing efforts are silent under laboratory growth conditions. It is therefore often necessary to refactor the regulation of a BGC using well-characterized promoters to provide expression in a heterologous host. BGC refactoring decouples gene clusters from native regulatory contexts by placing pathway genes encoded by the BGC downstream of known, characterized promoters in a production host. However, the field insufficiently understands the transcriptional regulation hierarchy to predict precisely the promoter refactoring events that induce secondary metabolite production from most silent biosynthetic gene clusters. Due to this uncertainty, each promoter of a small library of known, different promoters is placed in multiple strategic positions in the pathway in an attempt to identify a combination that activates the cluster, if any. Often times several hundred different combinations of promoters and insertion sites are constructed and screened to produce a compound. This process is lengthy and challenging. The amount of work and time involved in refactoring a single pathway is immense, and current tools that allow for controllable expression of BGCs do not scale to screening tens or hundreds of novel pathways.

In spite of advances in genome sequencing, bioinformatic discovery of BGCs, and cloning of BGCs into shuttle vectors for manipulation and experimentation, there is still no universal method to activate the expression of large NP pathways. Often the pathway does not produce sufficient or detectable metabolite in its surrogate heterologous host and additional extensive genetic manipulation is required, which may entail many months of effort by multi-functional teams. The current state of the art for expressing BGCs in *Streptomyces* involves genetic engineering of native or synthetic promoters located endogenously within a BGC to attempt to activate the entire pathway. Accordingly, a universal tool that activates quiescent pathways exogenously and/or facilitates over-expression of BGCs would have a major impact in accelerating NP drug discovery by giving researchers more control over expression pathways of interest in ways that were only previously achievable by laborious and time-consuming genetic refactoring.

It is well known in the art that individual genes can be expressed using constitutive or inducible promoters in nearly any host. For example, the inducible promotors Potr (1) and PnitA (2, 3) have been described for use in single-gene expression experiments and their respective oxytetracycline (OTC) and ε-caprolactam (ε-cap) inducers appear to have no effect on the physiology or growth rate of common *Streptomyces* expression strains. There are numerous examples of promoters being placed strategically in front of one or a few genes in a BGC to initiate expression of some of the proteins in the pathway (see, e.g., Int'l Pat. Pub. No. WO2017151059A1, incorporated herein by reference).

It is also well known in the art that dual promoter vectors have been used to transcribe DNA from one or both sides of a recombinant clone (see, e.g., U.S. Pat. Nos. 4,766,072 and 5,017,488, each of which is incorporated herein by reference) or to express one (see, e.g., U.S. Pat. No. 6,117,651, incorporated herein by reference) or several protein-encoding genes (see, e.g., U.S. Pat. No. 9,546,202, incorporated herein by reference) operably linked to said promoters. There are also multiple examples of uni-directional or bi-directional promoters used to express several genes in a BGC when inserted into the appropriate position between genes within a pathway (see, e.g., Int'l Pat. Pub. No. WO201715 1059A1, incorporated herein by reference).

Accordingly, the art would benefit from technology that improves the efficiency, simplicity, and/or throughput of expressing natural products from BGCs and/or from large inserts (e.g., comprising 5 to 10 to 100 kb or more).

SUMMARY

Accordingly, provided herein is a technology in which transcription of a BGC is placed under control of promoters that are present in a cloning vector and that are thus external to the BGC. There are no known examples of a promoter being used outside of the confines of a BGC, that is, placed exogenously outside of the BGC to activate expression of the entire pathway. The present technology teaches for the first time that non-strategically placed exogenous promoters can be used to activate endogenous regulatory components within a BGC that activate the production of a biologically active agent. In contrast to previous technologies, embodiments of the technology provided herein comprise cloning a BGC into an inducible dual-promoter vector to produce a small molecule metabolite. The dual-promoter vector provides transcription of pathway and/or pathway components (e.g., genes) from one or both directions. In some embodiments, the technology provided herein is a plug-and-play approach for heterologous expression that reduces the amount of time needed to produce a NP metabolite, e.g., from months to days.

Biosynthetic gene clusters (BGCs) encode multiple genes that produce small molecule compounds of considerable therapeutic value as drugs for fighting cancer, viral and bacterial infections, and more. BGCs often contain dozens of genes clustered in a functional unit and comprise multiple promoters and regulator elements in multiple orientations. Activating a BGC to discover novel small molecules or to over-express a BGC to produce more of a known compound, is technically difficult and very complicated.

Accordingly, the technology provided herein facilitates chemical analyses of the biosynthetic potential of gene clusters from genomic or metagenomic sources by improving heterologous expression of BGCs. In particular, embodiments of the technology provide a dual-promoter BAC vector that comprises two inducible promoters flanking a cloning site for heterologous expression of cloned inserts (e.g., comprising a BGC) in *Streptomyces* species. After cloning a BGC nucleic acid into the dual-promoter vector (e.g., in an *E. coli* host) and the presence of the cloned BGC sequence is verified, the recombinant clone is transconjugated to a *Streptomyces* spp. for heterologous expression. The transconjugant strain may now be capable of expressing the BGC using, e.g., basal expression (no inducer) from native promoters or BGC expression may be inducible using one or both of the non-native promoters of the vector that flank the cloned BGC nucleic acid.

During the development of the technology provided herein, experiments using the 21-kb ACT cluster and the 33-kb RED cluster from *Streptomyces coelicolor* (encoding a blue or red anti-microbial product, respectively) indicated that the technology expressed products of the cloned BGC inserts without the vector promoters being operably linked to any gene. In particular, after cloning each of these BGCs in both orientations into the dual-promoter BAC vector and transconjugating the recombinant clones to *Streptomyces lividans* ΔactΔred (comprising deletions of the chromosomal ACT and RED clusters), the expected blue or red products were produced in an inducible manner. In control experiments, the wild type promoters were not able to express either RED or ACT robustly or in an inducible manner in the heterologous host. During the development of embodiments of the technology, experiments also indicated that the technology also expressed two other BGCs, one encoding a Type I PKS and one encoding a NRPS cluster, that were discovered from a soil metagenomic library. When expressed in *S. coelicolor* M1154 from native promoters, these BGCs each weakly expressed an antibacterial metabolite(s) that inhibited the growth of multidrug-resistant bacterial pathogens (e.g., *Acinetobacter baumannii*). After transfer of these BGCs to the dual-promoter BAC vector and transconjugating to *S. coelicolor* M1154, a significant 2-3-fold increase in antibacterial activity against *A. baumannii* was detected when an inducible promoter in the vector was used to drive transcription relative to antibiotic activity due to expression of the BGCs from native promoters.

Accordingly, in some embodiments the technology provides an expression vector comprising a first promoter and a second promoter flanking a cloning site, wherein the first promoter and second promoter direct transcription toward each other and in opposite directions; and wherein the expression vector is configured to accept a biosynthetic gene cluster nucleic acid at the cloning site and express a product of the biosynthetic gene cluster nucleic acid under control of the first promoter and/or the second promoter. In some embodiments, the first promoter and/or the second promoter is an inducible promoter. In some embodiments, the first promoter and/or the second promoter directs transcription in a host cell that is different than the source of the biosynthetic gene cluster nucleic acid. In some embodiments, the first promoter and/or the second promoter directs transcription in *Streptomyces*. In some embodiments, the first promoter is Potr or Potr*. In some embodiments, the second promoter is PnitA. In some embodiments, the first promoter comprises a nucleotide sequence provided by SEQ ID NO: 1. In some embodiments, the first promoter comprises a nucleotide sequence provided by SEQ ID NO: 2. In some embodiments, the second promoter comprises a nucleotide sequence provided by SEQ ID NO: 6. In some embodiments, the expression vector further comprises OtrR. In some embodiments, the expression vector further comprises NitR. In some embodiments, the vector further comprises a nucleotide sequence provided by SEQ ID NO: 3. In some embodiments, the expression vector further comprises a nucleotide sequence provided by SEQ ID NO: 5.

In some embodiments, the cloning site comprises a restriction enzyme recognition site. In some embodiments, cloning site comprises a restriction enzyme recognition sequence comprising 6, 7, 8 or more nucleotides. In some embodiments, the cloning site comprises an integration sequence adapted to facilitate integration of a nucleic acid by recombination. In some embodiments, the cloning site comprises a multiple cloning site. In some embodiments, the cloning site comprises a selectable and/or screenable marker. In some embodiments, the expression vector further comprises a selectable marker for *Streptomyces*. In some embodiments, the expression vector further comprises a selectable marker for *E. coli*. In some embodiments, the expression vector further comprises an *E. coli* origin of replication. In some embodiments, the expression vector further comprises a *Streptomyces* origin of replication. In some embodiments, the expression vector further comprises a gene that stabilizes large plasmids. In some embodiments, the expression vector further comprises a sopA gene, a sopB gene, and/or a sopC gene. In some embodiments, the expression vector is configured to accept an insert comprising more than 10 kb, more than 20 kb, more than 50 kb, and/or more than 100 kb (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the expression vector is configured to accept an insert comprising 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)).

In some embodiments, the expression vector is configured to express a product of the biosynthetic gene cluster nucleic acid when the expression vector is present in a host cell. In some embodiments, the expression vector is configured to express a product of the biosynthetic gene cluster nucleic acid when the expression vector is present in a *Streptomyces* host cell. In some embodiments, the expression vector is configured to express a product of the biosynthetic gene cluster nucleic acid that is a nucleic acid or a polypeptide. In some embodiments, the expression vector is configured to express a product of the biosynthetic gene cluster nucleic acid that is a product of one or more enzymes encoded by the biosynthetic gene cluster. In some embodiments, the expression vector is configured to express a product that is a biologically active agent. In some embodiments, the biologically active agent has antiviral, antimicrobial, antifungal, antiparasitic, or anticancer activity. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a product of a polyketide synthase or nonribosomal peptide synthase.

In some embodiments, the technology provides a vector comprising a first promoter and a second promoter flanking a cloning site, wherein the first promoter and second promoter direct transcription toward each other and in opposite directions; and wherein the expression vector is configured to accept a nucleic acid comprising at least 10 kb ((e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)) at the cloning site and express a product of the nucleic acid under control of the first promoter and/or the second promoter. In some embodiments, the expression vector is configured to accept an insert comprising 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the first promoter and/or the second promoter is an inducible promoter. In some embodiments, the first promoter and/or the second promoter directs transcription in a host cell that is different than the source of the nucleic acid. In some embodiments, the first promoter and/or the second promoter directs transcription in *Streptomyces*. In some embodiments, the the first promoter is Potr or Potr*. In some embodiments, the second promoter is PnitA. In some embodiments, the first promoter comprises a nucleotide sequence provided by SEQ ID NO: 1. In some embodiments, the first promoter comprises a nucleotide sequence provided by SEQ ID NO: 2. In some embodiments, the second promoter comprises a nucleotide sequence provided by SEQ ID NO: 6. In some embodiments, the vector further comprises OtrR. In some embodiments, the vector further comprises NitR. In some embodiments, the vector further comprises a nucleotide sequence provided by SEQ ID NO: 3. In some embodiments, the vector further comprises a nucleotide sequence provided by SEQ ID NO: 5. In some embodiments, the cloning site comprises a restriction enzyme recognition site. In some embodiments, the cloning site comprises a restriction enzyme recognition sequence comprising 6, 7, 8 or more nucleotides. In some embodiments, the cloning site comprises an integration sequence adapted to facilitate integration of a nucleic acid by recombination. In some embodiments, the cloning site comprises a multiple cloning site. In some embodiments, the cloning site comprises a selectable and/or screenable marker. In some embodiments, the expression vector further comprises a selectable marker for *Streptomyces*. In some embodiments, the expression vector further comprises a selectable marker for *E. coli*. In some embodiments, the expression vector further comprises an *E. coli* origin of replication. In some embodiments, the expression vector further comprises a *Streptomyces* origin of replication. In some embodiments, the expression vector further comprises a gene that stabilizes large plasmids. In some embodiments, the expression vector further comprises a sopA gene, a sopB gene, and/or a sopC gene.

In some embodiments, the expression vector is configured to accept an insert comprising more than 10 kb, more than 20 kb, more than 50 kb, or more than 100 kb (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the expression vector is configured to accept an insert comprising 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the expression vector is configured to accept a biosynthetic gene cluster nucleic acid at the cloning site and express a product of the biosynthetic gene cluster nucleic acid under control of the first promoter and/or the second promoter. In some embodiments, the expression vector is configured to express a product of the biosynthetic gene cluster nucleic acid when said vector is present in a host cell. In some embodiments, the expression vector is configured to express a product of the biosynthetic gene cluster nucleic acid when said vector is present in a *Streptomyces* host cell. In some embodiments, the expression vector is configured to express a product of the biosynthetic gene cluster nucleic acid that is a nucleic acid or a polypeptide. In some embodiments, the expression vector is configured to express a product of the biosynthetic gene cluster nucleic acid that is a product of one or more enzymes encoded by the biosynthetic gene cluster. In some embodiments, the expression vector is configured to express a product that is a biologically active agent. In some embodiments, the biologically active agent has antiviral, antimicrobial, antifungal, antiparasitic, or anticancer activity. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a product of a polyketide synthase or nonribosomal peptide synthase.

In some embodiments, the technology provides a kit. For example, in some embodiments, the technology provides a kit comprising an expression vector as described herein. In some embodiments, the first promoter of the expression vector is an inducible promoter and/or the second promoter of the expression vector is an inducible promoter and the kit further comprises an inducer of said first promoter and/or an inducer of said second promoter. In some embodiments, the kit further comprises a restriction enzyme for cutting said expression vector at said cloning site and/or a composition for integrating a nucleic acid at said cloning site.

In some embodiments, the technology provides a system. For example, in some embodiments, the technology provides a system comprising an expression vector as described herein. In some embodiments, the first promoter of the expression vector is an inducible promoter and/or the second promoter of the expression vector is an inducible promoter and the system further comprises an inducer of said first promoter and/or an inducer of said second promoter. In some embodiments, the system further comprises a restriction enzyme for cutting said expression vector at set cloning site and/or a composition for integrating a nucleic acid at said cloning site. In some embodiments, the system further comprises a culture medium, an antibiotic, and/or a competent host for said expression vector.

In some embodiments, the technology provides an expression vector as described herein that further comprises an insert (e.g., a cloned insert). Accordingly, in some embodiments, the technology provides a nucleic acid comprising an expression vector and an insert, wherein said expression vector comprises a first promoter and a second promoter flanking said insert; the first promoter and second promoter direct transcription toward each other and in opposite directions; and the insert comprises a biosynthetic gene cluster nucleic acid. In some embodiments, the insert is 5 kb or more, 10 kb or more, and/or 20, 30, 40, 50, 60, 70, 80, 90, or 100 kb or more. In some embodiments, the insert is at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the expression vector is configured to accept an insert comprising 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)).

In some embodiments, the insert is from a cultured microorganism. In some embodiments, the insert is from a metagenomic library. In some embodiments, the insert comprises a nucleotide sequence encoding an amino acid sequence of a polyketide synthase (PKS) or a nonribosomal peptide synthase (NRPS). In some embodiments, the insert comprises a plurality of genes. In some embodiments, the insert comprises genes encoded by both strands of said insert. In some embodiments, the expression vector is configured to express a product of the biosynthetic gene cluster nucleic acid under control of the first promoter and/or the second promoter. In some embodiments, the first promoter and/or the second promoter is an inducible promoter. In some embodiments, the first promoter and/or the second promoter directs transcription in a host cell that is different than the source of the insert. In some embodiments, the first promoter and/or the second promoter directs transcription in *Streptomyces*. In some embodiments, the first promoter is Potr or Potr*. In some embodiments, the second promoter is PnitA. In some embodiments, first promoter comprises a nucleotide sequence provided by SEQ ID NO: 1. In some embodiments, the first promoter comprises a nucleotide sequence provided by SEQ ID NO: 2. In some embodiments, the second promoter comprises a nucleotide sequence provided by SEQ ID NO: 6. In some embodiments, the expression vector further comprises OtrR. In some embodiments, the expression vector further comprises NitR. In some embodiments, the expression vector further comprises a nucleotide sequence provided by SEQ ID NO: 3. In some embodiments, the expression vector further comprises a nucleotide sequence provided by SEQ ID NO: 5.

In some embodiments, the vector further comprises a selectable marker for *Streptomyces*. In some embodiments, the expression vector further comprises a selectable marker for *E. coli*. In some embodiments, the expression vector further comprises an *E. coli* origin of replication. In some embodiments, the expression vector further comprises a *Streptomyces* origin of replication. In some embodiments, the expression vector further comprises a gene that stabilizes large plasmids. In some embodiments, expression vector further comprises a sopA gene, a sopB gene, and/or a sopC gene. In some embodiments, the expression vector is configured to express a product of the biosynthetic gene cluster nucleic acid when said vector is present in a host cell. In some embodiments, the expression vector is configured to express a product of the biosynthetic gene cluster nucleic acid when said vector is present in a *Streptomyces* host cell. In some embodiments, the biosynthetic gene cluster nucleic acid comprises a nucleotide sequence encoding two or more genes of a biosynthetic pathway. In some embodiments, the biosynthetic gene cluster nucleic acid comprises a nucleotide sequence encoding two or more genes of a biosynthetic pathway that produces a biologically active agent. In some embodiments, the biologically active agent has antiviral, antimicrobial, antifungal, antiparasitic, or anticancer activity. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a product of a polyketide synthase or nonribosomal peptide synthase.

In some embodiments, the technology provides a nucleic acid comprising an expression vector and an insert, wherein the expression vector comprises a first promoter and a second promoter flanking said insert; the first promoter and second promoter direct transcription toward each other and in opposite directions; and the insert comprises at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the expression vector is configured to accept an insert comprising 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the first promoter and/or the second promoter is an inducible promoter. In some embodiments, the first promoter and/or the second promoter directs transcription in *Streptomyces*. In some embodiments, the first promoter is Potr or Potr*. In some embodiments, the second promoter is PnitA. In some embodiments, the first promoter comprises a nucleotide sequence provided by SEQ ID NO: 1. In some embodiments, the first promoter comprises a nucleotide sequence provided by SEQ ID NO: 2. In some embodiments, the second promoter comprises a nucleotide sequence provided by SEQ ID NO: 6. In some embodiments, the expression vector further comprises OtrR. In some embodiments, the expression vector further comprises NitR. In some embodiments, the expression vector further comprises a nucleotide sequence provided by SEQ ID NO: 3. In some embodiments, the expression vector further comprises a nucleotide sequence provided by SEQ ID NO: 5. In some embodiments, the expression vector further comprises a selectable marker for *Streptomyces*. In some embodiments, the expression vector further comprises a selectable marker for *E. coli*. In some embodiments, the expression vector further comprises an *E. coli* origin of replication. In some embodiments, the expression vector further comprises a *Streptomyces* origin of replication. In some embodiments, the expression vector further comprises a gene that stabilizes large plasmids. In some embodiments, the expression vector further comprises a sopA gene, a sopB gene, and/or a sopC gene. In some embodiments, the insert comprises more than 10 kb, more than 20 kb, more than 50 kb, or more than 100 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the expression vector is configured to accept an insert comprising 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)).

In some embodiments, the insert comprises a biosynthetic gene cluster. In some embodiments, the expression vector is configured to express a product of the biosynthetic gene cluster when said nucleic acid is present in a host cell. In some embodiments, the expression vector is configured to express a product of the biosynthetic gene cluster nucleic acid when said vector is present in a *Streptomyces* host cell. In some embodiments, the expression vector is configured to express a product of the biosynthetic gene cluster nucleic acid that is a nucleic acid or a polypeptide. In some embodiments, the expression vector is configured to express a product of the biosynthetic gene cluster nucleic acid that is a product of one or more enzymes encoded by the biosynthetic gene cluster. In some embodiments, the biosynthetic gene cluster nucleic acid comprises a nucleotide sequence encoding two or more genes of a biosynthetic pathway that produces a biologically active agent. In some embodiments, the biologically active agent has antiviral, antimicrobial, antifungal, antiparasitic, or anticancer activity. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a product of a polyketide synthase or nonribosomal peptide synthase.

In some embodiments, the technology provides a host cell comprising an expression vector as described herein. In some embodiments, the technology provides a host comprising an expression vector further comprising an insert. In some embodiments, the technology provides a host cell comprising a nucleic acid, wherein said nucleic acid comprises an expression vector as described herein and a nucleic acid insert. In some embodiments, the host cell expresses a product of a biosynthetic gene cluster encoded by the insert. In some embodiments, the host cell expresses a nucleic acid or a polypeptide encoded by the insert. In some embodiments, the host cell expresses one or more enzymes encoded by the insert. In some embodiments, the host cell expresses a biologically active agent. In some embodiments, the biologically active agent has antiviral, antimicrobial, antifungal, antiparasitic, or anticancer activity. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a polyketide or nonribosomal peptide.

In some embodiments, the technology provides a composition comprising a host cell as described herein. For example, in some embodiments, the technology provides a composition comprising a host cell as described herein, wherein the host cell comprises an expression vector as described herein (e.g., comprising an insert) and the composition further comprises an inducer of the first promoter and/or an inducer of the second promoter. In some embodiments, the composition further comprises a product expressed from the induced expression of said insert. In some embodiments, the product is a biologically active agent. In some embodiments, the biologically active agent is a polyketide or nonribosomal peptide. In some embodiments, the biologically active agent has antiviral, antimicrobial, antifungal, antiparasitic, or anticancer activity. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a terpene, saccharide, or alkaloid.

In some embodiments, the technology provides methods. For example, in some embodiments, the technology provides a method of expressing a product from a cloned biosynthetic gene cluster. In some embodiments, methods comprise providing an expression vector comprising a first promoter and a second promoter flanking a cloning site, wherein the first promoter and second promoter direct transcription toward each other and in opposite directions; and cloning a nucleic acid insert comprising a biosynthetic gene cluster at said cloning site. In some embodiments, the nucleic acid insert is 5, 10, 20, 30, 40, 50, 60, 70, 80, 90, or 100 kb or more (e.g., comprising more than 10 kb, more than 20 kb, more than 50 kb, and/or more than 100 kb (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the nucleic acid insert is 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)).

In some embodiments, the technology provides methods of expressing a product from a cloned nucleic acid insert comprising at least 10 kb (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the nucleic acid insert is 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, methods comprise providing an expression vector comprising a first promoter and a second promoter flanking a cloning site, wherein the first promoter and second promoter direct transcription toward each other and in opposite directions; and cloning a nucleic acid insert comprising at least 10 kb at said cloning site. In some embodiments, the nucleic acid insert comprises a biosynthetic gene cluster.

In some embodiments, the technology provides methods for expressing a product from a cloned biosynthetic gene cluster. In some embodiments, methods comprise providing an expression vector comprising a first promoter and a second promoter flanking a cloning site, wherein the first promoter and second promoter direct transcription toward each other and in opposite directions; cloning a nucleic acid insert comprising a biosynthetic gene cluster at said cloning site to provide a recombinant vector comprising said nucleic acid insert; transforming said recombinant vector comprising said nucleic acid insert into a host cell; and contacting said host cell with an inducer of said first promoter and/or an inducer of said second promoter to induce expression of a product from said nucleic acid insert. In some embodiments, the host cell is a *Streptomyces* spp. In some embodiments, the nucleic acid insert is 5 kb or more, 10 kb or more, or 20, 30, 40, 50, 60, 70, 80, 90, or 100 kb or more (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the nucleic acid insert is 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the nucleic acid insert is from a cultured microorganism. In some embodiments, the nucleic acid insert is from a metagenomic library. In some embodiments, the nucleic acid insert comprises a nucleotide sequence encoding a polyketide synthase (PKS) or a nonribosomal peptide synthase (NRPS). In some embodiments, the nucleic acid insert comprises a plurality of genes. In some embodiments, the nucleic acid insert comprises genes encoded by both strands of said nucleic acid insert. In some embodiments, the methods further comprise detecting expression of a product encoded by one or more nucleotide sequences of said nucleic acid insert. In some embodiments, the product is produced by a biosynthetic pathway encoded by the biosynthetic gene cluster. In some embodiments, the product is a biologically active agent. In some embodiments, the biologically active agent has antiviral, antimicrobial, antifungal, antiparasitic, or anticancer activity. In some embodiments, the biologically active agent is a polyketide or nonribosomal peptide. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a terpene, saccharide, or alkaloid.

In some embodiments, the technology provides methods for expressing a product from a biosynthetic gene cluster. For example, in some embodiments, methods comprise providing a host cell comprising a recombinant nucleic acid comprising an expression vector and an insert, wherein said expression vector comprises a first promoter and a second promoter flanking said insert; the first promoter and second promoter direct transcription toward each other and in opposite directions; and said insert comprises a biosynthetic gene cluster nucleic acid; and contacting said host cell with an inducer of said first promoter and/or an inducer of said second promoter to induce expression of a product from said biosynthetic gene cluster. In some embodiments, the host cell is a Streptomyces spp. In some embodiments, the insert is 5 kb or more, 10 kb or more, or 20, 30, 40, 50, 60, 70, 80, 90, or 100 kb or more (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the nucleic acid insert is 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the insert is from a cultured microorganism. In some embodiments, the insert is from a metagenomic library. In some embodiments, the insert comprises a nucleotide sequence encoding a polyketide synthase (PKS) or a nonribosomal peptide synthase (NRPS). In some embodiments, the insert comprises a plurality of genes. In some embodiments, the insert comprises genes encoded by both strands of said insert. In some embodiments, the methods further comprise detecting expression of a product encoded by the biosynthetic gene cluster. In some embodiments, the product is a biologically active agent. In some embodiments, the biologically active agent has antiviral, antimicrobial, antifungal, antiparasitic, or anticancer activity. In some embodiments, the biologically active agent is a polyketide or nonribosomal peptide. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a terpene, saccharide, or alkaloid.

In some embodiments, the technology provides methods for expressing a product from a nucleic acid insert comprising at least 10 kb (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the nucleic acid insert is 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, methods comprise providing a host cell comprising a recombinant nucleic acid comprising an expression vector and an insert, wherein said expression vector comprises a first promoter and a second promoter flanking said insert; the first promoter and second promoter direct transcription toward each other and in opposite directions; and said insert comprises at least 10 kb (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)); and contacting said host cell with an inducer of said first promoter and/or an inducer of said second promoter to induce expression of a product from said nucleic acid insert. In some embodiments, the nucleic acid insert is 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the host cell is a Streptomyces spp. In some embodiments, the insert comprises a biosynthetic gene cluster. In some embodiments, the insert is from a cultured microorganism. In some embodiments, insert is from a metagenomic library. In some embodiments, the insert comprises a nucleotide sequence encoding a polyketide synthase (PKS) or a nonribosomal peptide synthase (NRPS). In some embodiments, the insert comprises a plurality of genes. In some embodiments, the insert comprises genes encoded by both strands of said insert. In some embodiments, methods further comprise detecting expression of said product. In some embodiments, the product is a biologically active agent. In some embodiments, the biologically active agent has antiviral, antimicrobial, antifungal, antiparasitic, or anticancer activity. In some embodiments, the biologically active agent is a polyketide or nonribosomal peptide. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a terpene, saccharide, or alkaloid.

In some embodiments, the technology provides methods for identifying a nucleic acid comprising a biosynthetic gene cluster. For example, in some embodiments, methods comprise providing a host cell comprising a recombinant nucleic acid comprising an expression vector and an insert, wherein said expression vector comprises a first promoter and a second promoter flanking said insert; the first promoter and second promoter direct transcription toward each other and in opposite directions; and the expression vector is configured to express a product of the insert under control of the first promoter and/or the second promoter; contacting said host cell with an inducer of said first promoter and/or an inducer of said second promoter to induce expression of a product from said insert; detecting expression of said product; and identifying the nucleic acid as a nucleic acid comprising a biosynthetic gene cluster when said product is identified. In some embodiments, the host cell is a *Streptomyces* spp. In some embodiments, the insert is 5 kb or more, 10 kb or more, and/or 20, 30, 40, 50, 60, 70, 80, 90, or 100 kb or more (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the nucleic acid insert is 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the insert is from a cultured microorganism. In some embodiments, the insert is from a metagenomic library. In some embodiments, the product is a biologically active agent. In some embodiments, the biologically active agent is a polyketide or a nonribosomal peptide. In some embodiments, the biologically active agent has antiviral, antimicrobial, antifungal, antiparasitic, or anticancer activity. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent.

In some embodiments, the detecting step of the method comprises a selection or a screen.

In some embodiments, the technology provides a library of nucleic acids, e.g., a library of expression vectors as described herein comprising nucleic acid inserts, wherein the library comprises a plurality of different insert nucleotide sequences (e.g., a library of cloned inserts in the expression vector). In some embodiments, the technology provides a clone library in host cells. In some embodiments, the technology provides a library comprising a plurality of host cells as described herein (e.g., host cells comprising a library of expression vectors as described herein comprising nucleic acid inserts, wherein the library comprises a plurality of different insert nucleotide sequences (e.g., a library of hosts comprising cloned inserts in the expression vector).

In some embodiments, the technology finds use to express a product from a biosynthetic gene cluster, the expression vector comprising a first promoter and a second promoter flanking a cloning site, wherein the first promoter and second promoter direct transcription toward each other and in opposite directions; and wherein said expression vector is configured to accept a biosynthetic gene cluster nucleic acid at the cloning site and express a product of the biosynthetic gene cluster nucleic acid under control of the first promoter and/or the second promoter. In some embodiments, the technology finds use to express a product from a cloned nucleic acid insert comprising at least 10 kb (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)), the expression vector comprising a first promoter and a second promoter flanking a cloning site, wherein the first promoter and second promoter direct transcription toward each other and in opposite directions; and wherein said expression vector is configured to accept a nucleic acid comprising at least 10 kb (e.g., at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)) at the cloning site and express a product of the nucleic acid under control of the first promoter and/or the second promoter. In some embodiments, the nucleic acid insert is 10-200 kb (e.g., 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)). In some embodiments, the technology finds use to identify a nucleic acid comprising a biosynthetic gene cluster, the expression vector comprising a first promoter and a second promoter flanking a cloning site, wherein the first promoter and second promoter direct transcription toward each other and in opposite directions; and wherein said expression vector is configured to accept a nucleic acid at the cloning site and express a product of the nucleic acid under control of the first promoter and/or the second promoter. In some embodiments, the technology finds use to produce a bioactive agent produced by a biosynthetic gene cluster, the expression vector comprising a first promoter and a second promoter flanking a cloning site, wherein the first promoter and second promoter direct transcription toward each other and in opposite directions; and wherein said expression vector is configured to accept a nucleic acid comprising a biosynthetic gene cluster nucleic acid at the cloning site and express a product of the biosynthetic gene cluster under control of the first promoter and/or the second promoter.

The technology also relates to nucleic acids. For example, in some embodiments, the technology provides a nucleic acid comprising a nucleotide sequence provided by SEQ ID NO: 8. In some embodiments, the technology provides a nucleic acid comprising a nucleotide sequence provided by SEQ ID NO: 9.

Additional embodiments will be apparent to persons skilled in the relevant art based on the teachings contained herein.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, an "increase" or a "decrease" refers to a detectable (e.g., measured) positive or negative change in the value of a variable relative to a previously measured value of the variable, relative to a pre-established value, and/or relative to a value of a standard control. An increase is a positive change preferably at least 10%, more preferably 50%, still more preferably 2-fold, even more preferably at least 5-fold, and most preferably at least 10-fold relative to the previously measured value of the variable, the pre-established value, and/or the value of a standard control. Similarly, a decrease is a negative change preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above.

Unless otherwise defined herein, scientific and technical terms used in connection with the present technology shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics, and protein and nucleic acid chemistry and hybridization described herein are those well-known and commonly used in the art. The methods and techniques of the present technology are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y. (1989); Sambrook et al., Molecular Cloning: A Laboratory Manual, 3d ed., Cold Spring Harbor Laboratory Press, Cold Spring Harbor, N.Y. (2000); Ausubel et al., Current Protocols in Molecular Biology, Greene Publishing Associates (1992 and Supplements to 2000); Ausubel et al., Short Protocols in Molecular Biology: A Compendium of Methods from Current Protocols in Molecular Biology, 4th ed., Wiley & Sons (1999); Harlow and Lane, Antibodies: A Laboratory Manual, Cold Spring Harbor Laboratory Press, Cold Spring Harbor, N.Y. (1990); Harlow and Lane, Using Antibodies: A Laboratory Manual, Cold Spring Harbor Laboratory Press, Cold Spring Harbor, N.Y. (1998); and T. Kieser et al., Practical *Streptomyces* Genetics, John Innes Foundation, Norwich (2000); each of which is incorporated herein by reference in its entirety.

Unless specifically defined or described in a different way elsewhere herein, the following terms and descriptions related to the technology shall be understood as given below.

As used herein, the term "recombinant", when used with reference, e.g., to a cell, nucleic acid, protein, or vector, indicates that the cell, nucleic acid, protein, or vector has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed, or not expressed at all.

As used herein, the term "vector" refers to a DNA molecule used as a vehicle to carry a nucleic acid (e.g., an "insert" comprising foreign genetic material) into a cell where, in some embodiments, it is replicated and/or expressed.

As used herein, the term "configured to accept" or "adapted to accept" refers to the characteristic (e.g., by design, structure, and/or function) of a nucleic acid (e.g., a vector (e.g., an expression vector)) as being capable of being linked (e.g., by ligation, recombination, or other nucleic acid manipulation in vivo and/or in vitro) to another nucleic acid. For example, a vector "configured to accept" an insert means that the vector is capable of being joined with the insert to provide a recombinant nucleic acid comprising the vector and the insert. In some embodiments, a vector that is "configured to accept" an insert comprises a cloning site and the cloning site comprises a restriction enzyme recognition site, a site of homologous recombination, or other nucleic acid structure or sequence that facilitates introduction of an insert at the cloning site. In some embodiments, a vector is prepared to receive an insert nucleic acid by digesting the vector and a nucleic acid that comprises the insert with restriction enzymes. The digested nucleic acids are then spliced together by an enzyme called ligase (e.g., by a process known as ligation) to form a recombinant vector capable of expressing a nucleic acid of the insert. In some embodiments, "TA" cloning is used to produce a recombinant vector from a vector and an insert. In some embodiments, a vector comprises sites for in vitro recombination reactions (e.g., integration and excision) similar to those that occur when lambda phage infects bacteria. In some embodiments, the recombination reactions are facilitated by the recombination of attP and attB attachment sites directed by a "clonase" or "integrase" enzyme. Other strategies are known in the art for designing and producing a cloning site that is configured to accept an insert.

As used herein, the term "expression vector" refers to a vector used to introduce a specific nucleic acid into a target cell for expression of the nucleic acid by the cell, e.g., to produce one or more proteins encoded by the nucleic acid by a constitutive or an inducible promoter. In some embodiments, an expression vector is a nucleic acid comprising one or more promoters. In some embodiments, an expression vector comprises one or more convenient restriction sites to allow for insertion or substitution of a nucleic acid into the expression vector.

As used herein, "expression" refers to the process by which the information of a particular nucleic acid (e.g., a gene) is used to synthesize a product (e.g., a biomolecule (e.g., a nucleic acid, a polypeptide, a carbohydrate, a lipid, and combinations, derivatives, and/or metabolites of the foregoing); a metabolite (e.g., a primary metabolite, a secondary metabolite); a fatty acid; a polyketide; a nucleotide; an amino acid; a cofactor; and combinations, derivatives, and/or metabolites of the foregoing). The term "expression" includes but is not limited to one or more of the following: transcription of a gene into a precursor mRNA; processing of a precursor mRNA to produce a mature mRNA; mRNA stability; translation of a mature mRNA into a protein (including codon usage and tRNA availability); and/or glycosylation and/or other modifications of the translation product. The term "expression" also includes transcription of a non-coding RNA, e.g., a transfer RNA, a ribosomal RNA, a microRNAs, a siRNA, a piRNA, a snoRNA, a snRNA, an exRNA, a scaRNA, or a long ncRNA. The term "expression" includes production of a functional product and production of non-functional products that find use in producing functional products by subsequent chemical or biochemical manipulation or synthesis.

As used herein, the term "biologically active agent" refers to any substance that has activity in a biological system and/or organism. For instance, in some embodiments, a "biologically active agent" is a substance that, when administered to an organism, has a biological effect on that organism. In some embodiments, where a substance is biologically active, a portion of that substance that shares at least one biological activity of the whole substance is typically referred to as a "biologically active" portion. In some embodiments, a "biologically active agent" is a chemical substance or formulation that beneficially affects humans, animals, or plants or is intended for use in the cure, mitigation, treatment, prevention, or diagnosis of infection or disease, or is destructive to or inhibits the growth of microorganisms.

As used herein the term "exogenously" refers to the use of native or non-native promoters that are outside the boundaries of a cloned nucleic acid insert, e.g., flanking the outside boundaries of a cloned BGC.

As used herein the term "endogenously" refers to the use of native promoters within the boundaries of a cloned nucleic acid insert, e.g., within the boundaries of a cloned BGC.

As used herein, the term "shuttle vector" refers to a vector constructed so that it can propagate in two different host species, e.g., E. coli and another organism such as Streptomyces.

As used herein, the term "promoter" refers to a region of a nucleic acid that controls the binding of RNA polymerase and transcription factors (e.g., the sequence of the promoter region controls the binding of the RNA polymerase and/or transcription factors). In some embodiments, a promoter drives transcription of a target gene or genes and thus may determine the timing and/or amount of gene expression and determines the amount of a recombinant protein that is produced. The term "promoter" may refer to a combination of a promoter (e.g., the RNA polymerase binding site) and an operator (e.g., response elements). Promoters typically comprise approximately 100 to 1000 base pairs and are present upstream of their target genes. Many common promoters are always active and are thus referred to as constitutive promoters. Other promoters are only active under specific circumstances and are thus referred to as "inducible promoters", which can be switched between two discrete states, e.g., an OFF state and an ON state. Some inducible promoters provide control of expression over a continuous range that is a function of the amount of inducer provided and/or present.

As used herein, "inducible promoter" means that the recognition of the promoter by the RNA polymerase, and therefore the transcriptional activity of the promoter and its target gene, is controlled by the absence, presence, or amount of chemical or physical factors.

As used herein, the term "DNA transcription" refers to the process of synthesizing a RNA from a DNA molecule by a specialized enzyme that is an RNA polymerase.

As used herein, the term "constitutive gene" or "constitutively expressed gene" refers to a gene that is transcribed continually at a relatively constant level. This term implies that a constitutive promoter regulates DNA transcription for the gene and therefore that an encoded gene product (e.g., protein or RNA) is produced at a relatively constant level.

As used herein, "ribosome binding site" refers to an RNA sequence to which ribosomes can bind to initiate protein synthesis (translation) inside a host cell or organism as part of the process of expressing a protein, a product produced by the protein, and/or a product produced by a biosynthetic pathway in which the protein is a member.

As used herein, "foreign gene expression" means the entire process by which the information of a particular gene or biosynthetic pathway is used to synthesize a product in a heterologous host. As used herein in reference to gene expression, the term "foreign" means that the referenced gene is from an organism different than the host used for gene expression.

As used herein, "outward-reading" refers to the direction of transcription from a specific promoter that is located particularly within a defined region of a DNA and that is typically located near the 5' or 3' ends of the defined region of the DNA. In particular, "outward-reading" refers to transcription from the mentioned promoter at which RNA synthesis starts within the defined region of the DNA and that proceeds towards a boundary of the defined region of the DNA toward adjacent DNA.

As used herein, a biosynthetic gene cluster (BGC) can be defined as a physically clustered group of two or more genes in a particular genome that together encode a biosynthetic pathway for the production of a specialized metabolite and/or chemical variants thereof. Non-limiting exemplary BGCs encode multiple genes for biosynthetic pathways that produce polyketides, nonribosomal peptides (NRPs), ribosomally synthesized and post-translationally modified peptides (RiPPs), terpenes, saccharides, and alkaloids. Some BGCs comprise elements such as acyltransferase domain substrate specificities and starter units for polyketide BGCs, release/cyclization types and adenylation domain substrate specificities for NRP BGCs, precursor peptides and peptide modifications for RiPP BGCs, glycosyltransferase specificities for saccharide BGCs, and hybrids combining one or more of these units.

As used herein, the term "natural product" refers to biological products that can be found in nature. Embodiments of the technology disclosed herein find use as effective tools to discover unknown natural products.

As used herein, the term "small molecule" or "metabolite" refers to a composition that has a molecular weight of less than approximately 5 kDa and more preferably less than approximately 2 kDa. Small molecules can be, e.g., nucleic acids, peptides, polypeptides, glycopeptides, peptidomimetics, carbohydrates, lipids, antibiotics, lipopolysaccharides, fatty acids, polyketides, nucleotides, amino acids, cofactors, and combinations, derivatives, and/or metabolites of the foregoing, or other organic or inorganic molecules.

As used herein the terms "polyketide" and "nonribosomal peptide" refer to important classes of natural products. Polyketides are a large group of secondary metabolites that either comprise alternating carbonyl and methylene groups or are derived from precursors that comprise such alternating groups.

Non-ribosomal peptides have a chemical structure similar to proteins (e.g., comprise peptide bonds), but are biosynthesized without use of messenger RNA.

As used herein, the term "polyketide synthase" or "PKS" refers to a protein with modular enzymatic activities that can lead to production of a polyketide under certain conditions.

As used herein, the term "non-ribosomal peptide synthetase" or "NRPS" refers to a protein with modular enzymatic activities that can lead to production of a non-ribosomal peptide under certain conditions.

As used herein, the term "ribosomally synthesized and/or post-translationally modified polypeptide (RiPP)" refers to genetically encoded precursor peptides that undergo some degree of enzymatic post-translational modification (e.g., chemical transformations occurring after translation).

As used herein, the term "module" refers to a section of a polyketide synthase or non-ribosomal peptide synthetase protein comprising one or more domains and involved in at least one round (typically one round) of chain extension or chain transfer (more commonly chain extension), including but not limited to a ketosynthase, ketoreductase, dehydratase, enoyl reductase, acyl carrier protein, acyl transferase, thioesterase, condensation, thiolation, peptidyl carrier protein, methylation or adenylation domain.

As used herein, the term "microorganism" includes prokaryotic and eukaryotic microbial species from the domains Archaea, Bacteria, and Eukarya, the latter including yeast and filamentous fungi, protozoa, algae, or higher Protista. The terms "microbial cells" and "microbes" are used interchangeably with the term "microorganism".

The terms "bacteria" and "bacterium" and "archaea" and "archaeon" refer to prokaryotic organisms of the domain Bacteria and Archaea in the three-domain system (see Woese C R, et al., Proc Natl Acad Sci USA 1990, 87: 4576-79).

The term "Archaea" refers to a taxonomic domain of organisms typically found in unusual environments and distinguished from the rest of the prokaryotes by several criteria, including the number of ribosomal proteins and the lack of muramic acid in cell walls. On the basis of small subunit rRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophiles (prokaryotes that live at very high temperatures). Besides the unifying archaeal features that distinguish them from Bacteria (e.g., no murein in cell wall, ester-linked membrane lipids, etc.), these prokaryotes exhibit unique structural or biochemical attributes which adapt them to their particular habitats. The Crenarchaeota consist mainly of hyperthermophilic sulfur-dependent prokaryotes and the Euryarchaeota contain the methanogens and extreme halophiles.

The term "Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "genus" is defined as a taxonomic group of related species according to the Taxonomic Outline of Bacteria and Archaea (Garrity et al. (2007) The Taxonomic Outline of Bacteria and Archaea. TOBA Release 7.7, March 2007. Michigan State University Board of Trustees).

The term "species" is defined as a collection of closely related organisms with greater than 97% 16S ribosomal RNA sequence homology and greater than 70% genomic hybridization and sufficiently different from all other organisms so as to be recognized as a distinct unit.

The term "strain" as used herein in reference to a microorganism describes an isolate of a microorganism considered to be of the same species but with a unique genome and, if nucleotide changes are non-synonymous, a unique proteome differing from other strains of the same organism. Strains may differ in their non-chromosomal genetic complement. Typically, strains are the result of isolation from a different host or at a different location and time, but multiple strains of the same organism may be isolated from the same host.

As used herein, the term "naturally occurring" as applied to a nucleic acid, an enzyme, a cell, or an organism, refers to a nucleic acid, enzyme, cell, or organism that is found in nature. For example, a polypeptide or polynucleotide sequence that is present in an organism that can be isolated from a source in nature and that has not been intentionally modified by a human in the laboratory is naturally occurring.

As used herein, the term "non-naturally occurring" as applied to a nucleic acid, an enzyme, a cell, or an organism refers to a nucleic acid, an enzyme, a cell, or an organism that has at least one genetic alteration not normally found in the naturally occurring nucleic acid, enzyme, cell, or organism. Genetic alterations include, for example, modifications introducing expressible nucleic acids encoding metabolic polypeptides, other nucleic acid additions, nucleic acid deletions, and/or other functional disruption of the microbial genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon.

As used herein, the term "host cell", "host microbial organism", and "host microorganism" are used interchangeably to refer to any archaeal, bacterial, or eukaryotic living cell into which a heterologous entity (e.g., a biomolecule such as a nucleic acid, protein, etc.) can be, or has been, inserted. The term also relates to the progeny of the original cell, which may not be completely identical in morphology or in genomic or total DNA complement to the original parent, due to natural, accidental, or deliberate mutation.

The terms "modified microorganism," "recombinant microorganism", and "recombinant host cell" are refer to a non-naturally occurring organism that is produced by methods such as inserting, expressing, or overexpressing endogenous polynucleotides; by expressing or overexpressing heterologous polynucleotides, such as those included in an integrated and/or episomal vector; by introducing a mutation into the microorganism; or by altering the expression of an endogenous gene. In embodiments relating to the introduction of a polynucleotide into a microorganism, the polynucleotide generally encodes a one or more enzymes involved in a biosynthetic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "wild-type microorganism" describes a cell that occurs in nature, e.g., a cell that has not been genetically modified. A wild-type microorganism can be genetically modified to express or overexpress a target enzyme. This microorganism can act as a parental microorganism in the generation of a microorganism modified to express or overexpress a target enzyme. In turn, the microorganism modified to express or overexpress one or more target enzymes can be modified to express or overexpress another target enzyme.

Accordingly, a "parental microorganism" functions as a reference cell for successive genetic modification events. Each modification event can be accomplished by introducing a nucleic acid molecule into the reference cell. The introduction facilitates the expression or overexpression of a target enzyme. It is understood that the term "facilitates" encompasses the activation of endogenous polynucleotides encoding a target enzyme through genetic modification of, e.g., a promoter sequence in a parental microorganism. It is further understood that the term "facilitates" encompasses the introduction of heterologous polynucleotides encoding a target enzyme in to a parental microorganism.

The term "mutation" as used herein indicates any modification of a nucleic acid that results in an altered nucleic acid, e.g., that produces an amino acid "substitution" in a polypeptide (e.g., thus producing a "mutant" polypeptide or "mutant" nucleic acid). Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are the results of artificial mutation pressure. In still other embodiments, the mutations in the microorganism genome are the result of genetic engineering.

The term "biosynthetic pathway", also referred to as "metabolic pathway", refers to a set of anabolic or catabolic biochemical reactions for converting one chemical species into another. Gene products belong to the same "biosynthetic pathway" if they, in parallel or in series, act on the same substrate, produce the same product, or act on or produce a metabolic intermediate (e.g., a metabolite) between the same substrate and metabolite end product.

The term "gene module" refers to a group, set, or collection of genes, e.g., as provided in a BGC. In some embodiments, an operon comprises the genes of a gene module; in some embodiments, the genes of a gene module belong to the same biosynthetic pathway. In some embodiments, a BGC comprises the genes of a gene module. In some embodiments, the genes of a gene module are coexpressed, e.g., the same set of transcription factors binds to the genes of the gene module to modulate expression of the genes of the gene module. In some embodiments, the genes of a gene module are provided together on a nucleic acid. In some embodiments, the genes are provided together on a nucleic acid in the same arrangement as found in nature and, in some embodiments, the genes of the gene module are provided on a nucleic acid in an arrangement that is not found in nature. In some embodiments, a gene module comprises a novel group, set, or collection of genes that are not normally present in the same pathway in nature. In some embodiments, a gene module comprises a novel group, set, or collection of genes that are not normally present in the same organism in nature.

The term "heterologous" as used herein with reference to molecules and in particular enzymes and polynucleotides, indicates molecules that are expressed in an organism other than the organism from which they originated or are found in nature, independently of the level of expression, which can be lower, equal, or higher than the level of expression of the molecule in the native microorganism.

As used herein, the term "heterologous host" refers to a host organism, usually a bacterial strain, that can express one or more genes from another organism (e.g., "source organism") that is taxonomically classified as belonging to a different genus or species than the host organism. The "heterologous host" has the potential to express a product of the one or more genes from the other organism (e.g., "source organism") when cultured under appropriate conditions.

As used herein, the term "homologous host" refers to an organism, usually a bacterial strain, that can express one or more genes from an identical or essentially identical organism. The "homologous host" has the potential to express a product of the one or more genes when cultured under appropriate conditions.

As used herein the term "*Streptomyces* expression strains" or "heterologous *Streptomyces* expression strains" refers to bacterial strains including, but not limited to, commonly used species such as *Streptomyces avermitilis*, *Streptomyces venezuelae*, *Streptomyces albus*, *Streptomyces lividans*, and *Streptomyces coelicolor*.

As used herein, the term "*Streptomyces* spp." refers to any strain including but not limited to those isolated from one or more representatives of the *Streptomyces* genus. The Actinobacterium of the *Streptomyces* genus include, but are not limited to, *Streptomyces abietis*, *Streptomyces abikoensi*, *Streptomyces aburaviensis*, *Streptomyces achromogenes*, *Streptomyces acidiscabies*, *Streptomyces actinomycinicus*, *Streptomyces acrimycini*, *Streptomyces actuosus*, *Streptomyces aculeolatus*, *Streptomyces abyssalis*, *Streptomyces afghaniensis*, *Streptomyces aidingensis*, *Streptomyces africanus*, *Streptomyces alanosinicus*, *Streptomyces albaduncus*, *Streptomyces albiaxialis*, *Streptomyces albidochromogenes*, *Streptomyces albiflavescens*, *Streptomyces albiflaviniger*, *Streptomyces albidoflavus*, *Streptomyces albofaciens*, *Streptomyces alboflavus*, *Streptomyces albogriseolus*, *Streptomyces albolongus*, *Streptomyces alboniger*, *Streptomyces albospinus*, *Streptomyces albulus*, *Streptomyces albus*, *Streptomyces aldersoniae*, *Streptomyces alfalfa*, *Streptomyces alkaliphilus*, *Streptomyces alkalithermotolerans*, *Streptomyces almquistii*, *Streptomyces alni*, *Streptomyces althioticus*, *Streptomyces amakusaensis*, *Streptomyces ambofaciens*, *Streptomyces amritsarensis*, *Streptomyces anandii*, *Streptomyces angustmyceticus*, *Streptomyces anthocyanicus*, *Streptomyces antibioticus*, *Streptomyces antimycoticus*, *Streptomyces anulatus*, *Streptomyces aomiensis*, *Streptomyces araujoniae*, *Streptomyces ardus*, *Streptomyces arenae*, *Streptomyces armeniacus*, *Streptomyces artemisiae*, *Streptomyces arcticus*, *Streptomyces ascomycinicus*, *Streptomyces asiaticus*, *Streptomyces asterosporus*, *Streptomyces atacamensis*, *Streptomyces atratus*, *Streptomyces atriruber*, *Streptomyces atroolivaceus*, *Streptomyces atrovirens*, *Streptomyces aurantiacus*, *Streptomyces aurantiogriseus*, *Streptomyces auratus*, *Streptomyces aureocirculatus*, *Streptomyces aureofaciens*, *Streptomyces aureorectus*, *Streptomyces aureoverticillatus*, *Streptomyces aureus*, *Streptomyces avellaneus*, *Streptomyces avermitilis*, *Streptomyces avicenniae*, *Streptomyces avidinii*, *Streptomyces axinellae*, *Streptomyces azureus*, *Streptomyces bacillaris*, *Streptomyces badius*, *Streptomyces bambergiensis*, *Streptomyces bangladeshensis*, *Streptomyces baliensis*, *Streptomyces barkulensis*, *Streptomyces beijiangensis*, *Streptomyces bellus*, *Streptomyces bikiniensis*, *Streptomyces blastmyceticus*, *Streptomyces bluensis*, *Streptomyces bobili*, *Streptomyces bohaiensis*, *Streptomyces bottropensis*, *Streptomyces brasiliensis*, *Streptomyces brevispora*, *Streptomyces bullii*, *Streptomyces bungoensis*, *Streptomyces burgazadensis*, *Streptomyces cacaoi*, *Streptomyces caelestis*, *Streptomyces caeruleatus*, *Streptomyces calidiresistens*, *Streptomyces calvus*, *Streptomyces canaries*, *Streptomyces canchipurensis*, *Streptomyces candidus*, *Streptomyces cangkringensis*, *Streptomyces caniferus*, *Streptomyces canus*, *Streptomyces capillispiralis*, *Streptomyces capoamus*, *Streptomyces carpaticus*, *Streptomyces carpinensis*, *Streptomyces castelarensis*, *Streptomyces catbensis*, *Streptomyces catenulae*, *Streptomyces cavourensis*, *Streptomyces cello staticus*, *Streptomyces celluloflavus*, *Streptomyces cellulolyticus*, *Streptomyces cellulosae*, *Streptomyces chartreusis*, *Streptomyces chattanoogensis*, *Streptomyces cheonanensis*, *Streptomyces chiangmaiensis*, *Streptomyces chrestomyceticus*, *Streptomyces chromofuscus*, *Streptomyces chryseus*, *Streptomyces chilikensis*, *Streptomyces chlorus*, *Streptomyces chumphonensis*, *Streptomyces cinereorectus*, *Streptomyces cinereoruber*, *Streptomyces cinereospinus*, *Streptomyces cinereus*, *Streptomyces cinerochromogenes*, *Streptomyces cinnabarinus*, *Streptomyces cinnamonensis*, *Streptomyces cinnamoneus*, *Streptomyces cirratus*, *Streptomyces ciscaucasicus*, *Streptomyces clavifer*, *Streptomyces clavuligerus*, *Streptomyces coacervatus*, *Streptomyces cocklensis*, *Streptomyces coelescens*, *Streptomyces coelicoflavus*, *Streptomyces coelicolor*, *Streptomyces coeruleoflavus*, *Streptomyces coeruleofuscus*, *Streptomyces coeruleoprunus*, *Streptomyces coeruleorubidus*, *Streptomyces coerulescens*, *Streptomyces collinus*, *Streptomyces colombiensis*, *Streptomyces corchorusii*, *Streptomyces costaricanus*, *Streptomyces cremeus*, *Streptomyces crystallinus*, *Streptomyces cuspidosporus*, *Streptomyces cyaneofuscatus*, *Streptomyces cyaneus*, *Streptomyces cyanoalbus*, *Streptomyces cyslabdanicus*, *Streptomyces daghestanicus*, *Streptomyces daliensi*, *Streptomyces daqingensis*, *Streptomyces deccanensis*, *Streptomyces decoyicus*, *Streptomyces demainii*, *Streptomyces deserti*, *Streptomyces diastaticus*, *Streptomyces diastatochromogenes*, *Streptomyces djakartensis*, *Streptomyces drozdowiczii*, *Streptomyces durhamensis*, *Streptomyces durmitorensis*, *Streptomyces echinatus*, *Streptomyces echinoruber*, *Streptomyces ederensis*, *Streptomyces emeiensis*, *Streptomyces endophyticus*, *Streptomyces endus*, *Streptomyces enissocaesilis*, *Streptomyces erythraeus* (also known as *Saccharopolyspora erythraea*), *Streptomyces erythrogriseus*, *Streptomyces erringtonii*, *Streptomyces eurocidicus*, *Streptomyces europaeiscabiei*, *Streptomyces eurythermus*, *Streptomyces exfoliates*, *Streptomyces faba*, *Streptomyces fenghuangensis*, *Streptomyces ferralitis*, *Streptomyces filamentosus*, *Streptomyces fildesensis*, *Streptomyces fihpinensis*, *Streptomyces fimbriatus*, *Streptomyces finlayi*, *Streptomyces flaveolus*, *Streptomyces flaveus*, *Streptomyces flavofungini*, *Streptomyces flavotricini*, *Streptomyces flavovariabilis*, *Streptomyces flavovirens*, *Streptomyces flavoviridis*, *Streptomyces fradiae*, *Streptomyces fragilis*, *Streptomyces fukangensis*, *Streptomyces fulvissimus*, *Streptomyces fulvorobeus*, *Streptomyces fumanus*, *Streptomyces fumigatiscleroticus*, *Streptomyces galbus*, *Streptomyces galilaeus*, *Streptomyces gancidicus*, *Streptomyces gardneri*, *Streptomyces gelaticus*, *Streptomyces geldanamycininus*, *Streptomyces geysiriensis*, *Streptomyces ghanaensis*, *Streptomyces gilvifuscus*, *Streptomyces glaucescens*, *Streptomyces glauciniger*, *Streptomyces glaucosporus*, *Streptomyces glaucus*, *Streptomyces globisporus*, *Streptomyces globosus*, *Streptomyces glomeratus*, *Streptomyces glomeroaurantiacus*, *Streptomyces glycovorans*, *Streptomyces gobitricini*, *Streptomyces goshikiensis*, *Streptomyces gougerotii*, *Streptomyces graminearus*, *Streptomyces gramineus*, *Streptomyces graminifolii*, *Streptomyces graminilatus*, *Streptomyces graminisoli*, *Streptomyces griseiniger*, *Streptomyces griseoaurantiacus*, *Streptomyces griseocarneus*, *Streptomyces griseochromogenes*, *Streptomyces griseoflavus*, *Streptomyces griseofuscus*, *Streptomyces griseoincarnatus*, *Streptomyces griseoloalbus*, *Streptomyces griseolus*, *Streptomyces griseoluteus*, *Streptomyces*

*griseomycini, Streptomyces griseoplanus, Streptomyces griseorubens, Streptomyces griseoruber, Streptomyces griseorubiginosus, Streptomyces griseosporeus, Streptomyces griseostramineus, Streptomyces griseoviridis, Streptomyces griseus, Streptomyces guanduensis, Streptomyces gulbargensis, Streptomyces hainanensis, Streptomyces haliclonae, Streptomyces halophytocola, Streptomyces halstedii, Streptomyces harbinensis, Streptomyces hawaiiensis, Streptomyces hebeiensis, Streptomyces heilongjiangensis, Streptomyces heliomycini, Streptomyces helvaticus, Streptomyces herbaceous, Streptomyces herbaricolor, Streptomyces himastatinicus, Streptomyces hiroshimensis, Streptomyces hirsutus, Streptomyces hokutonensis, Streptomyces hoynatensis, Streptomyces humidus, Streptomyces humiferus, Streptomyces hundungensis, Streptomyces hyderabadensis, Streptomyces hygroscopicus, Streptomyces hypolithicus, Streptomyces iakyrus, Streptomyces iconiensis, Streptomyces incanus, Streptomyces indiaensis, Streptomyces indigoferus, Streptomyces indicus, Streptomyces indonesiensis, Streptomyces intermedius, Streptomyces inusitatus, Streptomyces ipomoeae, Streptomyces iranensis, Streptomyces janthinus, Streptomyces javensis, Streptomyces jietaisiensis, Streptomyces jiujiangensis, Streptomyces kaempferi, Streptomyces kanamyceticus, Streptomyces karpasiensis, Streptomyces kasugaensis, Streptomyces katrae, Streptomyces kebangsaanensis, Streptomyces klenkii, Streptomyces koyangensis, Streptomyces kunmingensis, Streptomyces kurssanovii, Streptomyces labedae, Streptomyces lacrimifluminis, Streptomyces lacticiproducens, Streptomyces laculatispora, Streptomyces lanatus, Streptomyces lannensis, Streptomyces lateritius, Streptomyces laurentii, Streptomyces lavendofoliae, Streptomyces lavendulae, Streptomyces lavenduligriseus, Streptomyces leeuwenhoekii, Streptomyces lavendulocolor, Streptomyces levis, Streptomyces libani, Streptomyces lienomycini, Streptomyces lilacinus, Streptomyces lincolnensis, Streptomyces litmocidini, Streptomyces litoralis, Streptomyces lomondensis, Streptomyces longisporoflavus, Streptomyces longispororuber, Streptomyces lopnurensis, Streptomyces longisporus, Streptomyces longwoodensis, Streptomyces lucensis, Streptomyces lunaelactis, Streptomyces lunalinharesii, Streptomyces luridiscabiei, Streptomyces luridus, Streptomyces lusitanus, Streptomyces lushanensis, Streptomyces luteireticuli, Streptomyces luteogriseus, Streptomyces luteosporeus, Streptomyces lydicus, Streptomyces macrosporus, Streptomyces malachitofuscus, Streptomyces malachitospinus, Streptomyces malaysiensis, Streptomyces mangrove, Streptomyces marinus, Streptomyces marokkonensis, Streptomyces mashuensis, Streptomyces massasporeus, Streptomyces matensis, Streptomyces mayteni, Streptomyces mauvecolor, Streptomyces megaspores, Streptomyces melanogenes, Streptomyces melanosporofaciens, Streptomyces mexicanus, Streptomyces michiganensis, Streptomyces microflavus, Streptomyces milbemycinicus, Streptomyces minutiscleroticus, Streptomyces mirabilis, Streptomyces misakiensis, Streptomyces misionensis, Streptomyces mobaraensis, Streptomyces monomycini, Streptomyces mordarskii, Streptomyces morookaense, Streptomyces muensis, Streptomyces murinus, Streptomyces mutabilis, Streptomyces mutomycini, Streptomyces naganishii, Streptomyces nanhaiensis, Streptomyces nanshensis, Streptomyces narbonensis, Streptomyces nashvillensis, Streptomyces netropsis, Streptomyces neyagawaensis, Streptomyces niger, Streptomyces nigrescens, Streptomyces nitrosporeus, Streptomyces niveiscabiei, Streptomyces niveiscabiei, Streptomyces niveoruber, Streptomyces niveus, Streptomyces noboritoensis, Streptomyces nodosus, Streptomyces nogalater, Streptomyces nojiriensis, Streptomyces noursei, Streptomyces novaecaesareae, Streptomyces ochraceiscleroticus, Streptomyces olivaceiscleroticus, Streptomyces olivaceoviridis, Streptomyces olivaceus, Streptomyces olivicoloratus, Streptomyces olivochromogenes, Streptomyces olivomycini, Streptomyces olivoverticillatus, Streptomyces omiyaensis, Streptomyces osmaniensis, Streptomyces orinoci, Streptomyces pactum, Streptomyces panacagri, Streptomyces panaciradicis, Streptomyces paradoxus, Streptomyces parvulus, Streptomyces parvus, Streptomyces pathocidini, Streptomyces paucisporeus, Streptomyces peucetius, Streptomyces phaeochromogenes, Streptomyces phaeofaciens, Streptomyces phaeogriseichromatogenes, Streptomyces phaeoluteichromatogenes, Streptomyces phaeoluteigriseus, Streptomyces phaeopurpureus, Streptomyces pharetrae, Streptomyces pharmamarensis, Streptomyces phytohabitans, Streptomyces pilosus, Streptomyces platensis, Streptomyces plicatus, Streptomyces plumbiresistens, Streptomyces pluricolorescens, Streptomyces pluripotens, Streptomyces polyantibioticus, Streptomyces polychromogenes, Streptomyces polygonati, Streptomyces polymachus, Streptomyces poonensis, Streptomyces prasinopilosus, Streptomyces prasinosporus, Streptomyces prasinus, Streptomyces pratens, Streptomyces platensis, Streptomyces prunicolor, Streptomyces psammoticus, Streptomyces pseudoechinosporeus, Streptomyces pseudogriseolus, Streptomyces pseudovenezuelae, Streptomyces pulveraceus, Streptomyces puniceus, Streptomyces puniciscabiei, Streptomyces purpeofuscus, Streptomyces purpurascens, Streptomyces purpureus, Streptomyces purpurogeneiscleroticus, Streptomyces qinglanensis, Streptomyces racemochromogenes, Streptomyces radiopugnans, Streptomyces rameus, Streptomyces ramulosus, Streptomyces rapamycinicus, Streptomyces recifensis, Streptomyces rectiviolaceus, Streptomyces regensis, Streptomyces resistomycificus, Streptomyces reticuliscabiei, Streptomyces rhizophilus, Streptomyces rhizosphaericus, Streptomyces rimosus, Streptomyces rishiriensis, Streptomyces rochei, Streptomyces rosealbus, Streptomyces roseiscleroticus, Streptomyces roseofulvus, Streptomyces roseolilacinus, Streptomyces roseolus, Streptomyces roseosporus, Streptomyces roseoviolaceus, Streptomyces roseoviridis, Streptomyces ruber, Streptomyces rubidus, Streptomyces rubiginosohelvolus, Streptomyces rubiginosus, Streptomyces rubrisoli, Streptomyces rubrogriseus, Streptomyces rubrus, Streptomyces rutgersensis, Streptomyces samsunensis, Streptomyces sanglieri, Streptomyces sannanensis, Streptomyces sanyensis, Streptomyces sasae, Streptomyces scabiei, Streptomyces scabrisporus, Streptomyces sclerotialus, Streptomyces scopiformis, Streptomyces scopuliridis, Streptomyces sedi, Streptomyces seoulensis, Streptomyces seranimatus, Streptomyces seymenliensis, Streptomyces shaanxiensis, Streptomyces shenzhenensis, Streptomyces showdoensis, Streptomyces silaceus, Streptomyces sindenensis, Streptomyces sioyaensis, Streptomyces smyrnaeus, Streptomyces Streptomyces somaliensis, Streptomyces sudanensis, Streptomyces sparsogenes, Streptomyces sparsus, Streptomyces specialis, Streptomyces spectabilis, Streptomyces speibonae, Streptomyces speleomycini, Streptomyces spinoverrucosus, Streptomyces spiralis, Streptomyces spiroverticillatus, Streptomyces spongiae, Streptomyces spongiicola, Streptomyces sporocinereus, Streptomyces sproclivatus, Streptomyces spororaveus, Streptomyces sporoverrucosus, Streptomyces staurosporininus, Streptomyces stelliscabiei, Streptomyces stramineus, Streptomyces subrutilus, Streptomyces sulfonofaciens, Streptomyces sulphurous, Streptomyces sundarbansensis, Streptomyces synnematoformans, Streptomyces tacrolimicus, Streptomyces*

*tanashiensis, Streptomyces tateyamensis, Streptomyces tauricus, Streptomyces tendae, Streptomyces termitum, Streptomyces thermoalcalitolerans, Streptomyces thermoautotrophicus, Streptomyces thermocarboxydovorans, Streptomyces thermocarboxydus, Streptomyces thermocoprophilus, Streptomyces thermodiastaticus, Streptomyces thermogriseus, Streptomyces thermolineatus, Streptomyces thermospinosisporus, Streptomyces thermoviolaceus, Streptomyces thermovulgaris, Streptomyces thinghirensis, Streptomyces thioluteus, Streptomyces torulosus, Streptomyces toxytricini, Streptomyces tremellae, Streptomyces tritolerans, Streptomyces tricolor, Streptomyces tsukubensis, Streptomyces tubercidicus, Streptomyces tuirus, Streptomyces tunisiensis, Streptomyces turgidiscabies, Streptomyces tyrosinilyticus, Streptomyces umbrinus, Streptomyces variabilis, Streptomyces variegatus, Streptomyces varsoviensis, Streptomyces verticillus, Streptomyces vastus, Streptomyces venezuelae, Streptomyces vietnamensis, Streptomyces vinaceus, Streptomyces vinaceusdrappus, Streptomyces violaceochromogenes, Streptomyces violaceolatus, Streptomyces violaceorectus, Streptomyces violaceoruber, Streptomyces violaceorubidus, Streptomyces violaceus, Streptomyces violaceusniger, Streptomyces violarus, Streptomyces violascens, Streptomyces violens, Streptomyces virens, Streptomyces virginiae, Streptomyces viridis, Streptomyces viridiviolaceus, Streptomyces viridobrunneus, Streptomyces viridochromogenes, Streptomyces viridodiastaticus, Streptomyces viridosporus, Streptomyces vitaminophilus, Streptomyces wedmorensis, Streptomyces wellingtoniae, Streptomyces werraensis, Streptomyces wuyuanensis, Streptomyces xanthochromogenes, Streptomyces xanthocidicus, Streptomyces xantholiticus, Streptomyces xanthophaeus, Streptomyces xiamenensis, Streptomyces xinghaiensis, Streptomyces xishensis, Streptomyces yaanensis, Streptomyces yanglinensis, Streptomyces yangpuensis, Streptomyces yanii, Streptomyces yatensis, Streptomyces yeochonensis, Streptomyces yerevanensis, Streptomyces yogyakartensis, Streptomyces yokosukanensis, Streptomyces youssoufiensis, Streptomyces yunnanensis, Streptomyces zagrosensis, Streptomyces zaomyceticus, Streptomyces zhaozhouensis, Streptomyces zinciresistens,* or *Streptomyces ziwulingensis.*

As used herein, the term "silent" or "quiescent", when used in reference to a gene, refers to a gene that has no phenotypical effect on the host and/or has no detectable expression. This non-effect of a silent gene can be due to the either low or non-existent expression of the silent gene. The term "silent gene" may also refer to a transcriptionally inactive gene. As used herein, "silent gene" refers to a gene that is unable to express the associated gene product from its coding sequence, either during transcription or translation processes in the cellular host.

As used herein, the term "activation" refers to an upregulation of gene expression or transcriptional activation of a gene that was previously not expressed or only expressed in small amounts. Conversely, the term "suppression" or "repression" refers to a downregulation of gene expression or transcriptional activity of a gene.

As used herein, the term "co-linear" refers to open reading frames that are transcribed in the same direction.

As used herein, the term "trans-conjugation" or "conjugation" refers to the transfer of genetic material between bacterial cells by horizontal gene transfer, e.g., by direct cell-to-cell contact or by a bridge-like connection between two cells.

As used herein, the term "antimicrobial" includes antibiotics and chemicals capable of inhibiting or preventing the growth of, or capable of killing, microbes, especially bacteria. An example of an antimicrobial chemical is a disinfectant. Classes of antimicrobials are known in the art. See, e.g., Vittorio Tracanna, Anne de Jong, Marnix H. Medema, Oscar P. Kuipers; Mining prokaryotes for antimicrobial compounds: from diversity to function, FEMS Microbiology Reviews, Volume 41, Issue 3, 1 May 2017, Pages 417-429, at Table 1, incorporated herein by reference.

As used herein, the term "antibiotic" refers to an agent produced by a living organism (e.g., a bacterium) that is capable of inhibiting the growth of another living organism (e.g., another bacterium) or that is capable of killing another living organism (e.g., another bacterium).

As used herein, the term "artificial DNA" refers to a DNA molecule or a portion of a DNA molecule that is different from any found in nature or that is produced by non-natural processes, for example, as the result of in vitro techniques or solid-phase DNA synthesis.

As used herein, the term "isolated DNA sequence" refers to any DNA molecule, however constructed or synthesized, that is locationally distinct from its natural location in genomic and/or episomal DNA. The definition includes the isolated DNA sequence in all its forms other than the natural state. For example, the DNA sequence may be inserted into a plasmid or phage vector or inserted into the genome of the organism from which it came or any other organism.

As used herein, the term "gene" refers to a polynucleotide comprising coding sequence for at least one polypeptide or non-coding RNA. When referring to protein-coding genes, the term "gene" refers to a polynucleotide comprising at least one open reading frame that is capable of encoding a particular polypeptide or protein after being transcribed and translated. Any of the polynucleotide sequences described herein may be used to identify larger fragments or full-length coding sequences of the gene with which they are associated.

As used herein, the term "synthetic gene" refers to a DNA fragment synthesized in the laboratory by combining nucleotides without preexisting DNA sequences. In particular, the term refers to a completely synthetic double-stranded DNA molecule.

As used herein, the term "recognition site" refers to a location on a DNA molecule containing specific sequences of nucleotides that are recognized by specific proteins or enzymes or by specific nucleic acids.

As used herein, the term "restriction endonuclease" refers to an enzyme that cuts a double-stranded DNA molecule at a specific recognition site. In some embodiments of the present technology, the term relates to restriction endonucleases or enzymes that specifically recognize DNA sequences of 6, 7, or 8 nucleotides, in which the nucleotide sequence of one DNA strand reads in reverse order to that of the complementary DNA strand (palindromic). However, the technology is not limited to use of such enzymes and includes restriction endonucleases that have recognition sequences of other sizes.

As used herein, the term oriV refers to the origin of replication (e.g., derived from the bacterial F plasmid) that finds use in some embodiments of the expression vector as described herein; ori2 refers to the secondary origin of replication, which is also known as oriS (e.g., derived from the bacterial F plasmid) that finds use in some embodiments of the expression vector described herein; repE refers to a gene encoding the replication initiation protein (e.g., derived from the bacterial F plasmid) that finds use in some embodiments of the expression vector described herein; incC refers to the incompatibility region (e.g., derived from the bacterial F plasmid) that finds use in some embodiments of the expression vector described herein; sopA refers to a gene encoding a partitioning protein (e.g., derived from the bacterial F plasmid) that finds use in some embodiments of the expression vector described herein; sopB refers to a gene encoding a partitioning protein (e.g., derived from the bacterial F plasmid) that finds use in some embodiments of the expression vector described herein; sopC refers to a gene encoding a partitioning protein (e.g., derived from the bacterial F plasmid) that finds use in some embodiments of the expression vector described herein; oriT refers to the incP origin of transfer for some embodiments of the expression vector described herein; ApramR refers to the aac(3)-IV apramycin resistance gene that finds use in some embodiments of the expression vector described herein; the phage φC31 attP site allows integration to genomic attB sites and is a component that finds use in some embodiments of the expression vector described herein; the phage φC31 integrase allows integration between attP and attB sites and is a component that finds use in some embodiments of the expression vector described herein; cos refers to the lambda cos site, which allows packaging into phage lambda particles, that finds use in some embodiments of the expression vector described herein; and Kanamycin-r refers to a gene encoding the kanamycin resistance gene that finds use in some embodiments of the expression vector described herein.

As used herein, the term "Cas9" (CRISPR associated protein 9) refers to an RNA-guided DNA endonuclease enzyme associated with the CRISPR (Clustered Regularly Interspaced Short Palindromic Repeats) adaptive immunity system in *Streptococcus pyogenes*, among other bacteria. Cas9 can be used to cleave DNA in vitro or in vivo by use of sequence specific guide RNA to target a known region of DNA.

As used herein, the term "target DNA" or "target vector" refers to a double-stranded DNA that is suitable to be modified using molecular biology techniques. In this technology, the definition relates to episomal DNA sequences that include specific recognition sites for restriction endonucleases or that can be modified by transposases as a result of the inclusion of transposable DNA elements.

As used herein, the term "origin of replication" or "replication origin" refers to particular sequences in episomal DNAs at which replication is initiated, based on recruiting proteins involved in DNA replication.

As used herein, the term "selectable marker" refers to a gene whose expression allows one to identify cells that have been transformed or transfected with a vector containing the marker gene (e.g., by antibiotic resistance on antibiotic medium, fluorescence, color generation, or other detectable signal). For instance, a recombinant nucleic acid may include a selectable marker operably linked to a gene of interest and a promoter, such that expression of the selectable marker indicates the successful transformation of the cell with the gene of interest. In some embodiments, a "selectable marker" refers to a gene located inside bacteria (at genomic or episomal level) that confers a feature for artificial selection. The term is typically associated with antibiotic resistance genes (e.g., a chloramphenicol resistance gene) provided in vectors or artificial vectors for selection of bacterial isolates after transformation.

As used herein, the term "transformation" refers to the process of introducing genetic material into a cell, e.g., to bacterial cells. In some embodiments of the present technology, the term is associated with introducing vectors, expression vectors, modified artificial vectors, and clones (e.g., comprising a vector and in insert) into bacterial cells.

As used herein, the terms "upstream" and "downstream" refer to relative positions of portions of nucleic acids or nucleic acid sequences (e.g., DNA or RNA) and are often used to differentiate relative positions in DNA or RNA sequences. As used herein, the terms "upstream" and "downstream" are defined relative to the 5' to 3' direction in which RNA transcription takes place. "Upstream" is toward the 5' end of the RNA molecule and "downstream" is toward the 3' end. For double-stranded DNA, "upstream" is toward the 5' end of the coding strand for the nucleic acid and downstream is toward the 3' end. Thus, in exemplary use, "upstream" is a position towards the 5' from another nucleic acid segment (e.g., promoter, gene, restriction site, etc.) in a single strand of DNA or in a RNA molecule and "downstream" is a position towards the 3' from another nucleic acid segment in a single strand of DNA or in a RNA molecule.

As used herein, the term "metagenome" is defined as "the collective genomes of all microorganisms present in a given habitat" (Handelsman et al., (1998) Chem. Biol. 5: R245-R249). However, this term is also intended to include clones, including the genomes or genes extracted from environmental samples.

As used herein, "metagenomic DNA" refers to the whole microbial-associated genomic DNA isolated from complex samples like open natural environments (e.g. soil, water) or from microbiomes of multicellular organisms (e.g. humans).

As used herein, "metagenomic library" refers to a clone collection of whole microbial-associated genomic DNA isolated from complex samples like open natural environments (e.g. soil, water) or from microbiomes of multicellular organisms (e.g. humans) in a recombinant vector.

As used herein, "genome" refers to the genetic material (e.g., chromosome) of an organism.

As used herein, "PCR" refers to the polymerase chain reaction method of amplifying DNA or RNA.

As used herein, "antiSMASH" refers to a software program used to identify motifs commonly found in BGCs.

As used herein, "insert" or "DNA insert" refers to a piece or fragment or sequence of DNA that is inserted, by molecular biology techniques, into a vector or an artificial vector for its subsequent selection, propagation, manipulation, or expression in a host organism.

As used herein, the term "large plasmid" or "large vector" refers to a plasmid or vector (e.g., an expression vector) that is larger than 10 kb and/or that comprises an insert greater than 5-10 kb. Large inserts (e.g., greater than 5-10 kb) are unstable (e.g., through recombination) at high copy numbers. In some embodiments, partitioning factors (e.g., sopA, sopB, and/or sopC) help maintain a plasmid or vector at single copy number to minimize and/or eliminate recombination instability.

As used herein, "reporter gene" means a gene whose expression in a bacterial host can be easily monitored or detected. In some embodiments of the present technology, the reporter gene encodes for a green fluorescent protein (GFP) variant.

As used herein, the term "gene" refers to a nucleic acid molecule that comprises a nucleic acid sequence that encodes a polypeptide or non-coding RNA and the expression control sequences that are operably linked to the nucleic acid sequence that encodes the polypeptide or non-coding RNA. For instance, a gene may comprise a promoter, one or more enhancers, a nucleic acid sequence that encodes a polypeptide or a non-coding RNA, downstream regulatory sequences and, possibly, other nucleic acid sequences involved in regulating the transcription of an RNA from the gene.

A nucleic acid molecule or polypeptide is "derived" from a particular species if the nucleic acid molecule or polypeptide has been isolated from the particular species or if the nucleic acid molecule or polypeptide is homologous to a nucleic acid molecule or polypeptide isolated from a particular species.

As used herein, "kilobase" (kb) or "kilobase pairs" (kbp) refers to 1000 nucleotides or 1000 base pairs of a nucleic acid (e.g., DNA or RNA).

As used herein, the term "in vitro" refers to studies that are conducted using components of an organism that have been isolated from their usual biological surroundings to permit a more detailed or more convenient analysis than can be done with whole organisms. Colloquially, these experiments are commonly called "test tube experiments". In contrast, in vivo studies are those that are conducted with living organisms in their normal intact state.

A used herein, the term "in vivo" refers to experimentation using living cells or a whole living organism as opposed to a partial or dead cell or organism, or an in vitro ("within the glass", e.g., in a test tube or petri dish) controlled environment.

As used herein, the term "molecular cloning" refers to the method of preparing or assembling exogenous, homologous, and/or heterologous DNA for propagation, selection, and/or expression within a host organism. In a conventional molecular cloning experiment, the DNA to be cloned is obtained from an organism or metagenome of interest and subsequently treated with enzymes such as Cas9 or restriction enzymes in to generate smaller DNA fragments. Subsequently, these fragments are then combined with vector DNA to produce recombinant DNA molecules. The recombinant DNA is then introduced into a host organism (typically an easy-to-grow, benign, laboratory strain of $E. coli$ bacteria) to produce a population of organisms in which recombinant DNA molecules are replicated along with the host DNA. This process takes advantage of the fact that a single bacterial cell can be induced to take up and replicate a single recombinant DNA molecule. This single cell can then be expanded exponentially to generate a large amount of bacteria, each of which contains a copy of the original recombinant molecule. Thus, both the resulting bacterial population, and the recombinant DNA molecule, are commonly referred to as "clones".

The method of molecular cloning can also be used to regulate gene expression. In general, regulation of gene expression comprises and includes a wide range of mechanisms that are used by cells to increase or decrease the production of specific gene products (protein or RNA). Sophisticated programs of gene expression are widely observed and known in the art, for example, as a mechanism to trigger developmental pathways, respond to environmental stimuli, or adapt to new food sources. Virtually any step of gene expression can be modulated, from transcriptional initiation, to RNA processing, and to the post-translational modification of a protein. Often, one gene regulator controls another, and so on, resulting in a complex gene regulatory network. The process of gene expression itself can be divided into two major processes, transcription and translation. One place in which the production of specific gene products can be influenced is during transcription, which is the process of transcribing DNA to RNA, which ultimately has an effect on the protein expressed during a later process called translation (also known as protein synthesis). Transcriptional regulation is the means by which a cell regulates the conversion of DNA to RNA (transcription), thereby orchestrating gene activity. A single gene can be regulated in a range of ways, from altering the number of copies of RNA that are transcribed to the temporal control of when the gene is transcribed. Transcriptional regulation also influences temporal expression of particular proteins. This control allows the cell or organism to respond to a variety of intra- and extracellular signals and thus mount a response. Some examples of this include producing the mRNA that encode enzymes to adapt to a change in a food source, producing the gene products, including proteins, involved in cell cycle specific activities, and producing the gene products, including proteins, responsible for cellular differentiation in higher eukaryote.

Percentage identity determinations can be performed for nucleic acids using BLASTN or standard nucleotide BLAST using default settings (Match/Mismatch scores 1, −2) Gap costs linear, Expect threshold 10, Word size 28, and match matches in a query range 0) and for proteins using BLAST using default settings (Expect threshold 10, Word size 3, Max matches in a query range 0, Matrix Blosum62, Gap costs Existence 11, extension 1 and conditional compositional score matrix adjustment).

BRIEF DESCRIPTION OF THE DRAWINGS

These and other features, aspects, and advantages of the present technology will become better understood with regard to the following drawings.

In the drawings, oriV refers to the origin of replication for the bacterial F plasmid; ori2 refers to the secondary origin of replication for the bacterial F plasmid; also known as oriS; repE refers to a gene encoding the replication initiation protein for the bacterial F plasmid; incC refers to the incompatibility region of the bacterial F plasmid; sopA refers to a gene encoding a partitioning protein for the bacterial F plasmid; sopB refers to a gene encoding a partitioning protein for the bacterial F plasmid; sopC refers to a gene encoding a partitioning protein for the bacterial F plasmid; oriT refers to the incP origin of transfer; ApramR refers to the aac(3)-IV apramycin resistance gene; the phage φC31 attP site allows integration to genomic attB sites; the phage φC31 integrase allows integration between attP and attB sites; cos refers to the lambda cos site, which allows packaging into phage lambda particles; and Kanamycin-r refers to a gene encoding the kanamycin resistance gene.

Figure 1:
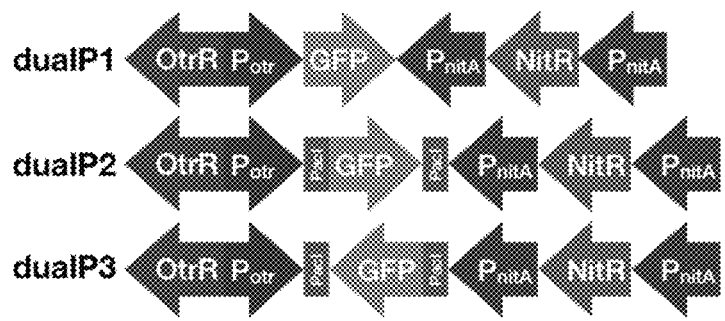
FIG. 1 shows three embodiments of the dual promoter cassette comprising OTC-promoter Potr and ε-cap promoter PnitA and the indicator GFP (green fluorescent protein) gene used in the BAC expression vector described herein. Variants 1 (dualP1) and 2 (dualP2) comprise GFP in an orientation for OTC induction while variant 3 (dualP3) comprises GFP in an orientation for ε-cap induction. Variants 2 and 3 comprise Pad restriction sites, which are rare and useful for cloning and subsequent modifications. OtrR encodes a regulator for Potr. NitR encodes a regulator for PnitA.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

For years it was assumed that S. coelicolor produces four compounds: actinorhodin (from the ACT BGC), undecylprodigiosin (from the RED BGC), methylenomycin, and a calcium-dependent antibiotic. Sequence analysis of the genome in 2002 revealed at least 25 pathways for potential secondary metabolites, which led to the discovery that S. coelicolor can produce 17 chemically distinct metabolite classes. Whole genome sequencing and computational analysis reveals nearly 1 million BGCs encoding NPs of unknown composition throughout the three domains of life. Decoding the genomes of antibiotic-producing microbes has revealed a surprisingly large number of new pathways, typically ten-fold higher than the number of molecules discovered by traditional approaches. Unfortunately, these pathways are mostly silent; efforts to turn them on have succeeded individually, but not as a large-scale platform. Computational tools to identify interesting pathways (e.g., polyketides, terpenes, nonribosomal peptides, etc.) are readily available, but identifying and finding the associated products is significantly more challenging.

As described herein, the present technology relates to the use of promoters (e.g., inducible promoters) provided in a vector (e.g., an expression vector) flanking a cloning site. In some embodiments, the technology provides a vector (e.g., an expression vector) comprising two promoters that flank a cloning site. After cloning an insert into the cloning site, the promoters flank the insert. Thus, the promoters provided by the expression vector are outside the boundaries of inserts cloned at the cloning site. Further, each promoter of the expression vector faces inward toward the insert and, accordingly, each promoter is upstream of nucleic acid sequences provided by the insert. That is, in some embodiments, the expression vector comprises two promoters (e.g., a first promoter and a second promoter) that direct transcription toward each other and in opposite directions. Accordingly, the two promoters are "face-to-face" promoters or, alternatively, "opposed promoters".

In some embodiments, one or both promoters is/are within 1 to 100 bases of the cloning site (e.g., within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 bases of the cloning site). In some embodiments, one or both promoters is/are within 10 to 500 bases of the cloning site (e.g., within 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 bases of the cloning site).

Accordingly, the promoters of the expression vector are capable of transcribing nucleic acids on one or both strands of a cloned insert. According to the technology provided herein, inserts are cloned into expression vectors provided herein without considering reading frame or other relationships between the expression vector promoters and nucleotide sequences of cloned inserts. Thus, the promoters in the expression vector not may or may not be operably linked to one or more genes of the insert. During the development of the technology provided herein, data collected surprising indicated that products were expressed from cloned inserts (e.g., comprising a BGC) without engineered placement of promoters within the insert and in operable linkage with a gene encoded by the insert. The data collected indicated that the promoters (e.g., inducible promoters) provided in the expression vector and outside cloned inserts transcribe nucleic acid of the insert and activate production of gene products (e.g., proteins, biosynthetic pathways comprising proteins, and products produced by biosynthetic pathways and/or proteins) in a heterologous host.

In some embodiments, the technology provides a vector (e.g., an expression vector) comprising a promoter flanking a cloning site, wherein the promoter directs transcription toward the cloning site; and wherein the expression vector is configured to accept a biosynthetic gene cluster nucleic acid at the cloning site and express a product of the biosynthetic gene cluster nucleic acid under control of the promoter.

In some embodiments, the technology provides a vector (e.g., an expression vector) comprising a promoter flanking a cloning site, wherein the promoter directs transcription toward the cloning site; and wherein the expression vector is configured to accept a nucleic acid of at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb) at the cloning site and express a product of the nucleic acid under control of the promoter.

In some embodiments, the technology provides a vector (e.g., an expression vector) comprising a first promoter and a second promoter flanking a cloning site, wherein the first promoter and second promoter direct transcription toward each other and in opposite directions; and wherein said expression vector is configured to accept a biosynthetic gene cluster nucleic acid at the cloning site and express a product of the biosynthetic gene cluster nucleic acid under control of the first promoter and/or the second promoter.

In some embodiments, the technology provides a vector (e.g., an expression vector) comprising a first promoter and a second promoter flanking a cloning site, wherein the first promoter and second promoter direct transcription toward each other and in opposite directions; and wherein said expression vector is configured to accept a nucleic acid comprising at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb) at the cloning site and express a product of the nucleic acid under control of the first promoter and/or the second promoter.

Figure 3:
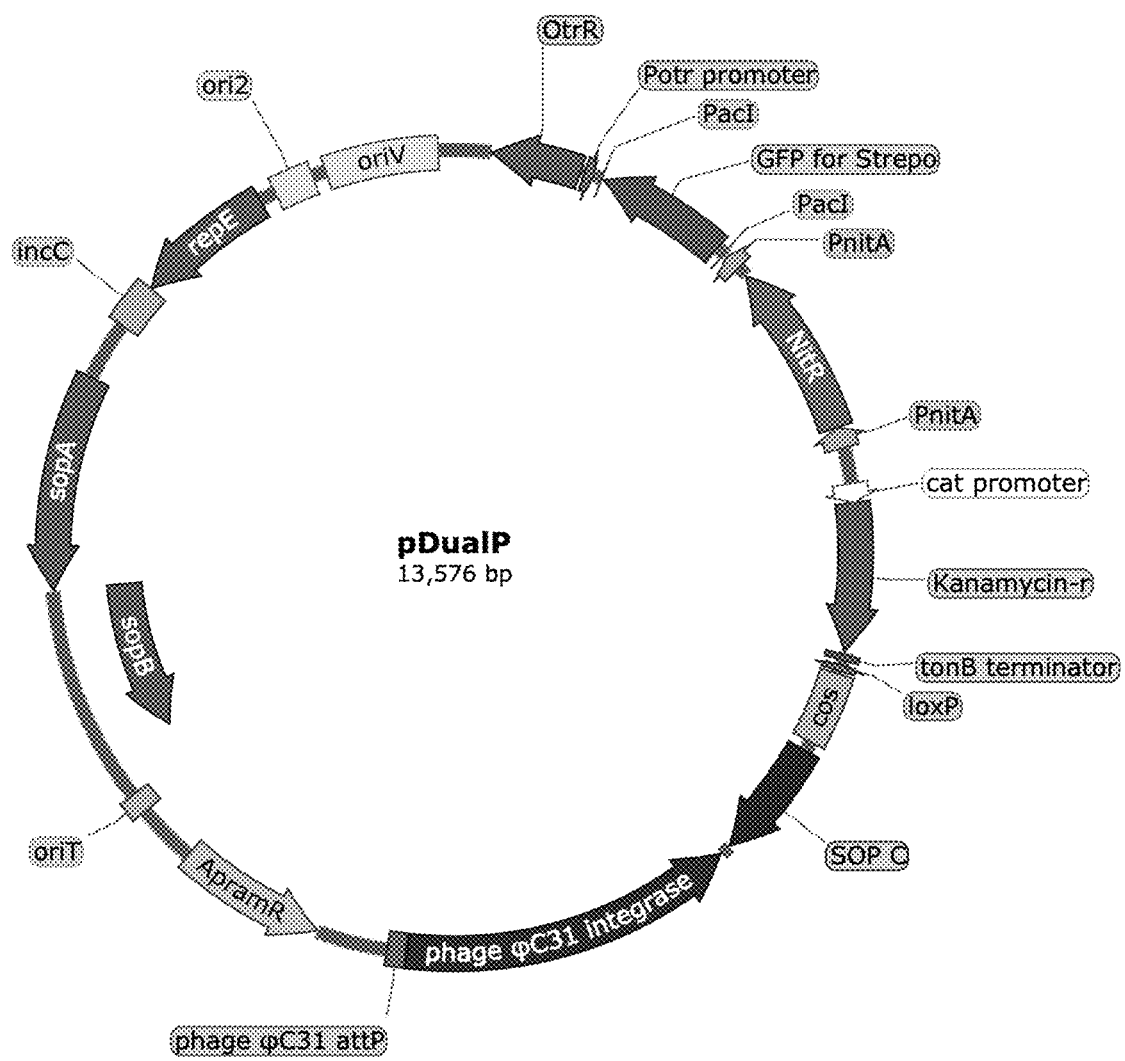
FIG. 3 shows a plasmid map of an embodiment of the dual inducible promoter expression vector described herein ("pDualP"). This expression vector is useful for cloning DNA to $E. coli$ and conjugation to, genome integration in, and inducible expression in Streptomyces and other organisms. Nucleotide sequences of Potr, OtrR, sfGFP, NitR, PnitA, and the dual promoter sequence comprising the sfGFP insert are provided by SEQ ID NOs: 1, 3, 4, 5, 6, and 7, respectively.

In some embodiments, one or both of the promoters is/are provided in multiple (e.g., 2, 3, 4, 5, or more copies), e.g., in a tandem arrangement or with other intervening nucleic acids (e.g., a gene (e.g., an activator and/or repressor gene)). See, e.g., the two PnitA promoters in FIG. 3, in which one promoter transcribes the regulator gene (e.g., NitR) and one promotor transcribes into the insert.

The technology comprises use of promoters that are capable of being introduced into a recombinant nucleic acid construct (e.g., a vector (e.g., an expression vector)) and direct transcription of a cloned insert in a host cell (e.g., a heterologous host cell).

Figure 4:
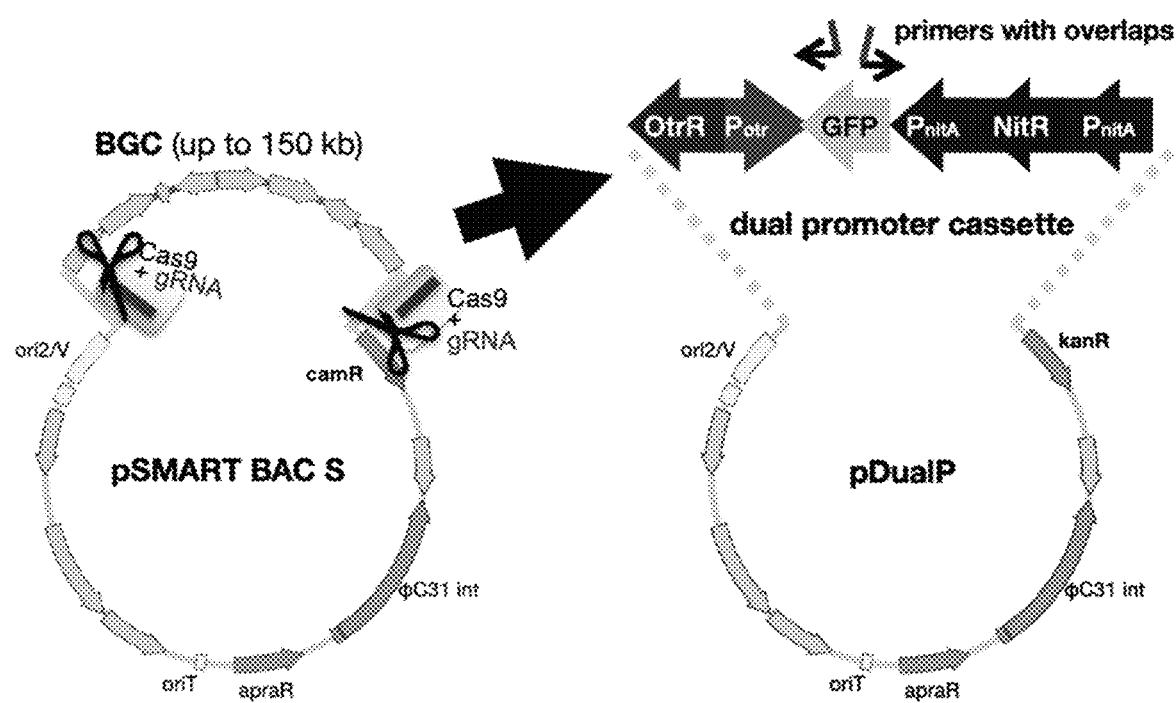
FIG. 4 is a schematic showing a method for subcloning metagenomic BGCs. Metagenomic BGCs from a BAC library clone are restricted by Cas9 at two unique sites flanking the BGC and assembled into a pDualP expression vector containing overlaps that match the ends of the restricted BGC.

In some embodiments, the present technology comprises use of the Potr or PnitA promoters. In particular, in some embodiments, the technology provides expression vectors, methods of using the expression vectors, and related systems, kits, and uses, wherein the expression vectors comprise a Potr and PnitA promoter flanking a cloning site and the Potr and PnitA promoters direct transcription toward each other and in opposite directions (see, e.g., FIG. 1, FIG. 3, and FIG. 4). As described herein, in some embodiments inserts are cloned into embodiments of the expression vectors provided herein and the technology is used to activate transcription of nucleic acids within the insert (e.g., one or more genes of a BGC and/or an entire BGC and/or a one or more genes of a nucleic acid insert comprising at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)) to express NP metabolites in a heterologous host.

Figure 5:
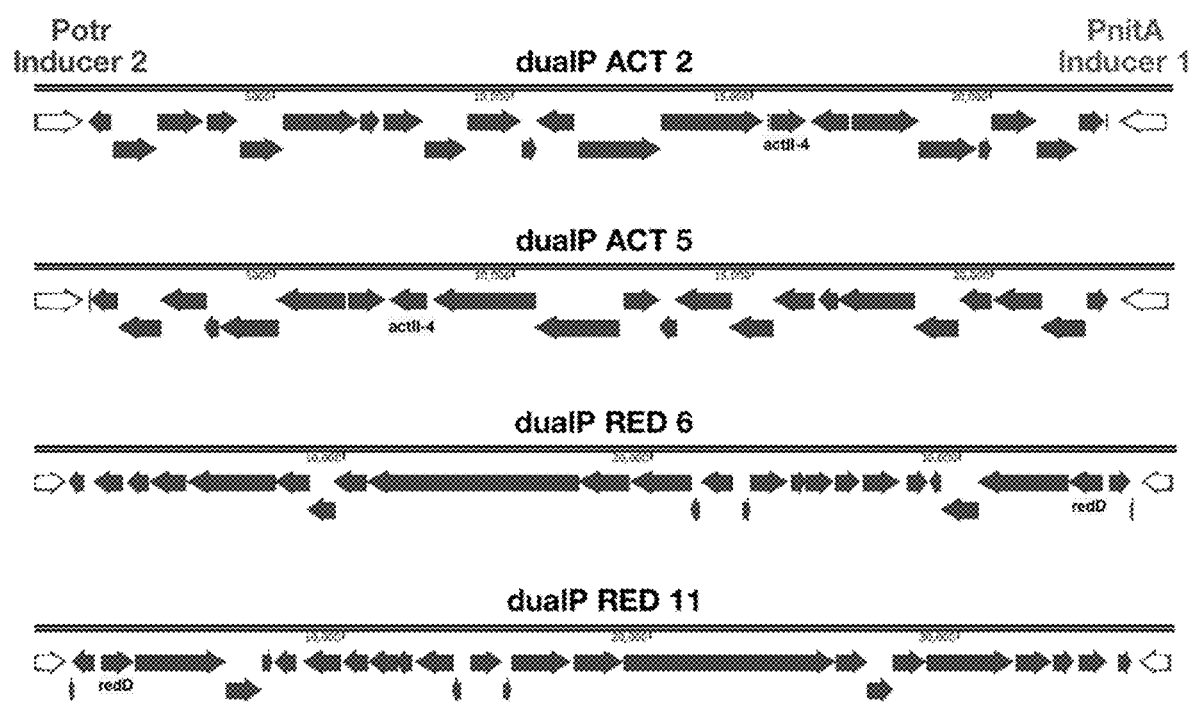
FIG. 5 shows ACT and RED BGCs cloned to pDualP in both orientations. Model S. coelicolor BGCs ACT and RED were cloned to pDualP in both orientations.
Figure 6:
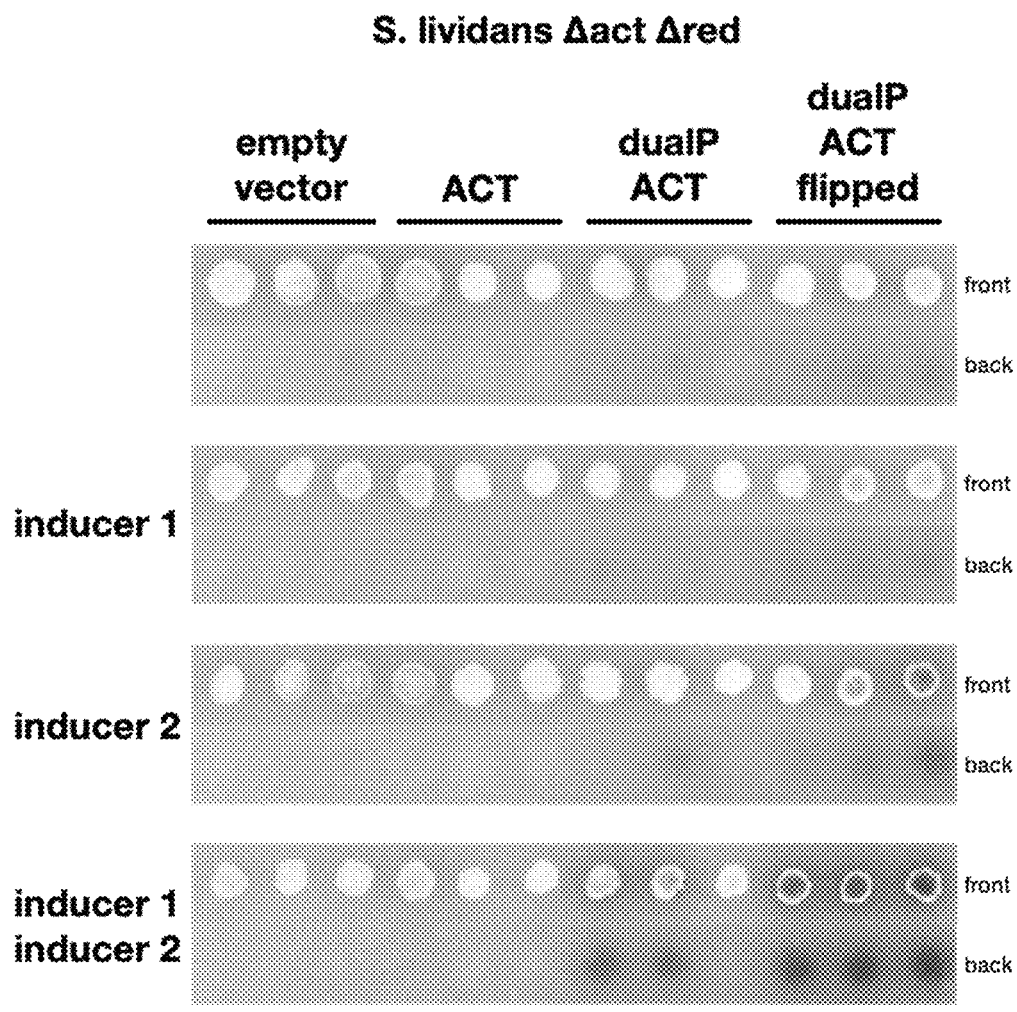
FIG. 6 shows pDualP ACT induction on MS agar imaged from either the front of the plate or the back of the plate, through the agar. In S. lividans ΔactΔred, the ACT BGC in both cloning orientations in pDualP is activated in response to inducers while the ACT BGC cloned without promoters is not activated.
Figure 7:
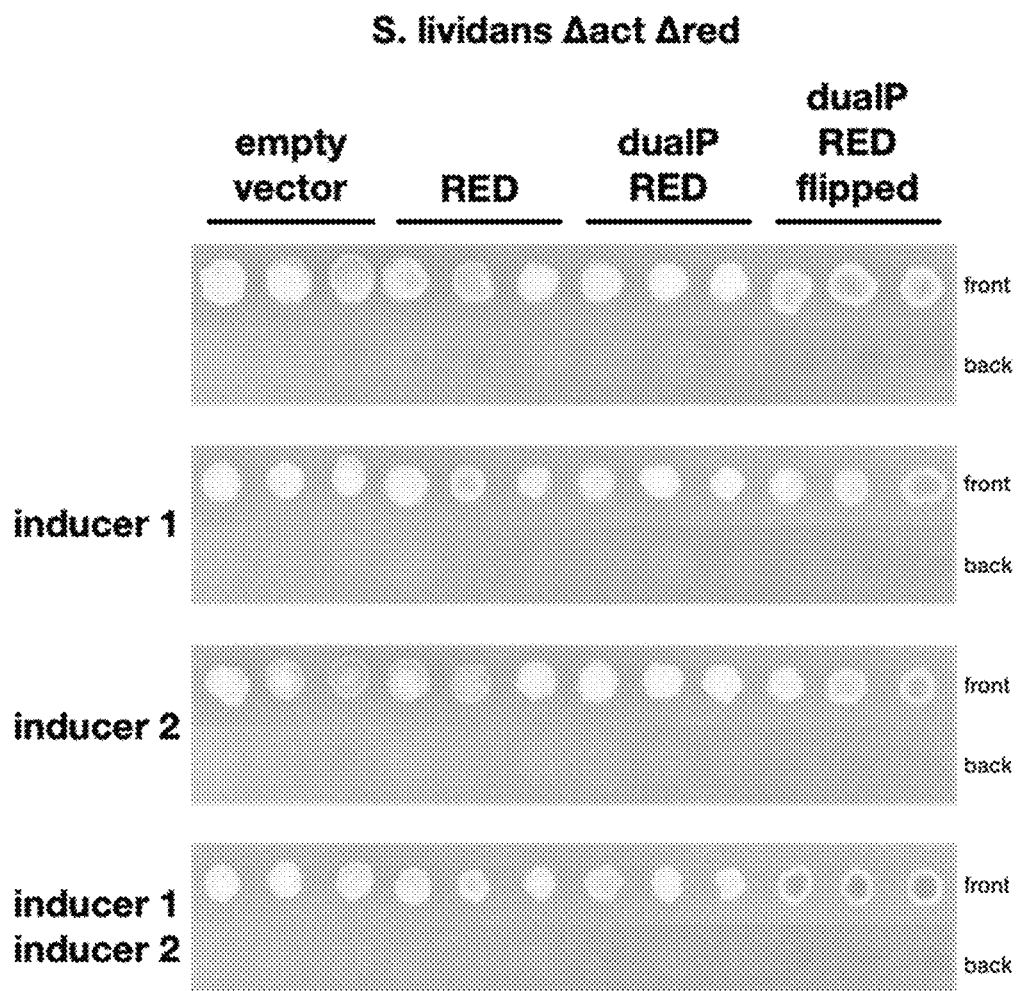
FIG. 7 shows pDualP RED induction on MS agar. In S. lividans ΔactΔred, the RED BGC in both cloning orientations in pDualP is activated in response to inducers while the RED BGC cloned without promoters is not activated.
Figure 8:
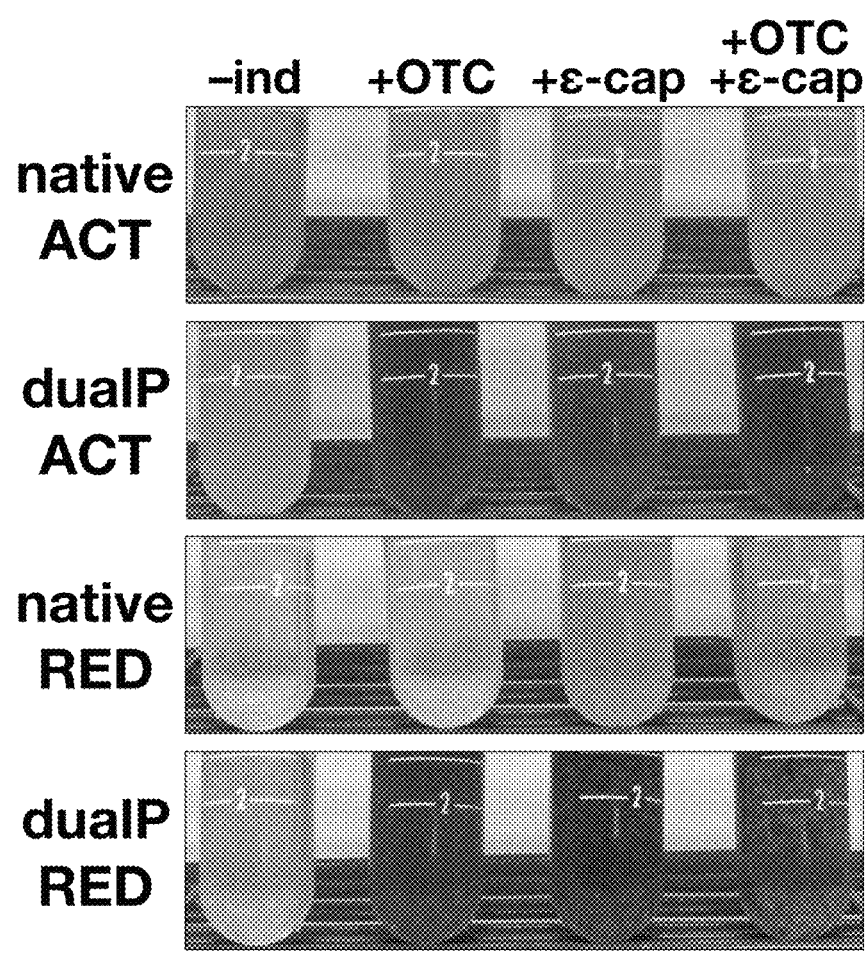
FIG. 8 shows pDualP induction of ACT in YEME broth or RED in R2YE liquid broth. In S. lividans ΔactΔred, the ACT and RED BGCs cloned to pDualP are activated in response to inducers while ACT and RED BGCs cloned without promoters are not activated.

For example, experiments conducted during the development of the technology indicated successful expression of metabolites from cloned inserts in two *Streptomyces* spp. hosts, *S. lividans* Δred Δact and *S. coelicolor* M1154. The 21-kb ACT cluster and 33-kb RED cluster were cloned from *S. coelicolor* A3 (2) into an embodiment of the dual inducible promoter BAC expression vector ("pDualP"; see, e.g., FIG. 4) in both orientations (see, e.g., FIG. 5). The same inserts comprising the ACT and RED clusters were also cloned into a standard vector without inducible promoters as a control. Both the pDualP constructs and the control constructs were conjugated into *S. lividans* Δred Δact (*S. lividans* comprising deletions of the endogenous nucleic acids (e.g., RED and ACT BGCs) that produce the RED and ACT products). Data collected during experiments described herein indicated that *S. lividans* Δred Δact comprising the control constructs did not produce significant quantities of the red or blue pigments from the RED or ACT native promoters from *S. coelicolor* (see, e.g., FIG. 6, FIG. 7, and FIG. 8). In contrast, expression of the pDualP RED and ACT inducible constructs was clearly activated in *S. lividans* Δred Δact when grown in the presence of one or both inducers of the Potr and PnitA promoters, OTC or ε-cap, respectively (see, e.g., FIG. 8). Wild type *S. lividans* is known to be a poor producer of native ACT or RED pigments (see, e.g., FIG. 8) and the data indicating minimal and/or undetectable expression of ACT or RED pigments by *S. lividans* Δred Δact comprising the control constructs is not unexpected. However, the data indicate the surprising result that inducible promoters placed outside of these cloned heterologous pathways were functionally able to activate both recombinant BGCs in the host cells.

Figure 9:
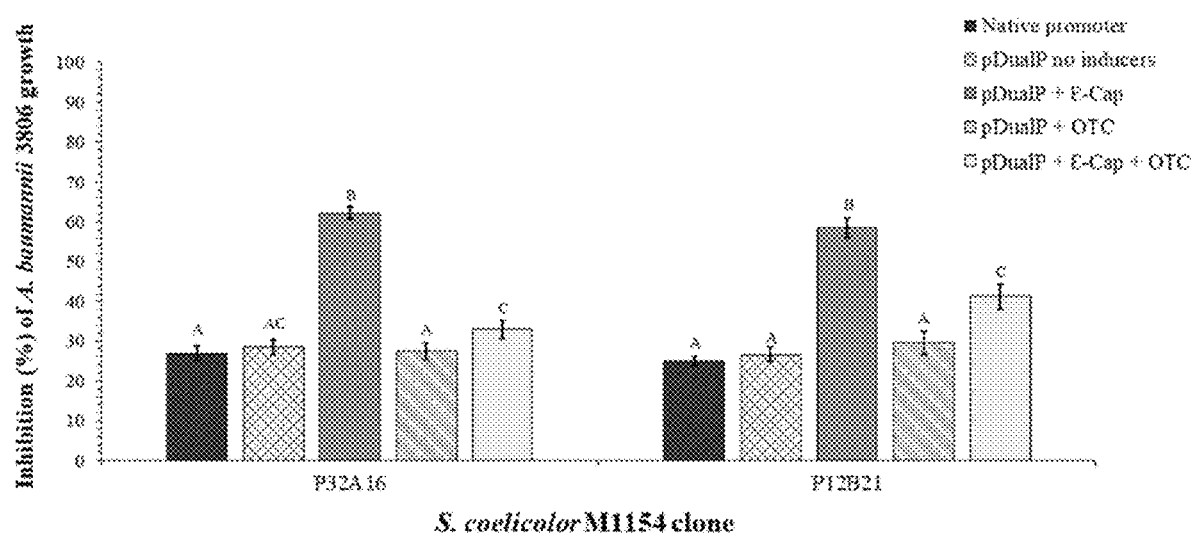
FIG. 9 shows a quantitative analysis of the pDualP inducible expression system in S. coelicolor M1154. Two metagenomic-derived BGCs were cloned to pDualP, introduced to S. coelicolor M1154, and extracts tested in an antibiosis activity assay against A. baumannii. Both BGCs show increased antibiosis activity in response to ε-cap. The growth inhibition of A. baumannii 3806 by supernatants of S. coelicolor clones harboring metagenomic BGCs with and without inducible expression is depicted. Inducible expression by pDualP is compared to the expression of the S. coelicolor native promoter (black bar). The values presented are the percent inhibitions of A. baumannii 3806 relative to the inhibition by the empty expression vector control from three replicates ±SD of each treatment group.

During the development of embodiments of the technology provided herein, data were collected indicating that novel BGCs discovered from a soil metagenomic library by a next-generation sequencing approach can be cloned into embodiments of the dual-inducible promoter BAC expression vector ("pDualP") to produce increased levels of an antibiotic metabolite relative to the native promoters present within the BGC (see, e.g., FIG. 9). Metagenomic clones P12B21 and P32A16 comprise BGCs that produce metabolites showing relatively weak (e.g., approximately 26%) inhibition of *Acinetobacter baumannii* under control of the unidentified native promoters within the BGC (see, e.g., FIG. 9, black bars). In contrast, the same inserts cloned into the pDualP expression vector and expressed from the pDualP expression vector were detected to produce strong inhibition of *A. baumannii* when activated by the ε-cap inducer (FIG. 9, grey bars labeled "B"). In particular, expression of the inserts from the pDualP expression vector produced approximately 59% inhibition of *A. baumannii* by clone P12B21 and approximately 62% inhibition of *A. baumannii* by clone P32A16, which represent a two-fold improvement relative to the control. It is contemplated that optimization of induction time and concentration may reveal even higher levels of inhibition.

Inducible Promoters

As used herein, the terms "Potr" and PnitA" refer to two distinct inducible promoters used for transcribing genes in *Streptomyces* using their cognate inducers oxytetracycline (OTC) and ε-caprolactam (ε-cap), respectively. See, e.g., Wang et al. (2016) "Development of a Synthetic Oxytetracycline-Inducible Expression System for Streptomycetes Using de Novo Characterized Genetic Parts" ACS Synthetic Biology 5: 765-73, incorporated herein by reference. The sequences of Potr and PnitA are provided by SEQ ID NOs: 1 and 6, respectively. An engineered derivative of Potr called Potr* is also described in Wang, supra, and is provided by SEQ ID NO: 2.

While the Potr and PnitA promoters are exemplary, the technology is not limited to use of these promoters. Accordingly, the technology includes expression vectors comprising other *Streptomyces* promoters. In some embodiments, the technology comprises use of a constitutive promoter. In some embodiments, the technology comprises use of an inducible promoter. In some embodiments, the technology comprise use of kasOp and its derivatives, synthetic tetracycline-inducible promoter tcp830, the constitutive erythromycin-resistance gene promoter ermEp*, phage 119 promoter SF14p, pstSp and xysAp promoters, thiostrepton-inducible promoter tipAp, synthetic resorcinol-inducible promoter PA3-rolO, actII orf4 promoter, the synthetic cumate-inducible promoter P21-cmt, and/or the 30S ribosomal protein S12 promoter PrpsL. Embodiments provide expression vectors comprising two different promoters flanking a cloning site wherein the two promoters are any two promoters chosen from kasOp and its derivatives, synthetic tetracycline-inducible promoter tcp830, the constitutive erythromycin-resistance gene promoter ermEp*, phage 119 promoter SF14p, pstSp and xysAp promoters, thiostrepton-inducible promoter tipAp, synthetic resorcinol-inducible promoter PA3-rolO, actII orf4 promoter, the synthetic cumate-inducible promoter P21-cmt, and/or the 30S ribosomal protein S12 promoter PrpsL. Further, the technology includes promoters (e.g., constitutive and/or inducible promoters) known in the art for heterologous hosts other than *Streptomyces* spp., e.g., Actinobacteria, Gram-negative hosts (e.g., proteobacterial hosts (e.g., *Pseudomonas* spp., *Agrobacterium* spp.), Hosts The technology is not limited in the host organism (e.g., that is transformed with an embodiment of the vector (e.g., an expression vector) provided herein (e.g., a vector comprising an insert (e.g., an insert comprising a BGC and/or an insert comprising at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb)))), e.g., to express a natural product (e.g., metabolite). The host organism is typically, but not necessarily, a genetically tractable (e.g., culturable under laboratory conditions and manipulable by molecular biological techniques) organism. The host organism may be a member of the domain Bacteria, the domain Eukarya, or the domain Archaea. In some embodiments of the technology, the host microorganism is from the domain Bacteria. In some embodiments, the host organism is a bacterium in the terrabacteria group. In particular embodiments, the host microorganism is from the taxa Actinobacteria, Streptomycetales, or Streptomycetaceae. In some embodiments, the host is from the genus *Streptomyces*. In some embodiments, the host is a *Streptomyces* expression strain, e.g., as defined herein (e.g., *Streptomyces avermitilis*, *Streptomyces venezuelae*, *Streptomyces albus*, *Streptomyces lividans*, and *Streptomyces coelicolor*). In some embodiments, the host organism is a *Streptomyces* spp., e.g., as defined herein.

Sources

Further, the technology is not limited in the source organism, organisms, and/or metagenome from which heterologous nucleic acids (e.g., comprising genes, operons, proteins, pathways, activities, etc.) are obtained for use in cloning as inserts in the expression vectors provided herein. For instance, in some embodiments, the source of the nucleic acid is a member of the domain Bacteria, the domain Eukarya, or the domain Archaea. In some embodiments, the source of the nucleic acid is a cultured Streptomycete. In some embodiments, the source is an organism, plurality of organisms, or metagenomic DNA obtained from the earth (e.g., soil, permafrost, sediments), water (e.g., fresh water, seawater, deep-sea vents), air, materials in the environment (e.g., decaying materials like rotting wood, compost), from the surface (e.g., skin) of animals (e.g., mammals, insects, worms), from inside (e.g., digestive tract, gut) animals (e.g., humans), from plants or plant-associated material (e.g., plant roots, plant seeds), possibly from outer space, and the like. In some embodiments, the source is an organism, plurality of organisms, or metagenomic DNA obtained from man-made or artificial environments (e.g., wastewater, activated sludge, hospitals, and ventilation systems). In general, the source may be procured from natural environments, artificial environments, from attempted replications of natural environments, and the like.

In certain embodiments of the technology, a source nucleic acid that is to be introduced into a host organism may undergo codon optimization to enhance expression of a product. Codon optimization refers to alteration of codons in genes or coding regions of nucleic acids for transformation of an organism to reflect the typical codon usage of the host organism without altering the polypeptide for which the DNA encodes. Codon optimization methods for optimum gene expression in heterologous organisms are known in the art and have been previously described (see, e.g., Welch et al (2009), PLoS One 4: e7002; Gustafsson et al (2004), Trends Biotechnol. 22: 346-353; Wu et al (2007), Nucl. Acids Res. 35: D76-79; Villalobos et al (2006), BMC Bioinformatics 7: 285; U.S. Pat. App. Pub. No. 2011/0111413; and U.S. Pat. App. Pub. No. 2008/0292918, each of which is incorporated herein by reference).

Methods

Some embodiments of the technology relate to methods, e.g., methods comprising one or more actions (e.g., steps) described herein. For example, in some embodiments, the technology provides a method of expressing a product from a cloned biosynthetic gene cluster. In some embodiments, methods comprise providing an expression vector comprising a first promoter and a second promoter flanking a cloning site, wherein the first promoter and second promoter direct transcription toward each other and in opposite directions. Some embodiments of methods comprise a subsequent step of cloning a nucleic acid insert comprising a biosynthetic gene cluster at said cloning site.

In some embodiments, the technology provides a method of expressing a product from a cloned nucleic acid insert comprising at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb). In some embodiments, methods comprise providing an expression vector (e.g., as described herein) comprising a first promoter and a second promoter flanking a cloning site, wherein the first promoter and second promoter direct transcription toward each other and in opposite directions. In some embodiments, methods further comprise cloning a nucleic acid insert comprising at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb) at said cloning site. In some embodiments, the nucleic acid insert comprises a biosynthetic gene cluster as described herein.

In some embodiments, methods relate to expressing a product from a cloned biosynthetic gene cluster. For example, in some embodiments, methods comprise providing an expression vector comprising a first promoter and a second promoter flanking a cloning site, wherein the first promoter and second promoter direct transcription toward each other and in opposite directions; cloning a nucleic acid insert comprising a biosynthetic gene cluster at said cloning site to provide a recombinant expression vector comprising said nucleic acid insert; transforming said recombinant expression vector comprising said nucleic acid insert into a host cell; and contacting said host cell with an inducer of said first promoter and/or an inducer of said second promoter to induce expression of a product from said nucleic acid insert.

In some embodiments, the technology provides a method of expressing a product from a biosynthetic gene cluster. For example, in some embodiments methods comprise providing a host cell comprising a recombinant nucleic acid comprising an expression vector and an insert, wherein said expression vector comprises a first promoter and a second promoter flanking said insert; the first promoter and second promoter direct transcription toward each other and in opposite directions; and said insert comprises a biosynthetic gene cluster nucleic acid; and contacting said host cell with an inducer of said first promoter and/or an inducer of said second promoter to induce expression of a product from said biosynthetic gene cluster.

In some embodiments, the technology relates to a method of expressing a product from a nucleic acid insert comprising at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb). For example, in some embodiments, methods comprise providing a host cell comprising a recombinant nucleic acid comprising an expression vector and an insert, wherein said expression vector comprises a first promoter and a second promoter flanking said insert; the first promoter and second promoter direct transcription toward each other and in opposite directions; and said insert comprises at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb); and contacting said host cell with an inducer of said first promoter and/or an inducer of said second promoter to induce expression of a product from said nucleic acid insert.

In some embodiments, the technology relates to a method of identifying a nucleic acid comprising a biosynthetic gene cluster. For example, in some embodiments, methods comprise providing a host cell comprising a recombinant nucleic acid comprising an expression vector and an insert, wherein said expression vector comprises a first promoter and a second promoter flanking said insert; the first promoter and second promoter direct transcription toward each other and in opposite directions; and the expression vector is configured to express a product of the insert under control of the first promoter and/or the second promoter; contacting said host cell with an inducer of said first promoter and/or an inducer of said second promoter to induce expression of a product from said insert; detecting expression of said product; and identifying the nucleic acid as a nucleic acid comprising a biosynthetic gene cluster when said product is identified.

In some embodiments, the methods comprise use of a host cell that is a *Streptomyces* spp.

In some embodiments, the nucleic acid insert is from a cultured microorganism. In some embodiments, the nucleic acid insert is from a metagenomic library. In some embodiments, the nucleic acid insert is 5 kb or more, 10 kb or more, or 10, 20, 30, 40, 50, 60, 70, 80, 90, or 100 kb or more (e.g., at least 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb).

In some embodiments, the nucleic acid insert comprises a nucleotide sequence encoding a polyketide synthase (PKS) or a nonribosomal peptide synthase (NRPS). In some embodiments, nucleic acid insert comprises a plurality of genes. In some embodiments, the nucleic acid insert comprises genes encoded by both strands of said nucleic acid insert.

In some embodiments, methods comprise detecting expression of a product encoded by one or more nucleotide sequences of said nucleic acid insert. In some embodiments, methods comprise detecting expression of a product encoded by a biosynthetic gene cluster. In some embodiments, the product is produced by a biosynthetic pathway encoded by nucleic acid and/or the biosynthetic gene cluster. In some embodiments, the product is a biologically active agent. In some embodiments, biologically active agent has antiviral, antimicrobial, antifungal, antiparasitic, or anticancer activity. In some embodiments, the biologically active agent is a polyketide or nonribosomal peptide. In some embodiments, the biologically active agent is a sterol, protein, dye, toxin, enzyme, immunomodulator, immunoglobulin, hormone, neurotransmitter, glycoprotein, radiolabel, radiopaque compound, fluorescent compound, cell receptor protein, cell receptor ligand, antiinflammatory compound, antiglaucomic agent, mydriatic compound, bronchodilator, local anaesthetic, growth promoting agent, or a regenerative agent. In some embodiments, the biologically active agent is a terpene, saccharide, or alkaloid. In some embodiments, methods comprise a detecting step that is a selection or a screen.

As used herein, the term "selecting" or "selection" refers to a process of using a selectable marker (e.g., antibiotic resistance gene) and/or selective culturing conditions to select and accordingly obtain host cells that comprise an expression vector and/or nucleic acid insert according to the present disclosure. Successfully transformed host cells can be obtained, e.g., by isolation and/or enrichment from a population of transformed host cells. Successfully transformed host cells are capable of surviving the selection conditions and, in some embodiments, are capable of expressing a product from a cloned insert. Selectable markers and selection systems are widely used to obtain host cells expressing a product of interest, e.g., at a high yield. Respective systems are also useful to generate and identify stably transformed host cells (e.g., clones). One goal of using respective selectable markers and selection systems is to introduce a selectable gene which upon exposure to selective growth conditions allows the identification of cells capable of production of the products of interest. Another goal of using selection systems is to identify a selectable gene present in a cloned insert which upon exposure to selective growth conditions allows the identification of cells capable of production of the products of interest.

As used herein, the term "screen" or "screening" refers to a process of using a screenable marker to identify and accordingly obtain host cells that comprise an expression vector and/or nucleic acid insert according to the present disclosure. Successfully transformed host cells can be obtained, e.g., by observation to detect a signal (e.g., fluorescence or color or some other phenotype) produced by a screenable marker and/or an insert and isolation from a population of transformed host cells. Successfully transformed host cells are capable of producing a detectable signal indicating successful transformation and are capable of expressing a product from a cloned insert. Screenable markers and screening systems are widely used to obtain host cells expressing a product of interest, e.g., at a high yield. Respective systems are also useful to generate and identify stably transformed host cells (e.g., clones). One goal of using respective screenable markers and screening systems is to introduce a gene allows the identification of cells capable of production of the products of interest. Another goal of using screening systems is to identify a gene present in a cloned insert that allows identification of cells capable of production of the products of interest. The terms "selecting" and "screening" apply both to nucleic acids present in the expression vectors as described herein and nucleic acids present in inserts cloned into the expression vectors as described herein.

Systems

In some embodiments, the technology relates to systems for cloning nucleic acid inserts comprising a BGC, nucleic acids encoding a biosynthetic pathway, and/or nucleic acids that are at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb); identifying nucleic acids that comprise a BGC or that encode a biosynthetic pathway; detecting biologically active agents produced by nucleic acids that comprise a BGC, nucleic acids that encode a biosynthetic pathway, and/or nucleic acids that are at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb); and/or expressing a product (e.g., a biologically active agent) from nucleic acid inserts comprising a BGC, nucleic acids encoding a biosynthetic pathway, and/or nucleic acids that are at least 10 kb (e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 kb).

In some embodiments, systems comprise a vector (e.g., an expression vector) as described herein. In some embodiments, systems further comprise a culture medium. In some embodiments, systems further comprise an inducer of one or more promoters provided on a vector (e.g., an expression vector) provided herein. In some embodiments, systems comprise one or both of the inducers OTC and/or ε-cap. In some embodiments, systems comprise a culture dish, tray, plate, or other vessel.

In some embodiments, systems comprise components for automated cell culture and clone management. In some embodiments, systems comprise a computer, e.g., programmed to direct automated cell culture and clone management.

In some embodiments, systems comprise an antibiotic for marker selection. In some embodiments, systems comprise a detector of a signal output by a cell (e.g., a fluorescence detector to detect and/or quantify GFP fluorescence; a colorimeter to detect and/or quantify a colored product; etc.) Some embodiments of the technology provided herein further comprise functionalities for collecting, storing, and/or analyzing data. For example, in some embodiments the device comprises a processor, a memory, and/or a database for, e.g., storing and executing instructions, analyzing data, performing calculations using the data, transforming the data, and storing the data. Moreover, in some embodiments a processor is configured to control a device or apparatus (e.g., a robot configured to perform one or more actions described herein). In some embodiments, the processor is used to initiate and/or terminate the measurement and data collection. In some embodiments, systems comprise a user interface (e.g., a keyboard, buttons, dials, switches, and the like) for receiving user input that is used by the processor to direct a measurement and/or to control a device or apparatus. In some embodiments, systems further comprise a data output for transmitting data to an external destination, e.g., a computer, a display, a network, and/or an external storage medium.

Uses

The technology finds use in natural products discovery, isolation of nucleic acids encoding BGCs, nucleic acids encoding biosynthetic pathways, and nucleic acids expressing biologically active agents. The technology finds use in metagenomic studies and analysis. The technology finds use in both the commercial and research settings.

Although the disclosure herein refers to certain illustrated embodiments, it is to be understood that these embodiments are presented by way of example and not by way of limitation.

Example 1—Construction of the Dual Inducible Promoter Vector

Figure 2:
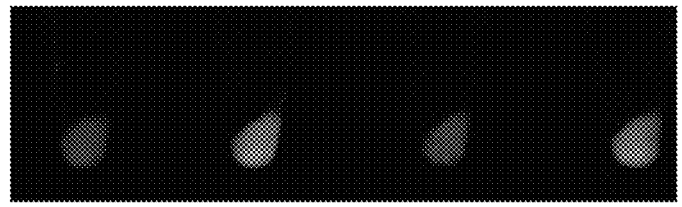
FIG. 2 shows sfGFP induction and fluorescence in $E. coli$. Presence of the inducers allows for expression of sfGFP and detection by UV fluorescence.

During the development of embodiments of the technology provided herein, a *Streptomyces* spp. expression construct was synthesized containing dual promoters facing each other with respect to their transcription direction. On one side of the construct are the two elements for oxytetracycline (OTC)-based induction, the OtrR gene and the Potr promoter adjacent to the cloning site (1). On the other side of the construct are the three elements of ε-caprolactam (ε-cap)-based induction, the PnitA promoter driving expression of the NitR gene, and a second copy of the PnitA promoter adjacent to the cloning site (2, 3). Both inducible promoters have been validated in multiple *Streptomyces* spp. Between these two promoters is sfGFP (super folder green fluorescent protein) as a control. The dual promoter construct was designed using published information from the individual components (1-3) and then synthesized, and the sequence was verified by ATUM (Newark Calif.) in an *E. coli* cloning vector. The dual promoter elements were subcloned into the *Streptomyces*-integrative BAC vector pBAC-S in three variants (see FIG. 1). Variant 1 contains the sfGFP under control of OTC. Variant 2 is identical to Variant 1 except that two PadI restriction sites flank the sfGFP. Variant 3 is identical to Variant 2 except that the sfGFP orientation has been flipped to come under control of ε-cap. Variant 2 and 3 were tested in *E. coli* with and without inducers and fluorescence indicating apparent expression of sfGFP was observed (see FIG. 2). To make the dual promoter system more useful for subcloning into the majority of BACs conferring chloramphenicol resistance, a version of Variant 2 named pDualP was created with the kanamycin resistance gene in place of the chloramphenicol resistance gene (see FIG. 3).

Example 2—Cloning and Heterologous Expression of Known Colored Antibiotic Genes RED and ACT During the development of embodiments of the technology provided herein, experiments were conducted to test the ability of the dual promoter system to activate clusters upon addition of inducer(s). In particular, the ACT and RED clusters, which encode for actinorhodin (blue pigment) and undecylprodigiosin (red pigment) production, respectively, were captured and cloned directly from *S. coelicolor* A3 (2) genomic DNA. The cells were lysed and genomic DNA (gDNA) extracted and purified. The gDNA was restricted in vitro using Cas9 and two guide RNAs that target sites upstream and downstream of each BGC. Linearized pBAC-S vector was prepared and PCR (polymerase chain reaction) amplification was used to add 40-bp overlaps identical to the ends of the BGC fragment left over after restriction. The linearized vector and the restricted gDNA were incubated together in a DNA assembly (e.g., "Gibson") reaction from New England Biolabs (Ipswich Mass.) or Synthetic Genomics (La Jolla Calif.) that uses the overlaps from the linearized vector and the fragment containing the BGC to produce a circular product. *E. coli* BacOpt 2.0 (Lucigen, Middleton, Wis.) transformants were screened by colony PCR, restriction digestion pattern of purified plasmid DNA, and Sanger sequencing to confirm cloning of ACT and RED clusters to pBAC-S. To generate dual-promoter versions of RED and ACT, purified plasmid was digested with PadI at sites upstream and downstream of the BGCs. The pDualP vector was restricted with PadI, dephosphorylated, gel purified, and ligated to the PacI-restricted ACT and RED fragments. In addition, two metagenomic BACs containing novel BGCs described below were subcloned in a similar manner using Cas9 restriction (see FIG. 4). After transformation and kanamycin selection, clones were identified by colony PCR for pDualP containing either ACT or RED in each orientation (see FIG. 5). Cultures of *E. coli* BacOpt 2.0 containing each of pDualP, pBAC-S ACT, pBAC-S RED, pDualP ACT (in both orientations), and pDualP RED (in both orientations) were mixed with *E. coli* conjugation helper strain HB101 (pRK2013) and *S. lividans* ΔactΔred and plated to MS agar (MS agar contains per liter: 10 g agar, 10 g mannitol, and 10 g soy flour). After 16 hours, the plates were flooded with apramycin to select for transconjugation and nalidixic acid to kill donor and helper *E. coli*. Transconjugants for each construct were isolated and tested on MS agar and R2YE agar (contains per liter: 10 g agar, 104 g sucrose, 0.26 g $K_2SO_4$, 10.2 g $MgCl_2·6H_2O$, 10 g glucose, 0.1 g tryptone, 0.25% yeast extract, 0.295 $CaCl_2·2H_2O$, 0.3% L-proline, 0.573% TES Buffer, 1 mL each trace elements solution, 2.5 mM NaOH) demonstrating inducible expression of pDualP ACT and RED BGCs (see FIG. 6 and FIG. 7). Additionally, YEME or R2YE liquid media were used to further demonstrate inducible expression of the pDualP ACT and RED BGCs (see FIG. 8).

Example 3—Cloning and Identification of Two Novel Metagenomic BGCS

Metagenomic Library Construction. During the development of embodiments of the technology provided herein, experiments were conducted to produce a metagenomic library and identify functional clones in the library. High molecular weight (HMW) metagenomic DNA was isolated from a Cullars Rotation (Auburn, Ala., USA) soil plot that had not been amended with fertilizers for the past 100 years. The isolation and purification of soil HMW DNA was conducted by isolating soil microorganisms that were embedded in low melting point agarose, treated with proteinase K, and washed extensively. The agarose was melted and the DNA was sheared by pipetting up to five times to generate DNA in the having a size of approximately 150 kb based on pulsed field gel electrophoresis. The agar was allowed to solidify again, and the DNA was end-repaired with the DNATerminator kit (Lucigen) in a total volume of 500 μL with 10 μL of enzymes and then heat killed at 70° C. for 15 minutes. The end-repaired DNA was ligated with BstXI adaptors (10 μL of 100 μM each) in a total volume of 700 μL comprising 10 μL of ligase (2 U/μL, Epicenter), followed by gel fractionation and isolation of large DNA fragments ranging from 100 to 200 kb by pulse-field gel electrophoresis. Purified large DNA fragments (about 100 μL, 1-3 ng/μL) were ligated into the cloning-ready BstXI shuttle vector pSmartBAC-S(16° C. for approximately 18 hours). The ligated DNA mixture was electroporated into competent *E. coli* cells (BAC-Optimized *E. coli* 10G Replicator Cells, Lucigen). Small scale ligations and transformations (1 μL of DNA per 20 μL of cells) were used to judge the cloning efficiency. The insert sizes of approximately 50 BAC clones were determined to find conditions that contained the desired insert size. Once the suitability of the trial ligation reaction was confirmed, large-scale ligations and transformations were conducted to achieve 19,200 clones for the BAC library (50×384-well plates arrayed).

Metagenomic Library Sequencing and Identification of novel BGCs. Individual clones from the BAC library were grown in triplicate in 96-well plates using 1 ml LB containing 0.01% arabinose to amplify BAC copy number (4). A three-dimensional pooling strategy was used to combine multiple clones for sequencing in such a way as to enable the location of individual BAC clones. Three pools were made; a row pool, a column pool, and a plate pool. The liquid cultures from each pool were combined as appropriate, the cells were pelleted and the BAC DNA purified as previously described (5). For plates 41-50, the initial pooling strategy merged all 384 clones from each original library plate into a single plate pool (10 plate pools); row clones from the 10 original library plates into single row pools (16 row pools A-P, each pool containing 240 clones); and column clones from the 10 original library plates into single column pools (24 column pools, each pool containing 160 clones). For the remainder of the library (plate no. 1-40), the 384-well plates were replicated in batches of 10 plates into 96 well quadrants. For each batch, 40 plate pools were made from each 96-clone quadrant; 8 row pools A-H were made, one from each 480-clone row (40 quadrant plates×12 wells/row); and 12 column pools were made, one from each 320-clone column (40 quadrant plates×8 wells/column).

Fragment libraries for sequencing on an Illumina instrument were constructed with 100 ng purified BAC DNA from each pool using the multichannel protocol and reagents from Lucigen (Middleton, Wis.). Unique indexes were used for each library pool within each batch of 10 library plates (Sets). Libraries were multiplexed and sequenced on Illumina HiSeq 2500 with v3 chemistry at 2×150 bp. The raw HiSeq reads per each column, plate or row pool were imported into the Alabama Super Computer (ASC) to be processed. Reads were filtered for high quality reads (Q score>30), trimmed, clipped and reads smaller than 30 bp were discarded using the software Trimomatric. To remove host and vector DNA sequences, all processed reads were mapped against E. coli DH10B and the vector pBAC-S sequences, and those that did not map to these reference sequences were then assembled using metaSPAdes implementation of SPAdes 3.9.0 software 6. Reads corresponding to each respective sequencing pool were assembled together resulting in 290 sets of contigs.

All contigs generated from SPAdes assembly were tentatively deconvoluted to a clone location using a custom bash script. Briefly, the deconvolution process consisted of renaming each individual contig to include their pool of origin and a unique number identifier. Contigs from the plate pools were compared to those in the column or row pools via BLASTn with 95% identity and a $10^{-6}$ e-value cut-off. The BLAST hits were extracted and annotated into 3 categories: 1) completely deconvoluted—plate contigs with hits in both column and row pools; 2) partially deconvoluted—plate contigs with hits in only one other dimension; or 3) singletons—contigs with no significant hits. Once each contig was annotated, the location information in the contig name was used to generate coordinates (plate, column and row) for the respective clone of origin.

A local version of antiSMASH 4.0 with prodigal (meta) for gene prediction was used to predict BGCs from plate pools, which had the greatest coverage per pool. The program was run on a Bioconda environment in the Alabama Supercomputer operating system to afford high-throughput detection. Annotations were conducted by importing the BiosynML antiSMASH 4.0 output into Geneious and manually inspecting BGCs. Selected clones identified as containing an intact BGC were individually grown from the E. coli cryostock and the presence of the targeted BGC was confirmed by insert DNA-specific PCR. The isolated BAC DNA was re-sequenced by standard single-end fragment sequencing using a MiSeq sequencer (Illumina, San Diego, Calif.). Trimming and assembly was conducted with CLC Genomics Workbench 8.5 followed by manual inspection and reassembly was conducted with SPAdes 3.9.0 when necessary. Analysis with antiSMASH 4.0 was conducted as described above for annotation of fully assembled clone insert sequences. Inserts with antiSMASH annotation matching that of their associated contig were considered validated. Clones exhibiting activities of interest were selected for further inspection. Their inserts were fully annotated using the RAST server (7). RAST and AntiSMASH annotations were combined using Geneious software and were manually inspected. Annotation figures were generated using the package GenoPlotR in R studio (8).

Annotation of Metagenomic inserts of interest (P12B21, P32A16). Inserts of the clones P12B21 and P32A16 were fully annotated in addition to the BGC annotation. Clone P12B21, with an insert of 60,007 bp, has a very short NRPS-like cluster with one complete module; however the "model" sequence prediction spans over 26 kb. The model is followed by efflux ABC-transporter genes possibly linked to antibiotic resistance, and their transcriptional regulator, with a noteworthy presence of a predicted tellurium resistance-linked gene. Clone P32A16 has genes that are most similar to a genomic origin from the phylum Acidobacteria upon RAST annotation. The insert had 59,698 bp and carried 48 features, including a predicted Type I PKS and cell-wall/cell-membrane metabolism genes such as permeases as well as gene sequences predicted to be involved in primary metabolism. The BGC was classified as Type I PKS and encompasses 9 domains distributed in 2 modules, containing condensation domains—suggesting a hybrid NRPS/PKS pathway—as well as a tailoring domain, which may contribute to the structural uniqueness of the compound. Clone P32A16 also contains a predicted TonB-linked transporter and an ABC-ATPase transporter, both with orthologous sequences identified from Acidobacteria taxa, that are in the vicinity of the BGC and may be involved in metabolite secretion.

Example 4—Expression of Antibacterial Activity of Two Metagenomic BGCS from Native or Dual Inducible Promoters Two BGCs (P12B21 and P32A16) derived from a soil metagenomic library that express an antibacterial metabolite that inhibits the growth of multidrug-resistant A. baumannii were subcloned into the pDualP dual-inducible vector and evaluated for inducible expression of antibacterial activity. These pDualP-BGC constructs were transferred by triparental intergeneric conjugation to an expression host (S. coelicolor M1154) that was engineered for heterologous expression of BGCs by the removal of four endogenous gene clusters to alleviate precursor competition and the addition of point mutations shown to pleiotropically upregulate antibiotic expression (9). To facilitate the conjugal transfer of each of the BGCs from the donor strain E. coli DH10B to the recipient S. coelicolor M1154, the helper strain E. coli HB101 10 bearing the plasmid pRK2013 11 was used.

Preparation of E. coli DH10B donor strains containing a pDual-BGC construct (or pDualP empty vector) for triparental mating was performed by culturing each donor in 2 ml LB liquid medium supplemented with apramycin (50 µg/ml) at 37° C. overnight. Overnight cultures were then diluted 1:100 in LB containing 50 µg/ml apramycin and cultured for 4-6 hours until the optical density at 600 nm ($OD_{600}$) reached 0.4 to 0.6. E. coli HB101 (pRK2013) was cultured in 1 ml LB supplemented with 30 µg/ml kanamycin, grown at 37° C. overnight, diluted 1:100 in LB containing kanamycin (30 µg/ml), and incubated until the $OD_{600}$ was between 0.4 and 0.6. Each E. coli donor harboring a separate pDualP-BGC construct and the E. coli HB101 (pRK2013) helper strain were pelleted by centrifugation and washed twice in an equal volume of LB to remove antibiotics. E. coli donor cells were resuspended in 100 µl of LB and E. coli HB101 (pRK2013) was resuspended in 300 µl of LB.

Mycelial fragments of S. coelicolor M1154 were used as recipients for intergeneric conjugation and were prepared by cultivating S. coelicolor M1154 in 20 ml of malt-extract yeast-extract maltose liquid medium (MYM contains per liter: 4 g maltose, 4 g yeast extract, 4 g malt extract) in a flask with a stainless-steel coiled spring, shaking at 200 rpm, 30° C. for 5 days. Mycelia was collected by centrifugation at 3,000×g, washed twice with 2× yeast extract tryptone (2×YT) medium, and resuspended in 400 µl 2×YT medium. Approximately $10^8$ E. coli donor cells (100 µl volume of each donor) were mixed with 100 µl of mycelia. The E. coli-S. coelicolor mixture was pelleted by centrifugation and the pelleted cells were resuspended in the residual liquid after removing most of the supernatant. The mating mixture was spread on mannitol soya flour (MS) agar supplemented with 20 mM $MgCl_2$ and incubated at 30° C. for 24 hours. The plates were overlaid with 1 ml of sterile water containing 0.5 mg nalidixic acid for counterselection against *E. coli* and 1 mg of apramycin for transconjugant selection. Plates were incubated for an additional 5-7 days at 30° C. until exconjugants were visible, after which exconjugants were replicated to MS plates supplemented with 30 µg/ml nalidixic acid and 50 µg/ml apramycin. Genomic integration of the BGC in each *S. coelicolor* M1154 pDualP exconjugant was validated using PCR analysis.

Screening *S. coelicolor* pDualP clones for inducible expression of antibacterial activity. Quantification of dual-inducible expression of antibacterial activity was performed using a bioassay format in which each metagenomic BGC (n=3) was treated with a single inducer (OTC or ε-cap), both inducers, or no inducers and compared to the expression by the native BGC promoters in *S. coelicolor* M1154. To prepare supernatants for bioassays, *S. coelicolor* pDualP clones were streaked onto MS agar plates and incubated at 30° C. for 4 days. A single colony of each clone was used to inoculate yeast extract-malt extract (YEME) broth and grown at 30° C., shaking at 200 rpm, for 72 hours. Similarly, each of the BGCs cloned in the non-inducible expression system (e.g., native promoter) were cultured in the same manner as the *S. coelicolor* pDualP clones to monitor antibacterial activity with and without promoter-expression capabilities. After 72 hours, *S. coelicolor* pDualP clones were treated with or without 2.5 µM OTC and/or 0.1% (w/v) ε-cap and grown for an additional 96 hours.

Following incubation, mycelium was removed from each *S. coelicolor* culture by centrifugation at 3,000×g for 15 minutes and supernatants were filtered through a 0.2 µm microporous membrane. A volume of 100 µl of cell-free supernatants from each *S. coelicolor* clone with and without the dual-inducible expression system were added to triplicate wells in a 96-well plate. Wells containing supernatants were then mixed with 100 µl of a 1:100 diluted log-phase culture of *A. baumannii* 3806 (12). Additionally, wells containing sterile growth medium (YEME broth containing per liter: 1.5 g yeast extract, 2.5 g Bacto-peptone, 1.5 g malt extract, 5 g glucose, 170 g sucrose, and 2.5 uM $MgCl_2$) with and without inducers, pathogen with and without inducers, and *S. coelicolor* empty vector treated with and without each inducer were included as negative controls. Plates were incubated for 24 h at 37° C. with shaking at 220 rpm, and the $OD_{600}$ was quantified for each well using a multi-well plate reader. Mean percent inhibition of the pathogen for each clone and treatment was determined relative to the *S. coelicolor* pDualP empty vector negative control. Statistical analyses using pair-wise comparisons derived from linear modeling were conducted in R (R-project.org) to evaluate significant differences (at $P<0.05$) among treatments.

Evaluation of inducible promoter expression and antibacterial activity. Data collected during these experiments indicated a significant increase (>two-fold) in the expression of antibacterial activity when induced with ε-cap (see FIG. 9) for both of the metagenomic BGCs cloned into the pDualP inducible-expression system in comparison to the expression by native promoters. No significant increase in antibacterial activity was observed from OTC induction alone for either of the metagenomic BGCs. Although induction with both ε-cap and OTC increased antibacterial activity for clones P32A16 and P12B21, it is contemplated that this effect was due to the enhanced expression by the ε-cap inducer alone and not by the combination of the two inducers. However, practicing the technology does not require knowledge of the mechanism and is embodiments of the technology are not limited by any particular theory of induction. Thus, induction with ε-cap demonstrated inducible heterologous expression of two metagenomic BGCs in *S. coelicolor* M1154 which is expected to aid in the detection and characterization of the over-produced antimicrobial metabolites.

REFERENCES

1. Wang, W. S., T. J. Yang, Y. H. Li, S. S. Li, S. L. Yin, K. Styles, C. Cone, and K. Q. Yang, *Development of a Synthetic Oxytetracycline-Inducible Expression System for Streptomycetes Using de Novo Characterized Genetic Parts*. Acs Synthetic Biology, 2016. 5(7): p. 765-773.
2. Herai, S., Y. Hashimoto, H. Higashibata, H. Maseda, H. Ikeda, S. Omura, and M. Kobayashi, *Hyper-inducible expression system for streptomycetes*. Proc Natl Acad Sci USA, 2004. 101(39): p. 14031-14035.
3. Matsumoto, M., Y. Hashimoto, Y. Saitoh, T. Kumano, and M. Kobayashi, *Development of nitrilase promoter-derived inducible vectors for Streptomyces*. Bioscience Biotechnology and Biochemistry, 2016. 80(6): p. 1230-1237.
4. Wild, J., Z. Hradecna, and W. Szybalski, *Conditionally amplifiable BACs: Switching from single-copy to high-copy vectors and genomic clones*. Genome Res, 2002. 12(9): p. 1434-1444.
5. Tellez, C. M. and K. D. Cole, *Preparative purification and library construction of BAC DNA using reversible electrophoresis gels*. Abstracts of Papers of the American Chemical Society, 2000. 219: p. U192-U192.
6. Bankevich, A., S. Nurk, D. Antipov, A. A. Gurevich, M. Dvorkin, A. S. Kulikov, V. M. Lesin, S. I. Nikolenko, S. Pham, A. D. Prjibelski, A. V. Pyshkin, A. V. Sirotkin, N. Vyahhi, G. Tesler, M. A. Alekseyev, and P. A. Pevzner, *SPAdes: A New Genome Assembly Algorithm and Its Applications to Single-Cell Sequencing*. Journal of Computational Biology, 2012. 19(5): p. 455-477.
7. Brettin, T., J. J. Davis, T. Disz, R. A. Edwards, S. Gerdes, G. J. Olsen, R. Olson, R. Overbeek, B. Parrello, G. D. Pusch, M. Shukla, J. A. Thomason, R. Stevens, V. Vonstein, A. R. Wattam, and F. F. Xia, *RASTtk: A modular and extensible implementation of the RAST algorithm for building custom annotation pipelines and annotating batches of genomes*. Sci Rep, 2015. 5.
8. Guy, L., J. Roat Kultima, and S. G. E. Andersson, *genoPlotR: comparative gene and genome visualization in R*. Bioinformatics, 2010. 26(18): p. 2334-2335.
9. Gomez-Escribano, J. P. and M. J. Bibb, *Engineering Streptomyces coelicolor for heterologous expression of secondary metabolite gene clusters*. Microb Biotechnol, 2011. 4(2): p. 207-215.
10. Boyer, H. W. and D. Roulland-Dussoix, *A complementation analysis of the restriction and modification of DNA in Escherichia coli*. J Mol Biol, 1969. 41(3): p. 459-72.
11. Figurski, D. H. and D. R. Helinski, *Replication of an origin-containing derivative of plasmid RK2 dependent on a plasmid function provided in trans*. Proc Natl Acad Sci USA, 1979. 76(4): p. 1648-52.
12. Taitt, C. R., T. A. Leski, M. G. Stockelman, D. W. Craft, D. V. Zurawski, B. C. Kirkup, and G. J. Vora, *Antimicrobial resistance determinants in Acinetobacter baumannii isolates taken from military treatment facilities*. Antimicrob Agents Chemother, 2014. 58(2): p. 767-81.

All publications and patents mentioned herein, both in this section and throughout the entirety of this application, are incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. An expression vector comprising a first promoter and a second promoter flanking a cloning site, wherein the first promoter and second promoter direct transcription toward each other and in opposite directions.

2. The expression vector of claim 1 wherein said first promoter is an inducible promoter and said second promoter is an inducible promoter.

3. The expression vector of claim 1 wherein said first promoter is Potr or Potr* and wherein said second promoter is PnitA.

4. The expression vector of claim 1 wherein said expression vector further comprises OtrR and NitR.

5. The expression vector of claim 1 wherein said cloning site comprises a restriction enzyme recognition site.

6. The expression vector of claim 1 further comprising:
a selectable marker for *Streptomyces*
and a selectable marker for *E. coli*.

7. The expression vector of claim 1 further comprising an *E. coli* origin of replication.

8. The expression vector of claim 1 wherein said expression vector accepts an insert comprising more than 10 kb.

9. The expression vector of claim 1 wherein said expression vector expresses a product of a biosynthetic gene cluster nucleic acid when said expression vector comprises an insert comprising said biosynthetic gene cluster and said expression vector is present in a host cell.

10. A kit comprising the expression vector of claim 1.

11. The kit of claim 10, wherein said first promoter is an inducible promoter and said second promoter is an inducible promoter and the kit further comprises an inducer of said first promoter and an inducer of said second promoter.

12. The kit of claim 10 further comprising a restriction enzyme for cutting said expression vector at said cloning site.

13. A host cell comprising an expression vector, wherein said expression vector comprises an insert, and wherein said insert comprises a biosynthetic gene cluster;
wherein said expression vector comprises a first promoter and a second promoter flanking said insert; and
the first promoter and the second promoter direct transcription toward each other and in opposite directions.

14. The host cell of claim 13, wherein the host cell expresses a product of a biosynthetic gene cluster encoded by the insert.

15. The host cell of claim 14 wherein said product of said biosynthetic gene cluster is a biologically active agent.

16. The host cell of claim 13 wherein said insert has a size that is greater than 5000 bp.

17. The host cell of claim 13 wherein said insert has a size that is greater than 10 kbp.

18. The expression vector of claim 1 further comprising an ori2 origin of replication.

19. The expression vector of claim 1 further comprising a selectable marker, wherein said selectable marker is a selectable marker for *Streptomyces* and said selectable marker is a selectable marker for *E. coli*.

20. The expression vector of claim 1 wherein said cloning site comprises a CRISPR cleavable sequence site.

* * * * *

```
                              SEQUENCE LISTING

<160> NUMBER OF SEQ ID NOS: 9

<210> SEQ ID NO 1
<211> LENGTH: 52
<212> TYPE: DNA
<213> ORGANISM: Streptomyces rimosus

<400> SEQUENCE: 1
gagaacgaca agaccttgtc aaaagccgcg gcggtgatta cgctcggcac cc            52

<210> SEQ ID NO 2
<211> LENGTH: 76
<212> TYPE: DNA
<213> ORGANISM: Streptomyces rimosus

<400> SEQUENCE: 2
gagaacgaca agaccttgtc aaaagccgcg gcggtgatta cgctcggcac ccgagaacga    60
caagaccttg tcaaaa                                                    76

<210> SEQ ID NO 3
<211> LENGTH: 492
<212> TYPE: DNA
<213> ORGANISM: Streptomyces rimosus

<400> SEQUENCE: 3
atggattcct cagcccctga cctggccgct ctgatcgagg tgaccgccga ggtcttcgcg    60
gtcaacggcc gcctgctccg cgaaggcgac agcctcaccg cccacgcggg gctgacctcg   120
gcgcgctggc aggtggccgg actgctgctg agcggcccct cgacggtcgc ccgcctggcc   180
cgcgagcggg ggctgcggcg gcaggcggtc cagcagaccg tcgagcggct gaaggccgag   240
ggcgtcgtca cgacccggcc caacccgcag gaccagcgca gccccctggt cgagctcacc   300
gcacgcggcc ggcaggcgct ggacgacctg cgtcccctgg aacggcggtg gctggagtat   360
ctggccgagg acattccggt cgaggacatg cgcgtggcga tcgcggtgct gagccgcctg   420
cgggagaagc tggacgcccg tccggcgacg gagttcggga ccggggccgg gtccgggcgg   480
cagtccgcct ga                                                      492

<210> SEQ ID NO 4
<211> LENGTH: 717
<212> TYPE: DNA
<213> ORGANISM: Aequorea victoria

<400> SEQUENCE: 4
atgcgtaaag gcgaagagct gttcactggt gtcgtcccta ttctggtgga actggatggt    60
gatgtcaacg gtcataagtt ttccgtgcgt ggcgagggtg aaggtgacgc aactaatggt   120
aaactgacgc tgaagttcat ctgtactact ggtaaactgc cggtaccttg gccgactctg   180
gtaacgacgc tgacttatgg tgttcagtgc tttgctcgtt atccggacca tatgaagcag   240
catgacttct tcaagtccgc catgccggaa ggctatgtgc aggaacgcac gatttccttt   300
aaggatgacg gcacgtacaa aacgcgtgcg gaagtgaaat ttgaaggcga tacccttgta   360
```

```
aaccgcattg agctgaaagg cattgacttt aaagaagacg gcaatatcct gggccataag      420
ctggaataca attttaacag ccacaatgtt tacatcaccg ccgataaaca aaaaaatggc      480
attaaagcga atttaaaat tcgccacaac gtggaggatg gcagcgtgca gctggctgat      540
cactaccagc aaaacactcc aatcggtgat ggtcctgttc tgctgccaga caatcactat      600
ctgagcacgc aaagcgttct gtctaaagat ccgaacgaga aacgcgatca tatggttctg      660
ctggagttcg taaccgcagc gggcatcacg catggtatgg atgaactgta caaatga        717

<210> SEQ ID NO 5
<211> LENGTH: 960
<212> TYPE: DNA
<213> ORGANISM: Rhodococcus rhodochrous

<400> SEQUENCE: 5
atgaacactt tcttctcctc agaccaggtc tcggcgcccg atcgcgtcgc gctctggcac       60
gatgtcatct gccgtagcta tgtcccgctc aacatcaccc tcacgagcga gcaacccttc      120
atcggtacgg tctcgacggg caacttgggc acggtacgta tcgcgacgtc ctcgtcactg      180
ccccaacaga tcacccgcac tcgtcgcttg atcaggcagg acgagcgtga gtacctcatg      240
gttggggtgc agtccgccgg ccatgcactc gtgcagcagc acggcagaac tgcacgagtc      300
ggtcgcggtg gactggtctt ctgggacacc cgccatccct acgacatcct cttcccgaca      360
gactggagga tgagcgtatt ccagttcccg cgatactctt tcggcttcac cgaagacttc      420
atcggcagga tgaccgcggt gaacgtcggg ggcgatcgcg gtatcggccg agtggtttca      480
tccttcatga caagcatcaa cgatgcgacc gacgcaggag acttggcgga ggtagcttca      540
ctccacaaca gtgctgtcga tcttctgtca gcggcgatac ggaccgagct tgccgatcaa      600
gccgccgcct ccgacggcct actcgagtgt gtgctcgcgt atatccgaca gaacctggcc      660
gacccgaacc tgtgtgcctc acagatcgcg gcggaacaca acgtctctgt gcggaccctc      720
caccgactgt tctcggccac gggacagggc gtggccgaac acatccgtaa cctccgactc      780
gagcgcatca agactgagct ggcagaccca acgagccggc gatatacgat cagcgctttg      840
gcgagaaaat gggggttcct cgatccctca acgttctcac gcgcgttcaa agacgcctac      900
ggcatcactg cccgagagtg ggcggcttct gcatcagcat caccgacgga ggtttcgtag      960

<210> SEQ ID NO 6
<211> LENGTH: 90
<212> TYPE: DNA
<213> ORGANISM: Rhodococcus rhodochrous

<400> SEQUENCE: 6
gcgaactccc ttatgcgggt ggcgcagaat gccaggaccc ttgtcattcc acgtcaattc       60
atgcgccttt tcacctcgta ctgtcctgcc                                       90

<210> SEQ ID NO 7
<211> LENGTH: 2654
<212> TYPE: DNA
<213> ORGANISM: Artificial Sequence
<220> FEATURE:
<223> OTHER INFORMATION: Synthetic construct

<400> SEQUENCE: 7
gcggccgctc aacgctatca ggcggactgc cgcccggacc cggccccggt cccgaactcc       60
gtcgccggac gggcgtccag cttctcccgc aggcggctca gcaccgcgat cgccacgcgc      120
```

```
atgtcctcga ccggaatgtc ctcggccaga tactccagcc accgccgttc caggggacgc    180
aggtcgtcca gcgcctgccg gccgcgtgcg gtgagctcga ccaggggggct gcgctggtcc    240
tgcgggttgg gccgggtcgt gacgacgccc tcggccttca gccgctcgac ggtctgctgg    300
accgcctgcc gccgcagccc ccgctcgcgg gccaggcggg cgaccgtcga ggggccgctc    360
agcagcagtc cggccacctg ccagcgcgcc gaggtcagcc ccgcgtgggc ggtgaggctg    420
tcgccttcgc ggagcaggcg gccgttgacc gcgaagacct cggcggtcac ctcgatcaga    480
gcggccaggt caggggctga ggaatccatg ccacagcgt atgtactccc cggagaacga     540
caagaccttg tcaaaagccg cggcggtgat tacgctcggc acccgagaac gacaagacct    600
tgtcaaaagg cctcggtgcc gatggtgaac caatgtgatg gcgtgtgtgt acggggccgg    660
aagcgccggc caggagagtg aggaaccatg cgtaaaggcg aagagctgtt cactggtgtc    720
gtccctattc tggtggaact ggatggtgat gtcaacggtc ataagttttc cgtgcgtggc    780
gagggtgaag gtgacgcaac taatggtaaa ctgacgctga agttcatctg tactactggt    840
aaactgccgg taccttggcc gactctggta acgacgctga cttatggtgt tcagtgcttt    900
gctcgttatc cggaccatat gaagcagcat gacttcttca gtccgccat gccggaaggc      960
tatgtgcagg aacgcacgat ttcctttaag gatgacggca cgtacaaaac gcgtgcggaa    1020
gtgaaatttg aaggcgatac cctggtaaac cgcattgagc tgaaaggcat tgactttaaa    1080
gaagacggca atatcctggg ccataagctg gaatacaatt ttaacagcca caatgtttac    1140
atcaccgccg ataaacaaaa aaatggcatt aaagcgaatt ttaaaattcg ccacaacgtg    1200
gaggatggca gcgtgcagct ggctgatcac taccagcaaa acactccaat cggtgatggt    1260
cctgttctgc tgccagacaa tcactatctg agcacgcaaa gcgttctgtc taaagatccg    1320
aacgagaaac gcgatcatat ggttctgctg gagttcgtaa ccgcagcggg catcacgcat    1380
ggtatggatg aactgtacaa atgatagcca ccacagtggg gcaggacagt acgaggtgaa    1440
aaggcgcatg aattgacgtg aatgacaag gtcctggca ttctgcgcca cccgcataag      1500
ggagttcgca atcaaaagaa aagcctatcg tctgaggaac ggtaggctct ttgtagcata    1560
tattactacg aaacctccgt cggtgatgct gatgcagaag ccgcccactc tcgggcagtg    1620
atgccgtagg cgtctttgaa cgcgcgtgag aacgttgagg gatcgaggaa cccccatttt    1680
ctcgccaaag cgctgatcgt atatcgccgg ctcgttgggt ctgccagctc agtcttgatg    1740
cgctcgagtc ggaggttacg gatgtgttcg gccacgccct gtcccgtggc cgagaacagt    1800
cggtggaggg tccgcacaga gacgttgtgt tccgccgcga tctgtgaggc acacaggttc    1860
gggtcggcca ggttctgtcg gatatacgcg agcacacact cgagtaggcc gtcggaggcg    1920
gcggcttgat cggcaagctc ggtccgtatc gccgctgaca aagatcgac agcactgttg     1980
tggagtgaag ctacctccgc caagtctcct gcgtcggtcg catcgttgat gcttgtcatg    2040
aaggatgaaa ccactcggcc gataccgcga tcgcccccga cgttcaccgc ggtcatcctg    2100
ccgatgaagt cttcggtgaa gccgaaagag tatcgcggga actggaatac gctcatcctc    2160
cagtctgtcg ggaagaggat gtcgtaggga tggcgggtgt cccagaagac cagtccaccg    2220
cgaccgactc gtgcagttct gccgtgctgc tgcacgagtg catggccggc ggactgcacc    2280
ccaaccatga ggtactcacg ctcgtcctgc ctgatcaagc gacgagtgcg ggtgatctgt    2340
tggggcagtg acgaggacgt cgcgatacgt accgtgccca agttgcccgt cgagaccgta    2400
ccgatgaagg gttgctcgct cgtgagggtg atgttgagcg ggacatagct acggcagatg    2460
acatcgtgcc agagcgcgac gcgatcgggc gccgagacct ggtctgagga aagaaagtg     2520
```

-continued

| | |
|---|---|
| ttcatgtccg tacctccgtt gcttgtgttt ggcaggacag tacgaggtga aaaggcgcat | 2580 |
| gaattgacgt ggaatgacaa gggtcctggc attctgcgcc acccgcataa gggagttcgc | 2640 |
| cttaaggcgg ccgc | 2654 |

<210> SEQ ID NO 8
<211> LENGTH: 59698
<212> TYPE: DNA
<213> ORGANISM: Unknown
<220> FEATURE:
<223> OTHER INFORMATION: Environmental clone

<400> SEQUENCE: 8

| | |
|---|---|
| gaccatgttg gtatgattta aattaatacg actcactata gggtcagtgc ggccgcgact | 60 |
| tcaagtcacg tgaattccaa gcttcggatc ccactgtgct ggaaagactc ctccgcgaag | 120 |
| ctcgcgtcga gtccagccag gccaacggcg tggcgaatgt ccaactgttc gacctgccgc | 180 |
| gcgagaccat cgaaccgcgc gcgcgccgcg tcgtcgtgga actgattgtt cgggcagcat | 240 |
| tcctgcatcg agcgcagcaa catctcacgc tgcgccgtgt ttctcgtacg ttccgcttga | 300 |
| ctcaacatca ccgctctcca ttcccccccga cagtgtttat cggcagaatg caacggctgg | 360 |
| agtcgcccga caaggggggtg cttttcgtcta cgaaagcacc gcgccaacgg ggcacgaagt | 420 |
| gaatcatcgc atcgcatcca agcgcctcgg ccagcgcggc gacggaactc agcttgacgt | 480 |
| ccccgccctt gagacaacga gcgagtgtcg cgctattcac gtcgagcgtt cgccaggacg | 540 |
| cgccacgcgt cgccatccac cggccgactt cgtcgcccac ttgaagcgcc agtgtcgtcg | 600 |
| ctgtcggctg atcatcacgc tgagcgacca gcagcgtttg aagccgcgcg cggcgcgcgg | 660 |
| cgtcgatgcg cacgcgctcg cccgtcgcgt cttcggccat cagtgcgtcc cctggacggg | 720 |
| caacgtcgcg agcgtgactt cctccgcaag cgatcgtgcg ccggcgtcga tcatcgcctg | 780 |
| gtgaccggcg ggatcggcgg acgccgcggc gccgtagagc agcgcggcca actcgcgcgc | 840 |
| gtcgtgaccg gtcagcggca cgcgcggcgc cgtcgcttcg tcggcgtcgt tcacgatcac | 900 |
| cacgagctgc acggtcgcgc cgtcacgcgc cacgccaagg cgaatcttta gcacgccggc | 960 |
| gagtggagac gtctccaccg cgggacgccg cttccaaaac cgaagtgact caaacatccg | 1020 |
| taaccccctc accccttacgc tttgagaaac acagcgcggc ggcctggacg tcgcgggcca | 1080 |
| actgcgccgc gtcctccggc gtcatccagc acgggatgcc gcgccaccca cacgtcagcg | 1140 |
| tcagccgaac cgccccagag tcagcggcat gtcgaatgcg ccggccactg gattgccacg | 1200 |
| cgtccaacgc ggactgcatg ttgatgactt cggggatcga cttcggaccg cagcgctgaa | 1260 |
| tgctgtcgcc gaacacgccg agcgcttccg ccttgcgcac agcggtttct gaaacaccaa | 1320 |
| gcacagcggc caacccgcgc aacgaccgaa cacgcgcatg catctttgcg aacctcccac | 1380 |
| cgcgcacccg cgaaccaaca acgcgaaccc accccgcgaa cccaaaaacc gaatggcgac | 1440 |
| tagcgcttgg atgcgccccc gctcaccgcg ataggcgcat agtcgaaga acctaagccg | 1500 |
| ccggggggtgg gggtatcaca atcaacaagc accaatagcg gcttccgctg ccgccggcaa | 1560 |
| ctcggtcgac aatgcaactg gctacggcgc accggcgtga accgatcgcc acaccctcga | 1620 |
| caacgaacag acctcacgcg cgcgcccctct ccacgccagc acaggacag ggcgcggcca | 1680 |
| cagggacacc ggctcgatat cggccctccc tggcttcccc gcaatgtccg caggtgacga | 1740 |
| acgtcagcgt tccatcagcc gtcagaccgc cgcggtctcg aacgctgtcc cgcaacacaa | 1800 |
| caagcacatc gaacggctct cgcgatgcaa cgaggcgtgc gtcaatcgcg gcataccact | 1860 |

```
gcctcagatc gacgccgtct aaggccttgc ccgcttcccg gacaatcaac tgctcctgcg    1920
caggtgttac acacaaaacc ttcccggtga acgcccattt cgcgcgcgcg agatctcgcg    1980
cgctcttggt tacctgtaca ggttgatcta ttggttttgg tgagccagac tcaccactag    2040
gcgtctcacg ctcaccacta gacgtctgcc gctcaccact aaggcagcca cttagcggtg    2100
agcggcgctc accactaaca ttgccaccca gtggtgagcg cggctcacca ctagcattgc    2160
tacccagcgg tgagcgcggc tcaccactgg cgacgagcgc tgagacgccg agcaccgaat    2220
aattgatgct gtagcgcggc ggccgcgttc cacagccggg ctcgatgttg atgtagccga    2280 gattttcag cgacgcgagt gctgacagca caccgcgatt cgacatcccg gaatcaacca    2340
ttagtcgacg gacaccaacg aacgtatcct gcgtgttgcg gttgattcgc caggcgatcc    2400
aaagcaggat catcttcgcg tggacactca gcgtcgtacc aggcagcgac ggaaacaccg    2460
cgcgaacatg ctcaaacgcc atcagacgac accccagcgc gacaagtgga gacgtctcca    2520
ctcgcgccac cagccgcgca agcagcagca cccgggcatt tctaccgatt cacgctctct    2580
gcgagctgtc gttcaatgcg ttcccgcaag gcagcaaccg ggacccgaag cgacccaccg    2640
acgcgcacgc taggaacatc accggacgcc atcaacccgt aaattttgt tcggctgatt    2700 cccatcgcgt cggcagcttc cgccggtcga tacagcagtc gttctgtagt gttcatatgc    2760
ctccgccgaa gttcagttag ataacggata gacattgaca gaattcacta tccaatgtaa    2820
ataacgcgtc atgaggttac agatgcctga aaaacgctat acgaggagac gcatggacac    2880
actgctacaa cggctgatcg atgtgacaca gtccgcggcg ccgcggcaag cgcgcggagt    2940
gctctctgac ctcgccaaag cgaatattgg agacatggca ccggatccac gcgcagcctc    3000
catactgacg acagccaacg atcgcgacgt tgcacgctgg acgaagcaac tccgcgatct    3060
gatacaggcc gtgaccgact atcagcagcg tccgatcggg ctgacttggt ccattcctcg    3120
ggtcaccatt cgcgcagcgt tgaaccgcgg cggcggatat cagatggaag tcgcgggaaa    3180
tccgggcgac ctacttcagc tccaggcaat tacgctcacc cgctcatttc gtggacggct    3240
tcagcgctgc ccatcaacct tcgccacggg aaatcgatgt ggacggattt tcttgcgcgc    3300
gggcaagcgg aaattctgtt cagaccggtg ccagcgacgc tactacatgc gggaagtttt    3360
cccgacgaag ggagcagagc aatgacgaca cgacgacgcg gccggggaga aggcagcatt    3420
cgccaacgaa aggacgggcg atgggaagtg cgcgttgata tcggacgcgg ccttgacggc    3480
aagcgtaggc gaagaagcgc tttcgccgat actcaggcgg ccgccgtgcg agaactcaag    3540
cgactcgccg gccggcaagt caccgggcag ctcgtaacca cgagcacacc caccgtcgcg    3600
acgtatctcg gcgagtggtt cgcgacgaac agcgacgcgt ggcggccgag cacgcgccgc    3660
ggctaccgtc gcgcgatcga cgggttcctc gtgcccgcct tcggcgcgct gcgcctggag    3720
caactcacgc cggcgatcgt acagcggtgg ctgctcgagc agaagacgca gcacggcgcc    3780
cggcgccgtc tggtgctcgc acacgcgacg ctgcgctccg cgctctccga cgcgcaacgg    3840
ctccagctcg tgacgatcaa cgccgccgcc ctggtcaagg tgccaaaggt gaccagccgc    3900
gcgatcgcgc cgctcgacgt cgaccaggcg cgggcgttcc tcgcgatcgc cggccggcat    3960
cgactcggcg cgctgttttc cgtcgcactc gcgtgcggcc tccgcctcgg cgaagcaacc    4020
ggcctcaaat gggaggacgt cgacctggag acgggcgacg tgcgcgtgcg ccagcagctc    4080
cagcgcgtca accgcgcgct ggtcctccag agtctcaaga cggcgcgcag ccgccgcacg    4140
ctctccctgc cacaggtctg catcgacgcg ctgcgcagca atcgcacgcg acagcgcgcc    4200
gaacggctca aggcgggtgc cgactaccag gagacgggcc tcgtgttcac gacctacgcg    4260
```

```
cgacgtggcg gcggccggaa ggtcgggacg gccctatccc cgcgcaacgt gctgcgcacg    4320
ctccacgagc tcctggacgc ggccacgctg ccgcgggtgc gcttccacga cctgcgccac    4380
tcggccgcga gcctcttgat cgcggaaggc gtgcagctgg ccgaagtcag catgctcctc    4440
ggtcactccg agctgcgcgt gacgtcggac ctctacgcgc acctcgcgaa gcagaccgcg    4500
gcgaaggccg cgcatcacat ggacgcggtg ttcaaagcgt gaggggggtca gttagggggt    4560 caaccggccg ccagcgcgcc gcgcgccggt tgaaagtcgc gaaattgttc aggaaactgg    4620
agccggcgat cggacttgaa ccgatgacct gctgattacg aatcagctgc tctaccaact    4680
gagctacgcc ggccggcggg tgagcgaaca cgcattctat cagattgcca tgagccggag    4740
aatacgcgtc ccgcgcctta ccggcgggag cgccatgac gcggtttgcg ctgctcgttc    4800
cactgatcgt cctggccggc gccccgacgg cggcggccca gacctcggga agcatgacgg    4860
tgctcaccgg tgtctactcc gccgcgaggg cgaagcccgc gatcgggtac gcgtggggct    4920
ttggcaaggc cggcggcggc ggggagctcg aatacgcggg aacacggggc agcggcgagg    4980
aggccgggtc gatcacccctc gcctggttca tcccaacgcc gctcaaggtg cgccgctcgc    5040
ccgtgtacgg catcgccgga ttcggcgcgt acgccgactc ccatcgcgcc gaactgcagg    5100
agacgatcgt ggccggcatg ggcaccaagg ttcaggtcgc cgggccgatc aaactccgga    5160
tcgagtaccg cctgttctg ttgcgcgacg cattccccc gccgcggcgc ctgtccgcgg    5220
gcctcagcgt cggcttctaa gcccccgggg gcatgctaa actagtcaat gactggttaa    5280
atcactgaca tgcctaaagt caccgcattc gaggccaaga cccgcttcgg cgaactcctg    5340
gagcgtgtgt cgcgcggcga agagatcgtg atcacccggc acgacaagcc cgtcgcgcgg    5400
ctggtgccgg aaggcgcgag gcgtctcgac gacgtgcgcc ggagcgtcca ggggttgcgg    5460
gaactgcagc agcggatccg cagacgcgcg aagtcgagac tcaccgatcg cgaggttcgc    5520
gccgccatcg aacacggccg gctgtgaccc gaaagttcgt cgcggacgcg tcggtcgccg    5580
tggcctggat tcatcccgat cagggaaccg acgaaaccga agcgatgctg gacgccctcg    5640
aagagggcgc cgcgttggaa gtcccggccc tctggccatt ggaggtcgcc aacgcgctgc    5700
tcgtgctcgt gcgacgccgc aagctcactg acgacgaccc cgtcctgggc cttcaatggc    5760
tcgccggtct cccggtccgc gtcgaccacg acatggccgc gctgacgcc ttcacccagc    5820 tctcggacat cgccgtcaaa cacggcctgt cggttacga tgcggcctat ctggagctcg    5880
cgcaacggcg cgcgttgtcg ttaggatgca aggacggccc gcttcgcacc ccgcccgcc    5940 gcgcgggcgt tccgctctgg acgtaatcac tccgaccgca gcgccgtcat cggatcgacg    6000
cgcgacgcgc ggcgcgcggg gacgagggcg gcgatcacgg cgacgaggac gatcagcacg    6060
gcaacgggcg tcagcgtgac cacgtcgggc cggcgcaccg cgaccggcgc ggactcgacg    6120
agcggcgccg ccgcgagcgc gccgagcacg ccgagcgcga gccccgccac ggtgagccac    6180 agccctggc cgatcacgaa ccgcaccacg cggccgcgat cggcgcccag cgcgacgcgg    6240
atcgcgaact cgcgcgtgcg cgaggacgcg agatacgaaa tcacgccgta ggtcccgccg    6300
agcgcgagac cgattgccag cgccgcgaac cccacgacga tccacagcga gagcgtgaac    6360
ccggcgagcg actcggcgac gacctgctcg atggtcttga tgccgaagac cgcgcgatcg    6420
ggcgcgccct cgcggatcgc cgcgcgatc ggatcgatga gcgcttccgg aggatcctgc    6480
gtccggacga cgagcgtcat gccgaggtcg gacacctgcg accagttctg cgcgatcggg    6540
taatacacct cgggaagcgc aggcgcgtcg agatgcacct gcctgacgtc cgcgatggtg    6600
```

```
ccgacgatcg tcccgcgggt ggtgacgagg ccgatcggat cctcgccggg aaacgccttc    6660
ttcgccagcg actcgttgac gacgatgacg cccggcgcgc cctcgatatc ggacgtcgtg    6720 aagcccggc cgcgccggat cgggatgccg agcgcgtcga ataacccgg cgtcacgtag     6780 cgcagctcga tctcgaactc ctgcgcgcgc ggcggacggc cgcggacgcg gaagtcggtc    6840
gagttgctgc tccacccca gctctggagc ggcagcatct gcgcgaagcc cgcggcgcgg     6900
acgccgggca gggccgtgac gcggtccgcc atgtcgtaga gcggcgcgc gccgccgggc    6960 gcgtcacgct gctggccgac gtggaacgtg atcacgttct cgcgcacgag ccccgcgtcg    7020
gtcgcatgga gacgcgccag ctcgcgcagc agcatcgtcg cgccgacgcc gagcatgaac    7080
gcgagcgcga cttcgacgac gacgagcgcg ctgcgcaggc ggcgctgcgc cggccccatc    7140
gtcccgcgat cgcccgcttc cgccagcgcg ccccgcggat cgcggcgcgc ggccatccac    7200
gcgggcacga cggcgacgag cacgccgcag gcgccacaga cgagcatcat gaacgcgaac    7260
acgcgccagt cgagcgtgac ctcgtgcgcg cgcggcaggt aggggccgc catcgcgacg     7320 agcttcgcca tgatccacca cgcgagcagc aggcccgcga tcccgccggc cgccgcgaga    7380
aagaggcttt ccgccagcag ctggcggacc agtcggaacg gcgacgcgcc gatcgccgcg    7440
cggaccgcga tctcgcggta gcgcagcgtc atccgcgcga gcgacaggtt cgcgacgttc    7500
gcgcacgcaa ggacgagcac gatgccgacg gcgccgaaca ggagcccgag cagccgccgc    7560
gtttcgcgcg ggaccacttc ctccgcgagc gcgacgacct cgatcccgcg tccggcgttc    7620
cgcgcgtctt ccgcctccag acgcgccgcg atgaggctca attccgcctg gcggccgcg     7680 atcgtcacgc cgggcttgag gcggcctgtc acgttgccgg cgttggcgag tgggcgcgtc    7740
agctccagcg gcatccagag atccgtgcgc gattcctcgg cggagccgcg gaggagcgat    7800
ccggcccgat acggatactg aaaccacttg ggcatgatgc cgacgatcgt gtaggcgcgg    7860
ccgtcgagat caatggcgct tccgaccgcg tcgccgcgcg acgagagacg gcgccgccag    7920
aaggactcgc tgacgacgat ggacgttgga ccgtcggcgg acgaatacgt gcggcgtag     7980 agcgccggca cgcgcagcac gccgaagaaa tccccttccg tgcgcaccgc catcacgcgc    8040
tccgcgttgc cgccctcgcg ccggtagcgc gcgccgacct catacgcggt catgccgtcg    8100
aacgacgtgc tctcgcgccg gtaccgatcg agattcctga cctggcggaa gaacggcggg    8160
cgcgcggtcg tgccgtggag ctgcacgagc cggtccggct gcggaaacgg cagcgggcgc    8220
agcatcagcg cgctcacgac ggtgaagagc gcggtcgtgg cgccgatgcc gatcgcgagc    8280
gtgagcagcg ccgtgatcgc gaaggtccgg tggctcgcga tgagggtccg cgcgccgtag    8340
cgcacgtcgt gcgccaggtc gtcgagccag cgccagcccc agacgtcccg cgcctcctcg    8400
cgcagccgca gcgtattgcc gaaccgcgac gggctcgcca gccgctcccg gtgcgcttcc    8460
atctcacggc gcacctgctc gtcgtgctcg ccgcggttga ggatgtactt cattcgccgg    8520
taccactctc ccggaagact catgcgctcc tcatgacggc gtcgatcgcg agcgccatcc    8580
gccggtattt cgtccgctcc gcgtcgagct gcttgcgccc gccggcgtc agcgtgtact     8640 cgcgcaccga acgcccgtc tccgagatcg ccggcgcagc cttcacccat cccttcagca    8700
gcagcttctg caacgccggg tagagcgatc cttcctcgac gctcagctcg tcgttcgaga    8760
gctgcgaaat gcgctgggcg atcgcgtagc cgtggagcgg acccgccgcg agcacgcgga    8820
ggatgagcat gatgagcgtt ccgggcggca ggccgtcttc acgaggcatc gtttacctag    8880
gcctcgtttt aacagggctg cgagtggttg tcaagcggca ggagtatgct ggggccgtcg    8940
agacgcgcgg atgcgagcac tcctcttctc gatgcccgac tcgttcgagc acacgcctgc    9000
```

```
gctcacgatg cgcatgccga acggcgccct cgcgtcgctg cgggcaacg ccgggccggg    9060
ccaccatgtc gccgtcgcgg acctgatcct ggcgcagcgc accgtcgccg cgaccgccgc    9120
gcgcctgatg cgcgagatcg atcccgacgt cgtcggcctc tcgatcatga ccttccagcg    9180
ccgtacggcg ctgcggctga tccggctgct tcgctcgatc aagccgtcga tcgccgccgt    9240
cgtgggcggg tacgatccca gcctcgcgac gcacgtgtat gaatcgccgg agagcggagt    9300
cgacttcgtc gtccgcggcg agggcgagct cacgttccgc gccttgctgg aggcgctcga    9360
ccgaaggcgg ccgttcgacg ggatacccgg gctcgcctac cgcgcgtcgc cgggcgccgg    9420
attcacgctg acgccgccgc ggcccgtcag cgatctggac ggcggcggca tcgcgctgcc    9480
gaagcgggac gcgcgggtcc tgtccggcta tacgttcctc ggccggccaa tcgacatcgt    9540
ggaaacgtcg cgcggctgca cgtacgactg cagcttctgc tcgatcatcg agatgcgcgg    9600
ccgcaacttc cacacgttcg atttcgagcg ggtgctcgcc gacatcgccg acgcgcgggc    9660
acgaggggcg cgcgcgatct ttctcgtcga cgacaacatc acgctcaacg tcgcgcggtt    9720
cgagacgctc tgccgcgcca tcgtcgacgc cggcctgaac gacatccact acatcgtgca    9780
ggcgatgacc tcctcgatcg cgtcgcacgg cgcgacgctc gcgccgctca tgcgccgggc    9840
cgggttccgc tacgtgttcc tcggcatcga gaacatcctg gacgaggatc tcgcgttcct    9900
gcgcgcctcg gcgaagaacg cgcagcgcga gtcaggccgg cgcgtgggga atgcgacgat    9960
ggcggcgatc gacgcgctgc accgcgaagg tctccacgtc gtcggcggca tcatcgtcgg   10020
caatccggac gacacgcggg aatcgatcga atcgaacctc gcgttcgcgc ggcagcacgt   10080
cgactggccc tacatccagc acccgacgcc gtatccgggc acgccgatga cgaacgactt   10140
ccgcgagcgc aacctgatcg tgaacgatcg gttcgaggag tacgacggga cgaccgcggt   10200
cgtgaagacg gcgcatctcg acgccgacga gatcgagttc ctgcggtggc gcgctgaacg   10260
gtggatgaag ctgcggcacc tgcccgccgt cctccggcat taccccggct tcgtcgcgcg   10320
gcacgcgccg gagatgctcg cgcacacgtt ccgcggcagc tcgtggcgat cggtgctcgg   10380
actcgagagc gagcgcgacg tgttcacgcg ctacaaggcg ctcagggcgc gggaacgaga   10440
gtatctgcca gcgtgacgcg aacgcgcccg tcccggactt cgaccggata ggtcgcgatg   10500
ccttcctccg cgggcccgtg cttcacggcg cccgtccgga cgtcgaactg cgagccgtgc   10560
cacgacact ggacgacgcc gcaggcgagc gcgccgtccg acagcggacc gccgcgatgc   10620
gtgcagcgat cgtcgaacgc cacgtatccc tcggccgtcc gcgcgaggac gagacggcgc   10680
gcgccgaagc gcagcagctt catctgatcg acctggaggt cgtccacgcc gcccacgtcc   10740
acgccgccgg catccttcgc gtcttcgaga aggcgcgtct cgacctgcca cttccccgct   10800
tccgcgtaac ggtgatccac ggaaatctgg ttgcgcgaca cgagcgtccc gcccatccat   10860
cctccggcgg cgagcgcggc agcccgcac gcttcggccg cgaaggccca cggcgcgggc   10920
ggcgcgtcgt catcggatcg ccgtcccgcc gcgcgcagcg cgaacagccc gagcgccgcg   10980
acgttggcga gcgcgtgatt ggtcgcgcgc ttgtgcgcgg agctcttcgg cggaaccgcg   11040
aagaggtagt cgatgatgcc ggggacggcc gcggcaagcg ccgtggcgag ccccatcgcg   11100
ttgaggtgac gccccgtccg gtacagctgg ggccggtccg tggcgcgcgc ccacgcgtcg   11160
accgccgcgc tgccgagcag gtacgcgaac gggaacggaa tcagcatcgg gtggatcggg   11220
tgtcccttga tatgggctga gctgcgcatg aaaacctcga ttctgcacgc tgcaatcgaa   11280
gttccagctg gcgccctcgg ataagaatag aatctcgcct gaatgcgcga ccttcccttc   11340
```

```
gactccgtgt atcgacacgg gttcgtccga cttgccgtct gcattccgtc cgtccgcctc    11400
ggcagtccgg cgcagaacgc cgcgcggacg atggagctgg cgcgcaaggc gggcaccgcc    11460
cacgcgaccg tcgcgctctt tccggagctc ggcctctcgg gctactcgaa cgaggatctc    11520
tttcatcaag acgcgctgct cgaagcgtcg ctcgcggccg tgcggacggt cgtcgaggag    11580
tcgcgcgaca tcgcatgcat gctcgtcgtc ggcgcgccgc tcaaggtcga gcagaaactg    11640
ttcaattgcg ccgtcgtcgt gcacaacggc gcgattctcg gcgtgacgcc gaagacatat    11700
ctccccaact accgcgagtt ctacgagcgg cgtcagttca cgcccggcgg ccacgcgggc    11760
acgcgcgaac tgacgctgtt cggccatacg gtgccgttcg gcagcgacat cctctatcgc    11820
ctcgagtcga cgcccgactg cgtcatccac accgagatct gcgaagacgt gtgggtgccg    11880
attccgccga gctcgcatgc ggcgctcgcc ggcgcgaccg tgctgctgaa tctctcggcg    11940
agcaacatca cgatcggcaa ggcggactac cgccgcacgc tgtgcgcctc gcagtccgga    12000
cggtgcgtgg cggcatacgc gtactcggcc gccggaaccg gcgagtcgac gacagacctc    12060
gcgtgggacg gccatggact cgtttacgag aacgggacac ggctcgcgga gacggaacgc    12120
tttgcctcca gcgatcagat ggtgcttgcg gacatcgaca tcgaacggct cgtccaggag    12180
cgcgtccgga tgacgagctt caacgacgcc gcggccgccg cccgatcgca cgcgtggcgg    12240
cacgtgaccg tcccgttcga acgtccgcgc gtgccggtgg cgctgcagcg gcacgtcgag    12300
cgcctgccct acgtgccgag cgatcccgcc gcgcgcgacg agcggtgccg cgaggcgtac    12360
aacatccagg tccagggtct tgcgtcgcgg ttcgcgagca cggggatcac gaaggcggtc    12420
atcggcgtct ccggcgggct cgactccgcg cacgcgctga tcgtcacggt ccacgcgatg    12480
gatcgtctgg ggcttccacg cgccaacgtg ctcgggttct cgatgccggg cttcgcgacg    12540
acggaccaca cgcgaaagaa cgcgctcgac ctgatgaagg cgctcggcat cacgagcgcg    12600
gagatcgaca tccgaccgtc gtgcctgcag atgttgaagg atctgcagca cccctacgcg    12660
gatggccagg aagtccacga catcacgttc gagaacgtcc aggccggcga gcgcacgtcg    12720
cacttgttcc ggctcgcgaa cctgcacaac gggatggtga tcggcaccag cgatctcagc    12780
gagctcgcgc tcggctggtg cacctacggc gtcggcgatc acatgtcgca ctacagcgtg    12840
aacgcgtcgg tccccaagac gctgatcaaa tacctgatcg gctggacgat cggcagcggc    12900
cagttcagcg agcaggcggg acgcgtgctg cagtcgatcc tcgacacgaa gatctcgccc    12960
gagctggtgc cgtcgcagtc gaccgaggac gtcctgggcc catacgagct gcacgacttc    13020
tttctctatt acgtgagccg gttcggccac cgcccgagcc gggtcgcgtt cctcgccgag    13080
cacgcgtggc gcgacgcgta cgatcgcgcc gcgatcaagc ggacgctggg cacgttcctg    13140
aagcgcttct tccagaccag ccagttcaag cgatccgcgc tgccgaacgg accgaaagtc    13200
gggtccggcg gctcgctgtc gccccgcagc gactggcggg cgcccagcga ctcgcacgcc    13260
gacgcgtggc tcgaagagct ggagcgccag gtccccgacc gctgagtcaa ccgtgagtca    13320
tggcacagcc gttgcctctc atcgttgcgg cggaggttgc agtgaggcag tgcgcgattc    13380
tgtacatcaa cgcgaacgga ctcgagcgga ctcatacgga tgcgctgcgg tcactcgggt    13440
tccacgtggt ggaaacggct gacgtacctg tcgacaaatc catcgaggac taccacgcgg    13500
tcatcgtccg gccgccatcg tcccaaggtc tgccgcaact ggcggcgcgc atgcgcgcaa    13560
agccgcgctt cggacgccgc gtgctggtcg cgctggtccc gcaggacacg ctgccgcagc    13620
agcggcgcga ggcggtcgac gcgggcttcg atctggccgt gaccgaaccg tgcagcgcgc    13680
gggatctcgc cgccgcgatc ctggggcgcc tgcggcgcta tccggagcat cactgcgtcc    13740
```

```
tacgcaccgt cacgggccgc cggaacgccg cgtgacgcag gactgctggg acgcgcgatt    13800
cgagcgttac gccagcgaca aagccgccgc cgcgctggcg gcgccgctgc cgccctatcg    13860
aaccgagatt gacgcggacc cggcatgggc ccgccacgtc ggcaacgcct ggacgcacgc    13920
gcgattcgga ggcccgttct acgtctccaa ctcgcacagc gatcggccgt cctgctcgct    13980
ggtgttcgtc cagtcggccg acggcaacac cggcacgtcg aaccctgcgt cgctcggagg    14040
cggcaccacc gacacgcatg tcatctacga aggcctctcg cgagtcgcgg cggacggcgt    14100
gctggcgggc gctgaaacga tccgatccgg aaacgcggtg ctgtcggtgt ggcatcccga    14160
gctcgtcgcg ctgcggacgt cgatgggggct tccgcgccac ccgtgcaga tcgtcgcgac    14220 gctgcgcggc ctgccgatcg acgacatgct gatgttcaac gtgccatcgg ccgccgcgat    14280
cgtgctgacc gtcccggccg cagccgaacg catgcgcgcc gcgatcgagg agcgtccgtg    14340
gatgcggatg ttcgtgatga ccgacgagca ccacttgccg gccgcgttcg cgtggctgcg    14400
gacctgcggg atcgatacgg tctcgtgcat cggcggccgc acgctcgcgg cgcagctgct    14460
cgatctgcgc ctcgtcgacg aggtgtatct gacgacgtcc ccgaaaaagg gaggcgatcc    14520
gggcacgccg atccatccag gcggctggcg cggcacggtg ctggttcgca agtgcggcac    14580
cggcgaggaa gccggtgtca cgttcgagca cgtgatcccg gctaacagct gacagccggc    14640
agccggcagc cggaagccgg aagccggaag ccggaagctg aagctggaa gctgaagct    14700 gcctactgtc ccccgcgtgc gcgctgttcg agcagccgcc gcatcgtgcc gttgagcgtc    14760
gctcgcgcga tcgcggcgcg cgcgcgctcg gccagcgcct gctgcagcac gggctcgtct    14820
tcctttcgcg acgcctgcac ggcgatcagc acgctgccca tctcgtcgaa cgactgctct    14880
ccccactgca cgcgcctggg cggcgcggcg ggattgtgcg gattgtcctc ggagttgtcg    14940
tacacgatcc ggacgtcgat ccgcgtgccc ttcggcagcg ccacgacgga cttgtaggta    15000
tagcgatcct gccagttgaa gtcccagtcc ttgatccaga gcagcggctg ggtgcggccg    15060
tccggcagcg tcgcttcggc cttcatctct ttggcgacgt agtgcgcgtg cgcggcgatc    15120
gagaacgcgt tgacgtccac cggcagtgtg agcgagtcct cgatcgtgaa gcgcttctcg    15180
cccgcgggaa tgtcgatacc ggcgccgaac ccgaacaacg cggggatctg gagggaccac    15240
agccggcgct cggcggtcg gtcggcgaag tagatgccga cggtcgactg ttcgacctcc    15300
ggtttcccgg tcgatggaa atgcatctgc agcacgaggt cggatcccctt cggcagcgga    15360 agcgccacgc ccggcggaaa cgactgcggg gtcgcgccga ccgcccagcc gccgagcggg    15420
ccggcgccgc ccgtcgccgc gccgacgccg acgcggccca tcccgccgaa cccaggcttg    15480
ccgtcgcggc cgtcgatctt cgccgacgcg ccggtcgcgt cgtacgcgaa cagcacgtgg    15540
tgcaccgcct tgcgggcgct cggccggaac tcgatcgcgc gcacccattt gtcttcgacg    15600
agtccggacg gcacgacgaa gttgcggtat acgtcggggc ccgacgccgg gatctcgaaa    15660
ccggccggca tccggaggat cacgtccggg gtgccgagct gccagccgtc gggaaacttc    15720
ggcagcttcg gcagcttcgc ggggtcgccc tcggcatgc cgcgcgcgac ccactcgcga    15780
atcgccgcga tctcggcgtc actcaggcgc cgttcgtcgg cgaactcgcc atagccgtgc    15840
gcggcatgcc acgcggcat gtagcgggac gcggtgacct tcgcgatgag cgtgcccgc    15900 ttttccacgt cagcgaatgt gatcaggaa aagggcgcgg cttcgccggg acgatggcac    15960
gtgacgcact tgtcgtagag gatcggcgca atggtctcgc tgaaagtcgg agaggccggc    16020
cgcgcggcgg cggcggcaag cgcggcgaca acgagcacgg gccacacacg cgtcatggcg    16080
```

```
atttccttct cttgtccggt ggaacgatga aacagcctgt tgcctgcgtt cgcgcggccg    16140
ccactcgccg gcccgcgagc accgcggcca gcgcgtcctc gagatcgtgc gccgtcacgg    16200
ttcggcgctg ccggccgatc gcgatgtacc ggtcgtcgat ccgtccgagg taccgcacgg    16260
cgccgcttcg atccacgacc gccacctcgg cgtcacggt cgctcccgcg cgggcggcga     16320
gccggccgtc gctgtcgtag acggccggca tggcgccgta gccaaactcc gtgcggtggc    16380
gtcgcagctc ctcgccgccg gcgccgacgt cctcgtacac gagcatgcag tcggaccccg    16440
ccgcggcgga cgcgcggcag atgcgctgga tctccggcgc gtagccgttg gagacgggac    16500
agtcggaggt cacgaacacg agcacgttca acgcgcgcgc gggctcgagc gggcggagga    16560
ccgcgccgtc caggccgcgc atctccagcg cggtcacgag cagggcgagc agcatccacg    16620
ggtacaacgc catggcccga caaatgtgac acaatccggc gcattccaac cgaccatctg    16680
aacccggagg aatcggcgtc gctgagcgcg caggtcgccc gggtggaagc ggcgaccggc    16740
gtgcagctcg ttccggcgat cgccggcaaa tccgacagct acgccgagct gccctggaag    16800
gcgttcgcgc tcgcgcgtc cctggcggcg ctcgcgctcg tcgccgccga tcggctgcag    16860
ccgcaatggg ccacgaacga caccgcgcgg ctgcacgtga tactcgtgct cggcgccggc    16920
gcgatcgcgg aactcgccgc catcttcatt ccggcgttcg cgcgattgct cctgcggccg    16980
gttcgcgccg aagtggaagt gcggcagtac gccgagtcgc tgttcctccg ccacgggctg    17040
tcgaagacca gcgggcgcgt cggcctcctc gtcttcgtga gcgtgttcga gcggaggatc    17100
gagatcgtgg ccgacacggg gttcgccggg gcgcgtgtcg ctgacgactg gcgcgccgtc    17160
atcgcgcgga tgacgccgca cctgcgcgat cgccgcccgt atgcggcgct gcaggacgcg    17220
ctcgccgcca tccaacagct gctcatcgcg aagggcttca cgcccacagc cggagaccgc    17280
aacgagctct ccgacatcgt catcgaggat cgcggcgaat gagacgcctt caccgcgccg    17340
cgctcgcgtg cctgctgatt gcgctcgtct cgtcgcgcgc gcggcgcag ccgaacatcc     17400
cgtttctcac gggccgcgtc gtggacgagg cgaacattct cagcgagggc gcgcgcacgc    17460
gtctcaccga cgtcctgaag gcgcacgaaa ccgcgaccac gaaccaggtc gtcgtcctca    17520
ccgtgccgac gatcggatcg aggagcatcg aggagtacgc ggtcaaggtg ttcgagtcgt    17580
ggaagctcgg gcagaaagag aaggacaacg gcgtcctggt cgtcgtcgtg ccgcaggatc    17640
gcaagatgcg catcgaggtc ggctacgggc tcgagggcac gctgcccgac ggcgccgccg    17700
gctcgatcat ccgcacgtgg atgacgcccg cgttcaaggc aggcaactac gacaagggga    17760
tcgaggacgg cgtcgcggcg attgtcgcgc ggctcgaagg ccgcggcgag ccgacggatc    17820
gcgcgccggc cgccgcgtcc gcctcgagcg gcggcgacgg cgccacgccg ctgccgtggt    17880
ggggcgccat cctgatcggc ggcttcatct tcgggatcct tggcctcttc acgttcatcg    17940
ggatcgccac accgggcgtc ggatggttca tctacgtgtt cctgatcccg ttctgggcca    18000
cgttcccgtc cgtcatcgtc ggctggtccg ggacgttcct gctgctcctc gtttacgcga    18060
tcggcttccc gatcgcgaag ctccgtctga agcgcacgcc ctggtacaag cagaaggcgt    18120
tcgagatgaa gacgaagggc acgacgtcga tcggcggctt cagcgtcggc gggagttcga    18180
gctccgacag cgggagcagc tggtcctctt ccgacacgcg tttctcggga ggcggcgaa     18240
gctccggcgg cggcggcgcg tcgggtagct ggtagctgga agctatttcc gtctcatctc    18300
cacgcgcacg cgacgctcca cttcgtgcgc ttcgtcggtc tcgtagctgt cgtgccccac    18360
ctgccggccg atcttcgcga agagccttcg catcgcgtcc tcgtcgcgca cgtccggccg    18420
ttcggcgatc tcgacggcgt gctggagctc atgcccaagg atcggcgtga tatcgggaaa    18480
```

```
ctgcacggtc gccttgattc ctactcgcag gaagcgcgcg tcggcgctcg cggtcacgag  18540
cttcgtccgc gccatcgccg cgctcggcga cgccatgatc tccacgtaga cgatggcgtc  18600
ggtgcacgcg agacgatcca tcaacccgcg aatcgtgacg gatcgccgcg cggcgtcgtc  18660
gagcagcgct tgcactcccg cgtccaccgc gcggacgcgc cggcccgggg cacaggccgg  18720
atcgggatcc gcggggccgg gcagtgtgat cagcagcaga atcgcgagcg ttccggcagc  18780
cgtcatagtg accgcataga cggagcacgc ccatcgcgca gcgcgggaat gtgacggttc  18840
gacggaacgc gggacggacg cgtgagtcag cgggacggcg cgccggcgtg gtcccaccgt  18900
ccgtctcacc ccgggcgaag accggatcgt cccacgacca atgcgatatg gtcttcacgt  18960
cgccggtgcc cagtgcgcga tactgacgct cacgcccgat ctcgcgggcg cgaccgcctc  19020
cagcaatcgc tcgcccgccg ctggtcctca gcggccgttg aagccgacgc ccgtctgttg  19080
ataacgcggc ggagcgggcg gcggaccgtc cttgtcatgc tcgagattgc cgggatcccg  19140
ggcatacatc gcgcgcgcga tcatcatttc gttcggcgtc agatcgaacg gccggcacgc  19200
gccgggaccg ccgcccatga tcgacggcgt cacccgcgtg tgccagtacc ccatcgcgtg  19260
gccgaactcg tggacgacgc cgagcgatcc gcacgtgtgg tcgaacccga gctgcaccca  19320
cccgggatct tctccgagca ggctccagtt gcccgagcgg ttgaactgga ggttgatcca  19380
ccctttctgc cgcgggcggt tcgtggcgct catctcgacc aggccgagct gcagccggcc  19440
gccgctccac tgcggaatcg cgcgccgcac gtcggacacg atgctctcga tgccggcggg  19500
attcaccgga aatccggtgt ccgtccacgt cgtccagacg aacagattcg ggttcgaggt  19560
ccagtgcctg gacggctcga cggccgtgcc ctggtacgtg ttccggacca tctcgcgata  19620
ttgatcgtgc gggaatttcg gatcgagcgc gatgagatcg aacaccaggc ccgtcttcgc  19680
ctcgcctcct gtcagcgacg tctcgcgcag caggtagcct ggcgacgcaa tcgtgagcgg  19740
cttcgtggaa ttgtccgtcg tcaggatcgt gaaaacgccg ctcgcgtccg tcgtcacggg  19800
cgcatcggtg ccgtaggtca ggacggcgcc ggagatcggc gtgacgaagt cggtggagct  19860
gacgaccgag ccgcggatcg cccagctcgt aggcgtcggc ggaaccggcg tgggcgccgt  19920
cggagacgat ggctgcgcgg gtgcagccgg ggacgccggc gccgggccgc cgcacgcggc  19980
gctgagcatg accgcggcga tcgccgccgc ggccgcgcgc gacagcgatc tacttgacgc  20040
gatagagccg cgactgggtg cggatgaaca ggccgtcgcg tgtaacgcc ggactggcga  20100 acgccagttc gcccaggctg ttcttcgcga cctcgtcata cgtgtctccg ggattgacga  20160
cgaaggtatc accctcttcg ctgaggaaga agatctttcc cccatacgtc cacggagacg  20220
cggagaaggt gttgccgacc ccgccgacgc gcgccttgta gatctccttg ccggctttgg  20280
cgtcgaacac ctggagcacg ccgttgtcgt tgacgacgta cacgcgcccg ccgtacgcga  20340
gcggcgacga cgtgtaggcg gccgcgcgcg gctggaacca tgcgacgaac gcgttcgatg  20400
tctcgccttg cgccagcgag atgtcgccgg aggcgccggg cttcaccgcg aacagcgggc  20460
ggttcgactc acccctgcgag cccgtgccga tgatcagcag gccatcggct tcggtcggcg  20520
tggggttcgc ctgcgtcgcc cccttcagcc gccacagttc cttgccgtcg agaccgtagc  20580
tgatcgtcac gcccgtgccg atggcgatga tttccgtgcg ctgcgcgttg gtccagatat  20640
acggcgtcga ccagccggac ttcatgatcc cgggcacgtg gttgcgcggc gtcttccaga  20700
tcgactggcc cgtcttcgcg tcgagcgctt cgatggagga cgcctcctgg ttgtcgtcga  20760
gcacgtagac gcgcccgtcg tggacgacgg gcgacgccgc cgtgccgaaa tcgagatacc  20820
```

```
gcgcgtgcgg ttcgatcttg tgcgcccaca gcagcttccc gtccatcgaa tagcagaaca   20880
ggccgatgtt gccgaacagc acgtagaggc gctcgccgtc ggtcgcgggc gtctccgacg   20940
cgtaggtgtt cttgcggtgg cggccgccga tcggcgggcc cttgtgcgcc tcctgctgcc   21000
agcgcggctt gcccgtggcg acgtcgaagc tgtagaccat gaactgcacg tcgcccgatt   21060
cctgcggcga ctcgagatcg cgctgccgca gcttctccat gatctggtct tccgagagcc   21120
cctgcttctg cagctccgcg acgtagtcgt tgccgtagat cccgggcgag ggctgcttga   21180
actccttcga actgatcgcc gtcgtcacga acacctgatc gccccacacg atcggcgagg   21240
accacgcgcg gccgggcacg tcgatcttcc acgccacgtt gatcgtcgtg gaccacttcg   21300
tcggcagcgt cgagaccgcg gacgtcgcgc ggccgccgtg cccgcggaac tgcggccacg   21360
tggtgtcggg cggcgccggc gcggccgtga tgaatgccgt gacgaataga atcgtcgaga   21420
ccaggatgct cacgcggaga gtgtatcgcg gctggccgtc agaactgcac cgacagcccg   21480
atcgacggcg tgacgccgaa gccgcgacgc agtccgctgg catactggcc ggtctgcgcg   21540
agcgacagga tcgtcgtctc cacgttgtac tcgttcatgc gattgagcac gttgagcacc   21600
tcgcccgaca aggtgaacac gccccagcgg ggaatgaaga cttttcggat gcgcagatcg   21660
agccggtcgt acgcgcgag gcggatgcga ttccgctccg tcccgatcgc cagcttcgcg   21720
ccgtcggcct gcaggaaccc cgtgcgcggc atgccgctcc catgacgcca ctgcgcgccg   21780
agcgcgagcg tcccggagag acgaaacgat ccgaccgcgt tcagcgtgtg ccgttgatcc   21840
gcgtcgctcg gaaacgcgag gttgtcgaag cgatccacga cggccgcgtc tccgtaggcg   21900
tagccaatcc atccgctgag tcgccgcgcg ctcgcgcggc ggatcgccac ctcgactcca   21960
cgcgccgtcg cgtcgagcgc gttctgaaac ggattgcgcg caatcgtcag gtgcccgtcc   22020
tcgacgcgcg gctcggcgag cgcgaacaag ccgtcgcggt cgcgccggcg atacacgtcg   22080
acgctcaggg tctggccggc gccgagcgca tggtcgaatc cgccgccgaa ctcgacggcc   22140
ctcggcatcc gcagtcccgg gttcgccagc aggccgtact gcgcggcgag cggcggaagc   22200
tgatactgcg ttccggccga cgcgcgcagc gtccagccgc gcgccacgcc ggtgacgatc   22260
acccgggggg cggcgaccgt ctcgccgtcg gcgctctcga tgcgcgcgcc ggcggtgacc   22320
gacacgcgcg acgacggcgt ccagcgatcc tgcacgtacc aggagatctc gttccgcccc   22380
gcgtcgaagg cgccgaggcc atccgcgcgc gggcgtgcg cgtcgacggc ctgcgcgtag   22440
acgccggcct gcagttgatg cgcggatgag gcctggaata cgacgtcggc gcggacgccg   22500
gcgctccgct gtccgttgtc caccgtctcc tgcccggcgt cgtcatgttc gcgatacgcc   22560
cgcgacagca cgaaccctg cacgcgcgtg aacacccgcg cgttcaccac cgccctccac   22620
gcggcgatgc cgagccggtt cgacgacttc gcatccgcgc cggagggctc gtcgctcgtg   22680
aacgcgccgg cgagccatga cgccgtgatc tggttccgcg cggacaggtc gatcacggcc   22740
ttgccgatga cgtcgccgaa ctgcaggtcg gtctcgtcgt catcgtcgtc gcccgtgccg   22800
gcgacggtgt cgacggcctg ctgaacgtag tcgagccgcg tggtccgtcc gcccagcagc   22860
caggagccgc gcttgcgcgg cagcggccct tcgagcacac cggacgagac gatgaacccg   22920
gtggagagat cgccgtcag gcgatcgcgg ttgccctcgc gcgtgtcgag cgccagcgcg   22980
ccggcggtca cgccgccgat gcgcgcgtcg ttgacgccgg gcgtcagcgc ggccgaggcg   23040
agcgtgtcct gattgacgac cgacagcgac aactcatccg tcgtcccga gtcggcgagc   23100 gcatgaacga acccgtccgt cctgacgccg tccacgtaca cgccgatctg atcgaacgcg   23160
gcgccccgga gcgagaactc ggccttcagg tcgttgttgg ccgccacgcc cggtaacgcg   23220
```

```
tgcacggacc ggagcggatc gtcgacgacc accatcgaca gcatctgcag atccactttc    23280
gtgagggtgc gtgcaggtaa ggcgtccgcg gccgcgccgc cgcggacctc gacgcgctcg    23340
gtgacgccgg ccgattcgcg gttcagacgg acctcgccga gatccgtgcc ggccgcggtc    23400
acgtccacac ggcgggtcac gaacgcatat cccacggcgg tgatcagcac gtcgatccgg    23460
cgcgccgcgc cggccggtag ggcgaaggcg ccgtccgggg ctgccgccgc ggcgttgcgg    23520
ccgtcgatga cgacggcggc gccggcgacc ggctcgcccg tctgcgcatc cagcacgcgg    23580
ccgctgatga gcggtccccc ctggagcccc ttcaacccga gcaccgccca caacgcgaac    23640
gcggccgcca taccgttcct cccttgttac tacgtttgta gtatttgacg ttactacatg    23700
tgtagtggtc tggcgtcgcg gctctatttc tggcgcgcgg gctcgagccc catgtactgg    23760
gcgaaccggc ttcgggcgcg ctcgtcggga cgggcgtgt cgagcttcgg gcgtgtgagg    23820
tcggccccga tgcgccggac ccagctcggg ccgcgctgct ccctctcggg aacctccagc    23880
cgcgtcccga tgtcgccgg ctgggcggga accgcgcgg cggcaatcgc gtcgcggagg    23940
gtgcccggcg cggctgccgg cgtggcaccc tgcggagggc tcggcgcagc ggccgtcgat    24000 gacgcgtcg cttgcgcgtc gagggcaacg gcggagaccg cttcgcgatc gaccggcgcg    24060
ggaatcggcg ccggggcaac cggcgccggc aaccgcaccg ggctcggcct cgtgccggcg    24120
cgcctggatg agggggctggc cgccgcgcc ggcgcctcgg aagcgggtac ctgcgtgatc    24180
agccgcaccg cgaccgcagg gatcacgcgg gagaaatccg cgaccgtcac cacaggtgcg    24240
agacagaccg caggcagcgc gaggaccgag accgcacgcc acggccgctc gcgccgatcg    24300
cggcgcggcc catcgtcgag cagcgactcg agtcgccgcc gcaaggctga cccacggctc    24360
gccatcgcgg cgaacgcagg cgcgggttcg tgcacgctcc attcggccac tctcaccaga    24420
caccgcgcca gcgccgcgcg ctcgcgcggt cccgcggcgg cccgctcatc gcagcacagc    24480
tccatggcga cccgcagacg cgccgcgcg aagagattgc acggctgcca ccatcccagc    24540
gtgcgaacag ccgccgcgac gatcaaccag gcggtgtcgc ggcgaacgac gtgcgcggct    24600
tcgtgggcca ggagtgcgcg gagctcgtcg cgcgggagct cgcgcagcgc ccggaccggc    24660
acgcagatct cgcgcgtaaa cgcgaccggc accgccagct gcggctgca cgtcagcgtc    24720 acgcgatcag cctggggccc gaggatctca tcgaggatcg cgcgcgccgg accgcgccga    24780
accgcacggc gacggcccgc gcagcgcgcg ctgaggtacc agacgccggc cgcgcgcagc    24840
gccagtaccg ccgtgatcgc gatccacgcc gcggcgagcc aggacggacg gccggtttcg    24900
atcgccggcg cgataccggc cggcgctgac aggcgaaccg ccgcgccgga cggcgcggag    24960
cccgcggcca ggaagacggt ggcggtgacg acgccgccca cgagcgccag tttccagagg    25020
gcatcgcggg gcgacggaac cgaccccccac ctcgtgcgct cggcggcggc cgcgagtacc    25080
gcgaaaagag cggcgtgcgc ggcgtaggtc aggagccacg tcgtcagagc gtgctccgtc    25140
atcatcgtcg cgccttgctg cgtaccaggc gctgcagatc ggcgacttcc tcacgtgtca    25200
gcttgcgcga gtcgagcagg tgactgacga acgccgtgac gtcgccgtcg aacagactgc    25260
ggagcagctc ccgcgtcacc gtttcgcgca cgtccgacgg cgacacgcac gatcgataga    25320
ggtattgccg cccttccacg cggtgggtga cgagtccgcg ctgctccagc cgcacgagca    25380
tcgtcgcgac cgtcgtgagc gcgagccgcc gtcccgtcat cgcgcgctgc acgtcggcca    25440
ccgacgcgtc gtcgcgcgac cacagcacct gcatcacggc cagttgcagc ggggtgagcc    25500
ccgacgcgtc gtcgcgcgac cacagcacct gcatcacggc cagttgcagc ggggtgagcc    25500
ggggaggcgt cccccccctta cgaggcatgc gccagatact acaccagtag gagtttcgcc    25560
```

```
gacgagctcg cgcggccaca cggcacagct cgggagaacg gctctgcttt ctcgcgcgaa    25620
cggatcccgc taccatcaac gtgattggga tgcgtactgc gaaccgaatc ctgatcgtgg    25680
aagacgatgc cgacctgcgg cggctcttcc gcacgacgct ttcgatggaa ggcttcctcg    25740
tcgacgaagc gagcgacggt atcgaagcgc tgccgtccat agagaaccac ccgcccgacc    25800
tggtcgtcct cgatctcgtg ttgcggtctc tcgacggagt gtccgtacag caggagcttg    25860
ccgccaaggc gatcacgagc agcacgccca tcgtcatcgt cacggggtcg acgatcgaca    25920
cgtccggcct cgcggtcgcc tgcgtgctgc acaagcccgt catgcccgac gagctgattc    25980
gcactgtgaa acgctgcctg gcgaaggggg agccggcggc cggcgcctga gtcctggagt    26040
atcatggccg cctccgaagg gaggaggctg actctatgcg ctcgaatgtt ctcaaggggc    26100
tcacggcgct ggcggcggtg gccgtcgtgg cggcggtgac ggcccacaac ccggcagtat    26160
ccccggtgtc ggcggcggct cccgccatgc agtcgattgg cgtcgtggcc ttcgcgcccg    26220
acggcacgct cttcgcggcg gacaacaagg gcggggcgat cttcgcgctg gatctcggcg    26280
cggcggcgaa cggcgccaag gccggttcgg ccgacatcga aggcgtcgat cagaagatcg    26340
cggcggcgct cggcaccgac gcggcgtcga tcgccgtgac ggatctggcg atccacccga    26400
agacgaagaa cgcctacatc gcggtgacgc gcggcacggg cgccgacgcg cagccggccc    26460
tgctccgcgt ggacggcgac ggcaagatca ccccgatcgc gctcgacacg ctgaagtcga    26520
cgagcgtcgc gctctcgaac gcgccggccg cggccgaagg ccgccgcaac ccgcgcaacg    26580
acgccgtgac cgacatggcg ttcgtgaaca cctcgaccgc gctcggtgca agcggcaggc    26640
taatcgtcgc gggcctctcg aacgaggagt tcgcctcgaa gctccgctcg ttcgcgtatc    26700
cgttcgcggc ggcggacccg ggcaccagcg tggagatctt ccacggcaac cacggggcgc    26760
tcgagacccg cgcgccggtc tacacgttca tcccgtacac catcgacgcg aagccgtacg    26820
tgatcgcgag ctacacctgc acgccgctcg tgaagttccc gatggacagc ctgaagggca    26880
ccaaggtcca gggcacgacg atcgcggagc tcggcgccgg caatcgtccg ctcgacatga    26940
tcctctaccg gaaggacggc agggaattcc tcctgatgtc gaacaacagc cgcggcgtca    27000
tgaagatccc gaccgccgac ttcggcaccg ccgccgccat cacggccaag gtgacgacgc    27060
cgaccggcgg catcgcgtac gagacgatca agtcgatgca gggcgtcgag cagatggacc    27120
tcctcgacgc gcagcgctcg atcgtgatcg cgcgcacggg agcgggcctc aacctctcgg    27180
cggtggcact gccctgatcc gtcttcccct cacggtgtcg tgcgcggcgg tcgctctcgc    27240
gatcgccgtg tgcggcgcgc cgtcccagct cgccatttcg ctcgacctct ccactccttc    27300
acgtcccgtc gtcctcgtca ccggcctctc gcgatccgaa gtcgaagcgc tcggtaccca    27360
gcagctcacc aacgaagggt gggcgcgcat cttccgcgtc acggtgctgg acgacaaggg    27420
caatcccgcc gcgacacccg tcgcgggcgc gtattccctc ggccgcgggg tcgcccgctt    27480
cacgccaatg tacccgctcg atccgggacg ccgctatcag gtcgtcttcg ccgacacgac    27540
gtcggtggtg acggtgccgg ccggcgcacc atcggcgccg acgagcgtct cggaggtata    27600
tccctccggc gacgtcgtcc cggccaacct gctgcgcatg tacgtcgcgt tctcgggtca    27660
aatgggatcg cgcgacggac aggactatct gagcgtcgcc gacgcggcgg ccgcgacct    27720
cgacgacgcg ctgctgccgc tcaacacgag tctctggaac gacgaccgca cgcgcttcac    27780
cgtgctgttc gaccccggcc gcgtgaaacg cggcatcctg ccgaaccggc gcgcggggcg    27840
cccgctcgcg caaggcatga cgttcaccct gtcggtgcgg cgcgactggc ccgacgcgca    27900
cggccgtcct ctggtctcgg atttccggcg cacgtttcga gtcggcgccg ccgtcgagcg    27960
```

```
tccgctcgac ccctcggcgt ggcaaatcac cgcgccggct gccatgtcga aggcgagct     28020 cgtggtccgc ttcccctggg cgctcgaccg cgggctcctg gcgcgaagcc tgcaggtgtc     28080
gacggacaat tccacagtcg acggcaccgt cgtcatcgag ggcgccgtca ccatcgacaa     28140
aggggaactc ggatggcggt tcactccggc cacacgcgcg tggctacccg cgcctatac     28200 gatcgtggtt cgtcccgagc ttgaagatgt ctccggaaac cgcatcgggc gtgctttcga     28260
gaccctcgac accagcgacg acacccgcat ccccccgttc cgaatcccct tcaccgtcac     28320
agcccggtga cacttcgtcc tccattcggt gttcaagtaa ccgagtgaag gacgccgacg     28380
tcgagggctt gagccggcgc tacgggccga tggtgctccg ccgctgccgg cggctgctcg     28440
ccgacgagaa cgaggcgctc gacgccagcc aggatgtgtt cgtgcaggtc ctgcggcaca     28500
aggcgcggct cgacgtccgg tatccctcga gcctgctgta ccgcatcgcg acgaacgtct     28560
gcctgaaccg gctgcgcgat cggacccgcg agccggtcac gcgcgacgaa gcggtgctct     28620
acgagatcgc gcgcgcggaa gaaccgggcg cggcaagcga cgcgcggatg ctgctcgagc     28680
ggctgttcgg gaaacaccag gaatcgaccc ggacgatcgc ggtgctgcac tacgtggacg     28740
ggctgacgct ggaggaagtg gccggcgaga tcgggatgtc ggtgtcgggc gtgcgcaagc     28800
ggctgcgcac gctgcgcgcg tcgctgacgg agatgatgca atgacacgaa ggatccccga     28860
cgtcgtgctg gagcggtacc ggctgaacga actgccggac gcctccgccc gggcggtgga     28920
gatgatgctc gccgcggatc ccgagctgcg agcgcggctg gacgcgctcg acggctcgga     28980
cgccgaaatc ctgcgcgact atccgcaggt gttcgtacac gacgtgccgg cgcgtccgcg     29040
ccgcgcggtc agccgctacg cgatggccgc ggcggcggtc gcggccgccg cgatcgcgat     29100
catcgccgtc ctgccccgcg cgccgatcgc cgaaccggac gatgcccgca tcaaaggcgg     29160
aagccccgcg ctggccgtct atcggcgcac gaattcgggg agcgagcggc tcgccgacgg     29220
cgccgtcgcg aggagcggcg atctgctgcg gtttgggttac gtgtccgcg gccgcggcta     29280 cggcgtgatc ctctcggtcg acggccgcgg cgcggtcacg atgcacctac cgccgtcagg     29340
cgatcgcgcg gtgccgctca cgccgggaaa gaccgtgctg ctcgacaacg cgtacgagct     29400
cgacgacgcg ccgcgggccg agcggttcta tttcgtgacg gccgacgaac cgtttcccgt     29460
gtcgccgatc gtgagcgccg cgaagcgcgc cgccgcggaa ggcgcgccgc cgcccgccgc     29520
gcttccactg ccccggggac tcgaacagtc gacgtttgcg attcagaaag aaggacggcc     29580
atgaagtccc gctgctttct ccatgccggc gcgctcggct tcgtcgtgct cgcgctctcc     29640
acgccggcgc ccgcgcagcc cgcgggaacc atccagcggt tcgtgctcgc gattggcgcg     29700
aacgcggcgg gagccgatcg tccgaagctg cagtacgccc tctcggacgc ggagcgtttt     29760
gcgcgcgtgt tgaccgagct gggcggagtg ccgccggcca acgagacgat cctgaggcag     29820
ccgaaggtca aggacctcat cgacgcgatc aacgcgctcg gcgcgcgcgc cgccggcgcc     29880
aggcgcgcgc cgggcaccgg ccgcgtcgag gtcatcgtgt attactcggg gcacgccgac     29940 gagcagggc tgctcctcgg cagcgagcgg tatccgtatc cgctgctgcg cgaccagctc     30000
gatcgcatcg gggccgacgt ccggatcgcc gtgctcgacg cctgcgcgtc cggcgccttc     30060
acgcgcatca agggcggccg cgcgcgtccg gccttcctcg tcgacgagtc gtcgaacgtg     30120
cggggccacg cgttcctgac gtcttccgcc gaaaacgagt ccgcgcagga tcggatcgc     30180 atccgcgcgt cgtacttcac ccacttcctc gtgtcgggtt tccgcggcgc gcggatctg     30240 tcgggcgacg gcaagatcac gctcaacgag gtctatcagt tcgcgtccac cgaaacgttg     30300
```

```
cgccggacgg tcgattcccg cggcggcgcg cagcacccct cgtacgacat caacctctcg    30360
ggcaccggcg acgtcgtcat gacgacgtg cgccagacga cggcgtcgct cgtgattccg    30420
gaggacatcg acggccggtt cttcgtccgc acgcccgcgc aggagctcgt cgtcgagctg    30480
tacaaaccgc tcggccgccg ggtggagctc gggctcgagc ccggttcgta cgacgtccgc    30540
ctggatcgcg agaagacgtc gatgatcgcg aagacgaaga tcgacgacgg cagccgcgtg    30600
acgctcgagg cgcgccagtt cggcgtggcc ccgctcgagc cgacgcggca gcggggcgac    30660
caccagccga agaatcctct tgccgtgtcg ggccgcaacc gcgtcgagct gcacttcggc    30720
ggacacgcca gcgcgcagcc ggccatcacg tcgggcatca cgccggtgg tttcgtggcc    30780 ggcatcgggt tcacgcactg ggcgcgcgaa gacatcgggc tctacttctc gattctggcg    30840
accggcgcgg agctcgggtc gtcggtcagc ccagggccg tattctcggg cgccacgggg    30900
atggtctcga ttccgatcgg cgtgaaatgg aacccgttcg tgcgccagat gccgccggcc    30960
atcaagccgt acctggcggc gtcgatcggc cccgtgatcg gatcgtcggc gggatcgttc    31020
atcggcaacg gcaccgtgag caacggcgag ttcgccgccg tcacgccgg cggactcatc    31080 ggcggcggcg tcgacttcca catgggacgc cccttctcga tcggtatcac ggccggctac    31140
aactggatgt ccgacttctc gcggccgatc ggctcgcgcg acaactacag cggcgccgaa    31200
atcggcatca cgttcggctt cctgttcggg aagggcactc ggtaggcagg gtcatggaat    31260
tcttgtgagg ccggtcgggg atcgtgaatc actcatccct gatcgtgaat ccttcgatcc    31320
gtcgatcgtt caatccgtcg atccaggatc cgcggatcct ggatcgtcga tccgaggatt    31380
ctgggatccg aggatcgcgg atcagggatg agtgatgcgg gattgtcgac aggactccgc    31440
ttctatcaca acgttcgtca catcgcggaa cccgactata cgccttaagc gtatagtcgg    31500
gtggtgaagc ccgaacagta ccttcccctc acgcccgtcg tcttcgagat cacgctggcc    31560
ctcgcgggcg gcgagcggca cggttacgac atcatgcaag acgtcgaacg ccgtaccgac    31620
ggccggatcg tcctgcatcc cggcacgctg tatcgcgcgc tcagccgtct gctcgaccag    31680
aaactgatcg aagagctcga cgaaagtcct gtgccgggtg acgacgagcg cggcggtat     31740 taccgcttga cggcgctcgg gcatgccgtc gcgcgggccg aagtcgagcg gctcgccagc    31800
caggtcagcg ccgcgcggcg cgcgttccgg ggaggcggcg cctgatcact ttctaccgtc    31860
ttctgctcct cgcctatccg gcggagttcc gcgcccgctt cggcgccgcg atgcggcagg    31920
tcttcctcga tcgctacgcg gcgtcgcggc ggcgaggctc gctcgcgacg atcgccttct    31980
tcttccgcac cctcgccgac gtcgcgtcca acgccgtggc cgtccgcatt caacagagag    32040
aaaccatgaa ctggtcctcg atcggcttcg acctccgcta cgcgctccgc atgttccgcg    32100
gcaatccggt cttcacggcc atggcgatcg cggcgctcgc gctcggaatc ggcgccaaca    32160
ccgccatctt caccatcgtg aacggcatcc tgctcaagcc gctgccttac gggaaccctg    32220
aggccctggt gatggtgtgg agcaccaacg ccgtcgagca tcgcgaccgc gacaccgtcg    32280
cgccgctcga cttcgtcgac taccggaagg ccgccgcgtt cgagcagctg cacgccacgt    32340
acagcttcct cgtgggcgcg gcgctcgcca cgccgggagg cacggagcag atcgtggtga    32400
cggccgtcac cccgggaacg ttcgagatgc tcggccgcag cccgctcatg gacgcactt     32460 tcgccgacag cgacatcacg accggcgtcg tgatcagcca cggcttctgg cagtcgcgcc    32520
tcggggggcg cgcgaacgcg atcggccagg tgctgaacat cgccggacag ccgcgcacgg    32580
tgctcggtgt gatgccgccg gacttcgtct tcccttacaa gacgatgctc ggcccgtccg    32640
gcttcacgcg cacgcagacg gtcgacgcgt ggctgccgct gcagttcgtg ccgggcaaca    32700
```

```
gccgggcgac gggcgtggcc atgctctcgc gaagcgcgcg tttcctgtcc gttgcgggc    32760
gtctcaagcc cggcgtgagc gtcgcgcagg ccaacgacga gatcgccggc atcgcaaagc    32820
aactgtccgc ctcgtatccc gactcgaacc gtctcgtcgg cgcttccgtc gtgccgattc    32880
acgagcaggc ggtcgggagc atgcgccccg cgctcgtgct gctgctcggc ggcgtcggct    32940
tcgtgctgct gatggcgtgc gtgaatctcg cgaacatgct gctcgcgcgc agcagcgtgc    33000
ggcagcgcga gatggccgtc cgctccgcgc tgggcgccgg acgccggcgg ctgatccggc    33060
aaacgctcgt cgaaacggtg ctgctcgccg ggctcggcgg catcgtggcg ctcgcgatcg    33120
tctactggac gattcccgcc ttgctcgcgc tcgcgccggc ggacctgcca aggatcggcg    33180
aggtgcgccc ggacgtgtcc gtcctcttct tcacgttcgc gctgtcgctc gcgacgggcg    33240
tcgtcatcgg catcgtcccc gcgctcgcgg gcacgcgccc cgcgctccag caacgctgc    33300
aggcctcggg acgcggatcg accgccggac gcgggcagcg gcgattgcgg agcggcctcg    33360
tcgtcgccga agtcgcgctt gcggtcgtcc tcacgctcgg cgccggcctg ctgatccgca    33420
gtttcctgtc ggtgctcgcg atcgatccgg gcttccgccc cgatcatctg ctcacgatgc    33480
agatcgcgat cccgcagaac taccgcacag cggacgagcg gcgcgcgctg tacgacaagc    33540
tgttctcgag gctggatgcg ctgccggcgcg tgacggcctc cggcggcacg acgcggctgc    33600
cgctcgggag cacgaacgtg tcggccaagg tcgcgatcga aggccgcgac gtccccgccg    33660
gcgagttgcc ggaagtcgaa ttccgccgcg cgtcgcacaa ctacttcgcg gcgatgggca    33720
tccccgtcct tcgcgggcgc ggtttcacgc gcgacgacgg cccgaacgcg ccgtcggtcg    33780
ccgtgatcaa ccaggccgcg tcgcgcaggc tgttcgggac cggggatccc gttggaaagc    33840
gcgtcagcat cggaggcccg cccgcgccgg cggctcccgg cgcaccgtca ccatggtcga    33900
cggtgatcgg cgtcatcggc gacatccgtc acagcgggct ggaggacgcg ccggcgccgg    33960
agatgtacat cccgtcccag cagggccgc cgaccaaccc cttcctcgtg atccggacgt    34020
cggccgatcc gtcggtcctg gcggcgaccg tgcgcggcga ggtacaggcg atcgacaagg    34080
ggatcgccgc gtacgacatt cgtccgatgt cgcaggtgcg ttccgaagcc gtgtcgcagc    34140
ggcgcttcat gctgctgctc gtgagcgcct tcggcgcgct ggcgctcgtg atggcggcgg    34200
tcggcgttta cggcgtgatg gcgctgacgg tcagcgagcg gacggcggaa atcggcgtgc    34260
gcctcgcgct cggcgcgcaa cccgcgcgcg tgctgcgcga cgtcatcgtg caaggcgtca    34320
ccctcgcggc gatcggcgtc atgtcggggcc tgctgctcgc gatcgcgtgc atgccgctgc    34380
tgtcgacgca gttgtatgga attcgcccgc tggatccgcc gacgctgctc gcgattccca    34440
cgctgctgct ggcagtcgcg gccgtggcgt gctcgattcc cgcgtggcgc gccatgagga    34500
tcgaccccgt cgacgcactt cgcacaagtt agacgagccc acggcatcgg ccacgaagat    34560
cacgaagctc acaaagacca caaagaaaac aaagtttggc ttcgtgatct ttgtgacctt    34620
cgtggccttt gtgccgctg ccgtcggccc gtctcacact gtgacgatcg ttagaggagc    34680
agcgcttcca cgcggtgggc gtggaccatc ccctcgcagg gcgaccacgc gaacacggtg    34740
aagcggccgt cctgcgaggc gacgagcgcg acggcgtcct gctgatcgtg acgaactgc    34800
gcggccgaga ggtgccgcgt gccgcccagt gaagagggt ggaccgtcga cgggacgaag    34860
ccttcgatcg gctcggtgac cgtggtctgc tccaccggcg gcgagccccg ccttctcgtg    34920
atcttggcac cgaaggcgag cagctcctga cgatcggtca cgatcgtcgc gccgtcgacg    34980
gccgtcagac ccgcgatcca ctcgatcgca tgatcgagcg caccctgcca gatgtgatcc    35040
```

```
cgcttgtcgc agctctgcgt catcaactcc gcaagcccgg agaacggcgg attcagcgcg    35100
taggagatcg gagagacgat cgactcgcgc cagcggtccg tgccgccggg gacgacgagc    35160
agcagcccgc cccgtttgtg cgcgcgcatc gacaccgcga actggacgag gacgttcacc    35220
gaatcggtcc atgacgccgg cgtgtcgaag ccaaccagcg acgacagcag ctgcgggcag    35280
tcgggcagcg ccgacgctcc ctcgtcgacg atcttcacct ggtcggcttc gagcacggcg    35340
atgttcgcga acttggtgtg ctcgccgccc cgatgctgct tcaccacgag caggcccggc    35400
gccgcgacct cgagaacgag cgcgtgcggc ggcagcccgc gcgtggagcc ccagatggcg    35460
agcgcgccgt cgtggtgcga gacgccgaga tgaatgcccg ggcgctcgac ggccggcgcg    35520
accttggaca gcaccgacgg atgcagcggc agcggacgcg cgaagagcag cggatccgtg    35580
gtcgagtccg gcggcacgag ggccagcgac acgatcggga cgtagccctc ttcgcggcgc    35640
agactggtcc agaacgcggc gtcgatcaac gcctcgatcg actcgacgtc gggcagcggg    35700
accgccgtcg cgaggaagcc caccgcggcg tgctccagat agcgcgcgaa gcactcgcgg    35760
acccgttccg ctacggcccg gcgcgccggg tagtccgcgt acgccataat cgttgaatct    35820
tatgacacca cgcggcgccc tcgggatcct ggcgacggct gcggccgcgg tcgggctgat    35880
cgcggtcatg gtcggctata ccaggcgggt cgaaacggat ttgttgaagg gcacggcctc    35940
gcgcgcgagc gtccggctgc tgaaggaccg cgcggcgatc ccggccttca ccgtgcccga    36000
cctcgcgggc cgccagatct cgaccgcgtc gctccgcggc aaagtggtgc tcgtgaattt    36060
ctgggcgacc tggtgcccgc catgccgtca ggaaatcccc gacctcgtcg cgctgcaggc    36120
gaagtacaag gaccacctgc agatcatcgg gatcgcgcag gactcgggct cgccggaaga    36180
cgtcaaggcg ttcgccgaca aatacgggat caactacccc atcgtcctca gcaccggcga    36240
gatcgagaag ctcttcccgc cggtatcggc gctcccgacc tcgttcttcc tggacaagga    36300
cggcaagctc gcgcagaagc acgtgggcat gctcaacgcg tcgctcacag agctcgagac    36360
gcaggcgatc gccggcatca atcccgatct ggaaatcgtc gacgcagaag acgaagacaa    36420
ggcgcgtgtc gcgagcgccg cgcaggcgaa caagattcca ggcatcgatc tcgcggcgct    36480 tccccggcc acgcgcgcga aggtgctcga agcgctcaac acggagcact gcacttgcgg    36540
atgcggcctc acgctcgcgc agtgccgcgt cgacgatccc agctgtgacg tcagcctccc    36600 ggtgcgcag gcgctcgtca agaaactcac ggcggccaag tgagcggaac ggagcgagcg    36660
gccgtgcgcg agcgtagtgg agtgaacctg agcgaggggc cggtgggcac cgccgaaggc    36720
ggccccgggc gccaaagatg aatcgcgacg cgctgctgac cgaactccgc gcgattctcg    36780
gcgatcgcct gtcgaccggc gattcggtcc gcgagcatca cagccgcggc gaatcgcatc    36840
acgcgcccgt ccttcccgac gccgtggcgt ttcccgcctc gaccgccgac gtgcaggcca    36900
tcgtcaaggc gtgcgccgcc gcgaagtgcc cgatgacgcc gttcggcgcg gcagctcgc    36960 tcgaagggca tgtgatcccg ctgaagggcg gcatcagcat cgatctgacg cgcatgaatc    37020
gcgtgctccg cgtcagcgtg gaggacctcg acgtcacggt cgaagcgggc atcacccgca    37080
agcagctcga caagcagctg cagacgaccg ggctgtggtt cccgctcgat ccgggcgccg    37140
acgcgacgat cggcggcatg gcggcgaccc gcgtcgggg acgacgcg gtgcgctacg    37200 ggacgatgcg cgaggccgtg ctcggattga cggtcgtcac cgcggacggc cgcgtcgtga    37260
agaccggctc gcgcgcgcgg aagtcgtcgg cgggctacga cctcacgagg ctcttcgtcg    37320
gcgcggaagg cacgctcggg atcatcacgg agctgacgct gcggctgcac ggccgtccgg    37380
aggcgatcgc gtcggcgaca tgctggttcg agtcgatcga agacgccgtg aacgcggtga    37440
```

```
tcctgatcgt ccagctcgga attcccgtcg cgcgcgtgga gctgctcgac gaaacccaga   37500
tcgacgcgtg caaccggcac tcgaaactga accggcaggt cgcgccgacg ctcttcttcg   37560
agttccacgg catgagcgac gccgcggtcg aggagcacct gacggcgacc gaggagatcg   37620
tcgcggacca tcgcgccggg gacttcctgc gcggcacgtc gcccgacgag cgcgcgaagc   37680
tgtggcaggc gcggcacgac tcgtactacg cgtcgctcgc gctgcgtccc ggcgcccgca   37740
gctggacgac cgacgcgtgc gtgccgatct cacgcctcgc ggactgcatc cgcgagacca   37800
agaaggacct caccgattcc cctctcatcg gcccgctcgt cggccacgtc ggcgacggca   37860
atttccacct gctgattccg gtgcacacgg actcgcccga ggagatggcg gccgcggagc   37920
ggctcacgag ccgcctcgcc gcgcgcgcga tcgcgatggg cggcacgtgc acgggcgagc   37980
acggcgtcgg gatggggaag atcaagttcc tcgaagcgga gcacggcgag gacgcgatcg   38040
ccgtcatgcg cgccatcaag cacgcgctcg atccgcacaa cctgatgaat cccgggaaag   38100
tcctgccggc ggagtcctga tgaaggcggc gcgcgtcctg accgtcgcgg gtgcggtcct   38160
gctgagcgga tgcagctcgc ccgccagcat gcccgcccgc ccggcggcgc ccccgacgtt   38220
caacaaggac atcgcgccga tcgtcttcga gcactgcgcg ccctgtcacc ggccgggcca   38280
ggcggcgccc ttcgcgctgc tcgactacaa ggacgcggtc gagcacgccg agaagatcgt   38340
caggatgacg aaggcgcgcc acatgccccc gtggctcccg gagccgggct tcggcgagtt   38400
cgagggcgag cggcggctga ccgacgcgca gatcgcgacg atcgagcgct gggcgaacga   38460
aggcacggtg gaaggcgctg ccgcggatct tccgaaaaag cctgagtggc ccgaaggctg   38520
gcagctcggg aagccggatc tcgtcatcac gatgccgcgg gcctacaccg tcaagccgtc   38580
cgacgaggat gtcttccgca acgtcgtgat gcgcgtcgcg cttccgtcgg gccggttcgt   38640
gcgcgccgtc gagttccgtc ccggccccgc gccgatcgtg caccacgccg tcatcagcat   38700
cgatcgcacg cgcgcctccc gccgccgcga cggcgcggac ggacaaccgg ggtacgacgg   38760
gatgatcacg cagggcgcgc agaacccgga cggccacttc ctcggatgga cgccaggccg   38820
cggtccgatc gtcgcgccgg ccggcatgcc atggcggctc gatcccggca gcgatctggt   38880
cgtgcagctg cacctcctgc cgcagagcga gcccaggcc gtgcaggcca gctcggcct   38940 cttcttcacc gacacgcctc cgcagttcgt gccgctgatg gtgaagctcg cctcgaaggc   39000
gatcgacatc cccgcgggcg agacggctta cgcgatcagc gatacctacg tcctgcccgt   39060
ggacgtggac gtgctgagcg tgtatccgca cgcgcactac ctcgggaagg aaatgcaggc   39120
gtccgcgaca ctgccggacg gcacgacgag accgctcctc tcgatcaagc actgggattt   39180
ccactggcag caggagtatc gctaccggac acccatcacg cttccccgcg gacgacgct   39240 gtcgatgaag tacacgtatg acaactcggc ggccaatccg cacaatcctc acaagccgcc   39300
gaagccggtc gtgtacgggc cgaactcgtc cgacgagatg ggcgacctct gggtccaggt   39360
cctcccgcga tcgcccgtgg acgccgccac cctcgtgcgc gggtttgccg agcgcgaaac   39420
gcgcgcgaac gtcgccggcg cggagctgct cgtccgccgg gtgccggagg acgcgaagaa   39480
ccaggcgttt ctcggaagca gctacgtgga gtcgggccgc ttcgccgagg cgatcgcgcc   39540
gctcgagcac gcgctgcggc tcgacccgcg ctccgcgaac gcgcacaacc agctcggcgc   39600
cgcgctgttc tcactgggac gcgcgcgcga ggcgatcccg cacttccgtc aggccgcggc   39660
gctctcgccc gacgacgagc ggatgcagtt caacctcggg tacgcgttga atgccacggg   39720
acagccgtcc gacgccgcgc tggccttccg gcgggccatc gcgatcaacc cggagttcgg   39780
```

```
agaggcgcac gacagcctcg gggtgttcct gctctcacgc aaccagctgg cggaagcgat    39840
cgcgcacctg acgaaagccg tcgctctgct gccgaactcg gccgaggcgc acagcaatct    39900
cggcggcgcg ctcgcgaacg cgggaaagat cgacgaggga atacaacacc tccggcgagc    39960
gctcgagctg cgccccgacc acgaggtggc gcgccacaac ctcgcgatcc tcgaacagcg    40020
ggcaaaacgg tagaaatttt gtcgggaggc ctgccgggga tcccgaatca ctaatcgctc    40080
atccgggatc cttcgatccc tgatcgacga tctccgatcg acgatctccg atcgacgatc    40140
cgacgatcgt ggatctgcga atccgaggat ccagggatcg aaggatctgc gatcagcgat    40200
tagtgattcg ggatccgata caatcccgcc ccatgcgcat cacactcatc gcgatagcag    40260
tttgcctgtc ctggacgacc ggcgcgtttg ctcaaggacg cggcggcggg caggggcccg    40320
gcggccgcc gcagacgatc gaggcccgca cgcagggctt ccagagaatc gacggctaca    40380
tgccgctcta ctgggacgag cggaccgggt cgctctggat ggagatcggg aagttcgaga    40440
ccgagatgct ctggtccacg tcgctgtcgg ccgggctcgg atcgaacgac atcggcctcg    40500
atcgcggcca ggccggccag gggcgcgtcg tgaagttcca gcgcatcggc ccgcgcgtga    40560
tgatggtgca gcccaattac acgtggcgcg ccgacagccc gaatcccgac gagcgccgcg    40620
cggtcgagga cgcgttcgcg aaatcgatcc tgtgggcctt cgcggtcggc gccgagagcg    40680
acggcaaggt cctcgtcgac gcgaccgact tcttcctgcg cgacgtctac aacgcggcgc    40740
cgcggctcgg cggctaccgg attgatcgga accgagcgc gatcgacatg ccgcgaacga    40800
aaggcttccc gaagaacacc gaggtcgaga cgatcctgac gttcaccaac gaaggcggcg    40860
ggggcgcgg cggcggcgga cgcggcgcg ccggcggcgg acgcggaggg ttcggcggcg    40920
ggatgttctc gggctccgtc ggcagcgtca cgcccaccgc ggactccgtc accctgcgcg    40980
agcatcagtc gttcgccgaa ctgcccgacg gcaactacaa accgcggtac gacgaccgc    41040
gcgcgggcta cggcggcctg cagtacatgg actatgccgc gccgctcggc tcgccgaacg    41100
tgaagcggtt cgtccgccgt caccggctgg agaaggtgga cccgacggcg cgcgtgagcg    41160
atgccaagaa gccgatcgtg tactacgtcg atcgcggaac gccggagccg attcgtaccg    41220
cgctgctcga aggggccgcg tggtggaacc aggcgttcga ggccgcgggg taccgcaacg    41280
cgttccgcgt cgagctcctg cccgcgggcg cggacccgat ggacatccgc tacaacatga    41340
tcaactgggt ccaccgctcg acgcgcggct ggagcaccgg cgcgacgatc tcggatccgc    41400
gcaccggcga gatcatccgc gcaaccgtca cgctcggatc gctgcgcgac cggcaggatt    41460
acctgatctt cgaaggcctg ctcgcgcccct acaagaacgg caccgagaaa cccgacatcc    41520
tcgagaagac cgcgatggcg cgcatccgcc agctcgcggc gcacgaggtc ggccacacgc    41580
tcggcctcgg gcatcagtac tacaacagca ccaaggggcg gatctcggtc atggactatc    41640
cgcacccgct cgagaagctg aacgcggacg gcacgatcga tctctcggac gcctacaccg    41700
tcggcatcgg accgtgggac aaggtcgcga tcgcgtacgg ctaccaggat ttcccgcagg    41760
gcaccgacga ggccgcctcg ctgcggaaga tcctggacga ggcgtggcag caggacctga    41820
tctacatgac gaatcaggat ctcgactcga cgccgaagtc ggaccagtgg aacaacgggt    41880
tcggcctcga ccaggccgcc gagttgaacc ggatcatgaa agtgcgacgc gcggcgctgg    41940
accgcttcga cgagaccgtg atcaggaaag acgcgccgat ggccacgatg gaagaggcgc    42000
tcgtgccgct ctacatgtat caccgctacg cggcgcagg cggcggcgtcg atggtcgcgg    42060
gccaggacta catctacgcg atgcgcgcg acgaccgggt cgcgacgcgc tgggtgccgg    42120
ccgcgcagca gaaggccgcg ctcgactcgc tcgcggtcgc gctcaagccg tcggagctcg    42180
```

```
ccttgccgaa agcggcgctc cagaagatcc cgccgcggcc gtcgggctgg ggcatgcacc    42240
gcgagctgtt cacgcgctac acgggcgaca ccttcgaccc gatcagtccg acggcggcg    42300 cggcggagat gacgatcggc ttcctgctcc agccggatcg cgccgcgcgc atggtggcgc    42360
agcacgccat ggatcccgcg ctgccggggc tcgacgaggt gatccgctcg ctgcgcaacg    42420
cgactttcat ggcgccggcg gcgacgccgt acgagcagga gatccggcgc gcgacgtcac    42480
gcgtcctcgt ggagcaggtc atggcgctcg ccgccaacgc gtcgatgccg caggtccgcg    42540
cgatcgcgac gctgcagctc gagggcctgc agaaccccgg catgccggcg ccgcccacgc    42600
gcgacgacac ggcgttccgc acgctgctcg cgggcgacat caagcgcttc ctcgagcgcc    42660
cgatggcgcc cgtcaccgcc ccgacgacgc ccgacgcgcc gcccggagcc ccgatcggcg    42720
atcccggcat ggattggctc gcgcgtcccg cgtggtcgtg cggctgggat gatcgcatcg    42780
gcggctggaa gcagtagccg gatgccggac gtcctcgtgc gagtgagggg cgatctgatg    42840
ccgctcgtgt tgcatcgaga ggcgacaatc accgcaagg gcgcgtggat ctccggcatc    42900
gcccccaacg aggtatccga ggcgaccgca ggcgtccgct gcgcgtgcgg ccggatcacc    42960
acgctgacga gccccgtcac gttcgaggat cacgatcccg atcgcgccga tcgcaggtca    43020
tggttccgct cggtccatcg aggggcgtgc gccgcatgcg cggccccgct ggacgtcgag    43080
ctcgtctacg tgtacggcga tttcacgatc acgccggcgg accgggaggt cttcagcctg    43140
gaggccatca ccgaacgagg cggcaccctc gcccgctaga gcctttcaa aagctctgta    43200 gcttccgcct tcaggcggaa atcgagcggt agaatagttc tgcgcgatgc cggtccccgt    43260
caaagtgaag atcgcgggtc agatggtccc cctggtcttc aacgaacccg tttccatcac    43320
ccatctgagc gacacgacgc cgaccgaggc gttcgcgccc gtgcgctgcg cctgcgccgt    43380
cgtcaacgtg ctgcaagccg atgtcgcctg catcgacacg tgctgccggt cgcgccacgt    43440
gggcacgtgc gaggcgtgcg gcgacgcgct ggagctcgag ctccaataca ccgtctcgga    43500
cgagcgcatc acgctggatg tcgtgcgcga gaagcgcggc acgttggtgc ggtgaagtac    43560
ttgggaggac agtcgtcgat cccgaatcac ttatcgctga tcgaggatcc aaggatcctc    43620
cgaaccccga tcagggatca tcgatccacc gatcaaggat ccaggatttg tggatcgacg    43680
gatcgatgga ttgacgatca gcgattagtg attcaggact cctgacaggc catggtctca    43740
ttcacccgca tcagcaagca gtacggcaag cagatcctct tcgtcgacgc ttcgttccag    43800
ctgaatcccg gcgagaaggt cggcctggtc ggcccgaacg gctccggcaa gacgacgctc    43860
ttccgcatga tcgtgggcga ggaagcgccg gacgaagggg acgtgtcggt cccgaagaag    43920
ctcacgatcg gctacttcaa gcaggacgtc gaggagatgt cgggccggtc cgtgctcgac    43980
gagacgatcg ccgcagcgg ccgcgtgggc ctgctccacc acgagctcga ggatctgaat    44040
cacgcgatgg cggatccgga tcgcgccggc gacatggaca ggatcctcgc gcgcttcggc    44100
gaagtgcagg aagagtacga gcacctgggc ggctacgcgc tcgaggcgca ggcgcgcgaa    44160
gtgctccacg gcctcgggtt cgaggacgac cggatcgacg gcgacgtcgg caacctgtcg    44220
ggcggatgga agatgcgcgt cgcgatggcg cgcgtgctcc tcagccggcc cgacatcctg    44280
ctgatggacg agccgacgaa ccatctcgac atcgagtcga tcatctggct cgaggagttc    44340
ctgaagacgc tgcccggctc cctgctcatg acgtcgcacg accgcgagtt catgaaccgc    44400
atcgtctcga agatcgccga aatcgacggc ggcgagatca ccgtctactc ggggaactac    44460
gatttctacg agcgggagcg cgccatccgc gaggcgaacc gcgaggccgc ctacgcgcgg    44520
```

```
cagcaggcga tgctcgcgaa ggaacagcgg ttcatcgagc gcttcgccgc gcacgccgcg   44580
aaagccgcgc aggtccagag ccgcgtgaag gcgctcgaga agatcgagaa gatcgagctg   44640
ccgaagaagc ggaaagtcgt caagttcgac tttcgccagc cgccgcgctc gggcgagcag   44700
gtcgcgacgc tcgaaggcgt cacgaagcag tacggcacgc gtgtcgtcca cgaccacatc   44760
aatctgtcga tccgccgcgg tgagcggtgg tgcgtcatgg gcaagaacgg cgcgggcaag   44820
tcgacgctgc tcaagatgat cgcgggcgcc gtgcagcccg acgaagggac cgttacgctc   44880
ggcgccagcc tccagatggg ctatttcgcg cagcagtcgc tcgacatcct cgaccccgcc   44940
ctcacgatcg aggagcagct gcagaaggac ttcccgcacg agggcatcgg cgtcctgcgc   45000
aacctcgccg gcgcgtttca gttctccggc gacgacaccg acaagaagat ccggatgctg   45060
tcaggcgggg agaagacccg cctcgtgatg gcgcgcatgc tcctgaaccc gccgaacttc   45120
ctcgtgctcg acgagccgac gaaccactc gatctcgcga cgaaggaaat gctgctggag   45180
gcgctccacg acttcgaggg gacgatgctg ttcgtgtccc acgatcggga gttcctgaag   45240
ggcctcagca accgcgtcct cgagctcggc ggcgagagcg cgtcgaggc gcagccgcac   45300 gcctatcccg gcacctacga ggaatacgtc gcccgcaccg gccacgaagc gccgggcgtt   45360
caccggtaag acggtcccaa gtccagggtc ccaagtcccg ggtcccaagt cccgggtccc   45420
aagtcacggg acccgagacg agggacgggg acgagggaca ctcgcgaaaa aaaagaggg   45480 gtgggccaca tggcccaccc ctcttttcgt ttgacgcgag tacttctaga actgcacgcg   45540
aatcgtgaac tgaaggacgc gctgatagtt gccgttgatc aggttcgtcg tccagctgtt   45600
cgccgcgccc aagccggcgt tcctgggcag gtcgcgtccg ggcgcgagga ccgtccccac   45660
cgcgccgggc gcgagcgtcg tgtcgcccgc gttcgcgacg tactgcgggt tgcgcagcgt   45720
catgtcggtc gggctggtga agttcgcgtt cgtttggcgg ccgttgacga acgcctggtt   45780
gaacgcgttg tacgcgtcca cgcggagctg cagctggcgg ttcccgccga ggcggatgtt   45840
gcgcgcgatg gcgaggtccg tccggtgcgt cgcgcacccg atcagcacgt tgcggcccga   45900
ctccagaccg acgctgttgt agcccggccc ggtgacgttg gcggtgtcga actgcacgta   45960
ctggttgctc gagcagccgt cgtcggtcgc ggacttgtag acgatacgcg cgccgtagtc   46020
cggcgaaccc gtcaggttcg tgttgctgcc attggcgttg tagctgaagc cgaggtcgta   46080
ccggttgccg gagctgccgg tgtagatccc cgagagctgc cagtcgttga tgacataccc   46140
gagcgctttc agccccgagt tgtcgctcga caccttcggc aggttccaca cccagttggc   46200
cttcagcagg tgacgctgga ggttcagcat gctgttcaga tcctcgtacg cctcctggtc   46260
gctgcgcacg ctgatcgaac cgtcggagtt gtgcaccaga cgcttcacca ggccggtgtt   46320
cccttccaac gagaggctca gcacgtagtt gacgccgaag ctgaaccgt tgcggaaccg   46380 gcggttgaag ttggtctgga tcgagtggta cgtgtcgctg aactcggtcg tctgctgatt   46440
gatgttaccc agcccccgat acgccctcag caacgcggtc tgcgtgtagg cgccggcgcc   46500
cggcaccgtc gccggtgcgt tcgtcgggtc ctgattctgc ggcaggtatg cggcgccgat   46560
gtcaatcgcg ttgagattgg tcggcgtgcc gttctgcggc gcgctcaggc ggttgtagcc   46620
gtggttgccg acgtaggaga cgtccaccac ggatgccac ggcagcgtct tctgacgcc   46680 cgcttcccac tgcgcggagg tcggaaccttt cgcgtcgtac tggaagatgt tcatgccggg   46740
gaccggcagg aagctcgtct gcggattcag gttctggaac tggccggtcc gcaggtcgat   46800
cgacgtcgcg atcggcgggt tgccggggat cgagaacacc gtgttgccgt cgggacggtc   46860
gtagaagatg ccgccgccgc cgcggaagat caggtcctgg ttcccggtca tgtcatacgc   46920
```

```
cacgccgaag cgcggcccga ccaccagggc cggccaggtg tagccgtact tcgagatgcc  46980
gtcgcccgcc cgcttgatgg cgttcagcgg attgccgacg cccggcacgg gcgtgccgat  47040
cgccgcctgg ctgttggccg agttcggcaa caccaggatc tggccggtga gcgggttcat  47100
ggcgttcttg acgttgcccg agcaggtggc cgcgccgttg ttgcagcccg cgacgtagag  47160
cacctgcgcc tgacccggga cccactggcc ggggaagaag ttcgacatct gctggaactg  47220
gtcgtactgc ggctgctggc gcgtgaagcg gacgcccgcg tccaccgtca gccggctgtt  47280
caccttccag ttgtcctgga tgtaggcctc ggtgttgttg tagagcatgc tgccctcgac  47340
gaacgtcgag ccctgcgtgt agcggcgaaa cacgcccgcc gccgcgttgg cgtagccgaa  47400
cgaggtgtcg agcgcgttgt tggtgtcgtt gtcgaattcg accgcgccct ggaacgcggt  47460
gccgccgatg ttctgcgcct tgaagctgtg gttgttgtag aacccggtct tcaaggtgtg  47520
ccggccggcg atcttcgtca agctgatcgc gacgtcctgc gtccggttga tgttcagcca  47580
gccgggatac tgctggttcg gcggcgcggc gccgatgcgg ccgccccacg agaacgtcgg  47640
cggcaggttc atgcgcgtgc cgtcccagaa gggcggcttc acgtcctgca gcacttcgta  47700
cgcgtacgag ccttcaggga ccttgcccgc gtcgggatac agcagcggga acgcggcgag  47760
gccgttgagc cggttcgacg aatcgttggt caggatgccg ccgttattgc ccccgtgag  47820 ctcgttgcgg atgaacccgt aggttccctc gaggaacgtc gacggcgtca gcatgtagtt  47880
cgcggtcagc gagtacttgg tgatgaacgg gtacgggaag tacgagtccg tgtatccggg  47940
aaggccgttg ttctgaacgc cgcccggcgt cgtcagcgcg cgctgccgat caccgccgta  48000
cgtaaagctg atacgcgtct tcggattgag ctgatagtcg aggcggaccg ccggctgctg  48060
gcgcagctga tcgacgatcg ggagcgggtc gccgcccgtg ccaccgagct cgtagttgta  48120
gttgctgccc ggcgtctgcg cccggttggg cgacgggtag cggttcagaa tcgcgatgcc  48180
gggcgcccac agcgcgcccg cggggatctt tccgatgacg ccgccgtcct ggaagcaggc  48240
cgtcgtgtcg gacgcgctac aggtgcccga gaccgcgggg ttcttgatgt acggatacag  48300
ggcgccgttg ttgtcgagcg tctgcgagaa gtcgcccgcg cgctccgcgg ccgtcggcac  48360
gcggaaccgg atcgggttgc cgttgttgat cgggttgctc gtcggaacgt actcgtggct  48420
gtagaagaag aacagcttgt tgttgccgcc gggctttccg atcggaccgc cgatcgagta  48480
gcccaggttc ttcgacttcg ccttcggctt cgggtcgccg ttcagctcgt tgaggatgcg  48540
gatcgagttc cagtcggagt tctgccagag ctcgtaggcg gatccgcgga agcggttggt  48600
gccgctcttc gacacggccg tgatctgaag gccgctcgac cggccgaact cggcctgata  48660
cccctgcgtc aggatcttca cttcggcgat cgactcgatg ttcaggttga tcatctggcc  48720
gttgttgccc gtgtccatgg ccgagatgcc gtccatcatg atgttgtcct ggctcgagcc  48780
gcccatgcgc gcgccgttct ggttggcacc gccgtcccgc acgccaggcg ccaactgaat  48840
gaggctcgtg aagttgccgt gattgatcgg caggttttcg acctgttcgg tcgtgaccgc  48900
gaacgatcgc tcaccgctct gtgcctgcac gagcggagac tcggcgacga cggtgaccgc  48960
ttcggtctga ccgccgactt cgagcgtgat tggcggcacc gacgcgcggt cgccgccgct  49020
gaccggcacg cctttgcgct gcgccgtctt gaagccgctc atcgtcactt cgaccgtgta  49080
ggtcgcggcc gtgacgttgg ggaatgtgta gttgccgttg ctgtcggtga ccgccggcgc  49140
ggacttcgta ttccgcgctt catcgatcag gaccaccgtc gcgccgggaa cgacgccgcc  49200
ttgcgcgtcc ttcacggaac ccgtgatgtt tcctgtcgtg atctgtgccg acgccggtac  49260
```

```
aaccatggcg ccgagtagca gcaggcccgc cgcaatcgat ttcagatacc cgtacttcgt   49320
cagactcaag cgatcctccc ttgcaagccg gcggcagtcg gaaaccgccg ggcattacac   49380
cacccacttg agggcgggct ggaggctacg ccctatgcgg ctggggtgtc aagacaaacc   49440
gtcatatgcc ccacaacccc tttcgatgcg tgtttgtggt aagcccggca attcgccagc   49500
taaggcgata tttgtcagct atttactgca agtatgaggg ggacgaatga ggcgcccgga   49560
agttgccctc ggccgcgaat tccttactgt gggttacgag cttttagttcg cgaggcgaat   49620 gatctctgct cgaggccggc gatcgcgagc gatatcggat cgccgcccgc cgcgacgtcg   49680
cctgtcacgc cgtacaggat cgccggagcg gggacgcccg gagacgccgc cgcgtgggcg   49740
ttcgccacgc tcgattcgag gtcccgcaga aacggatcga cgatgcggtc gtgggcggcc   49800
gtgatgatga gatggatcga atccggattc tgtaatcgat cgatctccca tccacgcgcg   49860
gtcatgccgc ccgcgatggc gtccatgggc gggccgtcgg atccgaacgc gaacacgctg   49920
atcggcgggt cgccgaacac gcgcagcccg agacgcgcga tgccggcccg caatcgtgtc   49980
gcggtgtcga gcgcacgctc gacgagtcgg ccatacccgt cctcgccgag gacatgcagc   50040
gcggcccacg ccgccgcgat cgcgccgccg ggccgcgtgc ccaggacgcc ggggctcgcg   50100
aagacgccgc ccgaccactg gtcggtcgcg aagaactgat accgccgcag cgccgcgtcg   50160
cgatagagca cgacggacgc gcccttcgcc gcatacccga acttgtgaag atcgatcgac   50220
agcgacgtca cgccgggcac gcggaaatcc cacgcgggcg cggtcccctt catacgctcg   50280
agaaacggca gcacgaaccc gccgagcgac gcatcgacgt gcagcccgac accccgcgcg   50340
cgcgcgatct cccccagctc cgcgatcgga tcgaccacgc cgtgcggaaa ggacggcgcc   50400
gacgcgacca gcgcgatcgt gtccgacgag cacgcgcgat ccatcgcggc ggcatccgcc   50460
ctggaatcgc cgccgcactc cacgacgacg ggctcgagat cgagatacgc cgcggccttg   50520
aggaacccgg gatggaccga gcgcggaagc acgatctcgc accgcgcgcg cggccccgc    50580 tccgctcgcg cgcgatcgcg gtacgccttc atcgcgagga tgatgctctc ggtcccgccg   50640
gacgtcatcg cgcccgccgc ggacgcgtcg cgcacgcgcga gatccgcgac gatcgcgacg   50700
acctcggact cgagcgccgc caggctggga aacgcgcgtg aggacaggcc gttcgcggcg   50760
agatacatcc cgtacgccga ccgcatcagc gactcgtgct cgtcgcccgc gtgatagacg   50820
agactgaacg atcgcccttc gcgccacggc cagtcgcccg cctggcgcga cgcgagatcg   50880
cggagcacct cctccgccgc gagtccggtt gcgggaaggc gccggctcat accacctccg   50940
ccgcgatgga tcgcgcgggc gcgtcggggt tcagcgcgac cgcttccacc gtccgcgcga   51000
acgcctcgac gatcgccgcg gcgcccgcgg gcgtgaacac gtcggcgtca tactcgagac   51060
gtcccgagag cgcgccgttc gattcgtaca ggtggaaggt ccagtcccgc ttcgcgccgt   51120
cattgtcgta ctcgaggaat tcgacatcga gcgcggcgag cgacgtgcgg tatctcgcga   51180
ggcttcccat ctcgttgtgg aggatgagca cgacggggag cgacggcatc tcgccggact   51240
cgccggcgag cgcggacgcg agcatcgcga acggcagttc cgcgagcgcg agcgcgtcga   51300
gcgcggcgtg ccggacgcgg cccagcagcg tccgcgccga cggatcgccg tggagatcga   51360
tccgcaccgg cagctggttg atgtagcagc ccacgacgtc gcgatcctcg gggcgcgcgc   51420
ggttcgcgct gaacgtgccg aggcagaagt cctcgaggcc ggtcatgcgg gtgacgagga   51480
cggccagcgc ggtcatgagg ctcgcaaaca gcgtcgcctg ttccgagcgt ccaggcgcg    51540 cgagcgcggt cccgatctcc gccgggatcg cgatcgcgcg attcccccg cggaacgacc    51600 gcgccgccgg acgcggcctg tccaacggca gcggcagcgg gggcagccgg ccgccgagca   51660
```

```
cacgggtcca ctgcgcgatc aggtcctggc gccgctcacc gcggagacgc tcgcgctgcc    51720
agcggacgaa atccgcatac gtcgatgccg gccgcggaag cggatcgggt tgcgcggcag    51780
ccgcggcggc gtacagagcg agcccgtcac gcagcaggat cggcagcgac gcgccgtcgg    51840
ccgcgaggtg gtgcgccgaa atgaggagtg cgtgatcgtg ggcgtcgagc cgcagcaggc    51900
gcgcgcggaa catcggatcc gccgccggat cgaacggcgc cagcgcgaac gcacgcgcgc    51960
gctcgtcgag tgcctggtca cgttcacgat cgcctgcaga gagaacgtcg agcggcagcg    52020
aaaacgccag cggcggcgtc cgctgcgtcg tctcaccgcc ggcggtctcg atgctcgcgc    52080
gcagcatcgc gtgccgcgcg acgagcccgt cgatcgcgcg cgtgaacgcc ggcacgtcga    52140
gcggcccgcg cagccggatc gccgccgcga ggttgaacaa actgtgcccg gggttcgcgt    52200
ggaccagccg ccagattggc agttgctgcg gcgacaggtc gaacgcgtcc ggcgattcgg    52260
atcgcgaggc accgacgtcc gccacggccc cgcgtcgatc gagcagcgac ggcaccagct    52320
gcgcggccag ctccgtgacg gtcggccccg cgagcagccg gaccgacgag acgtcgatct    52380
ccaaatcggt gtgcagccgc gcgctcagct ccaccgccat cagcgagtcg agcccgaggc    52440
tcgtcatcgg aaccgcgcga tcgacggcct cggccggcat gcgcagcacc gccgcggccg    52500
ccgtcgcgat ctgatccgcg acgagcgcgg tctgctcttc cggcgacgcg cgtcgcaca    52560 cgaggctcgc cagcgatcgg cgtccggccg actcgctcgc cgcgccgcca aattccgaga    52620
aacgcggcgg aacacccgat ggcagccgcc gctcccagtc gaccgccatg atcgaggcgg    52680
gcggcccgtc gagccgcagg agaacgccga gcgcgcgcac cgcgtcggca ggcgcgaggg    52740
gcggcaggcc ctgttcgacg aagtagtcgt gcagccacgc gcggcgcgcc acctcgccga    52800
tgtccgcaat cggcgaccac gccaccgccg tcgccggcag tccctgcgac cggcgatact    52860
cggcaagccc gtcgagaaag gcgttcgccg ccgcgtagac gccctggccc gcgcttccga    52920
accacgccgc gatcgacgaa tacacgacga agaagtcgag cgcgcgcccc ttcgtcagca    52980
cgtgcaggtt ccacgcccca ctcaccttcg cgcgccaggc cttcgcgaag gtgtctgcgt    53040
cgaccgccgc cagcgtcgcg tcggcgtaag cggccgcggc atgcaccacg ccggcgagcg    53100
gcggcatcga cgcgtcgagg tcgcgcaggg cggccgcgag atcgccggca cgcgcgacgt    53160
cacacgacac gagcctgacg tccgcgccgc gcgggcgcat cgcgtcgagc gtcgcgcgat    53220
ccgagtcgct gacgcggccg cggcgcgaga cgagcgccac gtgccgcgcg ccgcgctcga    53280
cgagccaggc cgcggtcgcc aaccccagtc cgctcgttcc gcccgtgacg agatacgtcg    53340
cgtcgccgcg caggcgcggg ccttccgtgt ccgagacgtc caccctcacg ggcgcggccg    53400
gttccggtac gagcaccagc ttgccgacgt gctgcgcctg cgccatcaac cggaacgcgt    53460
ccgccgcctg ccccagggga aacgcgcggt gcggcacggg cgcgagaccg cggtcattga    53520
cgagccgcat cgccgcgcgg aacatcgccg ccacggcgtc cggatcggtg cgcatcaact    53580
gatcgagatc gaacgccgtg accgtgagcc ccttctggaa cgcgcgcaag tcgacgatc    53640 cgccggtgta gatgttggcg atgtcgacga gccgtccgcg cggacggagc accgcgatgc    53700
tccgcggcag cgtggacgcc ggaagcgtgt tcaggacgat gtcgacgccc gcgccgcccg    53760
tcgcggcgag tgtctcgtcc gcgaacgcgg tggacctcga gtccatcacg tgcgcgaccc    53820
cttgctgacg gagcagggcg cgcttcgcct cgcttccggc cgtcgcgaac acttcgagat    53880
cgagcgcgcg cgcgatggcg attgcggcct gccccacgcc gcccgtcgcc gagtggatca    53940
gaatgcgctc ccccgcgcgc gcccgcgccg cgtcgcagat gaccgcgtac gccgtgaggt    54000
```

```
acgcgatcgg cagcgtcgcg gccgcctcga acgtgatgcc cgccggcttc gccgcgacgt    54060
agcgcgcgtc ggcgaaggcg aacggtccga aacacggcgc ggcaatcgcg atgacgtcat    54120
cgcccgggcg gaactcggtg acgttcgctc cagcggcgac gacgcggccg gcgcactcgc    54180
ctcccagcga ctgcccgccc ctgatgcgct gcaggctctc gccgtcgatc agcccgagcg    54240
tcttgacgac gtccttgaaa ttcaatccgg cggcctcgac ggcgatgcgc acgtcgtccg    54300
gtcccggatc gcgcgtcccg ccgtcgacga actcgagact ctcgatcaga cccggtgtcc    54360
ggatcgcgag gtggtacggc gcgtcgcccg cgggacggct cagcgccgcg cgggtgattc    54420
gcggcaccca ccgccgcccg ttcctcagcg ccacttccgt ttcggcatcg ccggacgaca    54480
attccgcgag caacgcgtct ccgtcgacgg cctcgtcgtg tccaacgtcg atcagacgac    54540
cgcgaagggc gggatactcg ttggcgacga cacggccgag cccccacagc gcgaacggcg    54600
gcatcacgct gacgggctcg tcgtctatgc ggcacgcacc gcgcgtgacg acgcacagcg    54660
tgacggctgg gtcgcgtgac tggatcgtct ggacggcacg aatgagatcg aggcactcgt    54720
cttcgagcgc ggcgtccggc gcctcgctcg atcggttcaa cgcgagatac acgacgcgcg    54780
agaccgggtc cgccgtgatg ccggtcgatc gcgccgcgag cgagacgcgg gcgccggacg    54840
cgcggagccg cgaggccaga cgctcgccgg cgccgtcacg cccgccggcg atcgcccaca    54900
ccgtgtcctg aacgggcgcg gtggtttcga gcggcacctg ttcccatcgc gtgtgatacg    54960
ccagatcgcg cggcgcgcgg cggctctcac gcgcgtcgac ggcgcgaaac gtgaagtggc    55020
gaatccgcga cgtgatccgg ccgtcggcat ccgcaatgtc cgagtgctcc gcgaaggtcg    55080
tcgcggtatg cgcgaacgtc cgcacgtatc cccagccgcg tcgcggcgtc gcgtcgaacc    55140
actggatttc gtccgcgccg atcggaatcc agagcacggg cctcggcgcg agcagcgggg    55200
cgccgttcaa gtacgcgtcc tggacggccg ggtgcgcgaa aaacggcgtc tgctcgggca    55260
ggctgtcggg ccaggcgact tcgaacagcg cttcgccgtc ccccagccac gcgtgccgga    55320
tgccgcggca ggccggtccg tactcgtagc cgcgctcccg caaacgccga tacacctcgt    55380
cgccgtcgat gcgcgctgcg caccgcacgc ggatcgcgtc gatgtcgagc gccggcgcgg    55440
gcgcgggcga gccctcgaag cggcggagaa agtgccgcgt gaaccgtccg ccggcgtagc    55500
tggagacggc gaacgtcgtc cgatcggcgg acgcgatcgt gtagagcgtc gtttcctcgc    55560
cggcgcggag gaggagcggc gcgtccacct tgagatccgc gggcaggcgc atcgctcccg    55620
ggaacagttc gcgcgacgcg gcaaccgcca tctcgcagta cgccgtccac ggaaacacga    55680
cgtcgccgcg gatcgcgtga tcccggagga acggcatccg atcgagatcg atcgtgctcc    55740
gccaggcggg aacggcagc ggcaccggca atccgagcag ggggtgcgcg gcgtcctcta    55800
cgcggaagcg ccgcatctgc tccccttcga tccagtgcgc ggttctctgc cacgcgatggc   55860 ctggcagccg cgcgatcgag ccggacggat acagacgcga gagatcgacc gcgtgtcccg    55920
acacgaacag ctcgccgatc gccgtgagca gcgccgcgcg ctcgcggcga tcgccgcgca    55980
gcgacgcgac cacggccccc tgagaaccgg cgttctcgcg cagcgccgcg ccgagtaccg    56040
gatgcgcgcc gatctcgacg aagcagcgcg agccgtcttc acgcagcgag cgcagcgcct    56100
cttcgaaccg gaccgtcgcg cgcatgttgt cggcccagta atggccgtcg agctcggtgc    56160
ccgcgagcgc ctcaccggtc acggtagaga cgagacggat cgccgtgggg gcggccgga    56220 tgccgcgcaa acgctcgacg agccgcggca tcaatggcgc catcgccgga ctgtggtacg    56280
gcacctcgac gttgaggacg cggttgaaca cgcccgcgcc ggtcaatcgc gccgacagcc    56340
gctgcagttc cgccgtgtcg cccgcgagcg tcaccgagcg cggactgttg cgcgccgcga    56400
```

```
ccgagacgac ccccgtgtcg aacggaaacc gcgcttgcaa atcgtcttcg ccgaggcctg    56460
ccgcgagcat gcctccgaga cccgccgctt ccgactgcag ttgagagcgc gcggcgatca    56520
cggccgccgc gtcgtcgaga tcgagcgcgc cgctcacgta cgccgccgcc acctcgccga    56580
cactgtggcc gacgatcgcc tcgggctcga cgccccacga gcgcagcagc gccgcgatgc    56640
cggcctggag cgcgaagatc gacacctgcg cgacgtcggt gcgatcgaca tcgacgccgc    56700
cgccggccgc aatcgcgtga cagaccgacc aatcgatatg cggcgcaac gcgcgatcgc     56760 acgcctccac ctcggcgcgg aacaccggct caccggcgaa cagctcgcgt cccatgccgg    56820
cacgctgctg tcccatgccc gagaacacga acaccggacc gcgcggcgca ccgcctttcag   56880 gcgcgcgtcc gctgacgagg ccctgctgcg cggaccctcg cgcacatgcg gcggccatcg    56940
cggccatctc ggcccgcgag ccgcccgcga tggcgacgcg gtgacgcaga cggcttctcc    57000
gccgcgcacc cgtgtacgcg atgtcggcga gccgatcgct cgtcgcatcg agatactcgg    57060
cggtcgtcct cgccagttcc gcgagcgccg cctcgcttcg cgccgacagc acgagcagct    57120
ccgctttcga ggcggcgccc ggcccgcctt cccgcgccgg ctgcgcgctc gcttcagtca    57180
ggaccgcgtg cgcgttggtg cccccgaagc cgaacgagtt cactgcgccg gcgcgcgggg    57240
cgccgccggc attggcgggc cactcctcga tcccggtgac gacgcgcagc cgcagctcgc    57300
gcatcggtat cctcgggttc ggctcgcgaa agtgcagcgt cggcggaatc tgccggtgcc    57360
acagcgacag cgcgagcttg atcacgcccg ccacgccggc cgcggactcg agatggccga    57420
tgttcgtctt caccgacccg acggcgagcg gttcctgccg tccgccggcg agcgtcgcgc    57480
cgagcgcgtg cgcctcgatc ggatcgccgg cctgcgtgcc agggccgtgc gcctcgacga    57540
actgcacgag atgcggcggc acgtcggcct gatcgagcgc cgatcggatc gccgccacct    57600
gcgcgtcgaa gctcggcatc gtgaggctgg gcgtacggcc gtcctgattg acggcgacgc    57660
cgcggatcac cgcgtagacg cgatcgccgt cgcgttcggc gtccgacagc cgcttgagca    57720
cgacgaggcc ggcgccttct ccgcggacga acccgtcggc gcccgcgtca aggcgcggc    57780 agcggccggt cggcgacagc atcgtcgcct tggagtacat gatgaacggg cccggcatga    57840
agttgagctg cacgccgccg gcaagcgccg tctcgcaggt gccgctccag atcgcctggc    57900
acgcctggtt gatcgccacg agcgagccgg aacaggcggt gtcgaccgtc aggctcgggc    57960
cgcgcagatc gaatgcgtag gaaatgcgat tcgagatcag gctcatgctg atgccggacg    58020
cgctgtgcga gtccaggttg ccgagcgagt cgcgatcgag ggccaggccg gcgagatcgg    58080
gcaccgcggc ggcgacgaag acgccgaccg gcgcgccggc cacgcggtcg agcgggatgc    58140
cggcgtcctc gagcgcctcc cacgccactt ccagcagtaa gcgctgctgc ggatccatgc    58200
gcgcggcttc gcgcggcgcg atcgcgaaga actgcgcgtc gaaccgatcg acgtgctcga    58260
ggaacgcgcc gtggcgcgcg taggtcttcc ccgaccgtga ttgatcgtcg ctttgaaacc    58320
gatcgagact ccaccggtcc ggcggaatct ccgtgacggc gtcgccgccg gactgcaaca    58380
gtttccagaa acgctcgggc ccgtcggcgc ctccgggaa gcggcagccg atgccggcaa     58440
tggcgatcgg ctcacgagtg tcgcgcgcg cccgcgcggc cagcacgcg cgcgtgcgcg       58500 gcggagcgat cgcggacaac cgctgttccg gattggcggt gccggtgtcg agaatccgca    58560
ggaagtccgc gatccaccga tccgcgtat cgcggtcgaa gaggtcggtg cggtactcca      58620
ggaacgcgta gatgtcggaa ccgcggacgg cgaactgcca gaggatcggc gcgcgcgcta    58680
catcgagcag atcgaaccgc atctcgggtg cgaaccagac cccggcggcc tcgatcgccg    58740
```

```
gcgcgatcgc gtcctgaaac gcgaagcctg gctgaatgag cgtggaagac gccgtgccgc   58800
tcgccgtgct cttgcgccga tccgcgtaca gccgttgatc gacgacgtgg agcggcacgt   58860
cctggcgtcg aaggccgcgt cgcaccgcgc gctgcgagcg ggcgatcaac tcggcgaagg   58920
ccggatcgtc cgccgcctgc acgcgcaacc ggatctcctg cgcgaggcac ccgacgatcg   58980
gcttccatcg cgccgcgcgc cggttggcca ccggtacggc cgcccagaga tccgtgctgc   59040
cgctgacgtg atgaagccac gccagatacg cggcgaacat gacgctgaac agcgtcgcgc   59100
cttcggccgc ggctctcgcg tgcgcttgcg cggccagcgg cgccggaatg gtgaaacgcg   59160
cgacgcggcc ggggcacgcg ctgtcgggac cgcccggccg atccgtcgga atgtcgagcg   59220
acagcggcgc gtcctgaaaa tcgtcgatcc agtaggcgat ctgcgcgtcg agctcgccgg   59280
acgccaggcg ccgccgctca tccaccgcaa aatcgaacgg cgtcgtctcg aggagcgcga   59340
gatcaggctc gacgccaagg cacgcggcgc gatagcactc ggccagctcc gtgagcgcga   59400
tgcgctgcga ccacgcgtcg aacacgagat gatgcccgac cagacagagc tcgtggcgat   59460
cgtcctcgac tctgatcaac agcgcgcgcc aaagcggctc gctcgccagc gcgaagggct   59520
ggctgatggc gcgtcgcgcg agccgctcga cctcggcgtc gcggcgctcg cgcggcacgt   59580 cccgacgtc tttccagcac attgggatcc taagcttaga attccacgtg gacaagttgt   59640
cgcggccgct tctatagtgt cacctaaata ctagtgactc agcgtaacct ggactggc   59698
```

<210> SEQ ID NO 9
<211> LENGTH: 60007
<212> TYPE: DNA
<213> ORGANISM: Unknown
<220> FEATURE:
<223> OTHER INFORMATION: Environmental clone

<400> SEQUENCE: 9

```
ggagtcacta gtatttaggt gacactatag aagcggccgc gacaacttgt ccacgtggaa     60
ttctaagctt aggatcccaa tgtgctggaa agcctgctgc tgaaccccga caccgtcgtg    120
ctcgacggtg cggtcgacgc gctgcgcacc ttctcgctcg accacccctc gtacggcctc    180
tacggcggca ggaccctgcg ccccgacggc acggtcgatc cgagctcctg ctggggcgat    240
atgacgctgt ggtcgctcgt gtcgttcgcc gcggggctgt cgaccgcgtt caagcgctcg    300
cgcgtcttcg accccgagtc gctcggatca tggcagcgcg acagcgtgcg ggaggtgccc    360
atcatcacgg ggtgcctgct gctgatctcc cgcgacggct ggaaccgcct cggcggcatg    420
gacgagcagt acttcctcta cggcgaagac gcagacttct cgctgcgcgc gcggcgggcg    480
ggcctgcgcc cggtcatcgt gccggacgcc gagatcgtgc acgccgtggg cggatccacc    540
tcgtcgagcg gccgcaagat gtgcatggtc atggccggca aggccaccgt gctgtgcaag    600
aactggccgg cgcccaggc cgcggtgggc atcgccctgc tgcaggccgg tgccgccacc    660
cgaacgctcc tcgcccgtgt gcgaggacga cgccacacca cctgggacga agtctggcgc    720
cgccgccggg actggcgccc gggataccgg ctcgcccggc agacgatctt cggtttcgac    780
ccgtcgaccg gctccgaggc gccggagaga acacccgcgt aacccgatac gtcgaatcct    840 ttgggggaa ccatgacgtc cgcaacactc atcaccgcac tacgcaccac cgccgccacc    900
gtcggggacg agaaaggggt ccgcttctac gccgacccca cgacctcgat cttccgggc    960 tggcgcgaac tcgacgagcg cgcccgtcgc atcgcccagt cgctgcaggc gccggtcac   1020 cagcccggcg agcgcgtgat cgtcgcgctc gcaccggac tccagtggcc ggatgccgcg   1080
tacggcgcgc tctacgccgg gctcgtgctc gttccggcgc ccgtcgtcgg ctacggcacc   1140
```

```
acgggggcgc tcgccgctcg gatcaacggg ttggccgcgg catccgaggc ctcgctggtg      1200
ctcaccgagc cggccatcct ctccgccctc ggcgaggacg ccgacgcgat cgagctcccc      1260
gtgcgggtga tcgacgacct cctcgccggc gatgccgatg cctgggtcga gccggggatc      1320
gacggcgatg cgccgtcgtt cctgctctac acctcggggt cgaccggcga cccgaagggc      1380
gtcatcggca cccacgccac gttcctcgcg acgaccgaga cctgcgccga gctgttctcg      1440
ctcgactcga gctcggtgct cgtgggctgg gctccgcttc accacgcgat gggcctgatg      1500
atccaggtga tccttcccgc cgttctcgga gccgactcga tcatgctcgc gaccgatcag      1560
ttccagcgac gcccgatcgt ctggctgcag ttgatcagcc gccaccgcgc cacgatgagc      1620
gtcgcgggca acttcgcgtt cggactcagc gcgaagctgg cgaccgacgc gcagatcgcc      1680
gagctcgacc tgtcgagtct caccacgctg ctgtgcggca gtgagccggt gcgggccgag      1740
acgctcgatg cgttcctcac ccggttcgcc tcgaccggga tcaccgccga ggcggtgctg      1800
ccggccttcg gcatgaccga ggcgatgctc atcaccagca agcgcccgg ccgtcccatc      1860 cgcttcacga gcttcgacgc cgccgaggtc gcggcgggtc gcctcgtcgg cgccgagggc      1920
gagggcagcg tcgcgatggt gtcgaacggc cagccggcga gcaacacgag cgtcgtcatc      1980
gtcgatcccg acacgctcga gccggtgccc gacggcacgg tgggagaggt ctgggtgtcg      2040
tcgccgatgg tcggcccggg ctacttcctg cgccccgacg ccaccgccga gaccttcggt      2100
caccacctgc ccggctccga gcacgagtac ctccgcaccg gcgacctggc atcggtcgtc      2160
gacgacgagc tctacgtcac cggacgactc aaagaggtca tcatcgtccg cggtcgcaat      2220
ctctacccgc aggacatcga ggccgccgcc gccgcggtgc accccgccgt cgggatcgcc      2280
gccgcgttcg agctcgacgg ccatccctcg gcggtgggca tcgtcgccga gtacgacgcc      2340
gaggcactgg gcgacaccac cctccccgac ctcgccgagg cgctgcgcgc gaccctcacc      2400
cagcgggtct cgctgccgtc ggtcgccgtc gcgctcgtcg agcccgggct gctgccgcgc      2460
acaccgacgg gcaaagtgcg ccgccgcccc accctcgcag caatcgaagc ggggcgctg      2520 accacgtcct tctcccgcgg ctaccgcgac acggtcgcga ccgcacactg atccatcaag      2580
gaagaccact catgtcgaac tcacctgaca ccaccacccc cacgtccgtc gccgcactcg      2640
gcgactggct catcgagcgc atccgcttct acgaccaggt cgatgcggcc gccgtgaccc      2700
tcgacgcgcc gctgagcgac ctcggtctcg actcgatcta cgtgctcacc ctctgcggag      2760
acatcgagga cacctacggg accgagatcg acccgacgtt cttcgagggc cgcgactcgc      2820
tcggacaggt cgccgtcgcc ctccacgaga ggctcgcccc ctcgtgaccg ccgtgacgtc      2880
gccgccgcgt ctgcgggcat ccgaggggtg cttgcagacg cgcggcggcg tcgtgcggtg      2940
gcgtctcggc ctccgcgatc ctgcggaggc ggcgtcgacg gtcgcacggg agtgggtcga      3000
acagatcgtc cgcgcccacg gcctgttcgc atggaccggc ttcgccgccg tgccgccgtt      3060
catgaagccg cgattcgcgt ccggcgggc cgacttctcc gtctcgcaca cggcgagtt      3120 cgtcctggtc gcggtgggag tggggcacg ggtcgggtc gacgtcgagg ccgcgccctt      3180
cgaggcgttc cgctccgcgg cgttgcgacg acggatgctg accccgccg agcacgacag      3240 gctcgcccgc gtaccggccg acgcgcgcct ccccaccctc gccgggtgt ggaccgcgaa      3300 ggaggccctc gtcaaagcga gtggcgaagg attgcggcgc gacttccgcc gcttcgccgt      3360
ccccgcactc ctcgatgccc ccgtctcgcc gctcgaggcc gctgtcgccg tgctctcccg      3420
cgacgcggcg cccgaggtgc tccgcctcac ccctcttctc gcggcgccga tgcccgaggc      3480
```

-continued

```
cccccctcccc acccctcttc ccgccgcacc cgaagcggcc ctcacggagt tgtcatgacg    3540
atcctcgaac accccggcac cgctgccgg aagaccgcct cccccgcccg acgcccctac    3600
gccgagttca tgaagatctg ggaggagggg tacgtgtcga accggatctc gttcgagatc    3660
atgcacacgc ccgggtctt catcgtcgcg ggtgcaccgc tgcgacgg cgacggtcgc    3720
ctccgacgcg agcgggtcct cgagcacctc gcggcgaccg tcgcgagcgc tccgatgttc    3780
cggctgcggc tgcaacggtc gctcctcggc ctcacaccgc ccgcctgggt gcccgacgag    3840
gagttcgacc tcgcccgcca cgtcgtcttc gccgacgagg tggccgacct cgacaccgcc    3900
gacctgcgac ggctctcggg tgacgacgac ggcgtgatgt cgatccggca cccgctgtgg    3960
cgcatccgcg tgacggagct gagcgacggc gacgtcgcca tcggcaacat gctccaccac    4020
gcgagcctcg acggcctgtc ggggatgaag gccatgtcgg tgatgaacgt caagtcgccc    4080
gacgaagacc tgcccacccc cgtcgacccg ttcgccggca tgcgcgccgc gagacggtgg    4140
gaactgccgg cactcgccat gaggcagtgg tgggacgacc tcgaggcgcc gcgtctgcgc    4200
gccgcctggc ggtcgtacac cgcgaagccc ttcgttcgga gggcgcgccg ggtggccgcg    4260
cgcctcctcc tcccgctccg ctacggcgcc ggcggcgagg cggcgcgcgc cgccgccctc    4320
cgccctcggc attcgtcgta ccgccgactc gacgccgccc tcgccgggcg gcgggcgcgc    4380
gagctcggcg gcaccctcag cgacctgctc atggcctcta cgatcggcgc ctggaacggg    4440
cgggagcgcg aggtcaagct gcgcttcccg gtgtcgttcc actcggagaa cgcgccgaag    4500
gcgcgcaaca acgtgcggga catggagatc cacggcgacg ccgacgcgcc gctcgccgag    4560
cgtgtcgcct cggtgcacgc ccaggtggcg gcgcgcgact ccgcctggga cggtcacgtc    4620
gtgcccggcg caccgatcgg ctacaccacc ctcctcccgt gggtctcgcg accgcggtac    4680
ttcgccggcg gcgaagtgct cgccatggtc cccttcccgg ccagcctggg aggcgaccgt    4740
ctcgcggcgg cggggatcat gtacaacggc tcgctcttca tcggcgcgaa catgcccacc    4800
gacctcgatg tcgaggcgac cgtggggcgc atcttcgcgc tcatgacggg atcggaagac    4860
cccggacggt accgaccacg cgacacgacg ggaaacgatg agccctgagc cgaagcgcat    4920
ccatgccgaa ttcatgaaga cgtgggagga gggctacgtc tcgacgcgga tcgcgtacga    4980
gaccatgcac accccctgct tcttcctcgt gcgcggcgat cagctgcgcg acgaggacgg    5040
gcgactcgac cgcacgcgca tcgacgactt cctccgcgcc acggcggcga gcgcgcccgt    5100
gttccgcctg cgcctgcagc gctcgttcct cggactgaca cctcccgcgt gggtgcccga    5160
cgacgacttc gacctcgccc ggcacgtgat ctacgccgac gccccgtcg acctcgccac    5220
cgccgacatc cggcggctcg ccggtgacga cggcaccctg ctgtcgatag cacacccgct    5280
gtggcggatg cgcgtgaccg agctgacaga cggcgacgtg gcgatcgggt gcgtgctgca    5340
ccacgcgatc ctcgacggcc aatcgatgat gaaggtgatg acgatgctca ccaccaaggc    5400
cgccggtgac gaccccgtcg gcccgacga cccttcgcc ggcacgcgcg ccgcacgcgc    5460
gaccgaactc cccgtcctgg ctgcggcgcg ctggtgcgc gggctcgccg atcgcgcgcc    5520
ccgcgccgcc gttcgttcgt acctctccaa gccctcgtc aagcgcgccc gccgtgtcgc    5580
cgggcgcctg ctgctgccgc tgcggttcga tgccggaggc gaggcggcac gcgccgctgc    5640
gctcccccg cgtatctcgg cctacacgcg cgtcgactac gcccgcgccc gtcagcacgc    5700
ccgagacctg ggaggcacgc tgagcgacct cctcgccgcc gccgccatcg gcgcctggga    5760
tggggcgaag cggcgcgtcg ccctgcggtt ccccgtgatg gtcagcgccg agagcggccc    5820
gaaagcacgc aacagcgtgc gcgacatctc cgtccaggcc gacgccgacg ctcctctcgc    5880
```

```
cgaccgggtg ctcgccgtgc acgagcagat cgcagcccgc gacgagatgg acgccccgc    5940 gccgtccgat gacgcgatcg gcttcaccac cgtcatcccg tgggtgtcgc gcccgcgcta    6000
cttcgcgggg agcgaggtgc gcgaggtcat cccgttcccc gcgagcctgg gctccgacaa    6060
gctcgccgcg gtcggcgtca tctacaacgg cgcgatgacc gtcggggcga acatgccggc    6120
gcgcagcgac atcgccgcga ccctcgaccg catcgcggcc cagctcacgc ccccgatga    6180 cggcgagcgc ccgtgaccga cccgatcgac agcagcgccg cggcgcagca tccgctctcc    6240
gtctccgtcg tcatcccgtc gtaccgccgc ctcgaccgga tcgccgacct cgtacgcgcc    6300
taccgcactc agggcgccga ccaggtcgtc gtcgtcctcg acgggccgca cccggatgg     6360 gagcacgccg tcgcaccggt cgccggaccc gatctcgatg tcgtcgcgct gcccgagaac    6420
gtcggtctgg cacgggcgcg catcgccggc ctccgggccg cgaccggcga catcgtgctg    6480
gccgtcgacg acgatgtcga acccgggccg gggctcgtcg accggcaccg cgcgttccac    6540
gccgtgcacg ccggggcgcgt gctgcagggg tacatgccga ccgccctccc cgcgagacgg    6600
caccgcgacc aggcgccgac ctacctctac gcccgcgagt acgaggcgca ggcacgggtg    6660
tggcgcgtcg gcgaccccgc cctgctcctg cgatcgctgt ggggcggcaa cctgagcctc    6720
cggcgcgagc tctacgagcg cgccgaggag ctcctcccct cggtgcggct cgagtacaac    6780
gaagacctcg acctgggcct gcgtctcgag aagctcggtg cggtcgcggt cttcgacccc    6840
gatgcccgcg ccgcgcacca ccacgcgcgc ggtctctcgg cgttcctgcg cgaatgcacc    6900
gcgcgcgggg gtgcgatcgc ccagatcgag gcacggtggg gcgagaggcc cgcgcagctg    6960
acgccgatca tcgacatccc gcgctcctac aaccgcgtgc tcgccgcgct gcagcgacgc    7020
atcgcggcac gcgacgaccc cggtgcgctc gagacctcga tcgtggcggt ctatcgggcg    7080
gccggtctgg tgggcgcgtg gcgcctgcag gacgggatcg cgcggatgct gcgtcggggc    7140
gtcgccatgc gcggctaccg gctcgcacgg cacgaggcct cggcggtgcc ggcacgatga    7200
cgcaccggcc ccgatcgggg agcggccgag gggccgacat acgatggtgg ggcgccacga    7260
ctgtcggagc cccccatact ccggtgctac agccccctg gctcggtcga cggcgtgagg     7320
agtctcatgc gtgtcgccca tcccgcccgc ctcggtgtga cggtctcggt cttcgcggcg    7380
gtgatcgcgt gcgccgccct cgtcggcgtg gcgaatctcg tccggcgctt ccgggaggac    7440
gaggcgcgcg agcgcgagtt cgacgactgg gccgccggca cctcgtcacg ggcgggtgca    7500
tccgaccgct aggttgtttc ctgtgtcctc ccgctcgtgc gggaggcgca tcgccgccaa    7560
cgatcgccgg cttccaggca gttccttccc gtccttctcg aggagtctca tgcgtctgtc    7620
cgtgatcggt tgtgggtatc tgggtgcggt ccatgccgcg gcgatggcgt cgatcggcca    7680
cgaggtggtc ggcatcgacg tcgacagcgc caagatcgcg cagctgtcgc ggggcgaggc    7740
gccgttcttc gagcccgacc tgcaggagct gctgacagcg ggcatcgcgt cgggcaacct    7800
caccttcacc accgacatgt cggcggccca gggcgcgagg gtgcacttca tcggcgtcgg    7860
gaccccgcag cagaaagacg gctacgccgc cgacctcacc tacgtcaacg ccgccgtcga    7920
cgggctcctg ccctacctga gcgagggcga cctcgtggcc ggcaagtcga ccgtgcccgt    7980
cggcaccgcc gcgcgcctgg ccgagagcgt caccccacc ggtgcgaccc tggtgtggaa     8040
ccccgagttc ctccgcgaag ggtgggcggt gcaggacacc atcgaccccg accgcctcgt    8100
cgccggcgtc ccctccgacg cgaacggcgc caccgaggag ggcgagcgcg cagcatccgt    8160
gctccgtgag gtctaccacc cgtcggtcgc gaagaacacg ccgttcatca tcaccgacta    8220
```

```
cgccaccgcc gagctcgtga aggtctccgc gaacgcgttc ctcgcgacca agatctcgtt    8280
catcaacgcg atggccgaga tcgccgaggt caccggcgcc gacgtcacca ccctcgccga    8340
cgcgatcggc cacgacgccc gcatcggccg ccggttcctc ggcgccggca tcggcttcgg    8400
cggcggctgc ctcccgaagg acatccgcgc cttcgccgcc cgcgccgaag aactcggccg    8460
cggcgaatcg gtcgcgttcc tccgcgagat cgacgcgatc aacctccgcc gccgcgaccg    8520
cgccgtcgac ctggtcgtgc aggccttcga cgggcaggtc ttcaagaaga acatcaccgt    8580
gctcggcgcc gcgttcaaac cccacagcga cgacatccgc gactcgcccg ccctcgacgt    8640
cgccgtccgc ctccacggcc tcggcgcctg ggtcaccatc accgaccctg cggcgatcga    8700
gaacgcccgc cgcatccacc cgcagctgaa ctacgtcgaa gaccgcgacg aagccctccg    8760
cggcgccgac gccgtcatcg tcgtcaccga gtgggacgaa taccgccggg agctgccccc    8820
cgagcacgcc gcgtccctca ccaacggcca catcgtcgtc gacggccgca actgcctcga    8880
cgcgaacgcc tggcgcgcgc ccggatggac ctactacggg atgggacgcc cctgacgggg    8940
ccgacccct aggctcagcg ccatggacac gctcagcagg atcaccgacc gcgccgacct    9000
cttcgcgctg aacggcgtga ccggtgttct caccttcgcc gtctacgtgg tcatcgtcat    9060
cgcgctctgg cgcgtcttct cgaaggcggg ctacccgggg tggctcgcga tcatcccgat    9120
cgtcaacgtc ttcacgctcg tgaagatcgc gggcttctcc gcctggttcg gcctgctcta    9180
catcgtcccc atcgtgggat tcgtcttcca cctcatcgtg tcgctgcgcg tcggccgggc    9240
gttcgggcac ggggcggtgt tctcggtgtt cttcctctgg atcttctaca tcatcgggtt    9300
cttcgtcgtc ggcttcggct ccgacaccta cgacgagcgc cgcatccgct cctgaaccac    9360
cggatgatcg agaccgacac ccgctcgcgc gacgcgcgcc gacggcgcat cgccctgcag    9420
ctcctcgtcg tctacggcat cgccgtcctc ctcatcgcct tctggccgt gccggtcgac    9480
agcggcgcgg tcgggctgct cgaccgcatc gagcgctggc tgccgtgggc gacctacgtg    9540
cgcatcgagg tcacgcgcaa cgtgctgttc ttcgtcccgc tcggactgct gctcagcttc    9600
gtgctcgagc gctcccgcta tctcgtcctg cccatcgggc tgctgacgac gatcacgatc    9660
gagggcctgc aggccgagct gctcgacaag cggacggcca gcatctccga catcctcgcc    9720
aacaccgccg gcacctgcat cggcatcctc atcgccgccg ccgtcacccg tcggctcgag    9780
ccccgccgga cgcctcaggg ccactcccgc tgagagtcca caacaccgg gcgcgccccg    9840
cgcagcatcc gggtgtcgtg gactctcagg ggggaaccgt agggtcgccc catgagcacc    9900
gacgagaacg acaccgcccc gaccggctcc gacaccgacc tcggcaagct gatcgcgcag    9960
gtcgacgacg agcacggcga ggacggcgcg gccgccatgg ccgaccagct ccgcggcaag   10020
gtcgaggaga ccgaggccga acccgaggcc cccggcgacc tcgaggactg aagccattcc   10080
gctgagagtc cacaacaccc ggacgcgctt cgcgcagcat ccgggtgtct tggactctca   10140
gtgcggagag acagcggtca gctcagtcga cgtcggtaga tggcgatcgc ggccgcgtac   10200
gcgaccacga ggatgcccac gagccacgcc agcgccaccc agatcgcgcc tccgacgggc   10260
tggccggcga acagcgcgcg caccgtgtcg acgaccgacg tcacgggctg gttctcggcg   10320
aaccacgcca ccgacccgg catcgaagcg gtcggcacga acgccgagct gatgaacggc   10380
aggaagatca gcgggtagct gaagccgctg gccccgtcga tcgtcttcgc cgagagtccc   10440
gcgaccaccg cgatccacgt gagagcgagc gtgaagagca ccaggatgcc ggcgaccgcc   10500
agccacgcgc cgatcgaggc gccggtgcgg aagccgagga gcagcgccac cccgacgacg   10560
atcaccaggg ccgcgacgtt cgccgcgaga gacgtgagca cgtgcgccca caggatgctg   10620
```

```
gatcgtgcga tcggcatcga ccggaaccgc tcgaagatcc cgccctgcag atcgaggaac   10680
agccggtagg cggtgtacgc cacccccgat gcgatggtga tcagcaggat gccgggcagg   10740
aggtagtcga cgtagccctc gctcgagccg gtgtcgatcg ctcccccgag cacgaagacg   10800
aagagcagca tgagcgcgac cggcgtcacc gcggtggtga tgatcgtgtc gggactgcgc   10860
aggatgtgac gcagcgagcg gccggtcagc actccggtgt cgctgaggac gtgggcggtc   10920
atgggaggtc cttccggtgc gcgggcgcgt cgcccgaacc gccgaccagg gcgaggaaga   10980
cgtcttcgag cgtcggctgc ttctcgacgt actcgacctg agcgggaggc agcagccgcc   11040
gcagttcgtc gagggtgccg ttctggatga tcctgccctc gtgcaggatc gcgatgcggt   11100
cggccagatg ctcggcctcg tcgaggtact gcgtggtcag gagcaccgtg gcgccgcccg   11160
cggcgagccg ggcgatcgtc ctccacacct cggcgcgcgc ctgagggtcc agacccgtgg   11220
tgggctcgtc caggaagatc accggaggat cgccgatcag gctcatcgcg atgtcgaggc   11280
gacgacgcat gcctccggag tagccgccgg cgcggcgatc gccggcgtcg acgaggtcga   11340
agcgctccac cagggcgtcg gcgatcgcgc gagggttctt caggtgccgg agcctcgcca   11400
ccagcacgag gttctcgcga ccgctgagca tctcgtcgac ggcggcgaac tgccccgtga   11460
gactgatcga ctcccgcacc tcgccgggct gagcgacgac gtcgaacccg tggacgctcg   11520
cgctccccgc gtcggcccgc gacagggtcg agaggatccg caccagggtc gtcttccccgg   11580 ccccgttcga gccgagaaga gccaggatgc tgccctctcg cacctcgagg tcgacaccgc   11640
gcagcacgtg cacgtcgccg tacgacttcg tgacccccg gacgtcgacg gcgttcatga   11700
ggatgcgctc ggctcatccg ccgcggcgtc gatcgccgag gtgagacgtg ctcgttcctt   11760
gtcgatccac tgcgcgcccg agtatgcgcg agcgaacgac tcggcgaact cgacggggtc   11820
gtcgccgacg atctcgcgga cgggcgtcgc gtcgaccgcg gcgcgttccc agaggtcggc   11880
gaggtcggcg gacatcgtca cgagcgtgtc gccgtctgtg acgccggcgt agtacatcag   11940
gtatcggctc agcgctttcg cggcctggtg gtacggctcg ggcagcgcct cgatgcgggc   12000
ggtcgcctga cggtactgct tcttctgctc cagcgacccg gtgagggtct cgatccactt   12060
cgcagccatg gctactctcc tcggtttctc gtgtgcgggg tgtggaggct ctcgatgcgt   12120
tcgacgagga agctccacga tctccagaac tcgtcgaggt actcgctccc ctgcgcgttg   12180
agcgaataga ccttgcgggg cggcccccttc tccgagggca ccttctcgac ggcgacgaga   12240
ccccgctgct cgacgcggat cagcagcgcg tagacggtgc cctcgacgat gtcggagaag   12300
ccctgctcgc gcagccgtgc ggtgatctcg tagccgtagg ccggttgcac ggccagcagt   12360
gccagcacga tgccctcgag cgtgcccttg agcatttcgg tcatctgttt cgccatgcga   12420
tccctcacta ctccgtgtca ttgagtaccg gtagatagta acgcagaata gcggtagctg   12480
gcaacaccga gtaccgagca cgtgagacag ctcgcccctt agcgcggcga cggtccggaa   12540
gtcgagcccg cgcaaggagt tggcgctccc tcgtggcggg ggtcagactg tggcgacacc   12600
gtgatgactt ttgtcgtcgc gagcaggtcc tgactgaggg ggaaccacga gaatgagcac   12660
ccgggtagcg gtcgtctgga acccgtcgaa gaccgagcgg gaggcgctcg agacgcctct   12720
gagcgcaact ctcggcgcgg acgccgacgt ccagtggttc gagaccagcg tcgacgaccc   12780
cggccagggg gcggcccgcc gcgccctcga ggcatcaccc gaggtgatca tcgtcgcggg   12840
cggtgacggc accgtgcgcg cggtcgcgga gcacctcgcc gacgagaagg ccgacgtcga   12900
cctcggcatc gtgccgctcg gaacgggcaa tctgctcgcg cgcaacctcg gcgttccgat   12960
```

```
caacgacatc gcgaaggcgg tcgaccgcgc cctcaccggc agcgccaccg ccatcgacgt   13020
cggctgggtc gacgtcgatc tcgacaccgg aaccgaacgc cacggcttcg tcgtgatgat   13080
cggcttcggc atcgatgcgc agatgatcgc cgagaccgac gacgagctca agagcaaggc   13140
cggctggctc gcctacgtcg agtcgctcgg gcgggccctc gcggccagcg acatcgtgcc   13200
cttccacctc accgtcgacg acgagcccgg ccgcgacgag cagggccaca cgctgctgat   13260
cgcgaactgc ggcacgctgc agggcggctt cacgctgctg cccgacgccg acccctccga   13320
cggcgaactc gacttcctgc tcctgagcgc cgagggactc ggccagtgga tgggaaccct   13380
caagacgatg atgtgggaca acgggctcat gcgcctgatc accaagaagg acgacacgac   13440
cagctccgag tcggtctcgc acggtcgggc gaagaagatc cgcgtcacgc tccccgaccc   13500
gcgggcgttc gagatcgacg cgcaggagat cggcagacg cggagttca ccgtgtctct   13560
```

```
gaggtggcgg aggcgctggt gaggctgacc gccgccatcg cgaacgacgg ccgcgcggag    15420
gcggtgacga ttccgatcgt ctcgcgcacg accgacgacg acggcacggc agagctcgtc    15480
atcggcgtcg gcaacgacgt gttgtccgcg cccgccgagt gggagggcga cgagctggac    15540
ttctccgagg ccgctgccgc tctccgctcg caccccggct atccccgcca cagcgcgccg    15600
ggccccgagc tctacgcggt gaacgatccc gactcgagct gggaccccga cctggacggt    15660
ttcacgcgcg cctgaccagg acagcgggag cggacggatg ccatgctgtt cgtggttggg    15720
gaaccggaac ggcgaatcgg agtacgcgtg gaacccgcct cgacccgacg accctcgatc    15780
gcctggagcg accaggtagc ggtcttcgcg atcgtcgaac tcgaccggtc cggcatcgtg    15840
cagagctgga actccggcgc cgaacgcatc aagggctaca cccgtgagga gatcgtcggg    15900
cagcacttct cccgcttcta ccggcccccca gaccgcgagc gcggtgtgcc cgagacgttg    15960
ctggcctcag cgctggccca cggctacgtc gaagacaccg gctggcgtgt gagatccgac    16020
ggcgccctct tctgggccca cgtcacgatc acggcggtgc gagacagcca cgggacgccg    16080
acggggttcg tgaagatcgt ccgagacctc accgcatcca agcgggccga cgacgagctg    16140
aacgctttcc tccgctcgtt cgtgcacgac ttcctctcgc ccgtcacagc cgtgcgcggc    16200
tacgtcgatc tactgcgcga agggatcggt gacgccgacg agatgctgca gcgtctcggc    16260
gcgaccagcg accacctgct ctcgatggcc accgcgctcg ccgagcgggt acgcgacgaa    16320
ccgccgccgc ggcgcgacca ggtcgtgcac gtcggcgcgc tggtgcggga ggccgcgagc    16380
ctggtgctcc ccggcgacct gttcggccgc ctgtcgttct cgatcaccga cgaccccgcc    16440
gtgcagggcg acgcgaccga actgcgccgt gccgttcaga acgtgctcga aacgcggcc    16500 aagtactccg agtcgaccat cgacgtgatc gtggagacgg ccgccgacac cgtcgacatc    16560
gtcgtgcgcg accgcggtcg cggcatccac cccgacgacc tgtcggcgat cctcgaggac    16620
ggcgtgcgcg gcggatggc cagggacgac gacggaggca gcggcatcgg actgccagt    16680 gccacccggg ccgtcgcgaa cgcgggcggc acgatcggac tggagagctc gctgggccac    16740
ggcacgacgg tgcgggtgcg tctgccccgc gccgccgacg aaaccgggcg gtaacagcac    16800
gaccccggcc cgaaacggga gtctgagagg ttgctggtac ccacacggga cgcgccgacg    16860
cgagcacgcg tcgacgcgtg cgtcagcgag tccctctacc cgtagaaggg cttcttccgc    16920
atgtctgaaa ccactggcag aggcaggatg ctgcagcctc gcggcatcgc gctgctcgtc    16980
accacgttcg ccctggcgag cggatcggtc gcgctggctc ccgcggcgtt cgccgcggcc    17040
cccgtcgcga gcatctcgat cgacgtctcc ccgacgagg cgaccgaggg cgacacgctc    17100
gaggtgaccg tgacctccac cggcacgacc gacctgtacg cgtacgacct gatcttcacg    17160
tacgaccccg cggtgctcga gttcgacgag gagtcggccg tcggccccga cggcggattc    17220
accaccggcg cgctcggcga cggcctgatc gccgtgaccc acacccgcct gggcacctcc    17280 cccgactct ccgggccggt cgaactcgcc tcgttctcgt tccgcgcgat cgacggcggc    17340
gacacggtcg tcgcactcgc ctcggccgag ctcgtcagct cgaccgacga atcggtgacc    17400
cagaccgacg tcgactccgc ctcggtctcg ctcgtcaccc tccccgaccc gtcgccgtcg    17460
ccgacgtcga ctccgaccga gagcgcgacg ccggacccga gcgcgagcgc ctcggcgacg    17520
gccgtcccgg tcggctcgaa cggccagccg ctggccgcca ccggcgccga cgcgaccccg    17580
tggctcatcg cgggtgcggg cgccgtcatc ctcatcgccg cgggcgcgct cctggtgatc    17640
cgtcgtcgtc aggcggtgtc cgaatgatcc gcacgcagag cacgacgccc tcctcccctt    17700
```

```
cgtcccgtaa aggccccctc gtgacagcat ccacccggcg catcctcgcc gtcgcggccg    17760
cgctgggaac ggtcgccgcc gcttccctcg ccgtccccgc caccgcggca cccgccgccg    17820
cggccgagag cgcaccgttc ctcgcgccgt actacaccga gctcgaccag accggcgacg    17880
atcaggtcac cgatgccgat ctggccgtac tgtcggccgc gatcggcgcg acgagcaccg    17940
acccgcagtg ggccgacgac gcggcgttcg acatcgacgc ggacggcgcc gtgaccgtgt    18000
ccgacctcgc tctgctgtcg cagcgcatca tctacgacga cggcccgttc cagctcgtcg    18060
aagccgacgt cgtcgagatg caggccgcga tgaacgccgg cgtcacgacg tcggtggagc    18120
tgacgcaggc atacatcgac cgcatcgcgg ccctcgacaa ggtcacggtc accggcggcg    18180
cacgaccgct caactcgatc atcacggtgg gcgagcaggc ggcgctgacc gccgccgcgg    18240
cggccgacgc cgtgcgcgcc gagaagggca tgacgagcat gctcctcggc gtgccgatcg    18300
cggtgaagga caactacaac accgtcgaca tgcccaccac ggccgggtgc ggatgctgga    18360
acgacaacca gaccacgacc gacgccacca tggtgaaagg cctccgcgca gacggcgcgg    18420
tcatcctcgc caaggcgagc atggacgagt tcgcgatcaa cctgtcgtcg cagtggtcgg    18480
cgttccagac gcccggcacg gcgctgacgg tctcgagccc gctcgacacg tcccgcacgt    18540
cgggaggctc gagcggcggc acgggcgcgt cgatctcggc gaacctcgcc gctatcggct    18600
tcggcaccga cacgggaggc tcgatccgcg tcccgtcgac gtacaactcc ctcgtgggcg    18660
tccgaccgac cgtcggtctc gccagccgcg ccggcatcgt gccgctcgcc ctgtcgcagg    18720
acaccggtgg tccgatcgcc cgttctgtga cggatgccgc cgtcgctctc gatgcggtcg    18780
tcggagcgga tgctgcggat ccgatcaccg cgaaccaggc cggcaaggtg ccgacgtcgt    18840
acacgtccta cctcgacgcg gactcgctcg ccggtaagac gttcggttac gtgccggcga    18900
tgttcggaac gaacgccagc accctcgccc tgtgggagaa gaccaagacg acgctcgtcg    18960
aacagggcgc gaaggtcgtc gaggtgaccc cgcccgaggg atggagcgcc atcctcggcg    19020
agggcagcgg cagcggcccg gagttcaacc acgacctcca ggagtacatc gccacctacc    19080
tcgaccccga cgtctcggcg aacagcctgc tgaagatcag ccagtcgacg aacatcgtcc    19140
ccggacgggg gagcaacccg tacgggcagc gtgcggccgt caccgaggag gcgtaccagg    19200
cctgggcggg tccgaccggc acccacacca cgcagctcgc caagggcaag acgctcgtga    19260
cgaagctgat ggacgacctg ggtctcgacg ccatcgtcta ccccagcggc aacgcgtaca    19320
gcacgatcag caccaacatg cgcctgagcc ccaacaccgg gctccccgcg gtgacggtgc    19380
cgatgggctg ggcggccgcg gtgggcgagt cgcccgcggg caacgtcaac ctcgagttcc    19440
tcgggcgcga cttcgccgaa ggtccgctgc tcgggtacgc gttcgcgctc gagcaggaga    19500
tcgacgcccg caccgcgccg gccctgtacg gcccgctggg gtgacccgca catgaaggaa    19560
gggcctcccg gtaccgaccg ggaggccctt ctctctgtcc gcggcgacga ccgcgtcaga    19620
tcattcgaag ttgcggtggc gggcgacgag gtcgtcgaac ttcgcccggg tgcgccgcac    19680
cagcatgagg tacagcacgt cccagaagat ccagagcgac tgctcgaaca ggctcccat    19740 cgcctggatg gtcggcacga gaccgctcgg gtcgtcggca ccgtaggtgt gggccggaac    19800
ggtcagcacg atgtcggcga gctgcgcggt cggcccgtcg ggtacggcgg tcgccacgag    19860
cagcgtcgcg ccggtcttct tcacctgctc ggcgatgtag tggaggtgag ggatgttcgc    19920
cggacccgac ggcatgatga acaggtcgtc cgctgtcacc gcggggtcg tgtcgtccca    19980 cccccagtgc acggtcttgc cgaaatgcgt caggcgcatc gcgaacgcct tcgacccag    20040 cccctcgcgc ccgataccga gcacgaagat gcgctggtgg ctctcgagcg cgtcgagggc    20100
```

```
ggcctcgatg ttctcgagcg gcacccggcg gaagacctcg ccgagctcct ggacgacggt    20160
ggcgctgatc tcgcggaact ccgacatgtc cactctctcc tcttcagatt cttcccggtg    20220
cttctcttcg gattctcccc ggtgctgttc accgagttcg tgctgatcgg gggtcatctc    20280
acacccggct tggcaccgag gcgcccgacg aggagggcga gcaggatgac ggcgccgtag    20340
acggcgttga tccagaaggt cgggacgccc gcgagggtga ggacgttggt cagcgtaccg    20400
agcagcagca cacccatgag tgcaccgacg atccggccct gtcctcccgt gagctgcacg    20460
cccccgatga cggcggcggc gagagcgctg aagatgaggt tctcccccat gccgctcgtg    20520
accgaggcga gacgcccggc gagcatcagg ccggcgaacg cggcgagcgc gctggccgcg    20580
acgaaggccg tgatgagcac gaagtcgacc cggatgccgg ccgcacgtgc ggcctcggcg    20640
ttgccgccga tcgcgtagag ggcgcgtccc cacgacgtgt agcgcaggag cagacccgcg    20700
atgaggaaga ggatgccggt gatccagatc gccgcgggga tccccgccca ccgcgccgac    20760
ccgacgtagc ggaaggcctc ggggaggccg gcgagggtct tgccctcgct gatgccgagc    20820
gtgatgccgc gcaggaggat cagcatcgcc agcgtgacga tgaagggatc gagtttcacc    20880
ttcaccacga ggaatccgtt gaacagtcct accagcatcc cgatcccgat cgtgatgccg    20940
atcgcaccga actcgttgat ctcggtgccg agaccgccga cggcggcggg gatgagcagc    21000
caggcggcga ccatgggcgc cagtcccacg gtcgattcga gagagatgtc gagcttgccg    21060
gtgaggagga tgaaggtgag gccgatcacg acgatgccga gctccgccga ctggcggagg    21120
atcagcgtga ggttcgccgc cgacaggaac gcggggctca cgacagcgcc gatgatcgcc    21180
acgatcacga gtccgggcag cacgctcagc tcgcggacgt tcttcacgac ggtgcgcgcg    21240
aaggggttct tcgcggcggg ggtacggatg acggtggttc gcacgatgtt cactccaggc    21300
cttcgatggc tcgaacgatg tcttcttcgg tcggttcgcg gagctcggcg ccgatgcgcc    21360
cctcccgcat gatgaggacg cgcgggctga cgagcagctc ctcgacgtcg tcggagatga    21420
ggaccacggc gacgccgtcg gcgagggcgc ggagcatgag ggcgtagatc gcgtccttcg    21480
ccgcgatgtc gacgcccgcg gtgggcgaga tgaggacgag cacgcgcgga ttgcgggcga    21540
gggcgcgcgc gagcaccacc ttctgctggt ttccaccgct gagtcccgac acggccaacg    21600
acggatccgg cggcaccagg gcgacgtcgg cgatgaggtc gcgcgagatc tcggtgcgcc    21660
tcttcggcga gaagaacccc cgcggggcga tctggtccat cacgcccatg gtcatgttct    21720
cggcgacgct gagctgcggc acgtatccgt ctcggtgccg gtcggcgggg acgaacccga    21780
tgccggcgcg ctgactggct ttgacgttgc ctgcggcgac gggctcgccg ttgacggtga    21840
tgctgccggt ggcggtcttg cgcaggcccg cgatcgcctc ccccaccgag tacttgcccg    21900
acccgcccac cccgccgatc gctacgatct cgccgggcgc gaccgtgaac gacacgtcgg    21960
tgaacgcgcc ctcccggtcg gtggcgttct tcacggcgag ggccacggcg ggcgacgccg    22020
acgcgtccga cgcggatgac gactccgctc ggtgccgacg ctgttcctgg ccggcgagca    22080
gcgcgtcgac gagatcgtcg gatcggatct cgtcgcccag cctcgaccag agcagcttgc    22140
cgtcgcgcag cacggttgcg gagtcgcaga tcgccgtgac ctcgcggagg aagtgcgaga    22200
cgaagacgaa cgtcacgccc gccgcctgga gctcctgcac cttgtcgaac agtcgccgga    22260
tcgccgcgcc ctcgagctgc acggtcggct cgtccagcag cacgatgcgg gtgcccgcct    22320
ccagcgcctt cgcgatcgtc agcatctggc gctcttccag cggcgcgtcg gccagcagca    22380
tcttcgggtc gaggtggatg ttccactccg tgaggatgcg ctcggactcc tcctgcatgc    22440
```

```
gacgccacga caccccggca cctcgctgag gcagccgccc cgtgaagagg ttctccgcga   22500
tggtgaggtt cgcgaacacg gagggacgct ggtagacgca ggcgacgcgc tgctgccacg   22560
ccttcggatc ggacgcggga ggagcctccg acccgaagaa cttcacggtc ccggtgtcgg   22620
gggtctcgag acccgtgatc atgcgcagga gcgtggattt gccagcgccg ttgcggccga   22680
tgagaccgtg cacctgcccg gcaggatcg agacggagac gtcttggagg gctctcgtcg    22740
caccgtacgt cttgctgacg ccgtcgatct cgatggcggg cacggtgacg ggcacggtgg   22800
tcggtgaagc ggtcatgacg tctccgtctc ggatgctgcg cggtcgggcg gtggggtgtt   22860
acgcggcgcc gaaggcgtcc agggcgaact gcttgttgcc ccagaggtcc gggtcgtcga   22920
cgttctcctt ggtgacgacc ggggtcggca gcagatcgac gaggttgccg ttgcgctcct   22980
cgatgacgct gccgtgatcg gtctcaccgg gagcgaaggt ctcaccctcg atggcgcgcg   23040
tgaggtagtc cgcgccgtag tcgatgtagt cggtcatcgg ctgggcgatg gcggcgtcga   23100
gccagccgtc gcggatcgcg gtcatggcca tggggctcgc gtcgaccgag acctgcacga   23160
tgtgaccggg ctcgccgacc gggatgagct tgccgatcga ctcgagggtg tcgaggatcg   23220
tcgggaagaa ggtcgcgtcg ctctggttgt aaatgcccgc gacgttggag tactggttca   23280
gcgcggtctc gataccggtc gccgccttcg cggggtccca ctcggtggcg acgttcacga   23340
gctgcacgtc ggggtagttc tccttcatgc agtcgttgaa cccgttggtg cggtcgcggc   23400
cgttggaggt gaccgggtcg ccgtcgaggg tgatcacggc cgaacccgcg gcgacgcgcg   23460
agcccatctc ttcgcaggcg agggcgccca tgttgacgtt gtcggcgcgg acgatcatcg   23520
cgatgttgcc cgaggcagga gcctcgtcga tcgcgacgat cggaacaccg gcgtcgttgg   23580
cgtactcgat cgcgggcacg atcgcgtcgg cgtcgcccac cgagatgacg agacccttgg   23640 cgccttgtt gatgagcgtc tggatgtcgg tgatctgctg ggcggcgtcg cggtcggcgt    23700
tcgtcgcggg gatcgtggcg tagccgagct cggcgaagcg ctccatcgag ccgacgttct   23760
cggcgttctg gaacgggtcg gtgtgggggg ctgcgagtag ctcagcggcg tggacgccgg   23820
gtcgccgctg tcggttccgg agccggcggt gtcgccggag cacccggcga gcaggagggc   23880
gccggctccg aggagtgcga caccggtgat cattgaagtt cgcatgcgac ttcctctctg   23940
aagtgcggga caggtgacgg ctgctgccga cgtcattctg aacgtatcgt acgtcttgta   24000
cgtacagaat gtacagccat cgtcgcgaaa tgcaaaccgt gaactcccg accgctcggg    24060 tgcggcggga tcgtgcttgt ctgtacagtc ggacgacaac gtaccgatag atcattctcg   24120
gcccgttcat cgatgcaaag gagtgtggtc gtgtcccaga tcatcgagcg cacctctccg   24180
gtgccgtact acgaacagct cttcgagatc ctgcgcgccc gcatcgtcgc gggcgaggtg   24240
cccgccgacg agcgactccc cagcgagctg gagctctgcc gtgaatacgg cctgtcgcgc   24300
gcgacggtgc gccagacgct gtcgaagctc gagtccgacg gcttcgcccg tcgagtgccc   24360
cgccgggggg tgttcgccac gtcgccggag gccccctcgg ggtggaccgt gcaggaggga   24420
ttcctcgagt cccagatccg gcacggtcgc accggcatcg agaccgaggt caccgacgcc   24480
ggcttcgtcc gcccgcccga tcacgtcgcc gaggcgctgc gcgtcgcgtc gacgaccag    24540 gtgttcgcga tcaacgcgt ccgctcgctc aacggccgtg tggccatgtt cagcacgaac    24600
tggttcccgg atgcggtggg gcgcacgatg tcgaccgccg acgccgtgct cgacggcacc   24660
gggtcggtca acgagaggct ccgcgaagcc gggttcgtca cgagcggcgc acgtcgcctc   24720
atccacgcca cactgccccc cgcggccgtg gcgcaacacc tgcgcatcga gacggatcag   24780
cccgtcctgc gcgtgcggtc gctctcgtgg gaccacagcg acacgcgctt cgactactac   24840
```

```
gagacctggg tgctcaccga cgtcatcccg ctcgaggtca gcgtcgcggc gagctgacgc   24900
tcacccgagc atcgacgcgg tgaacccgcc gagcgagacg accgcatcgg gccgccatcc   24960
gcgagccgtc gctgccagca gggccgcgcc gaccgccgtc acctccggtt ccaggatggg   25020
tgcggcccgc aggccgtgca ccgccgactt gatctcgatc caccccggcg agcgcaccca   25080
cccgcccgcc aggcgcacct cgcctcgatc gggcatcccc gccgaaaccg cgtcgacggc   25140
atcgcgtccc gccaccgcca gcgcaccgag taccgccgac gcgcgggcgc gaggatcacg   25200
gggggcgtcg ggcgagtacg agggcgcacc accgcccctc tcccccggca cgaagtagcc   25260
cgagtcccac agcggcagcg gttcggccgc ccctcgagg agcgcgcgga cctccgcggc   25320
gacatccgca tcctgggacg cccactgcac gttgcgagcg agctcctcca cgcgcaggag   25380
cgtccgcccg tcggagcgga tgccggggc gacatcgacg tgctcaccgc gcacgaccgg   25440
catccccgga gcctgcgcga ccacgacctc ggcagtgccc atcgagtcga ggatcgcgcc   25500
gggcacgatc tgctgcacgc cccacccgc gatcgggtga tcgtggccgc ccgcgaccgt   25560
gacggcgtcg gccgcgatga caccgcctc gcgaagggtc ggcgaatcga gggggcccac   25620
gatctcgccc gtcgcgacga ccgggggcag cagctcgggc gagccgaggg tggcggcgac   25680
gcggtcgaac gcccacaccc ggtcgctcga tcgccacgcc gccgtgcgcg aggcgagggt   25740
gtcgctgaag aacggccgcg cggcccaccg gcacgccgcg aggtcggtca gcgcgagcca   25800
cgaccgcgcc cgaccggcgg tctcgtgcgt ccgcgcccac gcccacccga cgaccgtccg   25860
cacggggtcg gtctccgagt cgaacgtctc gtcgtcgacc agctgcggtc gaagcgcgcg   25920
gaacaggtcc tggcgacggg gatcgaacca cgtcagcgcc ggggtgagca cgccgagccg   25980
gtcgtcgacg agcacgccgt cctcgccgac tccggcgacg cagatggcgt gcacctcgaa   26040
gatctcgccg cagacctcga tcaccatctc ctcgacggcg tcgaagagac ggtcgaccct   26100
caccgacaga tcgaccgcgt cacgcggcgt cggacgactc gcacgagcga cgacggctcc   26160
cgactcgtcg atggcgacga ccttggaatt ggtgctcccg acatcgacgc cgcaggcgac   26220
gggcacgcgc gaaccagcgg acacgtgacc actcctcccc ggggcgcccc acgggcgacg   26280
acctgccgaa gacgccgacc gggcagtggc ggcacctcgt ccacgaccat aaccgcccgc   26340
acggcccccg accgtcggcg ggggtcagga ggagccgatg agaacggggt cgatgtagcc   26400
gagcgcgcgc tgcgcctcga cgtgctgccg ggcgatctgc ggctcgagct ccgcacgcgg   26460
gagctccgtc gcggcgagct cccacgacgg gaacgccccg tcgagggccg ccgccgcctg   26520
catggcggcc cccttcgtga cgtactcgtc gaactccggc acgacgatcg gcaggtcgac   26580
catctggctg agcacccgtt gcacggcgtg gttcttcgcc gccccgccga tcagcagcat   26640
ccgcgtcgtc ggcacggcgc aggcgtgcag cgcgtcgagc atggcgacct ggctcgcgag   26700
ggtcccctcg acgacggcgc gtgcgaagtt cgcgcgggtg aggttcgtga gcgtcgcccc   26760
ctgcagcgac ccgcgggcgt gcggcagatc cgggtgcgt tcgccctcga agtacgcag   26820 cagcgccagt ccgcccgcac cggcgggcgc ctgcagcgcc aggtccgaca gctcggcgta   26880 ggtgcaccg agcaggctcg ccccaggtg cagattccgc gcggcgttga gcgtggcgac   26940
cagcggcagg tgcgcaccgg tggcatcggc gtagctgcac acgtatcccg cgtagtcgtg   27000
caccggggcg gccgtgcggg cgtagacgac ccccgaggtg ccgaggctga gcaccgcgtc   27060
gccgtccgcg agtccgaggg ccagcgccgc ggccgcattg tcgccgcttc ccacgccgat   27120
cgggatgccc gcgggaaccc cggggatccc cgcgccggtc acgcccgcgc gaccgagcgg   27180
```

```
cccgagcacc tcgggcagga tcgccgacga cccgaaggcg tgcgcgaaca ggtcggggt    27240 gtaggcctcg tcctggcccg accagtaggc ggtgccggat gcttcggatc gatccgtcgt    27300
cagccgatcg acaccgcccg taccgggccc gaatccgcgg agtcgccagg tgagccagtc    27360
gtgcacgacc gcgacggcgg cggtgcgtcg agcggcatcc ggatcggtgt cgcgcagcca    27420
gcgcgctttg accaccgtgt cggagagcgt gagcggcagc ccgttcgac ggatccactc     27480 ctcccgcccg agctcggcgt tcagcgcgac catctgcggg tgcgaccggg tgtcgttcca    27540
caggggcgac cgcgcgacgg cggcacccga ggcgtcgagg aagatgggcg tgtgctgctg    27600
gccgctcacc gagacggccg cgacgtcgtc cagcccgccc gccgcgcgca cggcttccag    27660
cagcgccgtc caccagacct ccggatcgac gacggtcgcg tcggggtggg cggccttgcc    27720
ctctcgcacg cgcaggccgg tcgcgagatc gcgcaccgtg accttgcacg cctgcgtgga    27780
cgaatcgatt ccggcgacga gcgtcatcgc ttctccccct ggtcttcgtg aacatgtcg     27840 ccgccgtgcg gccgccgacg gctcaccacg gcgtggcttt caggtgctcc caacgcggac    27900
cgacggaggc ggcccaggcg gcgacccgct cggcgttgcg aggatcgacc tcgacctcgc    27960
gcggctcgct gcgggcccac ggcacgacct cgcccgatgc gagggcctga gccccgcgcg    28020
agaccacctc ggggaagcgc gagacgctca acgccacccc cagcaggtcg gccttcagct    28080
gcagccagag cggattcacg gcggccggcc cgatgacctt cacccgctcg accggatggt    28140
cgaacagtcc gagcacgtcg cggaactgca gggccatgcc gaggaagcag ccgagcacga    28200
tgtcggcggt ggtcgtgtcg ctgtgcaccc cggcgaccac gccccgtgcc gcggcgttct    28260
tgtccggcgg cgggctccct cggaactgcg gcagcacgag cggcacggtg tcgaggtcga    28320
gcgccccgcg ggcgtagcgc cgagcgaggt cgtcgacgca cgcggtgagc tcgtcggcgg    28380
tgagcgagag catgctctgg agcgtcgcga acgccgaccc gcccgtgggg atcgaggcga    28440
acagggtgaa cccctctccc gcgcagtcga tgccgttggc cagtttcgtc gcggcggcgg    28500
cctcgtcgag cctcgggcgc tgaccgacga agaggatgcc ctcggtcgtt ccggtggagt    28560
tgagcagttc gcctggccgg aggtctgctc ccgcaccgcc gaccatgtga tcgtggccgg    28620
cgacgtgcac catcacgtcg tcgccgagac ccagccgccg tgcggcggcg gcggtgatcg    28680 ccgaccectc gacggcggct cggagcggtg ggaacagcga cgtgtcgaga ccgacgagcc    28740
cgacgatctc ggccgaccag cggcgttcga cgaggtcgag cgccatcgtg cggctggcca    28800
gcgagtactc cgaccaccgg tccccggtca gcgcgccggc gaggtactcc gcgacgttga    28860
gccactgggc gtcgcccgcg tcgtcggcgt gggccacggc ccacgcgacc ttcgacaggc    28920
cgtagttggc gttgatcgga agcccggtga cctcgtagac gcgacgacgc tcgcgcgcgt    28980
ccagccggtt caggtagtcc gagccccggt ggtcgtgcca gaggatcatc ggcgacgcca    29040
gtgacatgtc gccgcggacg agaccccccg attcgccgac gccggtgatg gcgatccggc    29100
gcaccgtcgc ccgatcgtcc gcgtcgagag cgagcacgaa ccgatcgatg cccgccgcca    29160
gctcggcgag gtcgtagacc tcccccagc ggtcgtccgt cgtcggcgtg gccaggcggg     29220
cggtggcgcg cgggtcgccg gatgcgtcga acaggcagag cttgacgctg gtcgttccga    29280
cgtcgacggt gatcgtggga agcatggggc ccgaccgctc aggccgcgga gggattcagc    29340
atccggatgc gtcgctccac cacatccgag atcgctgcga cggcctgcgt ggagacgcgg    29400
atgagcgaca cctcctgcgg attggcggcg tacgcctcgc cgaaggcgcg gatcatggcg    29460
ttgcgcagat cgctggcgac gttgaccttc acgacgccga attcgtgcag gcgcccgagc    29520
tgctcgggcg ggagccccga tccgccgtgc accacgagcg ggacgctgct ggccgcccgc    29580
```

```
acctgcgcga gcaggtcgaa gtcgatcgcc gccgtcgggg agtacccgtg cacgttcccg    29640
accgacacgg cgagcatgtc ggggcgcacc gccgtcacga agccctcgac ctgagagggg    29700
tcggtgctca actccacctc ggggccgtgg tcatcctcct tgccaccgat gctgccgagc    29760
tccgcctcga gggccagatc ggccggggtc atctcgcgcg cgatcgacga gatgcgcacg    29820
ttctcgtcgt agggctcctc ggaggcgtcg atcatgatcg acgtgaaatc ggcggcgagg    29880
gcgtcttcga ccgctccgag cgacttgccg tggtcgaggt gcagcgcgac gggaacccgg    29940
gtctcggcga gccgtcggct gaccatgtcg tagatgtact cgaagcccga cagcgccgca    30000
ttggtcgggg cgacctggat gaaggtcggc actccgacct tctcgatggc atcgacgatc    30060
cccatcgtcg tctcgatgtt cgtggtgttg aaagcacccg cgacgagccc gcgcgcggtg    30120
cattcctgaa tgacgtcgag gccgctgacc agtggcatag ggggtccttt cgaagagaca    30180
gcgtcactct aacctgaaca gtacatatcg tccagtctgt acgtacaaaa gcctccctgc    30240
ttgttcgctc ataccccctg ggtggccgcg cgtccaggct cggggccgac cgaaggcacc    30300
cgcctaacct ggccggaacg tcggaaagga cgcccgtgct caccggactc gtcacctcgc    30360
tcaccctctt caccgcactc ctgtcggggg cgctcgccga cggcaccccc gagacccccg    30420
ccgacggcgc cgccggcgtc gtctacgtct tcgtcgccat cgcgggcctg gtcgccgtcg    30480
ccgtggtcgg cgggatcgcc ttcgtcctac tccgcgacg ccgcggccgc aagcggcgct    30540
gagtccacac ctccgcgctc ggatcaccac cgcgcggcgg cgtccgtgag tggactcgtg    30600
cggcggggtg tggattcgat cccgcgcacg cctcgcctag ggtcggaggc atgaccgcgc    30660
gcatctcgct cctcggccgg ttcgtcctcg cgctcctgat cgcggtcgcg gcggtgctcc    30720
tcccggccgc cgcggcgtcg gccgacgtcg acgacttcgc cttcgactcg ttccacgccg    30780
acatgctgct caccgcgcc gccgacgggc acgccgagct ctcggtcacc gagacgctcg    30840
tggcccgctt ccccgacagc gaccagaacc gcggcatcgt gcgcgcgatc cccgacgacg    30900
acgccggtgt gccgctgcac acgaccgtca cctcggtgac gtcgggcggt ggcgagccca    30960 tccccctacga ggtgagcgag cgcgacggct tcatcgaggt ggcgaccggc gacgactcct    31020
acgtgcgggg ggtgcagacc tacgtcatct cctacacgca gcgcgacacg atccgcgcgt    31080
tcgccgacac cgatgccgac gagttctacc gcgacctcaa cggcacggga tgggagcagc    31140
ccttcggcga ggtcagcgcc tacatcgtca tcgatccctc cctggccgac gcgctcacgg    31200
gaaacaccgc ctgctacgtc ggcgaaaagg gctcgagcga cacctgcgag atcgtcgagc    31260
gcgcgaccgc gccgggtgaa ccgaaggagt tcttcccgca ggcgttcgac ctcgagccgc    31320
gagagaacgt gacggtcgcc atcggcttcg agccggggac cttcgttccc ggcgaggtcg    31380
agcgcagtgc ggtgcaggac ttcgccaccg acgccgctcc cgtgttccag gtcggcgccg    31440
tcgccgcgat cgtcgcgagc atcgcggcgg cgtccgcggc tctcctcgcg cgacgccgta    31500
gccgcgacgc ggagggacgc ggcatcatcg tggccgagta cgacccgccg caggaggtct    31560
cggtcgtgca ggccgcgcac ctcgtcggac gcccgccgc agccgtcccc gccgcgatcg    31620
tcgatctcgc cgtcaccggt cacgcgcgcg tcatcgcgca cgacgatgcg gcgaccgacg    31680
tctcgctcga gtacctcgcg ccgagtcccg acgatccggc ccgtcagcgc accctcgacg    31740
ccgtgttcgg cctcgccccc gaacccggcc ggcggctgcg gctgaagggc gcggacgccg    31800
agatcgcgtc gcgtttcacg agcctctccg cctcggccgt cggcgagctc cacgcggccg    31860
gcctcacgca gaagcagtcg catcggctgc ccggctcggc cttcgccgtc gccttcgtcg    31920
```

```
ccttcgccgt cgcggtcgtc tgcgccgtgt tcgccgcgat gggcgacgcc ccgcggtggg    31980
tgcccggggc cgccgtcgtc gtggccgtcc tcgccgggat cgtgaccgtc accatgtggc    32040
gcacccgcga ccgcatcacc gatcgcggcg cgccggtccg cgaccatctc ctcggcctgc    32100
gcgactacct gcaactggcc gaggccgatc gcatccgcat gctgcagagc cccgaaggcg    32160
cggagcgcag cggaccggag gcggccgagg tcctgcacct ctacgagcgc ctgctcccct    32220
acgcgatcat ctggggcatc gagaaggagt gggcgggcgt gctcgcgacg caggccgagc    32280
ggacggatgc ttcgctggac tggtaccgcg gaacccaggc gttctcctcc actcagctgg    32340
tggccgtgat gacggcgtcg cgaacggcgg ccagcccgcc cgcgccgacc tgggccgcca    32400
gcggcggcag cagtttctcc gggggctcca tgggggcgg attctcgggc ggcggcgcag    32460
gaggcggcgg aggcggaggc cggtagcgtc cgcgtcacac acgcgtcacg tgcggcccct    32520
atgcttcgag catgtctgcc cgaagacgta ctcgccgccg cctctcgtcc acccgcccgc    32580
cccaccgcca gccggtgtgg ctcatcgtcg gggcggtgat cgtcgcgctc ggaaccgtcc    32640
tgctggtggc cgccgccctg ctgacccgat gaccgggtag ggataccccg gtatcggcgc    32700
gacgatcgcc ctcgctacgg tgggtggcat ggagttcctg tcgtgatcga agcccattcc    32760
ctgaccaagc gctacggcgc caagaccgcc gtcgacacca tcgacttcac cgtccgtccg    32820
gggcacgtca ccggattcct cggaccgaac ggtgccggaa agtccaccac gatgcgcatg    32880
atcgtgggtc tggaccgccc cacgaacgga tcggtcacgg tgaacggcaa gccgtacgcc    32940
gagcaccgcg cgccgcttca ccaggtcggc gcactgctcg acgcgaaggc ggttcacacc    33000
gggcggagcg cccgcaacca cctgctggcc atcgccgcca cccacaggat cggcgcgaag    33060
cgcgtcgacg aggtcatcgg cctcaccgga ctcgagtccg tcgcccgcaa gcgagtcggc    33120
gggttctcgc tcggcatggg gcagcggctc ggtctcgccg tggcgctgct cggcgatccg    33180
gccaccctca tcctcgacga gccggtcaac ggcctcgacc ccgagggcgt ggcatgggtg    33240
cgtcagttcg tccggcacct cgccggcgag gggcgcaccg tgttcctgtc ctcgcacctc    33300
atgagcgaga tggcccagac cgccgaccac atcatcgtgc tcggacgcgg acggatcgtc    33360
gccgacgccc ccgtcaacga gatcctcgcc aacgcctcgg gcggctcggt caaggtgcga    33420
acgccccaga tcgcgcagct cggcccgctt ctcgagagcg agggcgccag cgcgacggcg    33480
acggcgcccg acctgctgtc ggtgacgggc atcgtcgcgc agcgcgtcgg cgagatcgcc    33540
gcgagcgcgg gcgtcgtgct gtacgagctc acgccgctca ccggctcgct cgaggacgcc    33600
tacatggagc tcacacgcga cagcatcgag tacgccaccg ccgactacga cacccccacg    33660
accgcggagg cgacccgatg agcacctcga cccccacccc cgtgttcacc ccgaccggcc    33720
gcgacctcag cttcggcgga gtcgtggctt ccgagtggat caagttccgc agcatccgct    33780
cgacctggtg gtgcttcgcg atcctggtcg tgctgaccgt cggcttcagc ctgctgctgt    33840
ccgcatcgct cagcgtcgac cccgcgccca cgggcgactc cgcccagtcg ctgtccgtgc    33900
aggcggtgac gatcagcacc accttcgggg cgctcgtggt cagcgtgctc ggcgtgctca    33960
tcatctcggg cgagtacggc accggcatga tccgctccac gctcaccgcc gtgccgaagc    34020
ggacgcccgc gctccttgcg aaggcactcg tgttcgccat cgcgacgttc gtcgtcgccg    34080
tgatctcctt cggcatctcg atcgcggtct ccgtggcgct gctgtcgggc aaaggcctcg    34140
agaccgacct cgcagatccg cagtactggc tcgccatcct cggcggcgtg ggctatctcg    34200
tcctcgtcga actcatcgcg ttctcgcctc ggcgcgatcat ccgcaacacg gcggggagcg    34260
tcgccgtggc gctgggcctc gtcctcgccg cgccgatcgt gctgaacatc gtggggggtgc    34320
```

```
tgacacagct ggtgtggatg cagaacctcg agaagatcct gccctcgtcg gcgggaagcg   34380
ctctcgccgc ctatcccgtc gagtcgtcgg gcgcgcccac caccgagggg ctctggacca   34440
tcgagccctg ggccggcgga ctgatcctcg tcgcgtgggt cgtcgtgctg ttctcgacgg   34500
cgatcgtgct gctgaagcgc cgcgacgcat gacgctcgcg ctcgggcccc cttatcgcct   34560
cgggggcccg agcgcgaacc tgtgagcacg tacatgtgaa acgcatagcg ttcggtgatg   34620
gacaatccct cagaacgttc agccctcgt cccacccctc ccgccggcac ggagaggttc   34680
gaccccgcgg tcggatcgaa ccgcagagcc gcggcgccgg ccccgcccg ctcgaagaag   34740 ccgcggacca tcgtcggtcg tcagcccttc tgagtcccgg caggatgccc taacgcaacc   34800
gcttcggcaa ccccggcccg acgtcgtggt gccccgctta tcgtcggaac ccccgcagga   34860
gaactcagcg gcggacgacg acgagggagc acagcatgac ccgtttcggc tacacactga   34920
tgaccgagca gagcggtcct cgcgagctcg tgaggtacgc cgcatccgcc gaggacgccg   34980
gcttcgactt cctcgtctcg agcgaccact tctccccgtg gctcacgagc cagggtcacg   35040
ccccgtacgc ctggaccgtg ctgggtgcgg tcgcgaacgc gacgtcgacg gtcgagctga   35100
tgacctacgt cacctgcccc actctgcgct accaccccgc ggtcgtcgcg cagaaggcca   35160
cgacgctgca gatcctctcc gacaaccgtt tcacgctagg tctcggttcg ggcgagaacc   35220
tcaacgagca cgtcatcggc gagggctggc cgtcggtgca gccccgacag gagatgctcg   35280
tggaggcgat cgagatcatc cgggcgctcc acaccggtga tctcgtcacc tacgacggcg   35340
agtacttccg ggtggactcg gcccgtatct gggacgcacc cgacggcggc gtgcccatcg   35400
gggtcgcggt ctcgggggcg aagtcgatcg ctcagttcgc cccgctcggc gatcacctca   35460
tcaccaccga acccgacgcc gacctgatct cgtcgtggga tgcggcgcga aaggtgagc   35520 ccgcctcgcg gaagatcggc cagatcccga tcagctggga ccccgacaag gatgcggcga   35580
tcgcccgcgc ccacgatcag ttccgctggt tcgccggggg ctgggcggtg aactcggatc   35640
ttccgacgcc ggccggtttt gagggcgcga gccagttcgt ccggcccgag gacgtcgcgg   35700
agtccatcgc ctgcggcccc gacctcgacg ccctcgcaga gagcgtccgt ccgttcgtcg   35760
acgcgggctt caccgacatc gccatcgtgc aggtcggtga cgagcagcag gagcgcttcg   35820
tcgtcgagat cgccgaaccg ctgctcgaga agctccgcgc cctctgacgc cggtcagagg   35880
agcgaacgcg cgacggtgac cgagctgctc gtcgtcccgc ccgggccgcg gacggtcaac   35940
gtgtacagct gctcctcgtc acggcaggag aaggcgagcc cggtgtagcc cccggacgac   36000
ggcggcacgg cggcggacgg cacggccgac gcatccgtcg tcccgacccc gatccacgcc   36060
tcgccggcgc cggtggtgtt ccaggtgaag gagaggggca cggtcgccga gcggtcgtcc   36120
gtgcattcgg ccgcggtcgt gctcaccgcg aaggcatcga tgaccggcgc ggtggtggtc   36180
tcaggcgtac ccgaggcgtc cggcgcgtcg ctcgcggtgg gcggcggcgc agtcgacgac   36240 gccgaccgg cggacgggtc gacgatgcc gcggacgatc ccgcggcga cgacgatgcg   36300 gtcggcgtcg tcgaaacgga ggcagcggga ccgcggtcg cggccccgtt cgcgatcgcc   36360
caccaggcca gcagcaccgc gacgacgatc agcgtcgcgc cgcccacgta ccccagacg   36420 atccgtcgtc ggacggtcga cgcgacggtc tcggcatcgg tccgatcatc ctgctcggtc   36480
atgcggtact cctctgtcgt ggcgggacgg cgaggggag gacgggatgc gatgatcccg   36540
ccctccccct cgtcggatca ctcggcgaa cgcctcgccc gcgtgcgggc gagcacgaac   36600
gcgctcgctc cgaacatcat gagcgcggcg ggccccggccc agagcgaccc cgggctcgac   36660
```

```
ccacccgtcg ccgcgaggct cgagtcgttc ggcggcacca cgaccgccgg ggccccggtg    36720
gtcgtgggcg tcggcgtcgg ggccgtggtg ggctccgtcg tcggctccgg cgtcggggtc    36780
gccgtcggct cgggctgcac gacgggcggc tcgacggcgc tcgccgtctc ggtagcccag    36840
aagatcgacc gcgcgacgtc gctgaacgcg ccgaccgggt ggttgcggaa cgtcggagag    36900
gtaccgaaca ggaacacacg attacccgag atcgtcgacg tcgcagacac ggctgcggcc    36960
ttgccggcgg catcggtcgt ggagcggccg tcggttgccc gccagtgacc cgagaccagc    37020
gggtctgcga cgtagctcgc ttcgaccgac acattctccc cgagagcagt gaaccacgtc    37080
gccgggtaga cgaacgcggt gtcctgggcg aagtcgccca gcaccccgtc ctcgggagtg    37140
tcgatggaca cgatgccgtt ggaccccgac gtgcccgtcg tcgccgtcac agtggccagt    37200
ccgaaggtcg acacgaacga tgctccggcc gcgccgcgcc cgacgacggg cttgcccgag    37260
tccaggaacg tgcgcatcgc ggtatagccg gtcgcctgcg tcgtcgggtt gatgttcagt    37320
gtggcgccga cccacagcag atcgatcgag ccgaggtcga ccgcgcccga atcgatcgtc    37380
gccgcggtaa ccggtacgag atcggtgaag ccgagcttgg tgagcgcgtc gcggtcgtcg    37440
gtgctggtga cgtatccgac gcgaaccgga cggagtccga cgacgccctc ctcgcgcaga    37500
cccgatccat cggaggcggc gaagtcgacg ccgtagatgc ccgctgcggc ccgggccgca    37560
gcatccgccg tcgcgtcgcg ccggaacacc acggtgccgt cctcgagctg cgacagcgcg    37620
atgccctcgc ccagcagctc gttgatggcc tggtaatcgg cgacgccgcg cggctcgaac    37680
gagaggtagt cgctcgcggg agccaccgaa cccgtgagag gcgcctcgga gatgggctcg    37740
agtgccgtcg tcggggcggg atcggtcgtg tagccgaggg cctcgacatc ggctccccac    37800
agcagcgaca ggctccacgc ggagatgtcg tacatgtcgg gcacccgctc ggtgatgtcg    37860
gtgccgtcgc cgagcagcgc gttcgcgagt ccgcggaccg gctggtgcat gtcgacgtag    37920
taggagccgg ccgggtaggt gacgccctcg gcggtgaacg tgccgtcgt gcgcgagacc    37980 tcgatgccgt tgacgagcag ctgctgcacg agcgtctgcg cgtcggagtc ggagcgctga    38040
cccgcaccct gcgggatgac gtaggcgcgc gggaactcgg tcgtgtagat gtcgttctcg    38100
tcccagatgt cggtccactc cgtgggcacg ccctcggcga ggtcgtccgg cgagacgtcg    38160
gcggggatct cgacgctctc ggcgccggtg agcccgcgct cgaagatctc gatctggttc    38220
tccagcagcg aggcgctgtt ctcctgcacg tagtcggcga cggtgtcgat gaccacctcg    38280
gcgacctcga tgttcaccTT cgcgcgcgcc ggctggtcgc cgctgcgacc gagcgggagc    38340
tcgaccgtat tcgtgacggc accctggtag gcgacgtact gcggggcgaa gatcggcggc    38400
cagtcgtccc agcccgaacg ctggtcgcgg taggggatgt tgatgaagcc ggtgttggtc    38460
gacgtcactc ccgcggtctc ggggtcgtag taggtgttgc cggggatgtt cgcctcggtc    38520
acggccttct cgatgtcgag cgcggtcgcg taggcgtgcg gcacgaacag gtcgtactcg    38580
tagttctcgc cgtggggcgg accgcacggt tcgacctgca gcacgttggt gtaaccgtgc    38640
aggtcgatga aataggtcgg ctggatgatg ctggcgaggt cgcggacgat cgacgcctcc    38700
ttcgtcgcac cggtgatgaa gtcgcggttg gggtcgtacc cgttggcggt gccgcgctgc    38760
ccgagcgcgc gcccgtcggg gttgttcgtg accgtgaagt agatgcggtg gttgtcgagc    38820
aggtcctgga tgaccgggtc ggcgctggtg gcgagatcct cgatgtagtt gagggtggcg    38880
tccgtgccct cccactcgtt gccgtggatg ttcgcgttga accacagcgg caccttgtag    38940
ccctcggcga gcgccgcatc ggatgctgcg gcggcggggt cgtacttcac cttggtgcgc    39000
caggcgtcct gctgagccgt ctcagcgggg gtctcacgcg acgtcaccgt caccatgtag    39060
```

```
atctcgcggc cctggtagga ggtgcccacg acctgcgacg acacgcggtt gctgcggtcc   39120
atcaggcggt tcaggaacgg ggcgatctcg tcgtagggca tcacgccgcg cgcgatcgac   39180
gcgtccgtgg gcaggtcggg gacgacggtg agccggggct ggtacgggta ctgcgtcggc   39240
atctcgatcg acgacgtcgg tcggacgatc gagagcgcgg gcgggtcgac cgccgcgctc   39300
gccggcgcga acgccagcat ggaggaggcg atggcgacga cgccacctat ggacacgagg   39360
gcacgggttc gcacgaagcg gactccattc gagaggggga gctcgacgcg cgctcggagc   39420
tgagcgcgcg ggaccacgcc gtccggtggg acggggatcg atgagactgg cggttccccc   39480
accctaggaa gcgcgtgttt cgccctcgtg tcggccgggt gtcgagaaga ctatgcgcgg   39540
gctatgcggt gatcgcgctc gccggaccgg tgatcctcgc gatgcggtca ggttcgatcg   39600
tgaccacgag agacggtgtg cgggcgacac cgtcgaccgc cacggcgtag cgccccgggg   39660
cgagtccttc gaagagcacg cgaccggtgt ggtcggtgag tccgtcccgc tccacgcgga   39720
cgcacccctg ccgcgcgagc gtgacatcgg cctccgcggc gaacgccccg tcttctgcgc   39780
acaggagcag ctcgaccgcg ccggcggtcg gcacgacgac gggcgtcacc tcgacgtcgc   39840
ggcggctcga cagctccacg gtctcatcgg cgagcgcgta gggcagccag tcgtgaccgg   39900
aacgccggta cacgagaagc tcgtatctgc cggcgggagc ccgcaggacg aagcgtccgg   39960
tggggtcgct ctcggcgacg agggtgtcgc cgtcgaaggg atcgaccgga gtcggctcgt   40020
tcaggagcgc gacggcgtac cggccgtccg cacccgagat cgcgcccgtc acccggcccg   40080
ccgccgtcag cgccgcgtcg acggcgaggg tctcggctcc ggcatccacg atcacgcgcg   40140
tggcgtcgtc acctcggcgg acgttgggga accacgcctc cacatacccg aagggggcat   40200
ccgggagcgc gatctccaag ggacggaaca gcaccgcgta tcggccggcc gggacgtcgc   40260
tgatcgcgta gccgccatcg gatcgagctg tcgcgctgta cacctgaccg gtcgattcgt   40320
cgatcgcgac gacgtcgccg gcgaccgcct gcccggtgtc ggaggcgagg cgtccgagga   40380
tgcgcccggt gccgggctcc gccgccacgg ccgtcgcggg agcgaagaac gatcccgcga   40440
cgaccgccga cgccgaggag gcggcggctc gacgcaggga gcccggtcgg tgcgagccgt   40500
tcgagtggtt cacgtggccg ctcccgctga gatcgatcca ccgccgtggt cggccgcggt   40560
cgccgcaccg taacagcccc ggatggcgcg gaggtgacta ctcggtgtcg ctttcgtact   40620
cgatctcacc ggcgacgatg gcctcggcgt aggtgcgcag gtcgggtccg ggctcgtagt   40680
cgatgaaccg gtccttcagg cgcgcgttca gctcggcgaa cgcttcgtcg gccgtcgcgt   40740
cggggcgggt cttcgcgacg tcgacgaccg cctcgcgcag cacgcggtcg cgtcgtcga   40800
ggatcttcgc tcgtgcgggt tcgttccagg agatctctga ggtcttcatg gcgcgagcgt   40860
acgtcgcacg acaccggggg aagctggggt tgcgcgcgcg ctaccggcgg tgtgcggcag   40920
gatccgacgc ggtcttctcg tcgacccagc cctgcagctt ccacgccggc acccggaaga   40980
cccgcgcgat cgcggcgacc gagtagcgcg cctccatcac ggcggcaacg gcgaactgcg   41040
gcagggaatc gaacgagcgg tcggcgagcg ctcccttgcg cagatccgcg aacgtgcgag   41100
gggcgcgctc cgccggagag gccggatcgc tcgacggcgg ctccgcgacc gccgcgggca   41160
ccgtcggcgc gtgatcgccc acaggcggag gaagcgcagc atccaccgac gtctccccca   41220
ccgacacgaa cgaccgcacc gggaccccga gagcgtctgc cgccgcgaac agggtcgaga   41280
gcgacgtcgc cccttcgccg cgctcgagcg ccgacagcgc gggagcggcg acaccggcga   41340
gcgtcgcaaa ctcctgcagg gacagtccct gcgctgtccg atgatcatgg atgcggcggc   41400
```

```
ccagagcagc tactccgacg gccgcccgcg ccgccctgtc cgagcgaccg ttcgatgtga    41460
tcgtccccat acgatcctcc ccgcctcgga tcgtagcgct taccacacgg acggcgcatc    41520
cccaagcccc tccgccatgc cttatcctgg tggggcaagg ggagtactcc cactcgcggc    41580
gctgccgtca ttacggactc gacatcgagt cccggcacgt cggtcccgac cccggtcgtg    41640
atggaggaga ccttgacgtc gttgtaacgt cctctcaccc ctggagctct cccatggaga    41700
tcacgcctct catttggctt atcacgatcg cggtcaccat cgcgttcttc gtctacgaat    41760
tcttcgcgca cgtgcgcaca ccgcacgaac cgacagtggg cgaatccgcc cgctggtcgg    41820
cgttctacat cgggctggcg ctgctgttcg gtgtcgtcat cggagcggtg tggggctggg    41880
acttcggcgg cgagtactac gccggatacc tcaccgagaa ggcgttgtcg atcgacaacc    41940
tcttcgtgtt cctgctgatc atgaccggtt tcgcggtacc gaagaagtac cagcagaagg    42000
tgctcatgat cggcatcgtc atcgcgctca tcatgcgcgg cgcgttcatc gccgtcggcg    42060
ccgcgttgat cgacaacttc tcgtggatct tctacatctt cggcgccctg ctgctcttcc    42120
tcgcgtaccg tcaggcgttc tcccacggag agagcgaccc cgccaacggc aggttcatga    42180
agttcgtgcg ccgccacctg gccgtcaccg aggagtacca cggcgacaag ctcacggtga    42240
agctggacgg caagcgcttc gtcaccccca tgctgctcac gatcgtcgcg atcggcttca    42300
tcgatctcgt cttcgccgtc gactcgatcc ccgccatcta cggcctcacg aacgaggcgt    42360
acatcgtgtt cacggccaac gcgttcgcgc tgatgggtct cgccagctg tacttcctca    42420 tcggcggcct gctcgagcgc ctcgtctacc tcgcccaggg tctggcggtc atcctcgcgt    42480
tcatcggtgt gaagctcgtg ttccacgccc ttcacgtcaa cgagctgccg ttcatcaacg    42540
ggggcgaacc gctcctgtgg gtgcccgaga tcccgatctg gttctcgctg ctgttcatcg    42600
gcgcgaccat cgccgtcgcc accgtcgcga gtctcgcgaa gacccgcaac gacgaccgca    42660
agaaggatcg ctcccgcatc gagggcgagc ccgtcatcca cgccgacgac gagacgaagc    42720
gctagccccc gagcccgccg tcgcccggtg acgggcggcg gagacctcac gagcggagga    42780
cgatccccca gggattcgtc ctccgttcgt cgtttatccg cccgcggtga cggatgctgc    42840
gcccgcgcga tcagccgagc ggcgccttcg cctcgaccac ccggcgcgcg gcggcatcga    42900
ccttcgccgc gaacgcctcg tcggtctgcg cgcgggagag cacggccgcg tacatctcgg    42960
gaaacaccgt cggatcggcc gagacgagca ccaggtcgac tccagcctcg atcgacagga    43020
gggcacggtc ggcgggcgtc cagtcgcgga tctgtgcggc ggccgacaga tcgtcggtcg    43080
tgaccacccc ctcgaacccg agctggtcgc gcagcaggcc cgtcacgacg gtcggcgaga    43140
acgcggcggg cgcgctgggg tcgatccgcg cgtagacggc ggtcgacatc atcacgaccg    43200
ccggcccccc ggcgagcaga tcgcggtaga cggccacgtc ggccgagtcg gcaccgacga    43260
cgtcgtcgac gacacccgac cgggtgtcgg tgttctgcgt agcccgcccg agaccgggga    43320
agtgcttcag cgtcggcatg acgcccgagg cccgcatccc ggcggcgaag gctccggcct    43380
tgtcggcgac ggtggcctgg tcgaatccgt actcgcgatt gagggcgccg atcggcgggt    43440
tctgcggtcc ggcttcggca ctcgtgacga tgtcggccac cggggcgagg ttcatgttca    43500
cgccggcctg ggcgagctgc gcgcccagc gtgtcgcgtc cgcctggagc gtcgccgtgt    43560
cggagcgcgc ctgggtgaga gcggtgggga tgctgtcgaa accgggaccg gagagcacct    43620
gcacgtcgcc gccctcctgg tcggtcgcga tccacagcgg cgggtcgctg tcgacgcggg    43680
cgtcttcgaa ggccttcacg aacgcggcag ccgcctcgac ccccgcggag gagcggccgt    43740
ggaggaagac gccgccggcg tgctgctgcg acaccgcgtc gagcgtgatc ggatcgggtc    43800
```

```
caccgaccga ggtgcccacc atgaagagct gccccacccg ctgttcgagc gagaggccgg   43860
cgatcgggtc ggcggggtg ggggtgggcg tcggagacgc cggtgagcg ctcgacggag    43920 cgatgctcga cggttccgcg gtcggcgacg gtgccggagc cgagcatccg acgagtccga   43980
ggatcgcggc gacggccagg gctgcggtgg ggagggttct cgtcacccct ccatggtcgc   44040
aaccctcccc gtgcgcgcgg cacgggttgc gcgcgccgac gttaggctct caccgatgat   44100
cagcacccgg atcggctcga gcctcgccgc tctggggatc gtggcatgtg cactggtgtc   44160
gtgcgcatcg gtcgcctctc ctccgccggc cgccgttcct ccccggccg ccggggtgcc    44220 cgactaccag ctcggcgatg cctatccgcc cgatgaccgg gtgacgatcg tcggacgcga   44280
ccggtcggcc gagccggccg aggggctgta ctcgatctgc tacgtcaacg ggttccagac   44340
gcagcccgcc gaacgcgacg agtggcctga ggagctgctt ctccgcagcg ccgacggcga   44400
gccggtcatc gaccccgggt ggcccgacga ggtgatcctc gataccggct cgaccgcgaa   44460
gcgccaggcg atcgccgaca tcgtcggtcc gtggatcgag gggtgcgcag catccggtt    44520 ccatgccgtc gagttcgaca atctcgacac attcacgcgc acgggcggcg cactgacgct   44580
cgaggacaac ctcgcgttgg ccgcgacgct cgtcgacgtg gcgcacgggg cgggcctcgc   44640
cgcggggcag aagaacgcgg cggaattcgc gtccgacctg cgcggcgccg cgggcttcga   44700
tttcgccgtg accgaggagt gcgccgccta cgacgagtgc gcgagctacg ccgacgtcta   44760
cgggtcggcc gtgatcgata tcgaatacac cgatgcactg ccccgcacgt tcgacgagat   44820
gtgcgccgat cccgggtcgc cctcgtcgat ggttctgcgc gatcgacagc tctcggcgcc   44880
gggcgatccc gaccacgtct tcgcggtgtg ctgaccggcg gcggacccta ccgaaccggt   44940
atatcccgcg caacgttcac agcagacgtc caggttctgc cattctgggg tcgcggtgtc   45000
tgcccgggtg ccgcttctct cagccgtgaa ggatactcat gactcagcag cccgcagccg   45060
gaatcgacta ccccggcaag accctcggca tcgtcggcct cgtcgtcgcc atcttcttca   45120
acgtgatcgg tctgatcatc tcggcgatcg cttcaacca gtcgaagaag gccggctaca   45180
agaacacgcc cgccctcgtc ggtatcatca tcggcatcgt tctgaccgtg ctcggcatca   45240
tcatcggcat cgcgtccttc tcggccatga tgagcatggt cagcagctac tgaccgcgct   45300
tcccgccccg tcttcgcccc gcctcggcgg gcggggggcgg ggcggtcgct tttcaagcac   45360
tacgcggcgc gacgcgtcga ccaccacgcc catgccacca gcacgggctg gaagaacagg   45420
cgcacgtagc gccgccggtc ggtgtcgagc ccgaaggcgg agcggccttt gcgccactgg   45480
tcgagattgc cggggaacac ggcgatgaag aaccgccgcga ggagcgatcc gacccgtcgg   45540
cgttccccgg gcagggcgac cagcgcgacg ccgaaggcga cctcgaccac gcccgaggcg   45600
accacgatcg tgtccttgtc cagcggcatg ccgtcgacga gcgcgtcggg cacctgtgcc   45660
tggaaatcct tccgcgccca gagcaggtgg ctcagtccgg cgaagaccat ggcggcggcg   45720
agcgcccacc gggcgacagt tctcatgatt ccgagagtag ttgtcaaggg cggggcgcgc   45780
gacggcgggc cggcgagacc atgggaggaa accgcaacag gaaggcagac catggcccgg   45840
atcatcgaga ccatcgacgt ggacgtcccc gttcgtgtcg cctacaacca gtggacgcag   45900
ttcgaggagt tccccccagtt cctcagcttc gtggagtcga tcgtgcagac cgacgacaag   45960
acgcagcact ggaaggtgaa gatcggcggc caggagcgcg agttcgacgc cgagatcacc   46020
gaacagcacc ccgacgagcg cgtcgcgtgg aacagcatcg cgggcgagga aaccacgcc    46080 ggcgtcgtga ccttccacaa gctcagcgac accacttcgc gcgtcaccgt gcagatcgac   46140
```

```
tgggagccca ccgggctgct cgagaaggcg ggcgccctgg tcggcgtaga cgacatcgcc    46200
gtgaagcgcg acctcgcgaa cttcaagaag ttcatcgagt cgcgcggatc cgagaccggc    46260
gcctggcgag gcgacgtcga gaactgacgt ccccctgcgga tggacggcgg tcggagcgct    46320
ccggccgccg tccgtcgtgt caggctcgga agtccggcga acccagcacg cgctcggggc    46380
ggagctccaa cacgacccgc tcggggttca cgcgcggttg gcgatagcgc cgcgcgtaga    46440
gctcgacggc gtgcgcgacg gcgtcggcgt cgtcgagcac ggatgctgcg ccctcgaaac    46500
tgatccatcg cccgccgtcc accgagcaga tggacgcgcg cccgcggcgc tgggcgttca    46560
ggaacttctg cgagcccggg atccgatca ccctcaccac gtcgtcctcc catgtgaatc    46620
ccacgggaac cgcgtggatg cggtcgcgac gccccagggt cgagagcgtg gcgaggtggt    46680
attcggagag gaaggcgcgc gcttcggcgg tgatcatcgt cccagcgtgc cagagtggaa    46740
gttctttact cgcctagtaa tcaccgagcc taagtacaat gggccgggca cgaaccatgc    46800
accctgcgcc cacagggaag ggagtgaccg gtgaccgtca ccgacaccga dacaaacttc    46860
gatacgaacg aggccatcca cgacgccgcc cgatcggtgg agctgctccg actctccgag    46920
gcccgcctgt cgcgcaggcg acagaccgac tgcggcccca gcgagaacgc ccgcgccgcg    46980
atgcgttaca tcctcgagcg ggcggacgtc ggagagggag tgactccgag cgagatcgcg    47040
tcgcacctcg gcgtctcggg cgcctcggtc accggcatgc tcgatcggct ccacgccggg    47100
ggcatgatcg ctttcgcagc gcaccccga gaccggcgca gcaagctggt cgtccccttc    47160
gaccgctcga cggacgcgga cgacgtcgac ccggtgacgg ccaagatccg ccagttcgcc    47220
gctgacctct cccccgaggc ggcggcccag gtcgccgact tcctcgagcg cgtccgcgag    47280
gtcgtcgacg cggaatgcgc ctgagagcag ccggcgtcag ccgaccacag gctccatcgg    47340
agcgtcggcg tcgggctcgg gcgtcacggc cagcccgttc gggctcccgg cctcgagcat    47400
gagctgatcg acccagcggc ggttgagcgc cggcggccgg cttccgtaga agtggaagac    47460
cagcgggatc gacggatgga tccagatcga tcgcgaaccg cttccgtcgc cggcggcgaa    47520
ctggaacatg aacgactcgt tgcgacgcag cttgttcatg aacacgatcc gcaggtgaga    47580
caacgcgcgc tcctcgatgt cgaaggaatg acctgcgcg ttgtaaatca gtttgcccac    47640
gatcacagac taccgcgagc cctgacttaa ctagtcggat cgacgggagt taactatctc    47700
ccccacggcg ccgttccgcg gaatctcacg gccctccggg gtccaggcgc cttcccgcga    47760
gttccccggg aatcgatgca caagaattca cttttgtccc ccgaacgggg gactccgacc    47820
ctatgatggg cgggacggcc cggcaccggt cgtcagccct cgccggcgtg tgacctcgtc    47880 caccgacga gggcactttt tttccgctgc cgtccggatc gcaccggtcg gccccaccgc    47940
gagtagagtc ccttctgatg ggtacccccga cgtctcgtcc gacgatgcgc cgacggacaa    48000
agaagaccct gctgatcgcc gcttccgcgc tgctggccat cgggctcgtc gccgtgatcg    48060
cgttcgtcgg cgtcaacgcc cagatcttct tccatgcgct gggcgcccgc cctcccgcgg    48120
tcggcacgac gatcgtcgcc cccaccgagt cgaaagccgc cctctccgcc gcctctccga    48180
gcgggctgtc cgacgacgag gccgccgcgg ccgcctacct cgccgagcag ccgaccgcct    48240
actggctgac tccgagctc gacccgatcg acgaggtctg ggaccggatc gcacacctcg    48300
ccgacgaggc acgcgaacag gatgcggcgc tcgcggtggt cgtctacggc ctgccgggc    48360 gcgactgcgg caatcactcc gccggcggac tcgacccgga ggggtacgtg gagtggaccg    48420
acctcatcgg tcaggcgctg cgcaacgccc aggatgtgca gaagatcgtg atcctcgagc    48480
ccgacagcct cgccctcgcc cccgactgcg gcaacatcga cgagcgggtg ccgcagctct    48540
```

```
ccggcgccgc cgaccggttg gcgggcatcg acacctggat ctacctcgac ggcggtcact   48600
ccgattggct gcccgctgag cagatggccg atctgatccg ccaggtcggc gtgtccgacc   48660
atgtgcgcgg cttcgccacg aacgtgtcca actaccagtc cacgaccgcc gagttcgact   48720
acgcccacga ggtggccggc ctcctcgag gcgacgtgca cgcgatcgtc gacacgtcgc    48780
gcaacggcgc cggcccggcg gggagcgagt ggtgcaatcc cgcaggacga ctgatcggag   48840
accccggggg cacctacggc gacgacgtcg tcgacacgaa cctctggatc aagccgcccg   48900
gcgagagcga cggcacctgc aacggcggcc ccgatgccgg cgtctggtgg ccgagggct    48960 ccgcggagct caccccgcgaa gcgcggtgag ggccacgggg ggccgctcac aacatatgta   49020
caagtatgga atgataacgc tggaccgagc ggtgccaccg gtctgcgcga ccttcggttc    49080
gcagcatccg ctcacctaga ccagcccgga gagcagggac atgagcgatt cagcggacgt   49140
caagaccgca gtcatcgtcg aggacgatcc cgacatccgg catctcctcg tcgaggtcct   49200
cgaatcggcc ggcttctcga ccgtgtcggt cggcaacggc atcgacggcg tccgcgcggt   49260
catcgcgtac cagccgttga tcaccacgct cgacgtcaac atgcccggca tcgacggatt   49320
cgaggccgca cgccgcatcc gggcgcagag cgacacctac atcatcatgc tgaccggcct   49380
ggaggacgag gccgacgtcg tgctcggcct cggcgcgggg gccgacgaat acgtcgtcaa   49440
gccgttccgg ccgcgcgagc tccgggcgcg catcgaagcc cttctccgcc ggccgcgcgg   49500
cggagacgct caggcgaacg ctccgcgaca ggactccgtc ggcccgtcct tccccggcgc   49560
gcgtcccacc gggcagacgc aatccatccc gatcgtgcgc aacgcacccg atgcccctca   49620
gcagccctcg ggccagccct ccgttccggc gttcgacgag caccggctgc cgccgaccag   49680
cgccatgccc gggtcgcccg tgatcgtccc ctcctcgcag gggcccgcct cctacccgc    49740 tccgggttcc gaggtggccg ttcggccgag cggcgccctc gcgccgaccg cgacaactg    49800 ggtgctgcac cgcgaccttc agctcgaccc cgagacccgc atcgtgctgg tcgccggcca   49860
ggagatggat ctgacccgca ccgagttcga cctgctggcg acgctcctcg aatcgaagcg   49920
gcgcgtgcgc agcaaggccg atctcacgct ggtcctgcgg ggagagtcct acgtgacgag   49980
ctacttcgtc ggcgatgccg acaagcgtgc gatcgaggcg cacatgacga acctgcgccg   50040
caagctcggc gacaacccgg ccgcaccgcg ctacatcgag acggtgcggg gagtcggcta   50100
ccgtctcacc tccgagctca cctcggcgtg atccgcgcgc agcacgcata acggatgcct   50160
cgaccctccc cagggccgag gcatccgtgt ttctgaaacg acgggttcgt gttcagacct   50220
tgtatccgtg gtagcgacgg acgagcttga agaacattcc gagggtctgg aggacggtca   50280
cgacgccgac gatcggccac ccgatccaga ggatcgtgga ctgggccatc gggccgatca   50340
gcatccagac gatcgtcatc gcgatcgcga tggcgatgag cacgatgagc ggcgtccagt   50400
gtccgagacc gccgcccttc tcggccttgg cctgcatcgc ccagttgtcg accttcttgc   50460
gggagaagaa gcggctccag gaacggacga agtggctgag acgcacccac atgaacatct   50520
ctgcgggaag gaaggtcgcc gcgaacagga cgtcgcgact gttgctgtcc ttcatcgtcc   50580
gcgcgatgcg cacgttgagc aggatcgcca tccccgacgg gatgagccac acggtgaga    50640 acacgaaggc gttgatcgac agcgagcccg ccaggagcgt cacgaaggcg acgcggacga   50700
aaaggttggt gagcatgccg aagttctcca gccaccgcag gcgcaggttc gggtgcagcg   50760 gctgacccctt cgtgtcgccg cgctggccgg gccacatgag ctcgatcgcg ccgtaggtcc   50820
acttgacctg ctgagcgtcg taacccgaga gcgtggtcat gccgccgacg ttcgcgcggg   50880
```

```
cgtaagggct gatcttggtg aggtacccgg cgctcttgat ctgcagcgac aggagcgagt   50940
cctccacctc ggagtcgcgc acccacgggg agttctggtg gttctgccgc atggcttcgc   51000
gcagcgcgtg ggtggagaag atcgagaact gcccgccgag gacggccatg ttgcgtccgc   51060
gcagcaggtt ctggagattg aaggccgcga actgcgtgcg ctgcccggcg atgaggaact   51120
tcgcgatggt gcccttgatc gggcggtcgt cgatggagta aatcgccgag ataccgccga   51180
tgcgggagtc cgccacggct tcgctctcga ggtactcgac ggcctgcttg tcggcgatgg   51240
tgtcaccgtc gacgccgagc aggtagtcgt acccctccac cagcgagtag ccgtagttca   51300
gcgccccgac cttcttgtcg gggttcttgc cgatgtcgtg gacgaagacc tcggtgaact   51360
gctcccccag gtcggtcgtg atctcgtgcg gcccgctgta ctcggaggcg atcttcacgg   51420
tcgcgtcgga cgtgttgttg acgacgacgt ggatgacgtc gggcacgcgc gtctgcttca   51480
ggagagcctc gatcacctca gcgatcgact cctcctcgtt gtaggccggg atgacgcacc   51540
cgatggtcga gcggtgtccg ccgttgttct ccagcaccgc ggagaagtcg tcggcgaagc   51600
ctgccgtcga gttcgcctgg atgggctcgt gggcgaacga gggggggcgcg aacgcctgag   51660 tggcgaggga ggtgcgcgtg tcgctcatgg gtgtcttcca atcggattct tcgaccttcc   51720
ggccgagacc cactctggcg gacccccctc agggaatcag cgaacgtaca tcacgcgttt   51780
ccgcaagatt ccctcaagat caccccgggg tcatccggcc gagccggcgg gatagatggc   51840
gatgggcacg tactggtaca cggtctgctg ggagaacgag ttctcgtcgt tcgcaccgcc   51900
ctcgacccag atgttcatcg cgaactccag ggtgacgccg taggtgtcgt tcggcatctg   51960
gtggatcgtc gtctccggga cgtgcagacc gccctggaag ctgttcagca gcagtccacg   52020
gtcggatcgg ttcgtgtcgg ccggcacgag cgtgcgcggg tcggcactga actggaaggg   52080
gctctgcacc tgacccgacg tctgagcggt ctgcgacgtg atcgagatcg acgagatgta   52140
gacgcggcgc ttctgggtga gcacggcctt ctcgtccgtg cgctggtcgt aggcgttgac   52200
ggcgaacccg aagtcttcct cccgatcggt cgtccactcc tgggtgcgcc gcgagtcgac   52260
ggcccacatg tcgagcgtca cctcgaggcc gtcggcgacc tcggtggtga gcgagaccga   52320
tccgtcgtag gtgaactgcg atgcgaagtc catcgacgcc gaaggctgcg gctgcggggt   52380
gacgaccgag gtcggggcgc tcgccgggtt ggagattccc tggacgctgt tgaacgtgtc   52440
gacgagctgt gcgcacccgg tgagcgacag accggcgagg gcgaaagagg cgacgaaggc   52500
cgcgacgcgg actttccggc gcgaagaatt gcgaaggctc atgggcccac tcctgaggat   52560
gagacgcgcg ggtgcgcgag ggtcggttcg gcgaccatca cgctgcggga tgcaggcctc   52620
agggggagtc tgaccgggcg atgagccgag agcatacatc ggccggagca gagacaggat   52680
ggcgcgcaag agaatacacc accgtcgtag actcaccgca tgggtgccgc gattcgtctt   52740
ccggcgtcgt cgccggtcga cgtcgtggaa gacccagaca acgcgtctcc gagcagccgc   52800
acccgatcga tctggctgct ccagctcgtt ctcgccgcga gcgtgatcgt cacggtgatc   52860
gtggtgcagg ccctccagcc gcagctgttc cgtgagtgga ccttctccgc cggggtcatc   52920
acgatcatcg tgttgacggt cgtgaccctg gtcgtcccgt ggccgcgcgt gccgcgaagc   52980
tcgatcgtcc tcgtgccgtt cctcgatctg atcggcatcg gtctgctcgc ctacgacagc   53040
gagatgcgct tcgggttctt ctgggtcttc ccggtgatct ggatcgcctc ccactattcg   53100
ctgctgcacc tcggcggcgc gctcggaacg gtcggcgcga tcatcctcat cgacgccaac   53160
ctgaacggcc ccaccccgtt ctccgccctg cggctcctcg tcgtgatgct ctcgctcgcc   53220
ttcatcggcc tcaccaccta cctcaccgct cgccagaaca acgcgttcaa gaacctcctg   53280
```

```
cgccgtcagg catcgcgcct ccagagcacg ctgcagcgcg tgaccggcca ggagcgacgg    53340
gtgtcggaga tgctcaacgg cctcgacacc gggatcgcgc gcctgtcctc cgacggggag    53400
gtgctcgcgc tcaacgacac ctacgtcacg ctctacgccg tcgaccgcga cgaccccaag    53460
cgtccggggg cgtctgtgga gtacgcgacc ctgcgcggcg agcccctgcc cgagcccgac    53520
cggccgttca tgcgcgcggc tcggggcgag cagttcgagg acgagcgggt ctggctctac    53580
gacacgcgcg gacagtggca tgcgctgtcg gcgtcgaccc gtcgcctgac ctcgagcgat    53640
gacgagcccg ccacgacgct gctcatcatc cacgacgtca ccgctctgat cgaggcggag    53700
cgagccaggg agcagatcgc gacggtcgtc tcgcacgagc tgcgcaaccc gctcacggcg    53760
atcatcggtc acgccgacct ccttctcgac cacgacgacc tcccgccccg cgtccgggac    53820
cagatcgagg tcatcgacaa tgccggccag cgcatgcaga agctgatctc ggagatcctc    53880
gcgggctccc gcgctcgttc ggacgagtcg agcgctccga actccgccga cgtgcgtcgc    53940
gtcatcgacg cgtccgtcga gtccttccgc ccggcctccg acgggcggcg catcgcgatc    54000
ctcgtcgagg tgcccgatga cctcccgctg gtcggcgacg cgttccgact gcgtcaggcg    54060
ttcgacaaca tcctgagcaa cgccatcaag tacacaccgg gcggcggaac cgtgcgcatc    54120
agcgcgacga ggaccgacga ccgcctcgtc gtctcgttcg ccgacaccgg ggtgggcatc    54180
tcgcccgccg acctgccgcg catcttcgac ccgtacttcc gcacgcagtc cgcgcgcgag    54240
agccccaccc ccggcaccgg cctcgggatg gggatcgtcc gcgacatcgt ggagcagcag    54300
ggcggtacgc tcgacgtgga cagcgagcag gggaccggta cgaccgtgac ggtcacgctg    54360
ccgatcgaga ccgaggcata aacggggttc ttcatggggt cgttctccgt cgccaacctc    54420
ggcatcgcgc aggcggtcgt cgcctcgctg ggaaccgtga tgatcgtcgg cctcggcttc    54480
ctccagcgcc cgtcgcgggc gtcgctgatg tggtcgctcg ccttcatcct cgccatggtc    54540
agcacctggg tcaccctggc gggcgaggca ctggccctcg agggtctgcg tcgcctcggc    54600
ctcggactca tgctcggcgc gccggcgctc atctggtcgg gcttccgcgc ccggcgacgt    54660
gtgcccgcgc tcccgtggat cgccgccgtg caggctgccg tatccgccgc ggtcctgatc    54720
gtgctggccg acccgcaggc ctacagcctc ggtttccgcg ccctgttcct cgtcgcgggc    54780
gtcttcgccg cgctcaccgt cgtcgagatc cagcgttccc ccgaccggca cgaacggctg    54840
gtgctccccc tgctgctcgt ctcgtccgct ttcgtcgtgc tgggcgtgtt ctccctcctc    54900
gccggtctga tctcgtcgcc cggcaccagc gaggacctcg ctctcgtgcg gctgctgaat    54960
tcgctcggga tgctggtcta cctcgtgtgc gtgaccgtca ccctcctgtt cttcacctcc    55020
gtgtcgagcg tcggtgtgca gacggcgcgg tcgtggaccc agttcgccgt cgccgcgacc    55080
gaccgcctgg cgcgcgcccg cgcggccggc gagacgagct gggtgctgct ctccgtgcag    55140
atcgacgatc ccgacgagat ccgcgcggcc gccgggagg cgtcgttctc ccgcatcgcc    55200
gaacgcttcg atcaggccgt cgtctcctcg ttccccgccg aagccgacat cgggcgcgag    55260
gggcggggcc gcctggtcgt gctgatcgcc cgacccgggc ccgtcgtccg cgagcacatg    55320
cgcgcactcc tgcacgaggt gtcgatcatc gacgccgctc agcagatctc cgtgcagctg    55380
tcggccagca tcggctgggc accggcggat gtcgtgggct acgacttccc cgcgctgctc    55440
accgcggcgc agcaggcctc ggccgaggca tccgcgcgag gcggagaccg ctggcagcgg    55500
atcggggcct gactactgcg agccgcccgc gatggcgacg gtgagcgtgt cggtggcggt    55560
ctgcttcgcg tactcgctcg aggtcggcgt ggtctgcacg aggtactcgt aggtgaactg    55620
```

```
cagggtgacg aaggtcgcac tgtcgggcac ctcgcccacg ttgaacgtct gcgagtagct   55680 gtagggtcg agcaccgggt agccggggct caccgtcgac tggtcgacct gcgcggtcag    55740
cggagcgaac gactcggtcg cgttgcccgg cacggcgatc atcgacgcgc gctgcaggta   55800
gacctgctgg ccgtcgttgg gcgtgacggt ggtcaccatg gagagctgga tcggcttcag   55860
cgccgtcgcc gtccacctgt ccatcgacag ggtcgaccag tagttgacgt cggcggcgac   55920
ggaaccggcc tggatcttgc gctcggtcga gccgctcgag aggtcgttgg gaaccggctg   55980
cggcgccgcc gactgcaccg cggacggcga ggtcgagacc gccggcgcat cgctgctgcc   56040
gaccgcccag ggcggggttc cgcaacccgt catgagaagg gccgccgtca gcgcgagggc   56100
gcccgcaccc accgtgcggc gtcgattcga agcgaacatg tacgggcctc tcccctggat   56160
gactgcgatt ctatccgcgg gcgggtgatc ggcccgcgac cgcctagggt gatcgggtga   56220
gcgcatcgac ctccgacgcc ccccgcagcc tgccgggtcg catcgtcgcc tggacattgg   56280
cggcgatcct cgccctcgcc gtgctcgggt cgctgtggat cggcgtgcgc ggcgcgatgg   56340
cctacgggca cctgaccgac gcgcaggatg cggcggccga ggtcgccgcg agcctgaacg   56400
acccggcggc cgcggccgac gccatcgccg gcatctccgc cgacacgtcg gccgcgcggt   56460
ccctcacgag cgacccgatc tggcgggccg ccgaatcgct gccgtggatc ggcgcgcagc   56520
tgtcggcggt gtcgaccgtg accgcggcga tcgacgatgt cgcgagctcg gcgctcaccc   56580
cgctggcgga ggtcgcgtcg tcgttctcgg tcgacgccat ccgcccccgg gacggggcga   56640
tcgacgtctc gctcttcaca tcgctcgccc ccgcggcccg caccggtgcc gacgcgatcg   56700
gcgcggccga agcatccgtc gactcgatcg acacgtcgct gttgatcggc ccctgcagg   56760 ccccgatcat ccaggcgcag gagctgctcg cgacgaccac ggccggcgcc gagaccctcg   56820
ctcgcgcgac cgagctcatg ccggccatgc tcggcgccga cggtccgcgc aactatctcg   56880
tgatcttcca gaacaacgcc gagtggcgct cgcagggcgg catcgtgggc gccatggccg   56940
tgatcagcac cgacggtgga cggatgtcgc tcaccgcgca gggatcgtcg ggcgacttcc   57000
gccggtacga ctcgtcggtg gtgccgctgt cgccggagct cctcggcgtg tacggcgaga   57060
ggcccgggca gtacatccag aacgccaccc aggtggccga cttcgcgctc accgggcaga   57120
tcgcgaagga gatgtgggcg cgcgagttcg gcacccaggt cgacggcgtc atctccctcg   57180
acccggtcgc gctgtcctac ctgctgacgg cgacaggacc gatcacgctg ccgaccggcg   57240
acgtgctcac cagcgacaac gcggtcgatc tgctcctcaa cggcgtctac cagcggtacg   57300
agcgtccggc agaccaggac gccttcttcc aggccgcggc cgcgacggtc ttctcggctc   57360
tgtcgtcggg ctccgccgag cctcgcccgc tcctcgaggc gctgtcgcgc gcgagcgacg   57420
agaaccgcct cctgctgtgg agcgctcgag aagacgacca ggcgatcctc gacgaaccga   57480
ccctgcaggg tgggctgccg gtgacggatg cggcgcagac ggcgttcggc gtctacctca   57540
acgacggcac cggctcgaag atggactact atctccgccg gggggcgggt gcggggtggt   57600
gcaccgaccc cgacggcggc tcgaccgcgg aggccgtcgt cacgatccgc aacgacgcac   57660
ccgccgatgc ggcgaacctg ccgacgtaca tcaccggcgg gggcagcttc ggagtgccgg   57720
agggatcggc ccgctccgtc gcctacctct acctgccgtc ggggggccgag ctcgtctcga   57780 gcgaggcctc aaacgccggc ggaaccccgg tgttcggcgg gggtttcgac tcgggccgcc   57840
aggtgatctc gtggacgagc gagctcgccc cgggcgagga ggcgacgctg cgggtacggg   57900
tgaggacgcc tcagacaccg cagctggtca tgcagataac accgattgtt aacacgaatg   57960
aaacgccgcg agttgcaagt acctgtgagt aacctcgata atcgttcaaa ggggaccctc   58020
```

```
aggatccacc tccaccgtcg ttcccctgcc ttgcacaacg ctgccattcc gcggcgacat   58080
gctgaccaag agacaggtgc cccccatgaa gaccaacttt gcaaaggtag ccgcggtgat   58140
cgcgatcgcc gccgccgcca cattcgtccc gctcgctgcc cacgcctacc ccaccggtga   58200
ggaagccagc gtctccagca cgaccgtcac gcccggcggg accatcgagt tcaccgtcgc   58260
ggacggcacg ttcgttcccg gcgagcccgt cacgatctcc ctcacgggtg agagcgcctc   58320
gggtgcgagc ctggcggtcc tcaaggccgc cgtcgagacc gccacgctcg gaaccatccc   58380
ggccgcggcc gacggttcca tcagcaccgg catcaagttc ccggccaacg cctcgggcgt   58440
ctacaccatc accgcgacgt cccctcggt tcccgagggt gtcagcgtga ccgtcaccgc   58500
cgcaacggcg agcggtggcg ccggcggcac cggcggctcc aacgccggtg cagcctgcc   58560 ggccacgggt atggactccg gctcgctcct cggcctctgg gtcggcggcg gcgcgctcgt   58620
cctcgccggt ggtgccgtcg ccgtcggtgc cgcagtgcac cgtcagcgca agcacgccgc   58680
gtaagacaca gcggttcgca gagagggtcg tccggaaacg ggcggccctc tctcgttgtc   58740
tctcagaccg cgtcgtctcc gacggggcg tgagcgtcgg acaccttcgc cgtgatgagg   58800
atcgggaggt ggtccgacaa cccctgggc agcgtacgga tgcgttcgat gtcgaagccc   58860
gacgacgtcg cgaagtcgta gtgcccacgg aagaaccggt accgggtgta ggttcgcgag   58920
tcgctcagtg tcagctcgta gccctgcgcg cggatcttct gcccgaggta ctccttgaag   58980
acgggatagt tgtagtcgcc gaccatgagc gtcggcagcc cctcccccag gttctgcagg   59040
gccgacagcg ccgtgcggat ctgatgacgc cgaagcgagt tcagtgccgt cagcggcgcc   59100
gcgtggaacg acgcgacgat gatctcgcgt ccgtggtcga tgtcgaacag ccgcacgccc   59160
agcatccgct cctcggcggg cttgagaacg tagtcgtgca gcgacttctt cagggcgagc   59220
gagcgcacct cgacggcgcg gaaggtgttc gcccggtagt acaccgccag ccccagcctg   59280
ttgcgctgcg tggcctcggc gagacggagg ccggcgatct cggcgggaag gcccgtcgtg   59340
tcgcactcct gcaggcagag gacgtcggca ccgtgggctt cgacgagctc ggcgagctcg   59400
gtcgccgcac ggtgcttgcg caggttgtag gagatgacct tcatagcggg tccagcctag   59460
gcacacgatc gatggcctcg ggccaggttg acaccggctc gccgtcgacc ggcggcgatc   59520
actcctggtc tcggcgacgc cgggtctgct cggcacgatc ggccagcagg tcgagcgccg   59580
gatagcccac ctcgctgagc gtcagtcccc gcgccgcgag caccttcgtc tcgctcgtgc   59640
gcaccgcgcc gtcgcggatc gacaccacgt catcgacgcc gagccgcccc tccccgaccg   59700
cgacgcacgc gccgacgaga gcgcggacca tgctgtggca gaacgcgtcc gcccgcacgt   59760
gcgcgagaag caccccctcg tcggtgcggc gccagtcgaa ctccagcagg gtgcggatcg   59820
tcgtcgcctc gtcccgcggc ttgcagtacg ccgcgaagtc gtggagtccg atgagcgagc   59880
gtgccgcagc atccatgctc tcgacgtctt tccagcacag tgggatccga agcttggaat   59940
tcacgtgact tgaagtcgcg gccgcactga ccctatagtg agtcgtatta atttaaatca   60000
taccaac                                                              60007
```